US011013814B2

United States Patent
Novak et al.

(10) Patent No.: US 11,013,814 B2
(45) Date of Patent: May 25, 2021

(54) CARTILAGE-HOMING PEPTIDE CONJUGATES AND METHODS OF USE THEREOF

(71) Applicant: BLAZE BIOSCIENCE, INC., Seattle, WA (US)

(72) Inventors: Julia E. Novak, Sequim, WA (US); Natalie Winblade Nairn, Seattle, WA (US); Dennis M. Miller, Woodinville, WA (US); Scott Presnell, Tacoma, WA (US); Claudia Jochheim, Seattle, WA (US); Mark Stroud, Seattle, WA (US)

(73) Assignee: Blaze Bioscience, Inc., Seattle, WA (US)

( * ) Notice: Subject to any disclaimer, the term of this patent is extended or adjusted under 35 U.S.C. 154(b) by 0 days.

(21) Appl. No.: 16/492,914

(22) PCT Filed: Mar. 16, 2018

(86) PCT No.: PCT/US2018/023006
§ 371 (c)(1),
(2) Date: Sep. 10, 2019

(87) PCT Pub. No.: WO2018/170480
PCT Pub. Date: Sep. 20, 2018

(65) Prior Publication Data
US 2020/0069812 A1    Mar. 5, 2020

Related U.S. Application Data

(60) Provisional application No. 62/472,485, filed on Mar. 16, 2017.

(51) Int. Cl.
| | |
|---|---|
| *A61K 47/00* | (2006.01) |
| *A61K 47/64* | (2017.01) |
| *A61K 47/65* | (2017.01) |
| *A61P 19/02* | (2006.01) |
| *A61P 13/12* | (2006.01) |
| *A61B 5/00* | (2006.01) |
| *A61B 6/03* | (2006.01) |
| *A61B 6/00* | (2006.01) |
| *A61K 49/00* | (2006.01) |
| *A61K 51/08* | (2006.01) |
| *C07K 14/435* | (2006.01) |
| *C07K 14/47* | (2006.01) |
| *C07K 16/24* | (2006.01) |
| *A61B 5/055* | (2006.01) |
| *A61B 8/08* | (2006.01) |

(52) U.S. Cl.
CPC ........ *A61K 47/6415* (2017.08); *A61B 5/0071* (2013.01); *A61B 6/037* (2013.01); *A61B 6/4057* (2013.01); *A61B 6/481* (2013.01); *A61K 47/65* (2017.08); *A61K 49/0056* (2013.01); *A61K 49/0058* (2013.01); *A61K 51/08* (2013.01); *A61P 13/12* (2018.01); *A61P 19/02* (2018.01); *C07K 14/43518* (2013.01); *C07K 14/43522* (2013.01); *C07K 14/4726* (2013.01); *C07K 16/244* (2013.01); *C07K 16/248* (2013.01); *A61B 5/055* (2013.01); *A61B 8/481* (2013.01); *A61B 2505/05* (2013.01); *C07K 2319/30* (2013.01); *C07K 2319/33* (2013.01); *C07K 2319/50* (2013.01)

(58) Field of Classification Search
CPC ..... A61B 5/0071; A61B 6/037; A61B 6/4057; A61B 8/481; A61K 38/00; A61K 47/65; A61K 49/0056; A61K 49/0058; A61K 51/08; A61P 13/12; A61P 19/02; C07K 14/4726; C07K 16/22; C07K 16/244; C07K 16/248; C07K 16/2887; C07K 16/42; C07K 2317/21; C07K 2319/21; C07K 2319/30; C07K 2319/33; C07K 2319/43; C07K 2319/50; G01N 33/57484
See application file for complete search history.

(56) References Cited

U.S. PATENT DOCUMENTS

| | | | |
|---|---|---|---|
| 8,945,553 B2 | 2/2015 | Stevens et al. | |
| 9,944,683 B2 | 4/2018 | Olson | |
| 2003/0031669 A1 | 2/2003 | Goldenberg | |

(Continued)

FOREIGN PATENT DOCUMENTS

| | | |
|---|---|---|
| CA | 2993891 A1 | 1/2017 |
| CN | 101583370 A | 11/2009 |

(Continued)

OTHER PUBLICATIONS

English machine translation of JP2005511017A, obtained via Google patents on Sep. 28, 2020 (Year: 2005).*

(Continued)

*Primary Examiner* — James H Alstrum-Acevedo
*Assistant Examiner* — Mercy H Sabila
(74) *Attorney, Agent, or Firm* — Polsinelli PC

(57) ABSTRACT

Peptides that home, target, migrate to, are directed to, are retained by, or accumulate in and/or bind to the cartilage or kidney of a subject are disclosed. Pharmaceutical compositions and uses for peptides or peptide-active agent complexes comprising such peptides are also disclosed. Such compositions can be formulated for targeted delivery of an active agent to a target region, tissue, structure or cell in the cartilage. Targeted compositions of the disclosure can deliver peptide or peptide-active agent complexes to target regions, tissues, structures, or cells targeted by the peptide.

25 Claims, 17 Drawing Sheets
Specification includes a Sequence Listing.

(56) References Cited

U.S. PATENT DOCUMENTS

| | | | |
|---|---|---|---|
| 2006/0088899 | A1 | 4/2006 | Alvarez et al. |
| 2009/0142266 | A1 | 6/2009 | Ronjat et al. |
| 2010/0215575 | A1 | 8/2010 | O'Neill et al. |
| 2013/0028836 | A1 | 1/2013 | Sentissi et al. |
| 2013/0164220 | A1 | 6/2013 | Yu et al. |
| 2013/0280281 | A1 | 10/2013 | Castaigne et al. |
| 2014/0179560 | A1* | 6/2014 | Olson .......... A61P 31/00 506/12 |
| 2015/0182596 | A1* | 7/2015 | Lee .......... A61K 38/30 514/8.6 |
| 2019/0117728 | A1 | 4/2019 | Olson et al. |

FOREIGN PATENT DOCUMENTS

| | | |
|---|---|---|
| JP | 2009023993 A | 2/2009 |
| JP | 2013224283 A | 10/2013 |
| WO | WO-2001053342 A1 | 7/2001 |
| WO | WO-2003020751 A2 | 3/2003 |
| WO | WO-03082196 A2 | 10/2003 |
| WO | WO-2008063291 A2 | 5/2008 |
| WO | WO-2012064658 A1 | 5/2012 |
| WO | WO-2013078250 A2 | 5/2013 |
| WO | WO-2014063012 A1 | 4/2014 |
| WO | WO-2014093406 A1 | 6/2014 |
| WO | WO-2014180534 A1 | 11/2014 |
| WO | WO-2015013330 A2 | 1/2015 |
| WO | WO-2015075699 A1 | 5/2015 |
| WO | WO-2015100370 A2 * | 7/2015 .......... A61K 47/26 |
| WO | WO-2015100370 A3 | 7/2015 |
| WO | WO-2015179635 A2 | 11/2015 |
| WO | WO-2016112176 A1 | 7/2016 |
| WO | WO-2016112208 A2 | 7/2016 |
| WO | WO-2016118859 A1 | 7/2016 |
| WO | WO-2016210376 A2 | 12/2016 |
| WO | WO-2017044894 A2 * | 3/2017 .......... A61K 47/64 |
| WO | WO-2017100700 A2 | 6/2017 |
| WO | WO-2017143259 A1 | 8/2017 |
| WO | WO-2018049285 A1 | 3/2018 |
| WO | WO-2018119001 A1 | 6/2018 |
| WO | WO-2018136614 A1 | 7/2018 |
| WO | WO-2018170480 A1 | 9/2018 |
| WO | WO-2018232122 A1 | 12/2018 |

OTHER PUBLICATIONS

English machine translation of JP2003520808A obtained via Google patents on Sep. 28, 2020 (Year: 2003).*
AAAAI. Inhaled Corticosteroids: Are considered the most effective long term usage medication for control and management of asthma. © 2017 American Academy of Allergy, Asthma & Immunology. 6 pages. URL:< https://www.aaaai.org/conditions-and-treatments/treatments/drug-guide/inhaled-corticosteroids>.
ACR Press Release, Nov. 2015 regarding 2 year study in which IA THA or and saline was administered to patients with symptomatic knee OA.
Akdag, et al. The Uptake Mechanism of the Cell-Penetrating pVEC Peptide. J. Chem. 2013, 1-9 (2013).
Akhmedov, D., et al. Knock-in luciferase reporter mice for in vivo monitoring of CREB activity. PLoS One 11, 1-13 (2016).
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Altschul, et al. Optimal sequence alignment using affine gap costs. Bulletin of Mathematical Biology. 1986; 48(5-6):603-16.
Alves, et al. Animal Models of Bone Loss in Inflammatory Arthritis: from Cytokines in the Bench to Novel Treatments for Bone Loss in the Bedside—a Comprehensive Review. Clin Rev Allergy Immunol. Aug. 2016;51(1):27-47. doi: 10.1007/s12016-015-8522-7.
Appelbaum, et al. Arginine Topology Controls Escape of Minimally Cationic Proteins from Early Endosomes to the Cytoplasm. Chem. Biol. 19, 819-830 (2012).

Ashkenazi, et al. From basic apoptosis discoveries to advanced selective BCL-2 family inhibitors. Nature Reviews Drug Discovery, 16, 273-284 (2017). Published online:Feb. 17, 2017. doi:10.1038/nrd.2016.253.
Baar, et al. Targeted apoptosis of senescent cells restores tissue homeostasis in response to chemotoxicity and aging. Cell 169.1 (2017): 132-147.
Bagal, et al. Ion channels as therapeutic targets: a drug discovery perspective. J Med Chem. Feb. 14, 2013;56(3):593-624. doi: 10.1021/jm3011433. Epub Nov. 29, 2012.
Baik, et al. Fluorescence Identification of Head and Neck Squamous Cell Carcinoma and High-Risk Oral Dysplasia With BLZ-100, a Chlorotoxin-Indocyanine Green Conjugate. JAMA Otolaryngol Head Neck Surg. Published on line Feb. 18, 2016. doi: 10.1001/jamaoto.2015.3617; JAMA Otolaryngol Head Neck Surg. Apr. 1, 2016; 142(4): 330-338.
Baker et al. Electrostatics of nanosystems: application to microtubules and the ribosome. Proc Natl Acad Sci U S A.Aug. 28, 2001;98(18):10037-41.
Balayssac, et al. Comparison of Penetratin and Other Homeodomain-Derived Cell-Penetrating Peptides: Interaction in a Membrane-Mimicking Environment and Cellular Uptake Efficiency. Biochemistry 45, 1408-1420 (2006).
Bandaranayake, et al. Daedalus: a robust, turnkey platform for rapid production of decigram quantities of active recombinant proteins in human cell lines using novel lentiviral vectors. Nucleic Acids Res. Nov. 2011;39(21):e143. doi: 10.1093/nar/gkr706. Epub Sep. 12, 2011.
Bao, et al. The tripeptide phenylalanine-(D) glutamate-(D) glycine modulates leukocyte infiltration and oxidative damage in rat injured spinal cord. Neuroscience. Jul. 7, 2006;140(3):1011-22. Epub Apr. 3, 2006.
Barad, et al., Rolipram, a type IV-specific phosphodiesterase inhibitor, facilitates the establishment of long-lasting long-term potentiation and improves memory. Proc. Natl. Acad. Sci. 95, 15020-15025 (1998).
Barchetta et al. Neurotensin Is a Lipid-Induced Gastrointestinal Peptide Associated with Visceral Adipose Tissue Inflammation in Obesity. Nutrients 10, 526 (2018).
Bar-Or, et al. A randomized clinical trial to evaluate two doses of an intra-articular injection of LMWF-5A in adults with pain due to osteoarthritis of the knee. PLoS One. Feb. 3, 2014;9(2):e87910. doi: 10.1371/journal.pone.0087910. eCollection 2014.
Bar-Or, et al. Low Molecular Weight Fraction of Commercial Human Serum Albumin Induces Morphologic and Transcriptional Changes of Bone Marrow-Derived Mesenchymal Stem Cells. Stem Cells Transl Med. Aug. 2015;4(8):945-55. doi: 10.5966/sctm.2014-0293. Epub Jun. 3, 2015.
Barton, Geoffrey J. Protein secondary structure prediction. Curr Opin Struct Biol. Jun. 1995;5(3):372-6.
Bendtsen, et al. Improved prediction of signal peptides: SignalP 3.0. Journal of molecular biology 340.4 (2004): 783-795.
Benedek, T.G. History of the development of corticosteroid therapy. Clin Exp Rheumatol. Sep.-Oct. 2011;29(5 Suppl 68):S-5-12. Epub Oct. 21, 2011.
Berger, et al. Computationally designed high specificity inhibitors delineate the roles of BCL2 family proteins in cancer. Elife 5, (2016).
Berman, et al. The protein data bank. Nucleic acids research 28.1 (2000): 235-242.
Bernard et al. Identification of an interleukin-15alpha receptor-binding site on human interleukin-15. J Biol Chem. Jun. 4, 2004;279(23):24313-22.
Bernhard, et al. Should we use cells, biomaterials, or tissue engineering for cartilage regeneration? Stem Cell Research & Therapy 7(1). Dec. 2016. DOI: 10.1186/s13287-016-0314-3.
Beyder, et al. Targeting ion channels for the treatment of gastrointestinal motility disorders. Therapeutic advances in gastroenterology 5.1 (2012): 5-21.
Bhardwaj, et al. Accurate de novo design of hyperstable constrained peptides. Nature 538, 329-335 (2016).
Bjellqvist et al. Reference points for comparisons of two-dimensional maps of proteins from different human cell types

(56) References Cited

OTHER PUBLICATIONS defined in a pH scale where isoelectric points correlate with polypeptide compositions. Electrophoresis. Mar.-Apr. 1994;15(3-4):529-39.
Bjellqvist et al. The focusing positions of polypeptides in immobilized pH gradients can be predicted from their amino acid sequences. Electrophoresis. Oct. 1993;14(10):1023-31.
Bodenhofer, et al. msa: an R package for multiple sequence alignment. Bioinformatics31.24 (2015): 3997-3999.
Bohlen, et al. A bivalent tarantula toxin activates the capsaicin receptor, TRPV1, by targeting the outer pore domain. Cell 141, 834-845 (2010).
Boisseau, et al. Cell penetration properties of maurocalcine, a natural venom peptide active on the intracellular ryanodine receptor. Biochim. Biophys. Acta—Biomembr. 1758, 308-319 (2006).
Boswell, C. A. et al. Comparative Physiology of Mice and Rats: Radiometric Measurement of Vascular Parameters in Rodent Tissues. (2014).
Bouchaud et al. The exon-3-encoded domain of IL-15ralpha contributes to IL-15 high-affinity binding and is crucial for the IL-15 antagonistic effect of soluble IL-15Ralpha. J Mol Biol. Sep. 26, 2008;382(1):1-12.
Boules, et el, Diverse roles of neurotensin agonists in the centralnervous system; Front Endocrinol (Lausanne). 2013; 4: 36.
Brattsand, R. Overview of Newer Glucocorticosteroid Preparations for Inflammatory Bowel Disease. IDB: Trends in Medical Therapy. Canadian Journal of Gastroenterology. vol. 4 (1990), Issue 7, pp. 407-414.
Brüggemann, M. et al. Human Antibody Production in Transgenic Animals. Arch. Immunol. Ther. Exp. (Warsz). 63, 101-8 (2015).
Bruno, et al. Basics and recent advances in peptide and protein drug delivery. Ther Deliv. Nov. 2013;4(11):1443-67.
Burns, Christopher. The History of Cortisone Discovery and Development. Rheumatic Disease Clinics of North America. vol. 42, Issue 1, Feb. 2016, pp. 1-14.
Butoescu, et al. Dexamethasone-containing PLGA superparamagnetic microparticles as carriers for the local treatment of arthritis. Biomaterials. Mar. 2009;30(9):1772-80. doi: 10.1016/j.biomaterials.2008.12.017. Epub Jan. 8, 2009.
Butte, et al. Near-infrared imaging of brain tumors using the Tumor Paint BLZ-100 to achieve near-complete resection of brain tumors. Neurosurg Focus. Feb. 2014;36(2):E1.
Carver, et al. The design of Jemboss: a graphical user interface to EMBOSS. Bioinformatics. Sep. 22, 2003;19(14):1837-43.
Chaturvedi, et al. A review on mucoadhesive polymer used in nasal drug delivery system. J Adv Pharm Technol Res. Oct. 2011;2(4):215-22. doi: 10.4103/2231-4040.90876.
Chen, et al., A targeted IL-15 fusion protein with potent anti-tumor activity. Cancer biology & therapy. Sep. 2015. vol. 16 No. 8, pp. 1415-1421; abstract; p. 1416, 1st column, 1st paragraph; p. 1416.
Chen, et al. The application of aptamer in apoptosis. Biochimie. vol. 132, Jan. 2017, pp. 1-8. Available online Oct. 14, 2016.
Chen, et al. Toxin acidic residue evolutionary function-guided design of de novo peptide drugs for the immunotherapeutic target, the Kv1.3 channel. Scientific reports 5 (2015): 9881.
Chen, et al. Unusual binding mode of scorpion toxin BmKTX onto potassium channels relies on its distribution of acidic residues. Biochemical and biophysical research communications 447.1 (2014): 70-76.
Chen, J. et al., Protein-protein interactions: General trends in the relationship between binding affinity and interfacial buried surface area. Protein Sci. 22, 510-515 (2013).
Cheung, et al., Identification of chondrocyte-binding peptides by phage display. Journal of Orthopaedic research. Jul. 2013; 31:1053-1058.
Choi, et al. A general strategy for generating intact, full-length IgG antibodies that penetrate into the cytosol of living cells. MAbs 6, 1402-1414 (2014).
Collaborative computational Project, No. 4. The CCP4 suite: programs for protein crystallography. Acta Crystallogr. D Biol. Crystallogr. 50:760-763 (1994).
Compton, et al. A review of osteocyte function and the emerging importance of sclerostin. J Bone Joint Surg Am. Oct. 1, 2014;96(19):1659-68. doi: 10.2106/JBJS.M.01096.
Corbi-Verge, et al. Strategies to Develop Inhibitors of Motif-Mediated Protein-Protein Interactions as Drug Leads. Annu. Rev. Pharmacol. Toxicol. 57, 39-60 (2017).
Cordes, et al. Sequence space, folding and protein design. Curr Opin Struct Biol. Feb. 1996;6(1):3-10.
Correnti, et al. Screening, large-scale production, and structure-based classification for cystine-dense peptides. Nat Struct Mol Biol. Mar. 2018; 25(3): 270-278.
Craik et al., Potential therapeutic applications of the cyclotides and related cystine knot mini-proteins. Expert Opin. Investig. Drugs 16, 595-604 (2007).
Crook, Z. R. et al. Mammalian display screening of diverse cystine-dense peptides for difficult to drug targets. Nat. Commun. 8, 2244 (2017).
Crowley, P. J. et al. Bioorganic & Medicinal Chemistry The role of molecular modeling in the design of analogues of the fungicidal natural products crocacins A and D. Bioorg. Med. Chem. 16, 10345-10355 (2008).
Daly, et al. Bioactive cystine knot proteins. Curr Opin Chem Biol. Jun. 2011;15(3):362-8. doi: 10.1016/j.cbpa.2011.02.008. Epub Feb. 27, 2011.
Dancevic, et al. Current and emerging therapeutic strategies for preventing inflammation and aggrecanase-mediated cartilage destruction in arthritis. Arthritis Res Ther. 2014;16(5):429.
Daniels, T. R. et al. The transferrin receptor and the targeted delivery of therapeutic agents against cancer. Biochim. Biophys. Acta—Gen. Subj. 1820, 291-317 (2012).
Davis, et al. MolProbity: all-atom contacts and structure validation for proteins and nucleic acids. Nucleic acids research 35.suppl_2 (2007): W375-W383.
De Coupade, et al. Novel human-derived cell-penetrating peptides for specific subcellular delivery of therapeutic biomolecules. Biochem. J. 390, 407-418 (2005).
De Groot, et al. Glucocorticoid Therapy and Adrenal Suppression. 2000. South Dartmouth (MA): MDText.com, Inc. 27 pages.
Derakhshankhah H et al.; Cell penetrating peptides: A concise review with emphasis on biomedical applications; Biomed Pharmacother. Dec. 2018;108:1090-1096. doi: 10.1016/j.biopha.2018.09.097. Epub Sep. 28, 2018.
Derendorf, et al. Pharmacokinetics and pharmacodynamics of glucocorticoid suspensions after intra-articular administration. Clin Pharmacol Ther. Mar. 1986;39(3):313-7.
Di Munno, O. Effects of glucocorticoid treatment on focal and systemic bone loss in rheumatoid arthritis. J Endocrinol Invest. Jul. 2008;31(7 Suppl):43-7.
Dohmen, et al. Multifunctional CPP polymer system for tumor-targeted pDNA and siRNA delivery. Methods Mol Biol. 2011;683:453-63. doi: 10.1007/978-1-60761-919-2_32.
Dolinsky et al. PDB2PQR: expanding and upgrading automated preparation of biomolecular structures for molecular simulations. Nucleic Acids Res.Jul. 2007;35(Web Server issue):W522-5.
Dou, et al. Overview of proteasome inhibitor-based anti-cancer therapies: perspective on bortezomib and second generation proteasome inhibitors versus future generation inhibitors of ubiquitin-proteasome system. Curr Cancer Drug Targets. 2014;14(6):517-36.
D'Souza, et al. Structural parameters modulating the cellular uptake of disulfide-rich cyclic cell-penetrating peptides: MCoTI-II and SFTI-1. Eur. J. Med. Chem. 88, 10-18 (2014).
Drake, et al. Bisphosphonates: Mechanism of Action and Role in Clinical Practice. Mayo Clin Proc. Author manuscript; available in PMC Sep. 1, 2009. Mayo Clin Proc. Sep. 2008; 83(9): 1032-1045.
Drin, et al. Physico-chemical requirements for cellular uptake of pAntp peptide: Role of lipid-binding affinity. Eur. J. Biochem. 268, 1304-1314 (2001).
Drug Bank (https://www.drugbank.ca/drugs/DB01248 created Jun. 13, 2005, updated Nov. 22, 2019).

(56) References Cited

OTHER PUBLICATIONS

Duchardt, et al. A cell-penetrating peptide derived from human lactoferrin with conformation-dependent uptake efficiency. J. Biol .Chem. 284, 36099-108 (2009).
Ducry, et al. Antibody-drug conjugates: linking cytotoxic payloads to monoclonal antibodies. Bioconjug Chem. Jan. 2010;21(1):5-13. doi: 10.1021/bc9002019.
Dulhunty, et al. Multiple actions of imperatoxin A on ryanodine receptors: Interactions with the II-III loop 'A' fragment. J. Biol. Chem. 279, 11853-11862 (2004).
Elmallah, et al. Marine Drugs Regulating Apoptosis Induced by Tumor Necrosis Factor-Related Apoptosis-Inducing Ligand (TRAIL). Mar Drugs. Nov. 13, 2015;13(11):6884-909. doi: 10.3390/md13116884.
EMBOSS iep. Available at http://emboss.sourceforge.net/apps/release/6.6/emboss/apps/iep.html. Accessed on Dec. 26, 2018.
Emsley et al. Coot: model-building tools for molecular graphics. Acta crystallographica Section D, Biological crystallography 60:2126-2132 (2004).
EP16815459.9 Extended European Search Report dated Nov. 28, 2018.
EP16845226.6 The Extended European Search Report dated Mar. 28, 2019.
EP16874006.6 The Extended European Search Report dated Jul. 30, 2019.
EP16874006.6 The partial Supplemental European Search Report dated Apr. 24, 2019.
EP17849695.6 The Extended European Search Report dated Apr. 1, 2020.
Erazo-Oliveras, et al. Protein delivery into live cells by incubation with an endosomolytic agent. Nat. Methods 11, 861-867 (2014).
Esteve, et al. Critical amino acid residues determine the binding affinity and the Ca 2+ release efficacy of maurocalcine in skeletal muscle cells. J. Biol. Chem. 278, 37822-37831 (2003).
Everts, S. Can we hit the snooze button on aging?. Chemical & Engineering News 95.10 (Mar. 6, 2017): 31-35.
Farr, et al. Clinical cartilage restoration: evolution and overview. Clin Orthop Relat Res. Oct. 2011;469(10):2696-705. doi: 10.1007/s11999-010-1764-z.
Fidel et al. Preclinical Validation of the Utility of BLZ-100 in Providing Fluorescence Contrast for Imaging Spontaneous Solid Tumors. Cancer Res. Oct. 15, 2015;75(20):4283-91.
Finton, et al. Autoreactivity and Exceptional CDR Plasticity (but Not Unusual Polyspecificity) Hinder Elicitation of the Anti-HIV Antibody 4E10. PLoS Pathog. 9, e1003639 (2013).
Fischer, et al. Apoptosis-based therapies and drug targets. Cell Death Differ. Aug. 2005;12 Suppl 1:942-61.
Fu et al. Programmed Hydrolysis in Designing Paclitaxel Prodrug for Nanocarrier Assembly. Sci Rep. Jul. 13, 2015;5:12023.
Furtek, et al. Strategies and Approaches of Targeting STAT3 for Cancer Treatment. ACS Chem. Biol. 11, 308-318 (2016).
Garcia, et al. Constitutive activation of Stat3 by the Src and JAK tyrosine kinases participates in growth regulation of human breast carcinoma cells. Oncogene 20, 2499-2513 (2001).
Gasteiger, et al. Protein Identification and Analysis Tools on the ExPASy Server. Excerpt, available at: http://web.expasy.org/compute_pi/pi_tool-doc.html. Accessed Nov. 7, 2018.
Gasteiger, et al. Protein Identification and Analysis Tools on the ExPASy Server. (In) John M. Walker (ed): The Proteomics Protocols Handbook, Humana Press (2005; pp. 571-607).
Gautam, et al. Topical Delivery of Protein and Peptide Using Novel Cell Penetrating Peptide IMT-P8. Sci. Rep. 6, 26278 (2016).
Geissler, et al. American Society of Biomechanics Journal of Biomechanics Award 2013: cortical bone tissue mechanical quality and biological mechanisms possibly underlying atypical fractures. J Biomech. Apr. 13, 2015;48(6):883-94. doi: 10.1016/j.jbiomech.2015.01.032. Epub Feb. 2, 2015.
Gelly, et al. The Knottin website and database: a new information system dedicated to the knottin scaffold. Nucleic acids research 32.suppl_1 (2004): D156-D159.

Geng, et al. Peptide-drug conjugate linked via a disulfide bond for kidney targeted drug delivery. Bioconjug Chem. Jun. 20, 2012;23(6):1200-10. doi: 10.1021/bc300020f. Epub Jun. 12, 2012.
Gibson, et al. BCL-2 Antagonism to Target the Intrinsic Mitochondrial Pathway of Apoptosis. Clin Cancer Res. Nov. 15, 2015;21(22):5021-9. doi: 10.1158/1078-0432.CCR-15/0364.
Goldring, et al. Emerging Targets in Osteoarthritis Therapy. Curr Opin Pharmacol. Jun. 2015; 22: 51-63. Published online Apr. 10, 2015. doi: 10.1016/j.coph.2015.03.004.
Goodsell, David S. Multidrug Resistance Transporters: Many bacteria use multidrug resistance transporters to pump drugs and poisons out of the cell. Molecule of the Month. Web article. Protein Data Bank (PDB-101). Nov. 2007. 3 pages. URL:<https://pdb101.rcsb.org/motm/95>.
Gothard, et al. Tissue engineered bone using select growth factors: A comprehensive review of animal studies and clinical translation studies in man. Eur Cell Mater. Oct. 6, 2014;28:166-207.
Gould, et al. Cyclotides, a novel ultrastable polypeptide scaffold for drug discovery. Current pharmaceutical design 17.38 (2011): 4294-4307.
Gump, et al. TAT transduction: the molecular mechanism and therapeutic prospects. Trends Mol Med. Oct. 2007;13(10):443-8.
Guo, et al. Protection Against Th17 Cells Differentiation by an Interleukin-23 Receptor Cytokine-Binding Homology Region. PLoS One, Sep. 19, 2012, 7(9), e45625.
Gurrola, et al. Imperatoxin A, a Cell-Penetrating Peptide from Scorpion Venom, as a Probe of Ca-Release Channels/Ryanodine Receptors. Pharmaceuticals (Basel). 3, 1093-1107 (2010).
Guzman, Flavio. Mechanism of action, indications and adverse effects of: etanercept, infliximab and adalimumab. Pharmacoloy Corner. Available at: http://pharmacologycorner.com/mechanism-of-action-indications-and-adverse-effects-of-etanercept-infliximab-and-adalimumab. Accessed Nov. 7, 2018.
Haas, et al. Drug-targeting to the kidney: renal delivery and degradation of a naproxen-lysozyme conjugate in vivo. Kidney Int. Dec. 1997;52(6):1693-9.
Hainer, et al. Diagnosis, treatment, and prevention of gout. Am Fam Physician. Dec. 15, 2014;90(12):831-6.
Hammaker, et al. "Go upstream, young man": lessons learned from the p38 saga. Ann Rheum Dis. Jan. 2010;69 Suppl 1:i77-82. doi: 10.1136/ard.2009.119479.
Hamman, et al. Oral delivery of peptide drugs: barriers and developments. BioDrugs. 2005;19(3):165-77.
Han, et al. Structural basis of a potent peptide inhibitor designed for Kv1. 3 channel, a therapeutic target of autoimmune disease. Journal of Biological Chemistry 283.27 (2008): 19058-19065.
Harada, et al. Antitumor protein therapy; application of the protein transduction domain to the development of a protein drug for cancer treatment. Breast Cancer. 2006;13(1):16-26.
He, et al. Low molecular weight hydroxyethyl chitosan-prednisolone conjugate for renal targeting therapy: synthesis, characterization and in vivo studies. Theranostics. 2012;2(11):1054-63. doi: 10.7150/thno.3705. Epub Nov. 6, 2012.
Henikoff et al. Amino acid substitution matrices from protein blocks. PNAS USA 89(22):10915-10919 (1992).
Hermans et al., Phospholipase C Activation by Rat Neurotensin Receptor Expressed in Chinese Hamster Ovary Cells. Clin. Neuropharmacol. 15, 130B (2012).
Herzig, et al. The Cystine Knot Is Responsible for the Exceptional Stability of the Insecticidal Spider Toxin ω-Hexatoxin-Hv1a. Toxins (Basel). Oct. 2015; 7(10): 4366-4380.
Hochberg, et al. American College of Rheumatology 2012 recommendations for the use of nonpharmacologic and pharmacologic therapies in osteoarthritis of the hand, hip, and knee. Arthritis Care Res (Hoboken). Apr. 2012;64(4):465-74.
Hockaday, et al., Imaging Glioma Extent with 131I-TM-601, J. Nuc. Med. 46(4): 580-586 (2005).
Hollander, J.L. Intrasynovial corticosteroid therapy in arthritis. Md State Med J. Mar. 1970;19(3):62-6.
Huber-Lang, et al. Mesenchymal Stem Cells after Polytrauma: Actor and Target. Stem Cells Int. 2016;2016:6289825. doi: 10.1155/2016/6289825. Epub Jun. 2, 2016.

(56) References Cited

OTHER PUBLICATIONS

Hunziker, et al. An educational review of cartilage repair: precepts & practice—myths & misconceptions—progress & prospects. Osteoarthritis Cartilage. Mar. 2015;23(3):334-50. doi: 10.1016/j.joca.2014.12.011. Epub Dec. 19, 2014.

Hwang, et al. Chondrocyte Apoptosis in the Pathogenesis of Osteoarthritis. Int J Mol Sci. Nov. 2015; 16(11): 26035-26054. Published online Oct. 30, 2015. doi: 10.3390/ijms161125943.

IUPHAR/BPS. Guide to Pharmacology—Tumour necrosis factor (TNF) receptor family. Available at: http://www.guidetopharmacology.org/GRAC/FamilyDisplayForward?familyId=334. Accessed Nov. 7, 2018.

Iyer, et al. Tying the knot: The cystine signature and molecular-recognition processes of the vascular endothelial growth factor family of angiogenic cytokines. The FEBS journal278.22 (2011): 4304-4322.

Jain, et al. Current ADC Linker Chemistry. Pharm Res. Nov. 2015;32(11):3526-40. doi: 10.1007/s11095-015-1657-7. Epub Mar. 11, 2015.

Jang, et al. A nucleic acid-hydrolyzing antibody penetrates into cells via caveolae-mediated endocytosis, localizes in the cytosol and exhibits cytotoxicity. Cell. Mol. Life Sci. 66, 1985-1997 (2009).

Janzer, et al. Drug conjugation affects pharmacokinetics and specificity of kidney-targeted peptide carriers, Bioconjugate chemistry 27.10 (2016):2441-2449.

Jentoft et al. Labeling of proteins by reductive methylation using sodium cyanoborohydride. J. Biol. Chem. 1979 254: 4359-65.

Jentoft et al. Protein labeling by reductive alkylation. Methods in Enzymology, 91(C), 570-579 (1983).

Karlsson, R., et al., Analyzing a kinetic titration series using affinity biosensors. Anal. Biochem. 349, 136-147 (2006).

Kean, et al. Clinical pharmacology of gold. Inflammopharmacology. Jun. 2008;16(3):112-25. doi: 10.1007/s10787-007-0021-x.

Kern, et al. Enzyme-Cleavable Polymeric Micelles for the Intracellular De-livery of Pro-Apoptotic Peptides. Mol Pharm. May 1, 2017;14(5):1450-1459. doi: 10.1021/acs.molpharmaceut.6b01178. Epub Mar. 30, 2017.

Kikuchi, et al., High proteolytic resistance of spider-derived inhibitor cystine knots. Int. J. Pept. 2015, (2015).

Kim, et al. Chondrocyte apoptosis: implications for osteochondral allograft transplantation. Clin Orthop Relat Res. Aug. 2008;466(8):1819-25. doi: 10.1007/s11999-008-0304-6. Epub May 28, 2008.

Kimura, et al. Engineered cystine knot peptides that bind αvβ3, αvβ5, and α5β1 integrins with low-nanomolar affinity. Proteins Struct. Funct. Bioinforma. 77, 359-369 (2009).

Kintizing, et al. Engineered knottin peptides as diagnostics, therapeutics, and drug delivery vehicles. Current opinion in chemical biology 34 (2016): 143-150.

Kirkland, et al. Clinical strategies and animal models for developing senolytic agents. Exp Gerontol. Aug. 2015;68:19-25. doi: 10.1016/j.exger.2014.10.012. Epub Oct. 28, 2014.

Kirkland, James L. Translating Advances from the Basic Biology of Aging into Clinical Application. Exp Gerontol. Jan. 2013; 48(1): 1-5. Published online Dec. 10, 2012. doi: 10.1016/j.exger.2012.11.014.

Kirwan, et al. A randomised placebo controlled 12 week trial of budesonide and prednisolone in rheumatoid arthritis. Ann Rheum Dis. Jun. 2004;63(6):688-95.

Kolmar, H. Biological diversity and therapeutic potential of natural and engineered cystine knot miniproteins. Current opinion in pharmacology 9.5 (2009): 608-614.

Kolmar, H. Natural and engineered cystine knot miniproteins for diagnostic and therapeutic applications. Current pharmaceutical design 17.38 (2011): 4329-4336.

Kozminsky-Atias, et al. Isolation of the first toxin from the scorpion *Buthus occitanus israelis* showing preference for Shaker potassium channels. FEBS letters 581.13 (2007): 2478-2484.

Krezel, et al. Solution structure of the potassium channel inhibitor agitoxin 2: caliper for probing channel geometry. Protein Science 4.8 (1995): 1478-1489.

Kumari, et al. Cysteine-Rich Peptide Family with Unusual Disulfide Connectivity from Jasminum sambac. J Nat Prod. Nov. 25, 2015;78(11):2791-9. doi: 10.1021/acs.jnatprod.5b00762. Epub Nov. 10, 2015.

Kuyinu, et al. Animal models of osteoarthritis: classification, update, and measurement of outcomes. J Orthop Surg Res. Feb. 2, 2016;11:19. doi: 10.1186/s13018-016-0346-5.

Lal, et al. Targeting the podocyte to treat glomerular kidney disease. Drug Discov Today. Oct. 2015;20(10):1228-34. doi: 10.1016/j.drudis.2015.06.003. Epub Jun. 19, 2015.

Lange, et al. Classical Nuclear Localization Signals: Definition, Function, and Interaction with Importin α*,s. J Biol Chem. Feb. 23, 2007; 282(8): 5101-5105.

Larking, et al. Clustal W and Clustal X version 2.0. Bioinformatics applications note. 2007. 2947-2948; 23(21).

Li, et al. Mitochondria and apoptosis: emerging concepts. F1000Prime Rep. 2015; 7: 42. Published online Apr. 1, 2015. doi: 10.12703/P7-42.

Li, et al. Synergistic Effects of Vascular Endothelial Growth Factor on Bone Morphogenetic Proteins Induced Bone Formation In Vivo: Influencing Factors and Future Research Directions. Biomed Res Int. 2016;2016:2869572. doi: 10.1155/2016/2869572. Epub Dec. 13, 2016.

Li, et al. Three dimensional de novo micro bone marrow and its versatile application in drug screening and regenerative medicine. Exp Biol Med (Maywood). Aug. 2015;240(8):1029-38. doi: 10.1177/1535370215594583.

Li, Z. et al. Influence of molecular size on tissue distribution of antibody fragments. MAbs 8, 113-9 (2016).

Lim, et al. A Cancer Specific Cell-Penetrating Peptide, BR2, for the Efficient Delivery of an scFv into Cancer Cells. PLoS One 8, (2013).

Ling et al., Molecular mechanism of the sea anemone toxin ShK recognizing the Kv1.3 channel explored by docking and molecular dynamic simulations. J. Chem. Inf. Model. 47, 1967-1972 (2007).

Liu, et al., Dual receptor recognizing cell penetrating peptide for selective targeting, efficient intratumoral diffusion and synthesized anti-glioma therapy. Theranostics. Jan. 1, 2016. vol. 6, No. 2, pp. 177-191.

Liu, et al. Robust structural analysis of native biological macromolecules from multi-crystal anomalous diffraction data. Acta Crystallographica Section D: Biological Crystallography 69.7 (2013): 1314-1332.

Lv et al. HIV protease inhibitors: a review of molecular selectivity and toxicity. HIV AIDS (Auckl). Apr. 8, 2015;7:95-104. doi: 10.2147/HIV.S79956. eCollection 2015.

Ma, et al. Engineered nanoparticles induce cell apoptosis: potential for cancer therapy. Oncotarget. Jun. 28, 2016;7(26):40882-40903. doi: 10.18632/oncotarget.8553.

MacMahon, et al. Injectable corticosteroid and local anesthetic preparations: a review for radiologists. Radiology. Sep. 2009;252(3):647-61. doi: 10.1148/radiol.2523081929.

Maillere, et al. Immunogenicity of a disulphide-containing neurotoxin: presentation to T-cells requires a reduction step. Toxicon, 1995; 33(4): 475-482.

Mamelak, et al. Phase I single-dose study of intracavitary-administered iodine-131-TM-601 in adults with recurrent high-grade glioma. J Clin Oncol. Aug. 1, 2006;24(22):3644-50.

McCoy, et al. Phaser crystallographic software. J Appl Crystallogr. Aug. 1, 2007;40(Pt 4):658-674. Epub Jul. 13, 2007.

McNulty, et al. TRPV4 as a therapeutic target for joint diseases. Naunyn Schmiedebergs Arch Pharmacol. Apr. 2015;388(4):437-50. doi: 10.1007/s00210-014-1078-x. Epub Dec. 18, 2014.

Mehndiratta, et al. Quinazolines as Apoptosis Inducers and Inhibitors: A Review of Patent Literature. Recent Pat Anticancer Drug Discov. 2016;11(1):2-66.

Mewar, et al. Treatment of rheumatoid arthritis with tumour necrosis factor inhibitors. Br J Pharmacol. Feb. 2011;162(4):785-91. doi: 10.1111/j.1476-5381.2010.01099.x.

Mitchell, et al. Polyarginine enters cells more efficiently than other polycationic homopolymers. J. Pept. Res. 56, 318-25 (2000).

Mitragotri, et al. Overcoming the challenges in administering biopharmaceuticals: formulation and delivery strategies. Nat Rev Drug Discov. Sep. 2014;13(9):655-72.

(56) References Cited

OTHER PUBLICATIONS

Mobasheri et al. Potassium channels in articular chondrocytes. Channels (Austin). Nov. 1, 2012; 6(6): 416-425.
Mobasheri, et al. Potassium Ion Channels in Articular Chondrocytes. Mechanosensitive Ion Channels Mechanosensitivity inCells and Tissues vol. 1, 2008, pp. 157-178.
Montagne, et al. The max b-HLH-LZ can transduce into cells and inhibit c-Myc transcriptional activities. PLoS One 7, 2-10 (2012).
Moore, et al. Engineering knottins as novel binding agents. Methods Enzymol. 2012;503:223-51.
Moore, et al. Knottins: disulfide-bonded therapeutic and diagnostic peptides. Drug Discovery Today: Technologies vol. 9, Issue 1, Spring 2012, pp. e3-e11.
Moroni, et al. Synthetic Pharmacotherapy for Lupus Nephritis. Expert Opin Pharmacother 18 (2), 175-186. Jan. 2, 2017.
Moroz, et al. Oral delivery of macromolecular drugs: Where we are after almost 100years of attempts. Adv Drug Deliv Rev. Jun. 1, 2016;101:108-121.
Mortier, et al. Soluble interleukin-15 receptor alpha (IL-15R alpha)-sushi as a selective and potent agonist of IL-15 action through IL-15R beta/gamma. Hyperagonist IL-15 x IL-15R alpha fusion proteins.J Biol Chem. Jan. 20, 2006;281(3):1612-9. Epub Nov. 11, 2005.
Mouhat, et al. Diversity of folds in animal toxins acting on ion channels. Biochem. J. 378, 717-26 (2004).
Moura, et al. Relative amino acid composition signatures of organisms and environments. PloS one 8.10 (2013): e77319.
Moyse, E. et al. Distribution of neurotensin binding sites in rat brain: A light microscopic radioautographic study using monoiodo [125I]Tyr3-neurotensin. Neuroscience 22, 525-536 (1987).
Mullins, et al. Renal disease pathophysiology and treatment: contributions from the rat. Dis Model Mech. Dec. 1, 2016; 9(12): 1419-1433. doi: 10.1242/dmm.027276.
Murshudov et al. Refinement of macromolecular structures by the maximum-likelihood method. Acta Cryst D53:240-255 (1997).
Mustain, et al., The role of neurotensin in physiologic and pathologic processes. Curr. Opin. Endocrinol. Diabetes Obes. 18, 75-82 (2011).
Musumeci, et al. Biomarkers of Chondrocyte Apoptosis and Autophagy in Osteoarthritis. Int J Mol Sci. Aug. 31, 2015;16(9):20560-75. doi: 10.3390/ijms160920560.
Myszka, D. G. Improving biosensor analysis. J. Mol. Recognit. 12, 279-284 (1999).
Nagase et al.: Substrate specificity of MMPs; Matrix Metalloproteinase Inhibitors in Cancer Therapy; Clendeninn & Appelt Eds., Springer Science Media New York; 39-66 (2001).
Nayak et al. In Vitro and In Vivo Study of Poly(ethylene glycol) Conjugated Ibuprofen to Extend the Duration of Action. Sci Pharm. Apr.-Jun. 2011; 79(2): 359-373.
Needleman et al. A general method applicable to the search for similarities in the amino acid sequence of two proteins. J. Mol. Biol. 48:443-453 (1970).
Nelson, et al. Myristoyl-based transport of peptides into living cells. Biochemistry 46, 14771-14781 (2007).
Nicolaides, et al., Glucocorticoid Therapy and Adrenal Suppression. In: Feingold KR, Anawalt B, Boyce A, et al., eds. Endotext. South Dartmouth (MA): MDText.com, Inc.; Oct. 19, 2018.
Nielsen et al. NN-align. An artificial neural network-based alignment algorithm for MHC class II peptide binding prediction. BMC Bioinformatics.Sep. 18, 2009;10:296.
Nielsen, et al., Prediction of MHC class II binding affinity using SMM-align, a novel stabilization matrix alignment method. BMC Bioinformatics vol. 8, Article No. 238 (2007).
Njiojob et al. Tailored near-infrared contrast agents for image guided surgery. J Med Chem. Mar. 26, 2015;58(6):2845-54.
Oh, et al. Dimethylfumarate attenuates renal fibrosis via NF-E2-related factor 2-mediated inhibition of transforming growth factor-β/Smad signaling. PLoS One. 2012;7(10):e45870. doi: 10.1371/journal.pone.0045870. Epub Oct. 8, 2012.
Ojeda, et al. Lysine to arginine mutagenesis of chlorotoxin enhances its cellular uptake. Biopolymers 1-76 (2017). doi:10.1002/bip.23025.
Ojeda et al. (Review: Chlorotoxin: Structure, Activity, and Potential Uses in Cancer Therapy; PeptideScience vol. 106, No. 1; Sep. 29, 2015).
Otwinowski et al. Processing of X-ray diffraction data collected in oscillation mode. Method Enzymol 276:307-326 (1997).
Park, et al. In Situ Recruitment of Human Bone Marrow-Derived Mesenchymal Stem Cells Using Chemokines for Articular Cartilage Regeneration. Cell Transplant. 2015;24(6):1067-83. doi: 10.3727/096368914X681018. Epub Apr. 22, 2014.
PCT/US16/66007 International Search Report and Written Opinion dated May 24, 2017.
PCT/US2016/039431 International Search Report and Written Opinion dated Jan. 13, 2017.
PCT/US2016/051166 International Preliminary Report on Patentability dated Mar. 22, 2018.
PCT/US2016/051166 International Search Report dated Mar. 23, 2017.
PCT/US2018/023006 International Search Report and Written Opinion dated Jul. 27, 2018.
PCT/US2018/037544 International Search Report and Written Opinion dated Oct. 26, 2018.
PCT/US2018/066337 International Search Report and Written Opinion dated Apr. 30, 2019.
PCT/US2019/022630 International Search Report and Written Opinion dated Jul. 5, 2019.
Pearson et al. Improved Tools for Biological Sequence Comparison. PNAS USA 85:2444-48 (1988).
Pearson. Rapid and sensitive sequence comparison with FASTP and FASTA. Meth. Enzymol. 183:63-98 (1990).
Pillow et al. Site-specific trastuzumab maytansinoid antibody-drug conjugates with improved therapeutic activity through linker and antibody engineering. J Med Chem. Oct. 9, 2014;57(19):7890-9.
Plosker, et al. Sulfasalazine: a review of its use in the management of rheumatoid arthritis. Drugs. 2005;65(13):1825-49.
Poillot, et al. Small efficient cell-penetrating peptides derived from scorpion toxin maurocalcine. J. Biol. Chem. 287, 17331-17342 (2012).
Ponce, et al. Expression of voltage dependent potassium currents in freshly dissociated rat articular chondrocytes. Cell Physiol Biochem. 2006;18(1-3):35-46. Epub Aug. 14, 2006.
Pooga, et al. Cell penetration by transportan. FASEB J. 12, 67-77 (1998).
Portilla, Didier. Apoptosis, fibrosis and senescence. Nephron Clin Pract. 2014;127(1-4):65-9. doi: 10.1159/000363717. Epub Sep. 24, 2014.
Portilla, et al. Metabolomic study of cisplatin-induced nephrotoxicity. Kidney Int.Jun. 2006;69(12):2194-204.doi: 10.1038/sj.ki.5000433. Epub May 3, 2006.
Potterton et al., A graphical user interface to the CCP4 program suite. Acta Crystallogr.—Sect. D Biol. Crystallogr. (2003). doi:10.1107/S0907444903008126.
Pouyani et al. Functionalized derivatives of hyaluronic acid oligosaccharides: drug carriers and novel biomaterials. Bioconjug Chem. Jul.-Aug. 1994;5(4):339-47.
Procko, et al. A computationally designed inhibitor of an Epstein-Barr viral Bcl-2 protein induces apoptosis in infected cells. Cell 157, 1644-56 (2014).
Punzi, et al. Post-traumatic arthritis: overview on pathogenic mechanisms and role of inflammation. RMD Open. Sep. 6, 2016;2(2):e000279. doi: 10.1136/rmdopen-2016-000279. eCollection 2016.
Qian, et al. Early endosomal escape of a cyclic cell-penetrating peptide allows effective cytosolic cargo delivery. Biochemistry. Jun. 24, 2014;53(24):4034-46.
Quintas-Cardama, et al. Molecular pathways: JAK/STAT pathway: Mutations, inhibitors, and resistance. Clin. Cancer Res. 19, 1933-1940 (2013).
Ramos, et al. Designing drugs that combat kidney damage. Expert Opin Drug Discov. May 2015;10(5):541-56. doi: 10.1517/17460441.2015.1033394. Epub Apr. 3, 2015.

(56) References Cited

OTHER PUBLICATIONS

Rashid, M. H. et al. A potent and Kv1.3-selective analogue of the scorpion toxin HsTX1 as a potential therapeutic for autoimmune diseases. Sci. Rep. 4, 8-10 (2014).
Rau, Rolf. Glucocorticoid treatment in rheumatoid arthritis. Expert Opin Pharmacother. Aug. 2014;15(11):1575-83. doi: 10.1517/14656566.2014.922955. Epub May 26, 2014.
Raynauld, et al. Safety and efficacy of long-term intraarticular steroid injections in osteoarthritis of the knee: a randomized, double-blind, placebo-controlled trial. Arthritis Rheum. Feb. 2003;48(2):370-7.
Rees, et al. Refined crystal structure of the potato inhibitor complex of carboxypeptidase A at 2.5 A resolution. J. Mol. Biol. 160, 475-98 (1982).
Reines, Brandon P. Is rheumatoid arthritis premature osteoarthritis with fetal-like healing? Autoimmun Rev. Jun. 2004;3(4):305-11.
Reinwarth, et al. Chemical synthesis, backbone cyclization and oxidative folding of cystine-knot peptides—promising scaffolds for applications in drug design. Molecules 17.11 (2012): 12533-12552.
Ren, et al. Quercetin Inhibits Fibroblast Activation and Kidney Fibrosis Involving the Suppression of Mammalian Target of Rapamycin and β-catenin Signaling. Sci Rep. 2016; 6:23968. Published online Apr. 7, 2016. doi: 10.1038/srep23968.
Renisio, et al. Solution structure of BmKTX, a K+ blocker toxin from the Chinese scorpion *Buthus martensi*. Proteins: Structure, Function, and Bioinformatics 38.1 (2000): 70-78.
Rhee, et al. Mechanism of uptake of C105Y, a novel cell-penetrating peptide. J. Biol. Chem. 281, 1233-1240 (2006).
Ricci, et al. Chemotherapeutic approaches for targeting cell death pathways. Oncologist. Apr. 2006;11(4):342-57.
Rice, et al. EMBOSS: the European Molecular Biology Open Software Suite. Trends Genet. Jun. 2000;16(6):276-7.
Rossini, et al. Focal bone involvement in inflammatory arthritis: the role of IL17. Rheumatol Int. Apr. 2016;36(4):469-82. doi: 10.1007/s00296-015-3387-x. Epub Oct. 31, 2015.
Said, et al. The anti-HIV cytokine midkine binds the cell surface-expressed nucleolin as a low affinity receptor. J Biol Chem. Oct. 4, 2002;277(40):37492-502. Epub Jul. 29, 2002.
Samy, et al. Animal venoms as antimicrobial agents. Biochem Pharmacol. Jun. 15, 2017;134:127-138. doi: 10.1016/j.bcp.2017.03.005. Epub Mar. 10, 2017.
Sangphukieo, et al. Computational Design of Hypothetical New Peptides Based on a Cyclotide Scaffold as HIV gp120 Inhibitor. PLoS One 10, e0139562 (2015).
Sansone, et al. Targeting the interleukin-6/jak/stat pathway in human malignancies. J. Clin. Oncol. 30, 1005-1014 (2012).
Santos, et al. Thermofluor-based optimization strategy for the stabilization and crystallization of Campylobacter jejuni desulforubrerythrin. Protein Expr. Purif. 81, 193-200 (2012).
Schmidt, et al. Reactivity of dimethyl fumarate and methylhydrogen fumarate towards glutathione and N-acetyl-L-cysteine—preparation of S-substituted thiosuccinic acid esters. Bioorg Med Chem. Jan. 1, 2007;15(1):333-42. Epub Sep. 29, 2006.
Schwartz, et al. Characterization of hadrucalcin, a peptide from *Hadrurus gertschi* scorpion venom with pharmacological activity on ryanodine receptors. Br J Pharmacol. Jun. 2009; 157(3):392-403.
Sellers, Peter H. On the theory and computation of evolutionary distances. SIAM Journal on Applied Mathematics. 1974;26:787.
Shahbazzadeh, et al. Hemicalcin, a new toxin from the Iranian scorpion *Hemiscorpius lepturus* which is active on ryanodine-sensitive Ca2+ channels. Biochem. J. 404, 89-96 (2007).
Shao, et al. NLRP3 inflammasome and its inhibitors: a review. Front Pharmacol. 2015; 6: 262. Published online Nov. 5, 2015. doi: 10.3389/fphar.2015.00262.
Shen, et al. NLRP3 inflammasome mediates contrast media-induced acute kidney injury by regulating cell apoptosis. (2016) Scientific Reports 6, Article No. 34682. Published online: Oct. 10, 2016. doi:10.1038/srep34682.
Shen, et al. Prolyl hydroxylase inhibitors increase neoangiogenesis and callus formation following femur fracture in mice. J Orthop Res. Oct. 2009;27(10):1298-305. doi: 10.1002/jor.20886.
Shimoaka, et al. Regulation of osteoblast, chondrocyte, and osteoclast functions by fibroblast growth factor (FGF)-18 in comparison with FGF-2 and FGF-10. J Biol Chem. Mar. 1, 2002;277(9):7493-500. Epub Dec. 11, 2001.
Shire, et al. Challenges in the development of high protein concentration formulations. Journal of pharmaceutical sciences 93.6 (2004): 1390-1402.
Sillero et al. Isoelectric point determination of proteins and other macromolecules: oscillating method. Comput Biol Med. Feb. 2006;36(2):157-66. Epub Jan. 1, 2005.
Sillero et al. Isoelectric points of proteins: theoretical determination. Anal Biochem. Jun. 1989;179(2):319-25.
Simeon, Rudo et al., In vitro-engineered non-antibody protein therapeutics, Protein Cell 218, 9(1);3-14.
Singh, et al. Antibody-Drug Conjugates: Design, Formulation and Physicochemical Stability. Pharm Res. Nov. 2015;32(11):3541-71.
Sinha, et al. Oral colon-specific drug delivery of protein and peptide drugs. Crit Rev Ther Drug Carrier Syst. 2007;24(1):63-92.
Sinniah, R. et al., Serum iron, total iron-binding capacity, and percentage saturation in normal subjects. J. Clin. Pathol. 21, 603-10 (1968).
Solon, E.G. Autoradiography techniques and quantification of drug distribution. 2015 Cell Tiss. Res. 360(1): 87-107.
Song, et al. Small-molecule modulators of the OX40-OX40 ligand co-stimulatory protein-protein interaction. Br J Pharmacol. Nov. 2014;171(21):4955-69.
Soroceanu, et al. Use of chlorotoxin for targeting of primary brain tumors. Cancer Res. Nov. 1, 1998;58(21):4871-9.
Sottero et al. Pacifastin-derived Peptides Target Tumors for Use in In Vivo Imaging. Anticancer Res. Jan. 2018;38(1):51-60.
Steinert, et al. Major biological obstacles for persistent cell-based regeneration of articular cartilage. Arthritis Res Ther. 2007; 9(3): 213. Published online Jun. 5, 2007. doi: 10.1186/ar2195.
Stern, et al. Alternative non-antibody protein scaffolds for molecular imaging of cancer. Current opinion in chemical engineering 2.4 (2013): 425-432.
Sudo, et al. Human-derived fusogenic peptides for the intracellular delivery of proteins. J. Control. Release 255, 1-11 (2017).
Sugumar, et al. Targeted treatments for multiple myeloma: specific role of carfilzomib. Pharmgenomics Pers Med. Jan. 20, 2015;8:23-33. doi: 10.2147/PGPM.S39085. eCollection 2015.
Sutherland, R. et al. Ubiquitous cell-surface glycoprotein on tumor cells is proliferation-associated receptor for transferrin. Proc. Natl. Acad. Sci. U. S. A. 78, 4515-9 (1981).
Swanson, et al. Tyrosine kinases as targets for the treatment of rheumatoid arthritis. Nat Rev Rheumatol. Jun. 2009;5(6):317-24. doi: 10.1038/nrrheum.2009.82.
Tabrizi, et al., Biodistribution mechanisms of therapeutic monoclonal antibodies in health and disease. AAPS J. 12, 33-43 (2010).
Tait, et al. Die another way—non-apoptotic mechanisms of cell death. J Cell Sci. May 15, 2014;127(Pt 10):2135-44. doi: 10.1242/jcs.093575.
Takayama, et al. Enhanced intracellular delivery using arginine-rich peptides by the addition of penetration accelerating sequences (Pas). J. Control. Release 138, 128-133 (2009).
Tam, et al., Antimicrobial peptides from plants. Pharmaceuticals 8, 711-757 (2015).
Tangri, et al. Rationally engineered proteins or antibodies with absent or reduced immunogenicity. Curr. Med. Chem. 9, 2191-9 (2002).
Tesmer, J. J., et al. The structure, catalytic mechanism and regulation of adenylyl cyclase. Curr. Opin. Struct. Biol. 8, 713-719 (1998).
The UniProt Consortium. UniProt: The Universal Protein Knowledgebase. Nucleic Acids Research, 2017, 45, D158-D169. Published online Nov. 11, 2016.
Trenevska, I., et al., Therapeutic Antibodies against Intracellular Tumor Antigens. Front. Immunol. 8, 1001 (2017).
Trudeau, L. E. Neurotensin regulates intracellular calcium in ventral tegmental area astrocytes: Evidence for the involvement of multiple receptors. Neuroscience 97, 293-302 (2000).

(56) References Cited

OTHER PUBLICATIONS

Tsunemi, et al. Crystallization of a complex between an elastase-specific inhibitor elafin and porcine pancreatic elastase. J. Mol. Biol. 232, 310-1 (1993).
Tundo, et al. Effect of cisplatin on proteasome activity. J Inorg Biochem. Dec. 2015;153:253-258. doi: 10.1016/j.jinorgbio.2015.08.027. Epub Sep. 4, 2015.
Ueda, Norishi. Ceramide-induced apoptosis in renal tubular cells: a role of mitochondria and sphingosine-1-phoshate. Int J Mol Sci. Mar. 5, 2015;16(3):5076-124. doi: 10.3390/ijms16035076.
U.S. Appl. No. 15/739,669 Office Action dated May 14, 2020.
U.S. Appl. No. 15/758,320 Office Action dated Apr. 15, 2020.
U.S. Appl. No. 15/739,669 Office Action dated Nov. 27, 2019.
U.S. Appl. No. 15/758,320 Office Action dated Feb. 26, 2019.
U.S. Appl. No. 15/758,320 Office Action dated Jul. 25, 2019.
Van den Hoven et al. Optimizing the Therapeutic Index of Liposomal Glucocorticoids in Experimental Arthritis. JM van den Hoven et al. Int J Pharm 416 (2), 471-477. Apr. 2, 2011.
Van Walsem, et al. Relative benefit-risk comparing diclofenac to other traditional nonsteroidal anti-inflammatory drugs and cyclooxygenase-2 inhibitors in patients with osteoarthritis or rheumatoid arthritis: a network meta-analysis. Arthritis Res Ther. Mar. 19, 2015;17:66. doi: 10.1186/s13075-015-0554-0.
Vannucci et al. Glucocorticoids in the management of systemic juvenile idiopathic arthritis. Paediatr Drugs. Oct. 2013;15(5):343-9. doi: 10.1007/s40272-013-0038-0.
Varoga, et al. Human beta-defensin 3 mediates tissue remodeling processes in articular cartilage by increasing levels of metalloproteinases and reducing levels of their endogenous inhibitors. Arthritis Rheum. Jun. 2005;52(6):1736-45.
Varoga, et al. Production of endogenous antibiotics in articular cartilage. Arthritis Rheum. Nov. 2004;50(11):3526-34.
Vasalou, et al. A Mechanistic Tumor Penetration Model to Guide Antibody Drug Conjugate Design. PLoS One 10, (2015).
Veiseh, et al. Tumor paint: a chlorotoxin:Cy5.5 bioconjugate for intraoperative visualization of cancer foci. Cancer Res. Jul. 15, 2007;67(14):6882-8.
Vincent et al., Neurotensin and neurotensin receptors. Trends Pharmacol. Sci. 20, 302-309 (1999).
Vitt, et al. Evolution and classification of cystine knot-containing hormones and related extracellular signaling molecules. Molecular endocrinology15.5 (2001): 681-694.
Vives, et al. A Truncated HIV-1 Tat Protein Basic Domain Rapidly Translocates Through the Plasma Membrane and Accumulates in the Cell Nucleus. J. Biol. Chem. 1997 272(25):16010-16017.
Vordenbaumen, et al. Defensins potential effectors autoimmune rheumatic disorders. Polymers. 2011; 3:1268-1281.
Vyas, et al. Ketorolac-dextran conjugates: synthesis, in vitro and in vivo evaluation. Acta Pharm. Dec. 2007;57(4):441-50.
Wakankar, et al. Formulation considerations for proteins susceptible to asparagine deamidation and aspartate isomerization. Journal of pharmaceutical sciences 95.11 (2006): 2321-2336.
Wan, et al. EPO Promotes Bone Repair through Enhanced Cartilaginous Callus Formation and Angiogenesis. PLoS One. 2014; 9(7): e102010. Published online Jul. 8, 2014. doi: 10.1371/journal.pone.0102010.
Wang, et al. Flavonoid Compound Icariin Activates Hypoxia Inducible Factor-1α in Chondrocytes and Promotes Articular Cartilage Repair. PLoS One. Feb. 3, 2016;11(2):e0148372. doi: 10.1371/journal.pone.0148372. eCollection 2016.
Wang, et al. Annexin-mediated Ca2+ influx regulates growth plate chondrocyte maturation and apoptosis. J Biol Chem. Feb. 7, 2003;278(6):3762-9. Epub Nov. 22, 2002.
Wang, X. et al. Characterization of promoter elements regulating the expression of the human neurotensin/neuromedin N gene. J. Biol. Chem. 286, 542-554 (2011).
Ward, et al. American College of Rheumatology/Spondylitis Association of America/Spondyloarthritis Research and Treatment Network 2015 Recommendations for the Treatment of Ankylosing Spondylitis and Nonradiographic Axial Spondyloarthritis. Arthritis Rheumatol. Feb. 2016;68(2):282-98. doi: 10.1002/art.39298. Epub Sep. 24, 2015.
Weatherall, et al. Small conductance calcium-activated potassium channels: from structure to function. Prog Neurobiol. Jul. 2010;91(3):242-55. doi: 10.1016/j.pneurobio.2010.03.002. Epub Mar. 30, 2010.
Werle, et al. The potential of cystine-knot microproteins as novel pharmacophoric scaffolds in oral peptide drug delivery. J. Drug Targeting 2006; 14:137-146.
Winn, et al. Overview of the CCP4 suite and current developments. Acta Crystallographica Section D 67.4 (2011): 235-242.
Winnard, et al. Development of novel chimeric transmembrane proteins for multimodality imaging of cancer cells. Cancer Biol. Ther. 6, 1889-99 (2007).
Wiranowska, et al. Clathrin-mediated entry and cellular localization of chlorotoxin in human glioma. Cancer Cell Int. Aug. 12, 2011;11:27.
Wischnjow, et al. Renal Targeting: Peptide-Based Drug Delivery to Proximal Tubule Cells. Bioconjug Chem. Apr. 20, 2016;27(4):1050-7. doi: 10.1021/acs.bioconjchem.6b00057. Epub Mar. 30, 2016.
Wojdasiewicz, et al. The Role of Inflammatory and Anti-Inflammatory Cytokines in the Pathogenesis of Osteoarthritis. Mediators of Inflammation. vol. 2014 (2014), Article ID 561459, 19 pages. http://dx.doi.org/10.1155/2014/561459.
Xiao, et al. Mechanisms of Cyclosporine-Induced Renal Cell Apoptosis: A Systematic Review. Am J Nephrol 2013;37:30-40. https://doi.org/10.1159/000345988.
Yamada, et al. Internalization of bacterial redox protein azurin in mammalian cells: Entry domain and specificity. Cell. Microbiol. 7, 1418-1431 (2005).
Yang, et al. Protein-peptide interactions analyzed with the yeast two-hybrid system. Nucleic Acids Res. 23, 1152-1156 (1995).
Yang, J. et al. The I-TASSER Suite: protein structure and function prediction. Nat. Methods 12, 7-8 (2015).
Ye, et al. The scorpion toxin analogue BmKTX-D33H as a potential Kv1. 3 channel-selective immunomodulator for autoimmune diseases. Toxins 8.4 (2016): 115.
Yu, et al. A naturally occurring, soluble antagonist of human IL-23 inhibits the development and in vitro function of human Th17 cells. J Immunol. Dec. 15, 2010;185(12):7302-8. doi: 10.4049/jimmunol.1002410. Epub Nov. 12, 2010.
Yurkovetskiy, et al. A Polymer-Based Antibody-Vinca Drug Conjugate Platform: Characterization and Preclinical Efficacy. Cancer Res. Aug. 15, 2015;75(16):3365-72.
Zager, R. Marked protection against acute renal and hepatic injury after nitrited myoglobin+ tin protoporphyrin administration. Translational Research 166.5 (2015): 485-501.
Zamli, et al. Chondrocyte apoptosis: a cause or consequence of osteoarthritis? Int J Rheum Dis. May 2011;14(2):159-66. doi: 10.1111/j.1756-185X.2011.01618.x.
Zhang, et al. The Functions of BMP3 in Rabbit Articular Cartilage Repair. Int J Mol Sci. Oct. 29, 2015;16(11):25934-46. doi: 10.3390/ijms161125937.
Zhang, et al. Tumor-selective proteotoxicity of verteporfin inhibits colon cancer progression independently of YAP1. Sci. Signal. 8, ra98 (2015).
Zhao, et al. Chemical engineering of cell penetrating antibodies. J. Immunol. Methods 254, 137-145 (2001).
Zhou, et al. Kidney—targeted drug delivery systems. Acta Pharm Sin B. Feb. 2014; 4(1): 37-42. Published online Jan. 23, 2014. doi: 10.1016/j.apsb.2013.12.005.
Zhu, et al. Evolutionary origin of inhibitor cystine knot peptides. FASEB J. 17, 1765-1767 (2003).
Zhu, et al. Identification of a novel senolytic agent, navitoclax, targeting the Bcl-2 family of anti-apoptotic factors. Aging Cell. Jun. 2016;15(3):428-35. Epub Mar. 18, 2016.
Zhu et al. Precursor nucleotide sequence and genomic organization of BmTXKS1, a new scorpion toxin-like peptide from Buthus martensii Karsch. Toxicon. Sep. 2001;39(9):1291-6.
Zhu, Yi et al. The Achilles' heel of senescent cells: from transcriptome to senolytic drugs. Aging Cell. Aug. 2015;14(4):644-58. Epub Apr. 22, 2015.
JP2018-510741 Office Action dated Aug. 12, 2020 (in English).

(56) References Cited

OTHER PUBLICATIONS

Pi et al, Targeted delivery of non-viral vectors to cartilage in vivo using a chondrocyte-homing peptide identified by phage display, Biomaterials. Sep. 2011;32(26):6324-32. doi: 10.1016/j.biomaterials. 2011.05.017. Epub May 31, 2011.
Haseeb, A and Haqqi, T., Immunopathogenesis of osteoarthritis, Clin Immunol. Mar. 2013;146(3):185-96. doi: 10.1016/j.clim.2012. 12.011. Epub Jan. 6, 2013.
EP 18767105.2, Extended European Search Report dated Nov. 24, 2020.
Hu, et al., Chondrocyte affinity peptide modified PAMAM conjugate as a nanoplatform for targeting and retention in cartilage. *Nanomedicine (Lond)*. 2018;13(7):749-767. doi:10.2217/nnm-2017-0335.

* cited by examiner

Construct 1

```
                    *  *  *  *   *    *    * ********  *  **  ***
SEQ ID NO: 541  VPINVKCRGSRDCLDPCKKAGMRFGKCINSKCHCTP
SEQ ID NO: 316  VRIPVSCKHSGQCLKPCKDAGMRFGKCMNGKCDCTPK
```

FIG. 5A

```
                 *  ****   *     *    *       *  ***** ** *
SEQ ID NO: 541  VPINVKCRGSRDCLDPCKKA-GMRFGKCINSKCHCTP
SEQ ID NO: 542  VQTNVKCQGG-SCASVCRREIGVAAGKCINGKCVCYRN
```

FIG. 5B

```
                 * ********    **   **  *  *    ***  *  ** *  *
SEQ ID NO: 541  VPINVKCRGSRDCLDPCKKA-GMRFGKCINSKCHCTP
SEQ ID NO: 483  VFINVKCRGSPECLPKCKEAIGKSAGKCMNGKCKCYP
```

```
                       *    *  **  *       *       *      **  *****  ****  **
SEQ ID NO: 320 QVQTNVKCQGGS-CASVCRREIGVAAGKCINGKCVCYRN
SEQ ID NO: 484 VFINAKCRGSPECLPKCKEAIGKAAGKCMNGKCKCYP
```

Predicted Dyad

```
                            10        20        30
                   ....*....|....*....|....*....|....
SEQ ID NO:494   5  IKCSESYQCFPVCKSRFGKTNG-RCVNGFCDCF  36
SEQ ID NO:495   5  VKCSSPQQCLKPCKAAFGISAGgKCINGKCKCY  37
SEQ ID NO:496  26  VSCSASSQCWPVCKKLFGTYRG-KCMNSKCRCY  57
SEQ ID NO:497   5  ESCTASNQCWSICKRLHNTNRG-KCMNKKCRCY  36
SEQ ID NO:498   5  VSCTTSKECWSVCKLYNTSRG-KCMNKKCRCY  36
SEQ ID NO:499   4  MRCKSSKECLVKCKQATGRPNG-KCMNRKCKCY  35
SEQ ID NO:500   1  IKCTLSKDCYSPCKKETGCPRA-KCINRNCKCY  32
SEQ ID NO:501   1  IRCSGSRDCYSPCMKQTGCPNA-KCINKSCKCY  32
SEQ ID NO:502  27  IRCSGTRECYAPCQKLTGCLNA-KCMNKACKCY  58
SEQ ID NO:503   2  ISCTNPKQCYPHCKKETGYPNA-KCMNRKCKCF  33
SEQ ID NO:504   1  ASCRTPKDCADPCRKETGCPYG-KCMNRKCKCN  32
SEQ ID NO:505   3  TSCISPKQCTEPCRAK-GCKHG-KCMNRKCHCM  33
SEQ ID NO:506   2  KECTGPQHCTNFCRKN-KCTHG-KCMNRKCKCF  32
SEQ ID NO:507  27  IKCRTPKDCADPCRKQTGCPHA-KCMNKTCRCH  58
SEQ ID NO:508   5  VKCTTSKECWPPCKAATGKAAG-KCMNKKCKCQ  36
SEQ ID NO:509   8  LECGASRECYDPCFKAFGRAHG-KCMNNKCRCY  39
SEQ ID NO:510   5  EKCFATSQCWTPCKKAIGSLQS-KCMNGKCKCY  36
SEQ ID NO:511  27  VRCYASRECWEPCRRVTGSAQA-KCQNNQCRCY  58
SEQ ID NO:512  28  VKCSASRECWVACKKVTGSGQG-KCQNNQCRCY  59
SEQ ID NO:513   5  VKCISSQECWIACKKVTGRFEG-KCQNRQCRCY  36
SEQ ID NO:514   5  VRCYDSRQCWIACKKVTGSTQG-KCQNKQCRCY  36
SEQ ID NO:515   5  VDCTVSKECWAPCKAAFGVDRG-KCMGKKCKCY  36
SEQ ID NO:516   5  AKCRGSPECLPKCKEAIGKAAG-KCMNGKCKCY  36
SEQ ID NO:517  28  KKCQGGS-CASVCRRVIGVAAG-KCINGRCVCY  58
SEQ ID NO:518  28  KKCSNTSQCYKTCEKVVGVAAG-KCMNGKCICY  59
SEQ ID NO:519   6  VKCSGSSKCVKICIDRYNTRGA-KCINGRCTCY  37
SEQ ID NO:520  28  NRCNNSSECIPHCIRIFGTRAA-KCINRKCYCY  59
SEQ ID NO:521  28  KECNGSSECYSHCEGITGKRSG-KCINKKCYCY  59
SEQ ID NO:522   1  AFCNL-RRCELSCRSL--GLLG-KCIGEECKCV  29
SEQ ID NO:523  29  AVCNL-KRCQLSCRSL--GLLG-KCIGDKCECV  57
SEQ ID NO:524   1  AACYSS-DCRVKCVAM-GFSSG-KCINSKCKCY  30
SEQ ID NO:525  27  AICATDADCSRKCP---GNPP---CRNGFCACT  53
SEQ ID NO:526  28  TECQIKNDCQRYCQSVK------ECKYGKCYCN  54
SEQ ID NO:527   2  TQCQSVRDCQQYCLTPD------RCSYGTCYCK  28
SEQ ID NO:528  29  VSCRYGSDCAEPCKRLKCLLPS-KCINGKCTCY  60
SEQ ID NO:529  28  IKCRYPADCHIMCRKVTGRAEG-KCMNGKCTCY  59
SEQ ID NO:530  28  IKCSSSSCYEPCRGVTGRAHG-KCMNGRCTCY  59
SEQ ID NO:531   5  VKCTGSKQCLPACKAAVGKAAG-KCMNGKCKCY  36
SEQ ID NO:532   5  VSCKHSGQCIKPCKDA-GMRFG-KCMNRKCDCT  35
SEQ ID NO:533   6  VKCRGSPQCIQPCRDA-GMRFG-KCMNGKCHCT  36
SEQ ID NO:534   5  VKCTSPKQCLPPCKAQFGIRAGaKCMNGKCKCY  37
SEQ ID NO:535   5  VKCTSPKQCSKPCKELYGSSAGaKCMNGKCKCY  37
SEQ ID NO:536   5  VKCTSPKQCLPPCKEIYGRHAGaKCMNGKCHCS  37
SEQ ID NO:537  25  VKCTGSKQCWPVCKQMFGKPNG-KCMNGKCRCY  56
SEQ ID NO:538  28  VKCRGSRDCLDPCKKA-GMRFG-KCINSKCHCT  58
SEQ ID NO:539  28  VRCVTDDDCFRKCP---GNPS---CKRGFCACK  54
SEQ ID NO:540  28  VPCNNSRPCVPVCIREVNNKNG-KCSNGKCLCY  59
```

FIG. 7

SEQ ID NO: 494  --------IKCSESYQCFPVCKSRFGKTNGRCVNGFCDCF-
SEQ ID NO: 27   GSGVPINVKCRGSRDCLDPCK-KAGMRFGKCINSKCHCTP
                 :**    *  :*:    **  :  *      *:*:*.  *.*

FIG. 8

```
SEQ ID NO:                    10             20             30
   321    . E V . R C S G S K Q C Y G P C K Q Q T G C T N S K C M N K V C K C Y G C G
   543    . A E I . R C S G T R . C Y A P C Q K L T G C L N A K C M N K A C K C Y G C V
   544    . R P T D . K C S A S Y Q C F P V C K S R F G K T N G . C V N G L C D C F .
   545    . Q F T D V K C T G S K Q C W P V C K Q M F G K P N G K C M N G K C R C Y S .
   317    G V P . N V K C R G S R D C L D P C K K A . G M R F G K C T N S K C H C T P . .
   398    G V P . N V . C R G S R D C L D P C R A . G M R F G . C T N S . C H C T P . .
   340    . V G . N V K C H S G Q C L K P C K D A . G M R F G K C T N G K C D C T P K
   546    . V G . N V K C H S R Q C L K P C K D A . G M R F G K C T N G K C H C T P K
   316    . V R . P V S C K H S G Q C L K P C K D A . G M R F G K C M N G K C D C T P K .
   333    G V I . N V K C K I S R Q C L E P C K K A . G M R F G K C M N G K C H C T P K .
   337    G V P T D V K C R G S P Q C L Q P C K D A . G M R F G K C M N G K C H C T P K .
   486    . V P T D V K C R G S P Q C L Q P C K D A . G M R F G K C M N G K C H C T P .
   338    G V P . N V S C T G S P Q C L K P C K D A . G M R F G K C M N R K C H C T P K .
   483    . V F . N V K C R G S P E C L P K C K E A I G K S A G K C M N G K C K C Y P . .
   547    . V V . G Q . C Y R S P D C Y S A C K K L V G K A T G K C T N G R C D C . . .
   548    . N F K V E G A C S K P C R K Y C I D K . G A R N G K C T N G R C H C Y Y .
   549    Q . D T N V K C S G S S K C V K I C I D R Y N T R G A K C T N G R C T C Y P . .
   474    Q K I . S N . C N N S S . C I P H C I R I F G T R A A K C T N R K C Y C Y P . .
   295    . v i v k c  g s  q C l . p C k . a . g  r . g k C m N g k C . C  p
```

FIG. 11

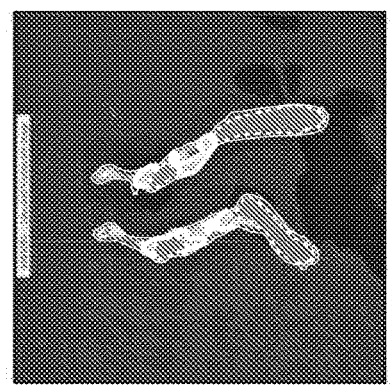
3 hours
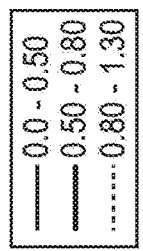
FIG. 13A
FIG. 13B
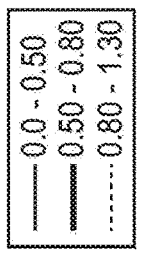
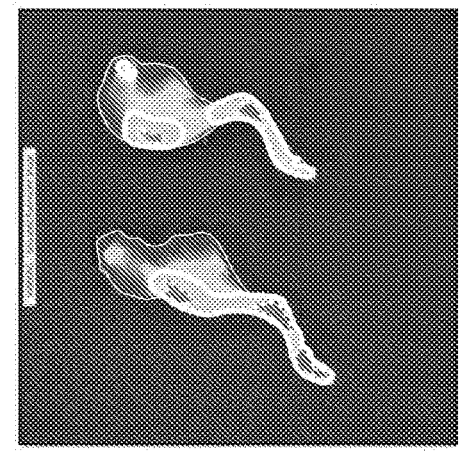
24 hours
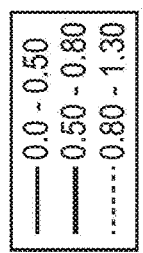
FIG. 13C
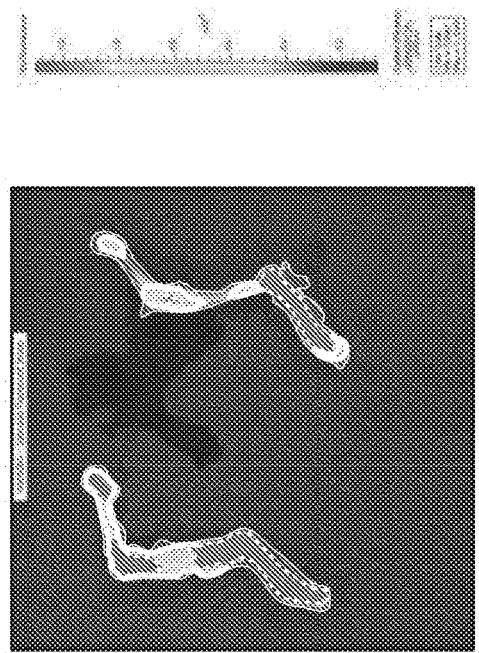
FIG. 13D
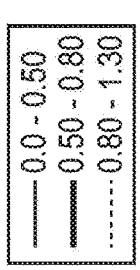

48 hours
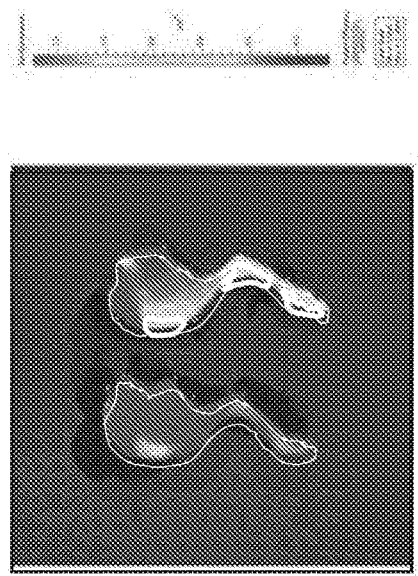
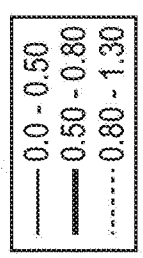
FIG. 13E
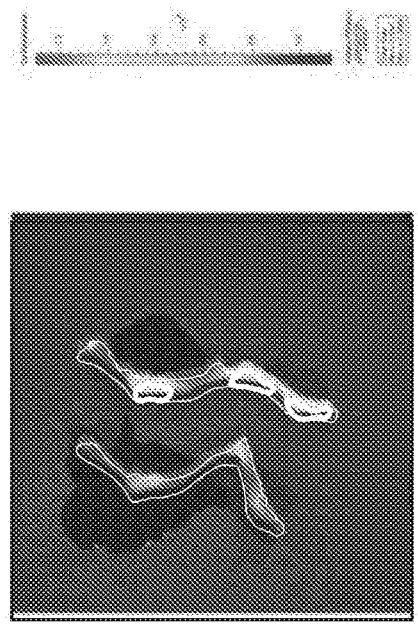
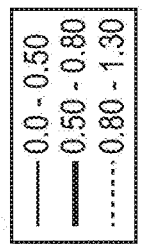
FIG. 13F
72 hours
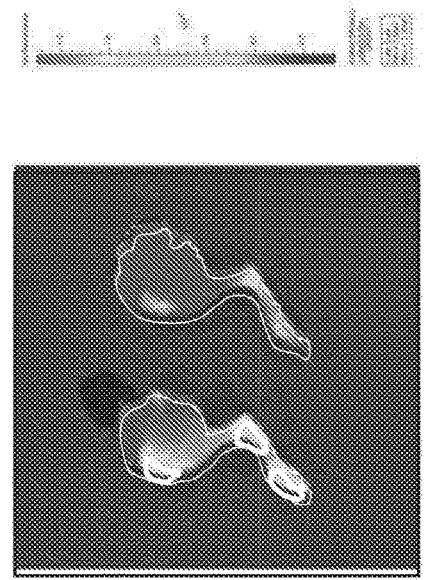
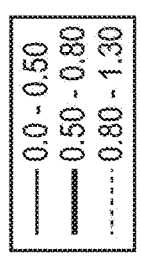
FIG. 13G
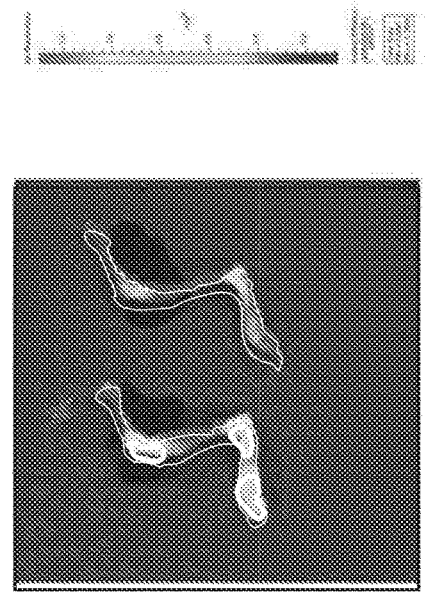
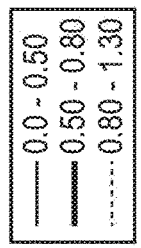
FIG. 13H

SEQUENCE LISTING

```
<160> NUMBER OF SEQ ID NOS: 570

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(8)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (17)..(17)
<223> OTHER INFORMATION: Any amino acid, amino acid analogue or null
<220> FEATURE:
<221> NAME/KEY: MOD_RES
<222> LOCATION: (22)..(24)
```

```
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (28)..(28)
<223> OTHER INFORMATION: Any amino acid, amino acid analogue or null
<220> FEATURE:
<221> NAME/KEY: MOD_RES
<222> LOCATION: (32)..(32)
<223> OTHER INFORMATION: Any amino acid, amino acid analogue or null
<220> FEATURE:
<221> NAME/KEY: MOD_RES
<222> LOCATION: (39)..(42)
<223> OTHER INFORMATION: Any amino acid, amino acid analogue or null

<400> SEQUENCE: 1

Gly Ser Gly Val Xaa Ile Xaa Xaa Lys Cys Xaa Gly Ser Lys Gln Cys
1               5                  10                  15

Xaa Asp Pro Cys Lys Xaa Xaa Xaa Gly Xaa Arg Xaa Gly Lys Cys Xaa
            20                  25                  30

Asn Lys Lys Cys Lys Cys Xaa Xaa Xaa Xaa
        35                  40

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: P or R
<220> FEATURE:
<221> NAME/KEY: MOD_RES
<222> LOCATION: (7)..(7)
<223> OTHER INFORMATION: P or N
<220> FEATURE:
<221> NAME/KEY: MOD_RES
<222> LOCATION: (8)..(8)
<223> OTHER INFORMATION: V or I
<220> FEATURE:
<221> NAME/KEY: MOD_RES
<222> LOCATION: (11)..(11)
<223> OTHER INFORMATION: S, T, R or K
<220> FEATURE:
<221> NAME/KEY: MOD_RES
<222> LOCATION: (17)..(17)
<223> OTHER INFORMATION: Y or L
<220> FEATURE:
<221> NAME/KEY: MOD_RES
<222> LOCATION: (22)..(22)
<223> OTHER INFORMATION: Q, R or K
<220> FEATURE:
<221> NAME/KEY: MOD_RES
<222> LOCATION: (23)..(23)
<223> OTHER INFORMATION: A, K or R
<220> FEATURE:
<221> NAME/KEY: MOD_RES
<222> LOCATION: (24)..(24)
<223> OTHER INFORMATION: T or A
<220> FEATURE:
<221> NAME/KEY: MOD_RES
<222> LOCATION: (26)..(26)
<223> OTHER INFORMATION: C or M
<220> FEATURE:
<221> NAME/KEY: MOD_RES
<222> LOCATION: (28)..(28)
<223> OTHER INFORMATION: F or N
<220> FEATURE:
<221> NAME/KEY: MOD_RES
```

```
<222> LOCATION: (32)..(32)
<223> OTHER INFORMATION: M or I
<220> FEATURE:
<221> NAME/KEY: MOD_RES
<222> LOCATION: (39)..(39)
<223> OTHER INFORMATION: Y or T
<220> FEATURE:
<221> NAME/KEY: MOD_RES
<222> LOCATION: (40)..(40)
<223> OTHER INFORMATION: G or P
<220> FEATURE:
<221> NAME/KEY: MISC_FEATURE
<222> LOCATION: (41)..(42)
<223> OTHER INFORMATION: May or may not be present

<400> SEQUENCE: 2

Gly Ser Gly Val Xaa Ile Xaa Xaa Lys Cys Xaa Gly Ser Lys Gln Cys
1               5                   10                  15

Xaa Asp Pro Cys Lys Xaa Xaa Xaa Gly Xaa Arg Xaa Gly Lys Cys Xaa
            20                  25                  30

Asn Lys Lys Cys Lys Cys Xaa Xaa Cys Gly
        35                  40

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(6)
<223> OTHER INFORMATION: Any amino acid, amino acid analogue or null
<220> FEATURE:
<221> NAME/KEY: MOD_RES
<222> LOCATION: (8)..(8)
<223> OTHER INFORMATION: Any amino acid, amino acid analogue or null
<220> FEATURE:
<221> NAME/KEY: MOD_RES
<222> LOCATION: (10)..(10)
<223> OTHER INFORMATION: Any amino acid, amino acid analogue or null
<220> FEATURE:
<221> NAME/KEY: MOD_RES
<222> LOCATION: (17)..(17)
<223> OTHER INFORMATION: Any amino acid, amino acid analogue or null
<220> FEATURE:
<221> NAME/KEY: MOD_RES
<222> LOCATION: (21)..(22)
<223> OTHER INFORMATION: Any amino acid, amino acid analogue or null
<220> FEATURE:
<221> NAME/KEY: MOD_RES
<222> LOCATION: (26)..(28)
<223> OTHER INFORMATION: Any amino acid, amino acid analogue or null
<220> FEATURE:
<221> NAME/KEY: MOD_RES
<222> LOCATION: (31)..(32)
<223> OTHER INFORMATION: Any amino acid, amino acid analogue or null
<220> FEATURE:
<221> NAME/KEY: MOD_RES
<222> LOCATION: (34)..(34)
<223> OTHER INFORMATION: Any amino acid, amino acid analogue or null

<400> SEQUENCE: 3

Gly Ser Xaa Xaa Xaa Xaa Ile Xaa Cys Xaa Gly Ser Lys Gln Cys Tyr
1               5                   10                  15

Xaa Pro Cys Lys Xaa Xaa Thr Gly Cys Xaa Xaa Xaa Lys Cys Xaa Xaa
            20                  25                  30

Lys Xaa Cys Lys Cys Tyr Gly Cys Gly
        35                  40
```

```
<210> SEQ ID NO 4
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(4)
<223> OTHER INFORMATION: May or may not be present
<220> FEATURE:
<221> NAME/KEY: MOD_RES
<222> LOCATION: (5)..(5)
<223> OTHER INFORMATION: E, G or null
<220> FEATURE:
<221> NAME/KEY: MOD_RES
<222> LOCATION: (6)..(6)
<223> OTHER INFORMATION: V, S or null
<220> FEATURE:
<221> NAME/KEY: MOD_RES
<222> LOCATION: (8)..(8)
<223> OTHER INFORMATION: R or S
<220> FEATURE:
<221> NAME/KEY: MOD_RES
<222> LOCATION: (10)..(10)
<223> OTHER INFORMATION: S or T
<220> FEATURE:
<221> NAME/KEY: MOD_RES
<222> LOCATION: (17)..(17)
<223> OTHER INFORMATION: G or D
<220> FEATURE:
<221> NAME/KEY: MOD_RES
<222> LOCATION: (21)..(21)
<223> OTHER INFORMATION: Q or R
<220> FEATURE:
<221> NAME/KEY: MOD_RES
<222> LOCATION: (22)..(22)
<223> OTHER INFORMATION: Q or K
<220> FEATURE:
<221> NAME/KEY: MOD_RES
<222> LOCATION: (26)..(26)
<223> OTHER INFORMATION: T or P
<220> FEATURE:
<221> NAME/KEY: MOD_RES
<222> LOCATION: (27)..(27)
<223> OTHER INFORMATION: N or Q
<220> FEATURE:
<221> NAME/KEY: MOD_RES
<222> LOCATION: (28)..(28)
<223> OTHER INFORMATION: S or A
<220> FEATURE:
<221> NAME/KEY: MOD_RES
<222> LOCATION: (31)..(31)
<223> OTHER INFORMATION: M or L
<220> FEATURE:
<221> NAME/KEY: MOD_RES
<222> LOCATION: (32)..(32)
<223> OTHER INFORMATION: N or Q
<220> FEATURE:
<221> NAME/KEY: MOD_RES
<222> LOCATION: (34)..(34)
<223> OTHER INFORMATION: V or S

<400> SEQUENCE: 4

Gly Ser Gly Ser Xaa Xaa Ile Xaa Cys Xaa Gly Ser Lys Gln Cys Tyr
1               5                   10                  15

Xaa Pro Cys Lys Xaa Xaa Thr Gly Cys Xaa Xaa Xaa Lys Cys Xaa Xaa
            20                  25                  30

Lys Xaa Cys Lys Cys Tyr Gly Cys Gly
            35                  40

<210> SEQ ID NO 5
<211> LENGTH: 42
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (13)..(14)
<223> OTHER INFORMATION: Any amino acid, amino acid analogue or null
<220> FEATURE:
<221> NAME/KEY: MOD_RES
<222> LOCATION: (16)..(17)
<223> OTHER INFORMATION: Any amino acid, amino acid analogue or null
<220> FEATURE:
<221> NAME/KEY: MOD_RES
<222> LOCATION: (20)..(20)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (33)..(33)
<223> OTHER INFORMATION: Any amino acid, amino acid analogue or null
<220> FEATURE:
<221> NAME/KEY: MOD_RES
<222> LOCATION: (35)..(35)
<223> OTHER INFORMATION: Any amino acid, amino acid analogue or null
<220> FEATURE:
<221> NAME/KEY: MOD_RES
<222> LOCATION: (38)..(38)
<223> OTHER INFORMATION: Any amino acid, amino acid analogue or null
<220> FEATURE:
<221> NAME/KEY: MOD_RES
<222> LOCATION: (42)..(42)
<223> OTHER INFORMATION: Any amino acid, amino acid analogue or null

<400> SEQUENCE: 5

Gly Ser Xaa Xaa Xaa Val Xaa Ile Xaa Val Xaa Cys Xaa Xaa Ser Xaa
1               5                   10                  15

Xaa Cys Leu Xaa Pro Cys Lys Xaa Ala Gly Met Arg Phe Gly Lys Cys
            20                  25                  30

Xaa Asn Xaa Lys Cys Xaa Cys Thr Pro Xaa
        35                  40

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(3)
<223> OTHER INFORMATION: May or may not be present
<220> FEATURE:
<221> NAME/KEY: MOD_RES
<222> LOCATION: (4)..(4)
```

-continued

```
<223> OTHER INFORMATION: G, S or null
<220> FEATURE:
<221> NAME/KEY: MOD_RES
<222> LOCATION: (5)..(5)
<223> OTHER INFORMATION: G, S or null
<220> FEATURE:
<221> NAME/KEY: MOD_RES
<222> LOCATION: (7)..(7)
<223> OTHER INFORMATION: P or R
<220> FEATURE:
<221> NAME/KEY: MOD_RES
<222> LOCATION: (9)..(9)
<223> OTHER INFORMATION: N or P
<220> FEATURE:
<221> NAME/KEY: MOD_RES
<222> LOCATION: (11)..(11)
<223> OTHER INFORMATION: K or S
<220> FEATURE:
<221> NAME/KEY: MOD_RES
<222> LOCATION: (13)..(13)
<223> OTHER INFORMATION: R or K
<220> FEATURE:
<221> NAME/KEY: MOD_RES
<222> LOCATION: (14)..(14)
<223> OTHER INFORMATION: G or H
<220> FEATURE:
<221> NAME/KEY: MOD_RES
<222> LOCATION: (16)..(16)
<223> OTHER INFORMATION: R or G
<220> FEATURE:
<221> NAME/KEY: MOD_RES
<222> LOCATION: (17)..(17)
<223> OTHER INFORMATION: D or Q
<220> FEATURE:
<221> NAME/KEY: MOD_RES
<222> LOCATION: (20)..(20)
<223> OTHER INFORMATION: D or K
<220> FEATURE:
<221> NAME/KEY: MOD_RES
<222> LOCATION: (24)..(24)
<223> OTHER INFORMATION: K or D
<220> FEATURE:
<221> NAME/KEY: MOD_RES
<222> LOCATION: (33)..(33)
<223> OTHER INFORMATION: I or M
<220> FEATURE:
<221> NAME/KEY: MOD_RES
<222> LOCATION: (35)..(35)
<223> OTHER INFORMATION: S or G
<220> FEATURE:
<221> NAME/KEY: MOD_RES
<222> LOCATION: (38)..(38)
<223> OTHER INFORMATION: H or D
<220> FEATURE:
<221> NAME/KEY: MISC_FEATURE
<222> LOCATION: (42)..(42)
<223> OTHER INFORMATION: May or may not be present

<400> SEQUENCE: 6

Gly Ser Gly Xaa Xaa Val Xaa Ile Xaa Val Xaa Cys Xaa Xaa Ser Xaa
1               5                   10                  15

Xaa Cys Leu Xaa Pro Cys Lys Xaa Ala Gly Met Arg Phe Gly Lys Cys
            20                  25                  30

Xaa Asn Xaa Lys Cys Xaa Cys Thr Pro Lys
        35                  40

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<223> OTHER INFORMATION: See specification as filed for detailed
      description of substitutions and preferred embodiments

<400> SEQUENCE: 7

Gly Ser Xaa Val Xaa Val Lys Cys Xaa Gly Ser Lys Gln Cys Xaa Pro
1               5                   10                  15

Cys Lys Arg Xaa Gly Xaa Arg Xaa Gly Lys Cys Ile Asn Lys Lys Xaa
            20                  25                  30

Cys Lys Cys Tyr Xaa
        35

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
```

```
<222> LOCATION: (20)..(20)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<223> OTHER INFORMATION: See specification as filed for detailed
      description of substitutions and preferred embodiments

<400> SEQUENCE: 8

Gly Ser Xaa Gly Cys Val Xaa Lys Cys Arg Pro Gly Xaa Lys Xaa Cys
1               5                   10                  15

Cys Xaa Pro Xaa Lys Arg Cys Ser Arg Arg Phe Gly Xaa Lys Lys Cys
            20                  25                  30

Lys Xaa

<210> SEQ ID NO 9
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid, amino acid analogue or null
<220> FEATURE:
<221> NAME/KEY: MOD_RES
<222> LOCATION: (5)..(7)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (17)..(18)
<223> OTHER INFORMATION: Any amino acid, amino acid analogue or null
<220> FEATURE:
<221> NAME/KEY: MOD_RES
<222> LOCATION: (23)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (28)..(28)
<223> OTHER INFORMATION: Any amino acid, amino acid analogue or null
<220> FEATURE:
<221> NAME/KEY: MOD_RES
<222> LOCATION: (36)..(36)
<223> OTHER INFORMATION: Any amino acid, amino acid analogue or null
<220> FEATURE:
<221> NAME/KEY: MOD_RES
<222> LOCATION: (41)..(43)
<223> OTHER INFORMATION: Any amino acid, amino acid analogue or null

<400> SEQUENCE: 9

Gly Ser Xaa Val Xaa Xaa Xaa Val Lys Cys Xaa Gly Ser Lys Gln Cys
1               5                   10                  15

Xaa Xaa Pro Cys Lys Arg Xaa Xaa Gly Xaa Arg Xaa Gly Lys Cys Ile
            20                  25                  30

Asn Lys Lys Xaa Cys Lys Cys Tyr Xaa Xaa Xaa
            35                  40
```

```
<210> SEQ ID NO 10
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (34)..(37)
<223> OTHER INFORMATION: Any amino acid
<220> FEATURE:
<221> NAME/KEY: MOD_RES
<222> LOCATION: (42)..(47)
<223> OTHER INFORMATION: Any amino acid

<400> SEQUENCE: 10

Gly Ser Xaa Xaa Xaa Gly Cys Val Xaa Xaa Xaa Xaa Lys Cys Arg Pro
1               5                   10                  15

Gly Xaa Lys Xaa Cys Cys Xaa Pro Xaa Lys Arg Cys Ser Arg Arg Phe
            20                  25                  30

Gly Xaa Xaa Xaa Xaa Lys Lys Cys Lys Xaa Xaa Xaa Xaa Xaa
        35                  40                  45

<210> SEQ ID NO 11
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(8)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (17)..(17)
<223> OTHER INFORMATION: Any amino acid, amino acid analogue or null
<220> FEATURE:
<221> NAME/KEY: MOD_RES
```

```
<222> LOCATION: (22)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (28)..(28)
<223> OTHER INFORMATION: Any amino acid, amino acid analogue or null
<220> FEATURE:
<221> NAME/KEY: MOD_RES
<222> LOCATION: (32)..(32)
<223> OTHER INFORMATION: Any amino acid, amino acid analogue or null
<220> FEATURE:
<221> NAME/KEY: MOD_RES
<222> LOCATION: (39)..(42)
<223> OTHER INFORMATION: Any amino acid, amino acid analogue or null

<400> SEQUENCE: 11

Gly Ser Gly Val Xaa Ile Xaa Xaa Arg Cys Xaa Gly Ser Arg Gln Cys
1               5                   10                  15

Xaa Asp Pro Cys Arg Xaa Xaa Xaa Gly Xaa Arg Xaa Gly Arg Cys Xaa
            20                  25                  30

Asn Arg Arg Cys Arg Cys Xaa Xaa Xaa Xaa
        35                  40

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: P or R
<220> FEATURE:
<221> NAME/KEY: MOD_RES
<222> LOCATION: (7)..(7)
<223> OTHER INFORMATION: P or N
<220> FEATURE:
<221> NAME/KEY: MOD_RES
<222> LOCATION: (8)..(8)
<223> OTHER INFORMATION: V or I
<220> FEATURE:
<221> NAME/KEY: MOD_RES
<222> LOCATION: (11)..(11)
<223> OTHER INFORMATION: S, T, R or K
<220> FEATURE:
<221> NAME/KEY: MOD_RES
<222> LOCATION: (17)..(17)
<223> OTHER INFORMATION: Y or L
<220> FEATURE:
<221> NAME/KEY: MOD_RES
<222> LOCATION: (22)..(22)
<223> OTHER INFORMATION: Q, R or K
<220> FEATURE:
<221> NAME/KEY: MOD_RES
<222> LOCATION: (23)..(23)
<223> OTHER INFORMATION: A, K or R
<220> FEATURE:
<221> NAME/KEY: MOD_RES
<222> LOCATION: (24)..(24)
<223> OTHER INFORMATION: T or A
<220> FEATURE:
<221> NAME/KEY: MOD_RES
<222> LOCATION: (26)..(26)
<223> OTHER INFORMATION: C or M
<220> FEATURE:
<221> NAME/KEY: MOD_RES
<222> LOCATION: (28)..(28)
<223> OTHER INFORMATION: F or N
<220> FEATURE:
```

```
<221> NAME/KEY: MOD_RES
<222> LOCATION: (32)..(32)
<223> OTHER INFORMATION: M or I
<220> FEATURE:
<221> NAME/KEY: MOD_RES
<222> LOCATION: (39)..(39)
<223> OTHER INFORMATION: Y or T
<220> FEATURE:
<221> NAME/KEY: MOD_RES
<222> LOCATION: (40)..(40)
<223> OTHER INFORMATION: G or P
<220> FEATURE:
<221> NAME/KEY: MISC_FEATURE
<222> LOCATION: (41)..(42)
<223> OTHER INFORMATION: May or may not be present

<400> SEQUENCE: 12

Gly Ser Gly Val Xaa Ile Xaa Xaa Arg Cys Xaa Gly Ser Arg Gln Cys
1               5                   10                  15

Xaa Asp Pro Cys Arg Xaa Xaa Gly Xaa Arg Xaa Gly Arg Cys Xaa
            20                  25                  30

Asn Arg Arg Cys Arg Cys Xaa Xaa Cys Gly
        35                  40

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(6)
<223> OTHER INFORMATION: Any amino acid, amino acid analogue or null
<220> FEATURE:
<221> NAME/KEY: MOD_RES
<222> LOCATION: (8)..(8)
<223> OTHER INFORMATION: Any amino acid, amino acid analogue or null
<220> FEATURE:
<221> NAME/KEY: MOD_RES
<222> LOCATION: (10)..(10)
<223> OTHER INFORMATION: Any amino acid, amino acid analogue or null
<220> FEATURE:
<221> NAME/KEY: MOD_RES
<222> LOCATION: (17)..(17)
<223> OTHER INFORMATION: Any amino acid, amino acid analogue or null
<220> FEATURE:
<221> NAME/KEY: MOD_RES
<222> LOCATION: (21)..(22)
<223> OTHER INFORMATION: Any amino acid, amino acid analogue or null
<220> FEATURE:
<221> NAME/KEY: MOD_RES
<222> LOCATION: (26)..(28)
<223> OTHER INFORMATION: Any amino acid, amino acid analogue or null
<220> FEATURE:
<221> NAME/KEY: MOD_RES
<222> LOCATION: (31)..(32)
<223> OTHER INFORMATION: Any amino acid, amino acid analogue or null
<220> FEATURE:
<221> NAME/KEY: MOD_RES
<222> LOCATION: (34)..(34)
<223> OTHER INFORMATION: Any amino acid, amino acid analogue or null

<400> SEQUENCE: 13

Gly Ser Xaa Xaa Xaa Xaa Ile Xaa Cys Xaa Gly Ser Arg Gln Cys Tyr
1               5                   10                  15

Xaa Pro Cys Arg Xaa Xaa Thr Gly Cys Xaa Xaa Xaa Arg Cys Xaa Xaa
            20                  25                  30

Arg Xaa Cys Arg Cys Tyr Gly Cys Gly
        35                  40
```

```
<210> SEQ ID NO 14
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(4)
<223> OTHER INFORMATION: May or may not be present
<220> FEATURE:
<221> NAME/KEY: MOD_RES
<222> LOCATION: (5)..(5)
<223> OTHER INFORMATION: E, G or null
<220> FEATURE:
<221> NAME/KEY: MOD_RES
<222> LOCATION: (6)..(6)
<223> OTHER INFORMATION: V, S or null
<220> FEATURE:
<221> NAME/KEY: MOD_RES
<222> LOCATION: (8)..(8)
<223> OTHER INFORMATION: R or S
<220> FEATURE:
<221> NAME/KEY: MOD_RES
<222> LOCATION: (10)..(10)
<223> OTHER INFORMATION: S or T
<220> FEATURE:
<221> NAME/KEY: MOD_RES
<222> LOCATION: (17)..(17)
<223> OTHER INFORMATION: G or D
<220> FEATURE:
<221> NAME/KEY: MOD_RES
<222> LOCATION: (21)..(21)
<223> OTHER INFORMATION: Q or R
<220> FEATURE:
<221> NAME/KEY: MOD_RES
<222> LOCATION: (22)..(22)
<223> OTHER INFORMATION: Q, R or K
<220> FEATURE:
<221> NAME/KEY: MOD_RES
<222> LOCATION: (26)..(26)
<223> OTHER INFORMATION: T or P
<220> FEATURE:
<221> NAME/KEY: MOD_RES
<222> LOCATION: (27)..(27)
<223> OTHER INFORMATION: N or Q
<220> FEATURE:
<221> NAME/KEY: MOD_RES
<222> LOCATION: (28)..(28)
<223> OTHER INFORMATION: S or A
<220> FEATURE:
<221> NAME/KEY: MOD_RES
<222> LOCATION: (31)..(31)
<223> OTHER INFORMATION: M or L
<220> FEATURE:
<221> NAME/KEY: MOD_RES
<222> LOCATION: (32)..(32)
<223> OTHER INFORMATION: N or Q
<220> FEATURE:
<221> NAME/KEY: MOD_RES
<222> LOCATION: (34)..(34)
<223> OTHER INFORMATION: V or S

<400> SEQUENCE: 14

Gly Ser Gly Ser Xaa Xaa Ile Xaa Cys Xaa Gly Ser Arg Gln Cys Tyr
1               5                   10                  15

Xaa Pro Cys Arg Xaa Xaa Thr Gly Cys Xaa Xaa Xaa Arg Cys Xaa Xaa
            20                  25                  30

Arg Xaa Cys Arg Cys Tyr Gly Cys Gly
        35                  40

<210> SEQ ID NO 15
<211> LENGTH: 42
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (13)..(14)
<223> OTHER INFORMATION: Any amino acid, amino acid analogue or null
<220> FEATURE:
<221> NAME/KEY: MOD_RES
<222> LOCATION: (16)..(17)
<223> OTHER INFORMATION: Any amino acid, amino acid analogue or null
<220> FEATURE:
<221> NAME/KEY: MOD_RES
<222> LOCATION: (20)..(20)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (33)..(33)
<223> OTHER INFORMATION: Any amino acid, amino acid analogue or null
<220> FEATURE:
<221> NAME/KEY: MOD_RES
<222> LOCATION: (35)..(35)
<223> OTHER INFORMATION: Any amino acid, amino acid analogue or null
<220> FEATURE:
<221> NAME/KEY: MOD_RES
<222> LOCATION: (38)..(38)
<223> OTHER INFORMATION: Any amino acid, amino acid analogue or null
<220> FEATURE:
<221> NAME/KEY: MOD_RES
<222> LOCATION: (42)..(42)
<223> OTHER INFORMATION: Any amino acid, amino acid analogue or null

<400> SEQUENCE: 15

Gly Ser Xaa Xaa Xaa Val Xaa Ile Xaa Val Xaa Cys Xaa Xaa Ser Xaa
1               5                   10                  15

Xaa Cys Leu Xaa Pro Cys Arg Xaa Ala Gly Met Arg Phe Gly Arg Cys
            20                  25                  30

Xaa Asn Xaa Arg Cys Xaa Cys Thr Pro Xaa
        35                  40

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(3)
<223> OTHER INFORMATION: May or may not be present
<220> FEATURE:
<221> NAME/KEY: MOD_RES
```

```
<222> LOCATION: (4)..(4)
<223> OTHER INFORMATION: G, S or null
<220> FEATURE:
<221> NAME/KEY: MOD_RES
<222> LOCATION: (5)..(5)
<223> OTHER INFORMATION: G, S or null
<220> FEATURE:
<221> NAME/KEY: MOD_RES
<222> LOCATION: (7)..(7)
<223> OTHER INFORMATION: P or R
<220> FEATURE:
<221> NAME/KEY: MOD_RES
<222> LOCATION: (9)..(9)
<223> OTHER INFORMATION: N or P
<220> FEATURE:
<221> NAME/KEY: MOD_RES
<222> LOCATION: (11)..(11)
<223> OTHER INFORMATION: R, K or S
<220> FEATURE:
<221> NAME/KEY: MOD_RES
<222> LOCATION: (13)..(13)
<223> OTHER INFORMATION: R or K
<220> FEATURE:
<221> NAME/KEY: MOD_RES
<222> LOCATION: (14)..(14)
<223> OTHER INFORMATION: G or H
<220> FEATURE:
<221> NAME/KEY: MOD_RES
<222> LOCATION: (16)..(16)
<223> OTHER INFORMATION: R or G
<220> FEATURE:
<221> NAME/KEY: MOD_RES
<222> LOCATION: (17)..(17)
<223> OTHER INFORMATION: D or Q
<220> FEATURE:
<221> NAME/KEY: MOD_RES
<222> LOCATION: (20)..(20)
<223> OTHER INFORMATION: D, R or K
<220> FEATURE:
<221> NAME/KEY: MOD_RES
<222> LOCATION: (24)..(24)
<223> OTHER INFORMATION: K, R or D
<220> FEATURE:
<221> NAME/KEY: MOD_RES
<222> LOCATION: (33)..(33)
<223> OTHER INFORMATION: I or M
<220> FEATURE:
<221> NAME/KEY: MOD_RES
<222> LOCATION: (35)..(35)
<223> OTHER INFORMATION: S or G
<220> FEATURE:
<221> NAME/KEY: MOD_RES
<222> LOCATION: (38)..(38)
<223> OTHER INFORMATION: H or D
<220> FEATURE:
<221> NAME/KEY: MOD_RES
<222> LOCATION: (42)..(42)
<223> OTHER INFORMATION: K, R or null

<400> SEQUENCE: 16

Gly Ser Gly Xaa Xaa Val Xaa Ile Xaa Val Xaa Cys Xaa Xaa Ser Xaa
1               5                   10                  15

Xaa Cys Leu Xaa Pro Cys Arg Xaa Ala Gly Met Arg Phe Gly Arg Cys
            20                  25                  30

Xaa Asn Xaa Arg Cys Xaa Cys Thr Pro Xaa
        35                  40

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

-continued

```
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<223> OTHER INFORMATION: See specification as filed for detailed
      description of substitutions and preferred embodiments

<400> SEQUENCE: 17

Gly Ser Xaa Val Xaa Val Arg Cys Xaa Gly Ser Arg Gln Cys Xaa Pro
1               5                   10                  15

Cys Arg Arg Xaa Gly Xaa Arg Xaa Gly Arg Cys Ile Asn Arg Arg Xaa
            20                  25                  30

Cys Arg Cys Tyr Xaa
        35

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
```

```
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<223> OTHER INFORMATION: See specification as filed for detailed
      description of substitutions and preferred embodiments

<400> SEQUENCE: 18

Gly Ser Xaa Gly Cys Val Xaa Arg Cys Arg Pro Gly Xaa Arg Xaa Cys
1               5                   10                  15

Cys Xaa Pro Xaa Arg Arg Cys Ser Arg Arg Phe Gly Xaa Arg Arg Cys
            20                  25                  30

Arg Xaa

<210> SEQ ID NO 19
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid analogue or null
<220> FEATURE:
<221> NAME/KEY: MOD_RES
<222> LOCATION: (5)..(7)
<223> OTHER INFORMATION: Any amino acid analogue or null
<220> FEATURE:
<221> NAME/KEY: MOD_RES
<222> LOCATION: (11)..(11)
<223> OTHER INFORMATION: Any amino acid analogue or null
<220> FEATURE:
<221> NAME/KEY: MOD_RES
<222> LOCATION: (17)..(18)
<223> OTHER INFORMATION: Any amino acid analogue or null
<220> FEATURE:
<221> NAME/KEY: MOD_RES
<222> LOCATION: (23)..(24)
<223> OTHER INFORMATION: Any amino acid analogue or null
<220> FEATURE:
<221> NAME/KEY: MOD_RES
<222> LOCATION: (26)..(26)
<223> OTHER INFORMATION: Any amino acid analogue or null
<220> FEATURE:
<221> NAME/KEY: MOD_RES
<222> LOCATION: (28)..(28)
<223> OTHER INFORMATION: Any amino acid analogue or null
<220> FEATURE:
<221> NAME/KEY: MOD_RES
<222> LOCATION: (36)..(36)
<223> OTHER INFORMATION: Any amino acid analogue or null
<220> FEATURE:
<221> NAME/KEY: MOD_RES
<222> LOCATION: (41)..(43)
<223> OTHER INFORMATION: Any amino acid analogue or null

<400> SEQUENCE: 19

Gly Ser Xaa Val Xaa Xaa Xaa Val Arg Cys Xaa Gly Ser Arg Gln Cys
1               5                   10                  15

Xaa Xaa Pro Cys Arg Arg Xaa Xaa Gly Xaa Arg Xaa Gly Arg Cys Ile
            20                  25                  30

Asn Arg Arg Xaa Cys Arg Cys Tyr Xaa Xaa Xaa
```

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (3)..(5)
<223> OTHER INFORMATION: Any amino acid analogue or null
<220> FEATURE:
<221> NAME/KEY: MOD_RES
<222> LOCATION: (9)..(12)
<223> OTHER INFORMATION: Any amino acid analogue or null
<220> FEATURE:
<221> NAME/KEY: MOD_RES
<222> LOCATION: (18)..(18)
<223> OTHER INFORMATION: Any amino acid analogue or null
<220> FEATURE:
<221> NAME/KEY: MOD_RES
<222> LOCATION: (20)..(20)
<223> OTHER INFORMATION: Any amino acid analogue or null
<220> FEATURE:
<221> NAME/KEY: MOD_RES
<222> LOCATION: (23)..(23)
<223> OTHER INFORMATION: Any amino acid analogue or null
<220> FEATURE:
<221> NAME/KEY: MOD_RES
<222> LOCATION: (25)..(25)
<223> OTHER INFORMATION: Any amino acid analogue or null
<220> FEATURE:
<221> NAME/KEY: MOD_RES
<222> LOCATION: (34)..(37)
<223> OTHER INFORMATION: Any amino acid analogue or null
<220> FEATURE:
<221> NAME/KEY: MOD_RES
<222> LOCATION: (42)..(47)
<223> OTHER INFORMATION: Any amino acid analogue or null

<400> SEQUENCE: 20

Gly Ser Xaa Xaa Xaa Gly Cys Val Xaa Xaa Xaa Xaa Arg Cys Arg Pro
1               5                   10                  15

Gly Xaa Arg Xaa Cys Cys Xaa Pro Xaa Arg Arg Cys Ser Arg Arg Phe
            20                  25                  30

Gly Xaa Xaa Xaa Xaa Arg Arg Cys Arg Xaa Xaa Xaa Xaa Xaa Xaa
        35                  40                  45

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (3)..(3)
<223> OTHER INFORMATION: Any amino acid, amino acid analogue or null
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:

```
<221> NAME/KEY: MOD_RES
<222> LOCATION: (14)..(14)
<223> OTHER INFORMATION: Any amino acid, amino acid analogue or null
<220> FEATURE:
<221> NAME/KEY: MOD_RES
<222> LOCATION: (18)..(18)
<223> OTHER INFORMATION: Any amino acid, amino acid analogue or null
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (28)..(28)
<223> OTHER INFORMATION: Any amino acid, amino acid analogue or null
<220> FEATURE:
<221> NAME/KEY: MOD_RES
<222> LOCATION: (37)..(37)
<223> OTHER INFORMATION: Any amino acid, amino acid analogue or null
<220> FEATURE:
<221> NAME/KEY: MOD_RES
<222> LOCATION: (39)..(39)
<223> OTHER INFORMATION: Any amino acid, amino acid analogue or null
<220> FEATURE:
<221> NAME/KEY: MOD_RES
<222> LOCATION: (41)..(42)
<223> OTHER INFORMATION: Any amino acid, amino acid analogue or null

<400> SEQUENCE: 21

Gly Ser Xaa Val Xaa Ile Xaa Val Lys Cys Xaa Gly Ser Xaa Gln Cys
1               5                   10                  15

Leu Xaa Pro Cys Lys Xaa Ala Xaa Gly Xaa Arg Xaa Gly Lys Cys Met
            20                  25                  30

Asn Gly Lys Cys Xaa Cys Xaa Pro Xaa Xaa
        35                  40

<210> SEQ ID NO 22
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid, amino acid analogue or null
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (11)..(11)
<223> OTHER INFORMATION: Any amino acid, amino acid analogue or null
<220> FEATURE:
<221> NAME/KEY: MOD_RES
<222> LOCATION: (14)..(14)
<223> OTHER INFORMATION: Any amino acid, amino acid analogue or null
<220> FEATURE:
<221> NAME/KEY: MOD_RES
<222> LOCATION: (18)..(18)
<223> OTHER INFORMATION: Any amino acid, amino acid analogue or null
```

```
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (28)..(28)
<223> OTHER INFORMATION: Any amino acid, amino acid analogue or null
<220> FEATURE:
<221> NAME/KEY: MOD_RES
<222> LOCATION: (37)..(37)
<223> OTHER INFORMATION: Any amino acid, amino acid analogue or null
<220> FEATURE:
<221> NAME/KEY: MOD_RES
<222> LOCATION: (39)..(39)
<223> OTHER INFORMATION: Any amino acid, amino acid analogue or null
<220> FEATURE:
<221> NAME/KEY: MOD_RES
<222> LOCATION: (41)..(42)
<223> OTHER INFORMATION: Any amino acid, amino acid analogue or null

<400> SEQUENCE: 22

Gly Ser Xaa Val Xaa Ile Xaa Val Arg Cys Xaa Gly Ser Xaa Gln Cys
1               5                   10                  15

Leu Xaa Pro Cys Arg Xaa Ala Xaa Gly Xaa Arg Xaa Gly Arg Cys Met
            20                  25                  30

Asn Gly Arg Cys Xaa Cys Xaa Pro Xaa Xaa
            35                  40

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: N, S or G
<220> FEATURE:
<221> NAME/KEY: MOD_RES
<222> LOCATION: (17)..(17)
<223> OTHER INFORMATION: L or Y
<220> FEATURE:
<221> NAME/KEY: MOD_RES
<222> LOCATION: (18)..(18)
<223> OTHER INFORMATION: D or E
<220> FEATURE:
<221> NAME/KEY: MOD_RES
<222> LOCATION: (25)..(25)
<223> OTHER INFORMATION: M or T
<220> FEATURE:
<221> NAME/KEY: MOD_RES
<222> LOCATION: (32)..(32)
<223> OTHER INFORMATION: N, Q, A, S, T or L
<220> FEATURE:
<221> NAME/KEY: MOD_RES
<222> LOCATION: (33)..(33)
<223> OTHER INFORMATION: S, G or R
<220> FEATURE:
<221> NAME/KEY: MOD_RES
<222> LOCATION: (36)..(36)
<223> OTHER INFORMATION: H or Y
<220> FEATURE:
<221> NAME/KEY: MOD_RES
<222> LOCATION: (38)..(38)
```

<223> OTHER INFORMATION: T or Y

<400> SEQUENCE: 23

Gly Ser Gly Val Pro Ile Xaa Val Arg Cys Arg Gly Ser Arg Asp Cys
1 5 10 15

Xaa Xaa Pro Cys Arg Arg Ala Gly Xaa Arg Phe Gly Arg Cys Ile Xaa
20 25 30

Xaa Arg Cys Xaa Cys Xaa Pro
35

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: See specification as filed for detailed description of substitutions and preferred embodiments

<400> SEQUENCE: 24

Gly Ser Gly Ile Val Cys Lys Val Cys Lys Ile Ile Cys Gly Met Gln
1 5 10 15

Gly Lys Lys Val Asn Ile Cys Lys Ala Pro Ile Lys Cys Lys Cys Lys
20 25 30

Lys Gly

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: See specification as filed for detailed description of substitutions and preferred embodiments

<400> SEQUENCE: 25

Gly Ser Ser Glu Lys Asp Cys Ile Lys His Leu Gln Arg Cys Arg Glu
1 5 10 15

Asn Lys Asp Cys Cys Ser Lys Lys Cys Ser Arg Arg Gly Thr Asn Pro
20 25 30

Glu Lys Arg Cys Arg
35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: See specification as filed for detailed description of substitutions and preferred embodiments

<400> SEQUENCE: 26

Gly Ser Val Arg Ile Pro Val Ser Cys Lys His Ser Gly Gln Cys Leu
1 5 10 15

Lys Pro Cys Lys Asp Ala Gly Met Arg Phe Gly Lys Cys Met Asn Gly
20 25 30

Lys Cys Asp Cys Thr Pro Lys

-continued

```
<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 27

Gly Ser Gly Val Pro Ile Asn Val Lys Cys Arg Gly Ser Arg Asp Cys
1               5                   10                  15

Leu Asp Pro Cys Lys Lys Ala Gly Met Arg Phe Gly Lys Cys Ile Asn
            20                  25                  30

Ser Lys Cys His Cys Thr Pro
        35

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 28

Gly Ser Ala Val Cys Val Tyr Arg Thr Cys Asp Lys Asp Cys Lys Arg
1               5                   10                  15

Arg Gly Tyr Arg Ser Gly Lys Cys Ile Asn Asn Ala Cys Lys Cys Tyr
            20                  25                  30

Pro Tyr Gly
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 29

Gly Ser Ile Ser Cys Thr Gly Ser Lys Gln Cys Tyr Asp Pro Cys Lys
1               5                   10                  15

Arg Lys Thr Gly Cys Pro Asn Ala Lys Cys Met Asn Lys Ser Cys Lys
            20                  25                  30

Cys Tyr Gly Cys Gly
        35

<210> SEQ ID NO 30
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: See specification as filed for detailed
      description of substitutions and preferred embodiments

<400> SEQUENCE: 30

Gly Ser Gln Val Gln Thr Asn Val Lys Cys Gln Gly Gly Ser Cys Ala
1               5                   10                  15

Ser Val Cys Arg Arg Glu Ile Gly Val Ala Ala Gly Lys Cys Ile Asn
            20                  25                  30

Gly Lys Cys Val Cys Tyr Arg Asn
        35                  40

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 31

Gly Ser Glu Val Ile Arg Cys Ser Gly Ser Lys Gln Cys Tyr Gly Pro
1               5                   10                  15

Cys Lys Gln Gln Thr Gly Cys Thr Asn Ser Lys Cys Met Asn Lys Val
            20                  25                  30

Cys Lys Cys Tyr Gly Cys Gly
        35

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 32

Gly Ser Ala Cys Lys Gly Val Phe Asp Ala Cys Thr Pro Gly Lys Asn
1               5                   10                  15

Glu Cys Cys Pro Asn Arg Val Cys Ser Asp Lys His Lys Trp Cys Lys
            20                  25                  30

Trp Lys Leu
        35

<210> SEQ ID NO 33
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 33

Gly Ser Gln Ile Tyr Thr Ser Lys Glu Cys Asn Gly Ser Ser Glu Cys
1               5                   10                  15

Tyr Ser His Cys Glu Gly Ile Thr Gly Lys Arg Ser Gly Lys Cys Ile
```

```
                     20                  25                  30

Asn Lys Lys Cys Tyr Cys Tyr Arg
            35                  40

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 34

Gly Ser Gly Cys Leu Glu Phe Trp Trp Lys Cys Asn Pro Asn Asp Asp
1               5                   10                  15

Lys Cys Cys Arg Pro Lys Leu Lys Cys Ser Lys Leu Phe Lys Leu Cys
            20                  25                  30

Asn Phe Ser Phe Gly
            35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Ser Asp Cys Val Arg Phe Trp Gly Lys Cys Ser Gln Thr Ser Asp
1               5                   10                  15

Cys Cys Pro His Leu Ala Cys Lys Ser Lys Trp Pro Arg Asn Ile Cys
            20                  25                  30

Val Trp Asp Gly Ser Val Gly
            35

<210> SEQ ID NO 36
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 36

Gly Ser Gly Cys Phe Gly Tyr Lys Cys Asp Tyr Tyr Lys Gly Cys Cys
1               5                   10                  15

Ser Gly Tyr Val Cys Ser Pro Thr Trp Lys Trp Cys Val Arg Pro Gly
            20                  25                  30

Pro Gly Arg
            35

<210> SEQ ID NO 37
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 37

Gly Ser Met Asn Ala Lys Phe Ile Leu Leu Val Leu Thr Thr Met
1               5                   10                  15

Met Leu Leu Pro Asp Thr Lys Gly Ala Glu Val Ile Arg Cys Ser Gly
            20                  25                  30

Ser Lys Gln Cys Tyr Gly Pro Cys Lys Gln Gln Thr Gly Cys Thr Asn
        35                  40                  45

Ser Lys Cys Met Asn Lys Val Cys Lys Cys Tyr Gly Cys Gly
    50                  55                  60

<210> SEQ ID NO 38
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Ser Met Asn Ala Lys Leu Ile Tyr Leu Leu Val Val Thr Thr
1               5                   10                  15

Met Thr Leu Met Phe Asp Thr Ala Gln Ala Val Asp Ile Met Cys Ser
            20                  25                  30

Gly Pro Lys Gln Cys Tyr Gly Pro Cys Lys Lys Glu Thr Gly Cys Pro
        35                  40                  45

Asn Ala Lys Cys Met Asn Arg Arg Cys Lys Cys Tyr Gly Cys Val
    50                  55                  60

<210> SEQ ID NO 39
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Ser Met Asn Ala Lys Leu Ile Tyr Leu Leu Val Val Thr Thr
1               5                   10                  15

Met Leu Thr Phe Asp Thr Thr Gln Ala Gly Asp Ile Lys Cys Ser
            20                  25                  30

Gly Thr Arg Gln Cys Trp Gly Pro Cys Lys Lys Gln Thr Thr Cys Thr
        35                  40                  45

Asn Ser Lys Cys Met Asn Gly Lys Cys Lys Cys Tyr Gly Cys Val Gly
    50                  55                  60

<210> SEQ ID NO 40
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Met Asn Thr Lys Phe Ile Phe Leu Leu Val Val Thr Asn
1               5                   10                  15

Thr Met Met Leu Phe Asp Thr Lys Pro Val Glu Gly Ile Ser Cys Thr
            20                  25                  30

Gly Ser Lys Gln Cys Tyr Asp Pro Cys Lys Arg Lys Thr Gly Cys Pro
```

```
            35                  40                  45
Asn Ala Lys Cys Met Asn Lys Ser Cys Lys Cys Tyr Gly Cys Gly
    50                  55                  60

<210> SEQ ID NO 41
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Ser Gly Val Pro Ile Asn Val Lys Cys Ser Gly Ser Arg Asp Cys
1               5                   10                  15

Leu Glu Pro Cys Lys Lys Ala Gly Met Arg Phe Gly Lys Cys Ile Asn
            20                  25                  30

Arg Lys Cys His Cys Thr Pro Lys
        35                  40

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Ser Gly Val Pro Ile Asn Val Lys Cys Thr Gly Ser Pro Gln Cys
1               5                   10                  15

Leu Lys Pro Cys Lys Asp Ala Gly Met Arg Phe Gly Lys Cys Ile Asn
            20                  25                  30

Gly Lys Cys His Cys Thr Pro Lys
        35                  40

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ser Gly Val Ile Ile Asn Val Lys Cys Lys Ile Ser Arg Gln Cys
1               5                   10                  15

Leu Glu Pro Cys Lys Lys Ala Gly Met Arg Phe Gly Lys Cys Met Asn
            20                  25                  30

Gly Lys Cys His Cys Thr Pro Lys
        35                  40

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Ser Gly Val Pro Ile Asn Val Lys Cys Arg Gly Ser Pro Gln Cys
1               5                   10                  15
```

```
Ile Gln Pro Cys Arg Asp Ala Gly Met Arg Phe Gly Lys Cys Met Asn
            20                  25                  30

Gly Lys Cys His Cys Thr Pro Gln
        35                  40
```

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gly Ser Gly Val Glu Ile Asn Val Lys Cys Thr Gly Ser His Gln Cys
1               5                   10                  15

Ile Lys Pro Cys Lys Asp Ala Gly Met Arg Phe Gly Lys Cys Ile Asn
            20                  25                  30

Arg Lys Cys His Cys Thr Pro Lys
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gly Ser Gly Val Glu Ile Asn Val Lys Cys Ser Gly Ser Pro Gln Cys
1               5                   10                  15

Leu Lys Pro Cys Lys Asp Ala Gly Met Arg Phe Gly Lys Cys Met Asn
            20                  25                  30

Arg Lys Cys His Cys Thr Pro Lys
        35                  40
```

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gly Ser Gly Val Pro Thr Asp Val Lys Cys Arg Gly Ser Pro Gln Cys
1               5                   10                  15

Ile Gln Pro Cys Lys Asp Ala Gly Met Arg Phe Gly Lys Cys Met Asn
            20                  25                  30

Gly Lys Cys His Cys Thr Pro Lys
        35                  40
```

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Gly Ser Gly Val Pro Ile Asn Val Ser Cys Thr Gly Ser Pro Gln Cys
1               5                   10                  15
```

Ile Lys Pro Cys Lys Asp Ala Gly Met Arg Phe Gly Lys Cys Met Asn
                20                  25                  30

Arg Lys Cys His Cys Thr Pro Lys
        35                  40

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Ser Gly Val Pro Ile Asn Val Pro Cys Thr Gly Ser Pro Gln Cys
1               5                   10                  15

Ile Lys Pro Cys Lys Asp Ala Gly Met Arg Phe Gly Lys Cys Met Asn
                20                  25                  30

Arg Lys Cys His Cys Thr Pro Lys
        35                  40

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ser Val Gly Ile Asn Val Lys Cys Lys His Ser Gly Gln Cys Leu
1               5                   10                  15

Lys Pro Cys Lys Asp Ala Gly Met Arg Phe Gly Lys Cys Ile Asn Gly
                20                  25                  30

Lys Cys Asp Cys Thr Pro Lys
        35

<210> SEQ ID NO 51
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Ser Val Gly Ile Asn Val Lys Cys Lys His Ser Gly Gln Cys Leu
1               5                   10                  15

Lys Pro Cys Lys Asp Ala Gly Met Arg Phe Gly Lys Cys Met Asn Gly
                20                  25                  30

Lys Cys Asp Cys Thr Pro Lys
        35

<210> SEQ ID NO 52
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Ser Val Gly Ile Pro Val Ser Cys Lys His Ser Gly Gln Cys Ile

```
                1               5                  10                  15
Lys Pro Cys Lys Asp Ala Gly Met Arg Phe Gly Lys Cys Met Asn Arg
                20                  25                  30

Lys Cys Asp Cys Thr Pro Lys
            35

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Ser Arg Lys Gly Cys Phe Lys Glu Gly His Ser Cys Pro Lys Thr
1               5                   10                  15

Ala Pro Cys Cys Arg Pro Leu Val Cys Lys Gly Pro Ser Pro Asn Thr
                20                  25                  30

Lys Lys Cys Thr Arg Pro
            35

<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Ser Ser Phe Cys Ile Pro Phe Lys Pro Cys Lys Ser Asp Glu Asn
1               5                   10                  15

Cys Cys Lys Lys Phe Lys Cys Lys Thr Thr Gly Ile Val Lys Leu Cys
                20                  25                  30

Arg Trp

<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Ser Leu Lys Gly Cys Leu Pro Arg Asn Arg Phe Cys Asn Ala Leu
1               5                   10                  15

Ser Gly Pro Arg Cys Cys Ser Gly Leu Arg Cys Lys Glu Leu Ser Ile
                20                  25                  30

Trp Ala Ser Lys Cys Leu
            35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Ser Gly Asn Tyr Cys Leu Arg Gly Arg Cys Leu Pro Gly Gly Arg
```

```
            1               5                  10                 15
Lys Cys Cys Asn Gly Arg Pro Cys Glu Cys Phe Ala Lys Ile Cys Ser
                    20                 25                 30
Cys Lys Pro Lys
        35

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Ser Thr Val Lys Cys Gly Gly Cys Asn Arg Lys Cys Cys Pro Gly
1               5                   10                  15
Gly Cys Arg Ser Gly Lys Cys Ile Asn Gly Lys Cys Gln Cys Tyr
                20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Ser Gly Cys Met Lys Glu Tyr Cys Ala Gly Gln Cys Arg Gly Lys
1               5                   10                  15
Val Ser Gln Asp Tyr Cys Leu Lys His Cys Lys Cys Ile Pro Arg
                20                  25                  30

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Ser Ala Cys Leu Gly Phe Gly Glu Lys Cys Asn Pro Ser Asn Asp
1               5                   10                  15
Lys Cys Cys Lys Ser Ser Ser Leu Val Cys Ser Gln Lys His Lys Trp
                20                  25                  30
Cys Lys Tyr Gly
        35

<210> SEQ ID NO 60
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Ser Arg Gly Gly Cys Leu Pro His Asn Arg Phe Cys Asn Ala Leu
1               5                   10                  15
Ser Gly Pro Arg Cys Cys Ser Gly Leu Arg Cys Lys Glu Leu Ser Ile
                20                  25                  30
```

```
Arg Asp Ser Arg Cys Leu Gly
        35

<210> SEQ ID NO 61
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Ser Arg Gly Gly Cys Leu Pro Arg Asn Lys Phe Cys Asn Pro Ser
1               5                   10                  15

Ser Gly Pro Arg Cys Cys Ser Gly Leu Thr Cys Lys Glu Leu Asn Ile
            20                  25                  30

Trp Ala Ser Lys Cys Leu
        35

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ser Gln Arg Ser Cys Ala Lys Pro Gly Asp Met Cys Met Gly Ile
1               5                   10                  15

Lys Cys Cys Asp Gly Gln Cys Gly Cys Asn Arg Gly Thr Gly Arg Cys
            20                  25                  30

Phe Cys Lys
        35

<210> SEQ ID NO 63
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Ser Ala Arg Gly Cys Ala Asp Ala Tyr Lys Ser Cys Asn His Pro
1               5                   10                  15

Arg Thr Cys Cys Asp Gly Tyr Asn Gly Tyr Lys Arg Ala Cys Ile Cys
            20                  25                  30

Ser Gly Ser Asn Cys Lys Cys Lys Lys Ser
        35                  40

<210> SEQ ID NO 64
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Lys Glu Leu Ser Ile
            20                  25                  30
```

```
Trp Asp Ser Arg Cys Leu Gly
        35

<210> SEQ ID NO 65
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Ser Arg Gly Gly Cys Leu Pro His Asn Arg Phe Cys Asn Ala Leu
1               5                   10                  15

Ser Gly Pro Arg Cys Cys Ser Gly Leu Lys Cys Lys Glu Leu Ser Ile
            20                  25                  30

Tyr Asp Ser Arg Cys Leu Gly
        35

<210> SEQ ID NO 66
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Ser Arg Gly Gly Cys Leu Pro His Asn Arg Phe Cys Asn Ala Leu
1               5                   10                  15

Ser Gly Pro Arg Cys Cys Ser Arg Leu Lys Cys Lys Glu Leu Ser Ile
            20                  25                  30

Trp Asp Ser Arg Cys Leu Gly
        35

<210> SEQ ID NO 67
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Ser Arg Gly Gly Cys Leu Pro His Asn Arg Phe Cys Asn Ala Leu
1               5                   10                  15

Thr Gly Pro Arg Cys Cys Ser Arg Leu Arg Cys Lys Glu Leu Ser Ile
            20                  25                  30

Trp Asp Ser Ile Cys Leu Gly
        35

<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Ser Ser Cys Ala Asp Ala Tyr Lys Ser Cys Asp Ser Leu Lys Cys
1               5                   10                  15

Cys Asn Asn Arg Thr Cys Met Cys Ser Met Ile Gly Thr Asn Cys Thr
```

```
                20                  25                  30
Cys Arg Lys Lys
        35

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ser Glu Arg Arg Cys Leu Pro Ala Gly Lys Thr Cys Val Arg Gly
1               5                   10                  15

Pro Met Arg Val Pro Cys Cys Gly Ser Cys Ser Gln Asn Lys Cys Thr
            20                  25                  30

<210> SEQ ID NO 70
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Ser Leu Cys Ser Arg Glu Gly Glu Phe Cys Tyr Lys Leu Arg Lys
1               5                   10                  15

Cys Cys Ala Gly Phe Tyr Cys Lys Ala Phe Val Leu His Cys Tyr Arg
            20                  25                  30

Asn

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Ala Cys Gly Ser Cys Arg Lys Lys Cys Lys Gly Ser Gly Lys
1               5                   10                  15

Cys Ile Asn Gly Arg Cys Lys Cys Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Ala Cys Gly Ser Cys Arg Lys Lys Cys Lys Gly Pro Gly Lys
1               5                   10                  15

Cys Ile Asn Gly Arg Cys Lys Cys Tyr
            20                  25

<210> SEQ ID NO 73
<211> LENGTH: 34
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 73

Gly Ser Ala Cys Gln Gly Tyr Met Arg Lys Cys Gly Arg Asp Lys Pro
1               5                   10                  15

Pro Cys Cys Lys Lys Leu Glu Cys Ser Lys Thr Trp Arg Trp Cys Val
                20                  25                  30

Trp Asn

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Ser Gly Arg Tyr Cys Gln Lys Trp Met Trp Thr Cys Asp Ser Lys
1               5                   10                  15

Arg Ala Cys Cys Glu Gly Leu Arg Cys Lys Leu Trp Cys Arg Lys Ile
                20                  25                  30

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Ser Asn Ala Lys Cys Arg Gly Ser Pro Glu Cys Leu Pro Lys Cys
1               5                   10                  15

Lys Glu Ala Ile Gly Lys Ala Ala Gly Lys Cys Met Asn Gly Lys Cys
                20                  25                  30

Lys Cys Tyr Pro
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Ser Asn Val Lys Cys Arg Gly Ser Lys Glu Cys Leu Pro Ala Cys
1               5                   10                  15

Lys Ala Ala Val Gly Lys Ala Ala Gly Lys Cys Met Asn Gly Lys Cys
                20                  25                  30

Lys Cys Tyr Pro
        35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Gly Ser Asn Val Lys Cys Arg Gly Ser Pro Glu Cys Leu Pro Lys Cys
1               5                   10                  15

Lys Glu Ala Ile Gly Lys Ser Ala Gly Lys Cys Met Asn Gly Lys Cys
            20                  25                  30

Lys Cys Tyr Pro
        35

<210> SEQ ID NO 78
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Ser Asn Ala Lys Cys Arg Gly Ser Pro Glu Cys Leu Pro Lys Cys
1               5                   10                  15

Lys Gln Ala Ile Gly Lys Ala Ala Gly Lys Cys Met Asn Gly Lys Cys
            20                  25                  30

Lys Cys Tyr Pro
        35

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Ser Arg Gly Tyr Cys Ala Glu Lys Gly Ile Lys Cys His Asn Ile
1               5                   10                  15

His Cys Cys Ser Gly Leu Thr Cys Lys Cys Lys Gly Ser Ser Cys Val
            20                  25                  30

Cys Arg Lys
        35

<210> SEQ ID NO 80
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Ser Glu Arg Gly Cys Lys Leu Thr Phe Trp Lys Cys Lys Asn Lys
1               5                   10                  15

Lys Glu Cys Cys Gly Trp Asn Ala Cys Ala Leu Gly Ile Cys Met Pro
            20                  25                  30

Arg

<210> SEQ ID NO 81
<211> LENGTH: 41
<212> TYPE: PRT
<213> ORGANISM: Artificial Sequence
<220> FEATURE:
<223> OTHER INFORMATION: Description of Artificial Sequence: Synthetic

```
                              polypeptide

<400> SEQUENCE: 81

Gly Ser Lys Lys Lys Cys Ile Ala Lys Asp Tyr Gly Arg Cys Lys Trp
1               5                   10                  15

Gly Gly Thr Pro Cys Cys Arg Gly Arg Gly Cys Ile Cys Ser Ile Met
            20                  25                  30

Gly Thr Asn Cys Glu Cys Lys Pro Arg
        35                  40

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Ser Gly Cys Lys Leu Thr Phe Trp Lys Cys Lys Asn Lys Lys Glu
1               5                   10                  15

Cys Cys Gly Trp Asn Ala Cys Ala Leu Gly Ile Cys Met Pro Arg
            20                  25                  30

<210> SEQ ID NO 83
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Ser Ala Cys Lys Gly Leu Phe Val Thr Cys Thr Pro Gly Lys Asp
1               5                   10                  15

Glu Cys Cys Pro Asn His Val Cys Ser Ser Lys His Lys Trp Cys Lys
            20                  25                  30

Tyr Lys

<210> SEQ ID NO 84
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Ser Ile Ala Cys Ala Pro Arg Gly Leu Leu Cys Phe Arg Asp Lys
1               5                   10                  15

Glu Cys Cys Lys Gly Leu Thr Cys Lys Gly Arg Phe Val Asn Thr Trp
            20                  25                  30

Pro Thr Phe Cys Leu Val
        35

<210> SEQ ID NO 85
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85
```

Gly Ser Ala Cys Ala Gly Leu Tyr Lys Lys Cys Gly Lys Gly Val Asn
1               5                   10                  15

Thr Cys Cys Glu Asn Arg Pro Cys Lys Cys Asp Leu Ala Met Gly Asn
                20                  25                  30

Cys Ile Cys Lys Lys Lys
            35

<210> SEQ ID NO 86
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ser Phe Thr Cys Ala Ile Ser Cys Asp Ile Lys Val Asn Gly Lys
1               5                   10                  15

Pro Cys Lys Gly Ser Gly Glu Lys Cys Ser Gly Gly Trp Ser Cys
                20                  25                  30

Lys Phe Asn Val Cys Val Lys Val
            35                  40

<210> SEQ ID NO 87
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Ser Gly Phe Cys Ala Gln Lys Gly Ile Lys Cys His Asp Ile His
1               5                   10                  15

Cys Cys Thr Asn Leu Lys Cys Val Arg Glu Gly Ser Asn Arg Val Cys
                20                  25                  30

Arg Lys Ala
        35

<210> SEQ ID NO 88
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Ser Cys Ala Lys Lys Arg Asn Trp Cys Gly Lys Asn Glu Asp Cys
1               5                   10                  15

Cys Cys Pro Met Lys Cys Ile Tyr Ala Trp Tyr Asn Gln Gln Gly Ser
                20                  25                  30

Cys Gln Ser Thr Ile Thr Gly Leu Phe Lys Lys Cys
            35                  40

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 89

Gly Ser Tyr Cys Gln Lys Trp Met Trp Thr Cys Asp Ser Ala Arg Lys
1               5                   10                  15

Cys Cys Glu Gly Leu Val Cys Arg Leu Trp Cys Lys Lys Ile
            20                  25                  30

<210> SEQ ID NO 90
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Ser Arg Gly Gly Cys Leu Pro His Asn Lys Phe Cys Asn Ala Leu
1               5                   10                  15

Ser Gly Pro Arg Cys Cys Ser Gly Leu Lys Cys Lys Glu Leu Thr Ile
            20                  25                  30

Trp Asn Thr Lys Cys Leu Glu
            35

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Ser Asn Val Lys Cys Thr Gly Ser Lys Gln Cys Leu Pro Ala Cys
1               5                   10                  15

Lys Ala Ala Val Gly Lys Ala Ala Gly Lys Cys Met Asn Gly Lys Cys
            20                  25                  30

Lys Cys Tyr Thr
        35

<210> SEQ ID NO 92
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Ser Gln Arg Ser Cys Ala Lys Pro Gly Glu Met Cys Met Arg Ile
1               5                   10                  15

Lys Cys Cys Asp Gly Gln Cys Gly Cys Asn Arg Gly Thr Gly Arg Cys
            20                  25                  30

Phe Cys Lys
        35

<210> SEQ ID NO 93
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93
```

Gly Ser Gly Cys Ile Pro Lys His Lys Arg Cys Thr Trp Ser Gly Pro
1               5                   10                  15

Lys Cys Cys Asn Asn Ile Ser Cys His Cys Asn Ile Gly Thr Leu
                20                  25                  30

Cys Lys Cys Arg Pro Gly
            35

<210> SEQ ID NO 94
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Ser Asn Tyr Cys Val Ala Lys Arg Cys Arg Pro Gly Gly Arg Gln
1               5                   10                  15

Cys Cys Ser Gly Lys Pro Cys Ala Cys Val Gly Lys Val Cys Lys Cys
                20                  25                  30

Pro Arg Asp
        35

<210> SEQ ID NO 95
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Ser Glu Arg Gly Cys Ser Gly Ala Tyr Lys Arg Cys Ser Ser Ser
1               5                   10                  15

Gln Arg Cys Cys Glu Gly Arg Pro Cys Val Cys Ser Ala Ile Asn Ser
                20                  25                  30

Asn Cys Lys Cys Arg Lys Thr
            35

<210> SEQ ID NO 96
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gly Ser Arg Tyr Cys Pro Arg Asn Pro Glu Ala Cys Tyr Asn Tyr Cys
1               5                   10                  15

Leu Arg Thr Gly Arg Pro Gly Gly Tyr Cys Gly Gly Arg Ser Arg Ile
                20                  25                  30

Thr Cys Phe Cys Phe Arg
            35

<210> SEQ ID NO 97
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Gly Ser Gln Arg Ser Cys Ala Lys Pro Gly Glu Met Cys Met Gly Ile
1               5                   10                  15

Lys Cys Cys Asp Gly Gln Cys Gly Cys Asn Arg Gly Thr Gly Arg Cys
            20                  25                  30

Phe Cys Lys
        35

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gly Ser Arg Arg Gly Cys Phe Lys Glu Gly Lys Trp Cys Pro Lys Ser
1               5                   10                  15

Ala Pro Cys Cys Ala Pro Leu Lys Cys Lys Gly Pro Ser Ile Lys Gln
            20                  25                  30

Gln Lys Cys Val Arg Glu
        35

<210> SEQ ID NO 99
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gly Ser Thr Val Lys Cys Gly Gly Cys Asn Arg Lys Cys Cys Ala Gly
1               5                   10                  15

Gly Cys Arg Ser Gly Lys Cys Ile Asn Gly Lys Cys Gln Cys Tyr Gly
            20                  25                  30

Arg

<210> SEQ ID NO 100
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Ser Glu Arg Arg Cys Glu Pro Ser Gly Lys Pro Cys Arg Pro Leu
1               5                   10                  15

Met Arg Ile Pro Cys Cys Gly Ser Cys Val Arg Gly Lys Cys Ala
            20                  25                  30

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Ser Arg Gly Gly Cys Leu Pro Arg Asn Lys Phe Cys Asn Pro Ser
1               5                   10                  15
```

```
Ser Gly Pro Arg Cys Cys Ser Gly Leu Thr Cys Lys Glu Leu Asn Ile
            20                  25                  30

Trp Ala Asn Lys Cys Leu
        35
```

<210> SEQ ID NO 102
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Gly Ser Cys Ala Lys Lys Arg Asn Trp Cys Gly Lys Asn Glu Asp Cys
1               5                   10                  15

Cys Cys Pro Met Lys Cys Ile Tyr Ala Trp Tyr Asn Gln Gln Gly Ser
            20                  25                  30

Cys Gln Thr Thr Ile Thr Gly Leu Phe Lys Lys Cys
        35                  40
```

<210> SEQ ID NO 103
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Gly Ser Val Arg Ile Pro Val Ser Cys Lys His Ser Gly Gln Cys Leu
1               5                   10                  15

Lys Pro Cys Lys Asp Ala Gly Met Arg Thr Gly Lys Cys Met Asn Gly
            20                  25                  30

Lys Cys Asp Cys Thr Pro Lys
        35
```

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Gly Ser Val Lys Cys Thr Thr Ser Lys Asp Cys Trp Pro Pro Cys Lys
1               5                   10                  15

Lys Val Thr Gly Arg Ala
            20
```

<210> SEQ ID NO 105
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gly Ser Gly Ile Val Cys Arg Val Cys Arg Ile Ile Cys Gly Met Gln
1               5                   10                  15

Gly Arg Arg Val Asn Ile Cys Arg Ala Pro Ile Arg Cys Arg Cys Arg
```

```
                    20                  25                  30

Arg Gly

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gly Ser Ser Glu Arg Asp Cys Ile Arg His Leu Gln Arg Cys Arg Glu
1               5                   10                  15

Asn Arg Asp Cys Cys Ser Arg Arg Cys Ser Arg Arg Gly Thr Asn Pro
            20                  25                  30

Glu Arg Arg Cys Arg
        35

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gly Ser Val Arg Ile Pro Val Ser Cys Arg His Ser Gly Gln Cys Leu
1               5                   10                  15

Arg Pro Cys Arg Asp Ala Gly Met Arg Phe Gly Arg Cys Met Asn Gly
            20                  25                  30

Arg Cys Asp Cys Thr Pro Arg
        35

<210> SEQ ID NO 108
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Ser Gly Val Pro Ile Asn Val Arg Cys Arg Gly Ser Arg Asp Cys
1               5                   10                  15

Leu Asp Pro Cys Arg Arg Ala Gly Met Arg Phe Gly Arg Cys Ile Asn
            20                  25                  30

Ser Arg Cys His Cys Thr Pro
        35

<210> SEQ ID NO 109
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gly Ser Ala Val Cys Val Tyr Arg Thr Cys Asp Arg Asp Cys Arg Arg
1               5                   10                  15

Arg Gly Tyr Arg Ser Gly Arg Cys Ile Asn Asn Ala Cys Arg Cys Tyr
```

```
                         20                  25                  30

Pro Tyr Gly
        35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Ser Ile Ser Cys Thr Gly Ser Arg Gln Cys Tyr Asp Pro Cys Arg
1               5                   10                  15

Arg Arg Thr Gly Cys Pro Asn Ala Arg Cys Met Asn Arg Ser Cys Arg
            20                  25                  30

Cys Tyr Gly Cys Gly
        35

<210> SEQ ID NO 111
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gly Ser Gln Val Gln Thr Asn Val Arg Cys Gln Gly Gly Ser Cys Ala
1               5                   10                  15

Ser Val Cys Arg Arg Glu Ile Gly Val Ala Ala Gly Arg Cys Ile Asn
            20                  25                  30

Gly Arg Cys Val Cys Tyr Arg Asn
        35                  40

<210> SEQ ID NO 112
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gly Ser Glu Val Ile Arg Cys Ser Gly Ser Arg Gln Cys Tyr Gly Pro
1               5                   10                  15

Cys Arg Gln Gln Thr Gly Cys Thr Asn Ser Arg Cys Met Asn Arg Val
            20                  25                  30

Cys Arg Cys Tyr Gly Cys Gly
        35

<210> SEQ ID NO 113
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Ser Ala Cys Arg Gly Val Phe Asp Ala Cys Thr Pro Gly Arg Asn
1               5                   10                  15
```

Glu Cys Cys Pro Asn Arg Val Cys Ser Asp Arg His Arg Trp Cys Arg
            20                  25                  30

Trp Arg Leu
        35

<210> SEQ ID NO 114
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gly Ser Gln Ile Tyr Thr Ser Arg Glu Cys Asn Gly Ser Ser Glu Cys
1               5                   10                  15

Tyr Ser His Cys Glu Gly Ile Thr Gly Arg Arg Ser Gly Arg Cys Ile
            20                  25                  30

Asn Arg Arg Cys Tyr Cys Tyr Arg
        35                  40

<210> SEQ ID NO 115
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gly Ser Gly Cys Leu Glu Phe Trp Trp Arg Cys Asn Pro Asn Asp Asp
1               5                   10                  15

Arg Cys Cys Arg Pro Arg Leu Arg Cys Ser Arg Leu Phe Arg Leu Cys
            20                  25                  30

Asn Phe Ser Phe Gly
        35

<210> SEQ ID NO 116
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gly Ser Asp Cys Val Arg Phe Trp Gly Arg Cys Ser Gln Thr Ser Asp
1               5                   10                  15

Cys Cys Pro His Leu Ala Cys Arg Ser Arg Trp Pro Arg Asn Ile Cys
            20                  25                  30

Val Trp Asp Gly Ser Val Gly
        35

<210> SEQ ID NO 117
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Ser Gly Cys Phe Gly Tyr Arg Cys Asp Tyr Tyr Arg Gly Cys Cys
1               5                   10                  15

```
Ser Gly Tyr Val Cys Ser Pro Thr Trp Arg Trp Cys Val Arg Pro Gly
            20                  25                  30

Pro Gly Arg
        35
```

<210> SEQ ID NO 118
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gly Ser Met Asn Ala Arg Phe Ile Leu Leu Val Leu Thr Thr Met
1               5                   10                  15

Met Leu Leu Pro Asp Thr Arg Gly Ala Glu Val Ile Arg Cys Ser Gly
            20                  25                  30

Ser Arg Gln Cys Tyr Gly Pro Cys Arg Gln Thr Gly Cys Thr Asn
        35                  40                  45

Ser Arg Cys Met Asn Arg Val Cys Arg Cys Tyr Gly Cys Gly
    50                  55                  60
```

<210> SEQ ID NO 119
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gly Ser Met Asn Ala Arg Leu Ile Tyr Leu Leu Val Val Thr Thr
1               5                   10                  15

Met Thr Leu Met Phe Asp Thr Ala Gln Ala Val Asp Ile Met Cys Ser
            20                  25                  30

Gly Pro Arg Gln Cys Tyr Gly Pro Cys Arg Arg Glu Thr Gly Cys Pro
        35                  40                  45

Asn Ala Arg Cys Met Asn Arg Arg Cys Arg Cys Tyr Gly Cys Val
    50                  55                  60
```

<210> SEQ ID NO 120
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gly Ser Met Asn Ala Arg Leu Ile Tyr Leu Leu Val Val Thr Thr
1               5                   10                  15

Met Met Leu Thr Phe Asp Thr Gln Ala Gly Asp Ile Arg Cys Ser
            20                  25                  30

Gly Thr Arg Gln Cys Trp Gly Pro Cys Arg Arg Gln Thr Thr Cys Thr
        35                  40                  45

Asn Ser Arg Cys Met Asn Gly Arg Cys Arg Cys Tyr Gly Cys Val Gly
    50                  55                  60
```

<210> SEQ ID NO 121
<211> LENGTH: 63

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gly Ser Met Asn Thr Arg Phe Ile Phe Leu Leu Val Val Thr Asn
1               5                   10                  15

Thr Met Met Leu Phe Asp Thr Arg Pro Val Glu Gly Ile Ser Cys Thr
            20                  25                  30

Gly Ser Arg Gln Cys Tyr Asp Pro Cys Arg Arg Thr Gly Cys Pro
        35                  40                  45

Asn Ala Arg Cys Met Asn Arg Ser Cys Arg Cys Tyr Gly Cys Gly
    50                  55                  60

<210> SEQ ID NO 122
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Ser Gly Val Pro Ile Asn Val Arg Cys Ser Gly Ser Arg Asp Cys
1               5                   10                  15

Leu Glu Pro Cys Arg Arg Ala Gly Met Arg Phe Gly Arg Cys Ile Asn
            20                  25                  30

Arg Arg Cys His Cys Thr Pro Arg
        35                  40

<210> SEQ ID NO 123
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Ser Gly Val Pro Ile Asn Val Arg Cys Thr Gly Ser Pro Gln Cys
1               5                   10                  15

Leu Arg Pro Cys Arg Asp Ala Gly Met Arg Phe Gly Arg Cys Ile Asn
            20                  25                  30

Gly Arg Cys His Cys Thr Pro Arg
        35                  40

<210> SEQ ID NO 124
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Ser Gly Val Ile Ile Asn Val Arg Cys Arg Ile Ser Arg Gln Cys
1               5                   10                  15

Leu Glu Pro Cys Arg Arg Ala Gly Met Arg Phe Gly Arg Cys Met Asn
            20                  25                  30

Gly Arg Cys His Cys Thr Pro Arg
        35                  40
```

<210> SEQ ID NO 125
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gly Ser Gly Val Pro Ile Asn Val Arg Cys Arg Gly Ser Pro Gln Cys
1               5                   10                  15

Ile Gln Pro Cys Arg Asp Ala Gly Met Arg Phe Gly Arg Cys Met Asn
            20                  25                  30

Gly Arg Cys His Cys Thr Pro Gln
        35                  40

<210> SEQ ID NO 126
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Ser Gly Val Glu Ile Asn Val Arg Cys Thr Gly Ser His Gln Cys
1               5                   10                  15

Ile Arg Pro Cys Arg Asp Ala Gly Met Arg Phe Gly Arg Cys Ile Asn
            20                  25                  30

Arg Arg Cys His Cys Thr Pro Arg
        35                  40

<210> SEQ ID NO 127
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Ser Gly Val Glu Ile Asn Val Arg Cys Ser Gly Ser Pro Gln Cys
1               5                   10                  15

Leu Arg Pro Cys Arg Asp Ala Gly Met Arg Phe Gly Arg Cys Met Asn
            20                  25                  30

Arg Arg Cys His Cys Thr Pro Arg
        35                  40

<210> SEQ ID NO 128
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Ser Gly Val Pro Thr Asp Val Arg Cys Arg Gly Ser Pro Gln Cys
1               5                   10                  15

Ile Gln Pro Cys Arg Asp Ala Gly Met Arg Phe Gly Arg Cys Met Asn
            20                  25                  30

Gly Arg Cys His Cys Thr Pro Arg

```
                35                  40

<210> SEQ ID NO 129
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Ser Gly Val Pro Ile Asn Val Ser Cys Thr Gly Ser Pro Gln Cys
1               5                   10                  15

Ile Arg Pro Cys Arg Asp Ala Gly Met Arg Phe Gly Arg Cys Met Asn
            20                  25                  30

Arg Arg Cys His Cys Thr Pro Arg
        35                  40

<210> SEQ ID NO 130
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Ser Gly Val Pro Ile Asn Val Pro Cys Thr Gly Ser Pro Gln Cys
1               5                   10                  15

Ile Arg Pro Cys Arg Asp Ala Gly Met Arg Phe Gly Arg Cys Met Asn
            20                  25                  30

Arg Arg Cys His Cys Thr Pro Arg
        35                  40

<210> SEQ ID NO 131
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Ser Val Gly Ile Asn Val Arg Cys Arg His Ser Gly Gln Cys Leu
1               5                   10                  15

Arg Pro Cys Arg Asp Ala Gly Met Arg Phe Gly Arg Cys Ile Asn Gly
            20                  25                  30

Arg Cys Asp Cys Thr Pro Arg
        35

<210> SEQ ID NO 132
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Ser Val Gly Ile Asn Val Arg Cys Arg His Ser Gly Gln Cys Leu
1               5                   10                  15

Arg Pro Cys Arg Asp Ala Gly Met Arg Phe Gly Arg Cys Met Asn Gly
            20                  25                  30
```

Arg Cys Asp Cys Thr Pro Arg
         35

<210> SEQ ID NO 133
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Ser Val Gly Ile Pro Val Ser Cys Arg His Ser Gly Gln Cys Ile
1               5                   10                  15

Arg Pro Cys Arg Asp Ala Gly Met Arg Phe Gly Arg Cys Met Asn Arg
            20                  25                  30

Arg Cys Asp Cys Thr Pro Arg
         35

<210> SEQ ID NO 134
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Ser Arg Arg Gly Cys Phe Arg Glu Gly His Ser Cys Pro Arg Thr
1               5                   10                  15

Ala Pro Cys Cys Arg Pro Leu Val Cys Arg Gly Pro Ser Pro Asn Thr
            20                  25                  30

Arg Arg Cys Thr Arg Pro
         35

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gly Ser Ser Phe Cys Ile Pro Phe Arg Pro Cys Arg Ser Asp Glu Asn
1               5                   10                  15

Cys Cys Arg Arg Phe Arg Cys Arg Thr Thr Gly Ile Val Arg Leu Cys
            20                  25                  30

Arg Trp

<210> SEQ ID NO 136
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gly Ser Leu Arg Gly Cys Leu Pro Arg Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Trp Ala Ser Arg Cys Leu
        35

<210> SEQ ID NO 137
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Ser Gly Asn Tyr Cys Leu Arg Gly Arg Cys Leu Pro Gly Gly Arg
1               5                   10                  15

Arg Cys Cys Asn Gly Arg Pro Cys Glu Cys Phe Ala Arg Ile Cys Ser
            20                  25                  30

Cys Arg Pro Arg
        35

<210> SEQ ID NO 138
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gly Ser Thr Val Arg Cys Gly Gly Cys Asn Arg Arg Cys Cys Pro Gly
1               5                   10                  15

Gly Cys Arg Ser Gly Arg Cys Ile Asn Gly Arg Cys Gln Cys Tyr
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gly Ser Gly Cys Met Arg Glu Tyr Cys Ala Gly Gln Cys Arg Gly Arg
1               5                   10                  15

Val Ser Gln Asp Tyr Cys Leu Arg His Cys Arg Cys Ile Pro Arg
            20                  25                  30

<210> SEQ ID NO 140
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gly Ser Ala Cys Leu Gly Phe Gly Glu Arg Cys Asn Pro Ser Asn Asp
1               5                   10                  15

Arg Cys Cys Arg Ser Ser Ser Leu Val Cys Ser Gln Arg His Arg Trp
            20                  25                  30

Cys Arg Tyr Gly
        35

<210> SEQ ID NO 141

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Arg Asp Ser Arg Cys Leu Gly
        35

<210> SEQ ID NO 142
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gly Ser Arg Gly Gly Cys Leu Pro Arg Asn Arg Phe Cys Asn Pro Ser
1               5                   10                  15

Ser Gly Pro Arg Cys Cys Ser Gly Leu Thr Cys Arg Glu Leu Asn Ile
            20                  25                  30

Trp Ala Ser Arg Cys Leu
        35

<210> SEQ ID NO 143
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Ser Gln Arg Ser Cys Ala Arg Pro Gly Asp Met Cys Met Gly Ile
1               5                   10                  15

Arg Cys Cys Asp Gly Gln Cys Gly Cys Asn Arg Gly Thr Gly Arg Cys
            20                  25                  30

Phe Cys Arg
        35

<210> SEQ ID NO 144
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Ser Ala Arg Gly Cys Ala Asp Ala Tyr Arg Ser Cys Asn His Pro
1               5                   10                  15

Arg Thr Cys Cys Asp Gly Tyr Asn Gly Tyr Arg Arg Ala Cys Ile Cys
            20                  25                  30

Ser Gly Ser Asn Cys Arg Cys Arg Arg Ser
        35                  40
```

```
<210> SEQ ID NO 145
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145
```

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Trp Asp Ser Arg Cys Leu Gly
        35

```
<210> SEQ ID NO 146
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Tyr Asp Ser Arg Cys Leu Gly
        35

```
<210> SEQ ID NO 147
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147
```

Gly Ser Arg Gly Gly Cys Leu Pro His Asn Arg Phe Cys Asn Ala Leu
1               5                   10                  15

Ser Gly Pro Arg Cys Cys Ser Arg Leu Arg Cys Arg Glu Leu Ser Ile
            20                  25                  30

Trp Asp Ser Arg Cys Leu Gly
        35

```
<210> SEQ ID NO 148
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148
```

Gly Ser Arg Gly Gly Cys Leu Pro His Asn Arg Phe Cys Asn Ala Leu
1               5                   10                  15

Thr Gly Pro Arg Cys Cys Ser Arg Leu Arg Cys Arg Glu Leu Ser Ile
            20                  25                  30

Trp Asp Ser Ile Cys Leu Gly
        35

<210> SEQ ID NO 149
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gly Ser Ser Cys Ala Asp Ala Tyr Lys Ser Cys Asp Ser Leu Arg Cys
1               5                   10                  15

Cys Asn Asn Arg Thr Cys Met Cys Ser Met Ile Gly Thr Asn Cys Thr
            20                  25                  30

Cys Arg Arg Arg
        35

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gly Ser Glu Arg Arg Cys Leu Pro Ala Gly Arg Thr Cys Val Arg Gly
1               5                   10                  15

Pro Met Arg Val Pro Cys Cys Gly Ser Cys Ser Gln Asn Arg Cys Thr
            20                  25                  30

<210> SEQ ID NO 151
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gly Ser Leu Cys Ser Arg Glu Gly Glu Phe Cys Tyr Arg Leu Arg Arg
1               5                   10                  15

Cys Cys Ala Gly Phe Tyr Cys Arg Ala Phe Val Leu His Cys Tyr Arg
            20                  25                  30

Asn

<210> SEQ ID NO 152
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ser Ala Cys Gly Ser Cys Arg Arg Cys Arg Gly Ser Gly Arg
1               5                   10                  15

Cys Ile Asn Gly Arg Cys Arg Cys Tyr
            20                  25

<210> SEQ ID NO 153
<211> LENGTH: 25
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 153

Gly Ser Ala Cys Gly Ser Cys Arg Arg Cys Arg Gly Pro Gly Arg
1               5                   10                  15

Cys Ile Asn Gly Arg Cys Arg Cys Tyr
            20                  25

<210> SEQ ID NO 154
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Ser Ala Cys Gln Gly Tyr Met Arg Arg Cys Gly Arg Asp Arg Pro
1               5                   10                  15

Pro Cys Cys Arg Arg Leu Glu Cys Ser Arg Thr Trp Arg Trp Cys Val
            20                  25                  30

Trp Asn

<210> SEQ ID NO 155
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Ser Gly Arg Tyr Cys Gln Arg Trp Met Trp Thr Cys Asp Ser Arg
1               5                   10                  15

Arg Ala Cys Cys Glu Gly Leu Arg Cys Arg Leu Trp Cys Arg Arg Ile
            20                  25                  30

<210> SEQ ID NO 156
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gly Ser Asn Ala Arg Cys Arg Gly Ser Pro Glu Cys Leu Pro Arg Cys
1               5                   10                  15

Arg Glu Ala Ile Gly Arg Ala Ala Gly Arg Cys Met Asn Gly Arg Cys
            20                  25                  30

Arg Cys Tyr Pro
        35

<210> SEQ ID NO 157
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gly Ser Asn Val Arg Cys Arg Gly Ser Arg Glu Cys Leu Pro Ala Cys

Arg Ala Ala Val Gly Arg Ala Ala Gly Arg Cys Met Asn Gly Arg Cys
            20                  25                  30

Arg Cys Tyr Pro
        35

<210> SEQ ID NO 158
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gly Ser Asn Val Arg Cys Arg Gly Ser Pro Glu Cys Leu Pro Arg Cys
1               5                   10                  15

Arg Glu Ala Ile Gly Arg Ser Ala Gly Arg Cys Met Asn Gly Arg Cys
            20                  25                  30

Arg Cys Tyr Pro
        35

<210> SEQ ID NO 159
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gly Ser Asn Ala Arg Cys Arg Gly Ser Pro Glu Cys Leu Pro Arg Cys
1               5                   10                  15

Arg Gln Ala Ile Gly Arg Ala Ala Gly Arg Cys Met Asn Gly Arg Cys
            20                  25                  30

Arg Cys Tyr Pro
        35

<210> SEQ ID NO 160
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gly Ser Arg Gly Tyr Cys Ala Glu Arg Gly Ile Arg Cys His Asn Ile
1               5                   10                  15

His Cys Cys Ser Gly Leu Thr Cys Arg Cys Arg Gly Ser Ser Cys Val
            20                  25                  30

Cys Arg Arg
        35

<210> SEQ ID NO 161
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

```
Gly Ser Glu Arg Gly Cys Arg Leu Thr Phe Trp Arg Cys Arg Asn Arg
1               5                  10                 15

Arg Glu Cys Cys Gly Trp Asn Ala Cys Ala Leu Gly Ile Cys Met Pro
            20                 25                 30

Arg
```

<210> SEQ ID NO 162
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Gly Ser Arg Arg Arg Cys Ile Ala Arg Asp Tyr Gly Arg Cys Arg Trp
1               5                  10                 15

Gly Gly Thr Pro Cys Cys Arg Gly Arg Gly Cys Ile Cys Ser Ile Met
            20                 25                 30

Gly Thr Asn Cys Glu Cys Arg Pro Arg
        35                 40
```

<210> SEQ ID NO 163
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Gly Ser Gly Cys Arg Leu Thr Phe Trp Arg Cys Arg Asn Arg Arg Glu
1               5                  10                 15

Cys Cys Gly Trp Asn Ala Cys Ala Leu Gly Ile Cys Met Pro Arg
            20                 25                 30
```

<210> SEQ ID NO 164
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Gly Ser Ala Cys Arg Gly Leu Phe Val Thr Cys Thr Pro Gly Arg Asp
1               5                  10                 15

Glu Cys Cys Pro Asn His Val Cys Ser Ser Arg His Arg Trp Cys Arg
            20                 25                 30

Tyr Arg
```

<210> SEQ ID NO 165
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Gly Ser Ile Ala Cys Ala Pro Arg Gly Leu Leu Cys Phe Arg Asp Arg
1               5                  10                 15

Glu Cys Cys Arg Gly Leu Thr Cys Arg Gly Arg Phe Val Asn Thr Trp
```

-continued

```
                 20                  25                  30

Pro Thr Phe Cys Leu Val
            35

<210> SEQ ID NO 166
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gly Ser Ala Cys Ala Gly Leu Tyr Arg Arg Cys Gly Arg Gly Val Asn
1               5                   10                  15

Thr Cys Cys Glu Asn Arg Pro Cys Arg Cys Asp Leu Ala Met Gly Asn
            20                  25                  30

Cys Ile Cys Arg Arg Arg
            35

<210> SEQ ID NO 167
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gly Ser Phe Thr Cys Ala Ile Ser Cys Asp Ile Arg Val Asn Gly Arg
1               5                   10                  15

Pro Cys Arg Gly Ser Gly Glu Arg Arg Cys Ser Gly Gly Trp Ser Cys
            20                  25                  30

Arg Phe Asn Val Cys Val Arg Val
            35                  40

<210> SEQ ID NO 168
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gly Ser Gly Phe Cys Ala Gln Arg Gly Ile Arg Cys His Asp Ile His
1               5                   10                  15

Cys Cys Thr Asn Leu Arg Cys Val Arg Glu Gly Ser Asn Arg Val Cys
            20                  25                  30

Arg Arg Ala
        35

<210> SEQ ID NO 169
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gly Ser Cys Ala Arg Arg Arg Asn Trp Cys Gly Arg Asn Glu Asp Cys
1               5                   10                  15
```

Cys Cys Pro Met Arg Cys Ile Tyr Ala Trp Tyr Asn Gln Gln Gly Ser
            20                  25                  30

Cys Gln Ser Thr Ile Thr Gly Leu Phe Arg Arg Cys
        35                  40

<210> SEQ ID NO 170
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gly Ser Tyr Cys Gln Arg Trp Met Trp Thr Cys Asp Ser Ala Arg Arg
1               5                   10                  15

Cys Cys Glu Gly Leu Val Cys Arg Leu Trp Cys Arg Arg Ile
            20                  25                  30

<210> SEQ ID NO 171
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Thr Ile
            20                  25                  30

Trp Asn Thr Arg Cys Leu Glu
        35

<210> SEQ ID NO 172
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gly Ser Asn Val Arg Cys Thr Gly Ser Arg Gln Cys Leu Pro Ala Cys
1               5                   10                  15

Arg Ala Ala Val Gly Arg Ala Ala Gly Arg Cys Met Asn Gly Arg Cys
            20                  25                  30

Arg Cys Tyr Thr
        35

<210> SEQ ID NO 173
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gly Ser Gln Arg Ser Cys Ala Arg Pro Gly Glu Met Cys Met Arg Ile
1               5                   10                  15

Arg Cys Cys Asp Gly Gln Cys Gly Cys Asn Arg Gly Thr Gly Arg Cys
            20                  25                  30

```
Phe Cys Arg
        35

<210> SEQ ID NO 174
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Ser Gly Cys Ile Pro Arg His Arg Arg Cys Thr Trp Ser Gly Pro
1               5                   10                  15

Arg Cys Cys Asn Asn Ile Ser Cys His Cys Asn Ile Ser Gly Thr Leu
            20                  25                  30

Cys Arg Cys Arg Pro Gly
        35

<210> SEQ ID NO 175
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gly Ser Asn Tyr Cys Val Ala Arg Arg Cys Arg Pro Gly Gly Arg Gln
1               5                   10                  15

Cys Cys Ser Gly Arg Pro Cys Ala Cys Val Gly Arg Val Cys Arg Cys
            20                  25                  30

Pro Arg Asp
        35

<210> SEQ ID NO 176
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Ser Glu Arg Gly Cys Ser Gly Ala Tyr Arg Arg Cys Ser Ser Ser
1               5                   10                  15

Gln Arg Cys Cys Glu Gly Arg Pro Cys Val Cys Ser Ala Ile Asn Ser
            20                  25                  30

Asn Cys Arg Cys Arg Arg Thr
        35

<210> SEQ ID NO 177
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Ser Gln Arg Ser Cys Ala Arg Pro Gly Glu Met Cys Met Gly Ile
1               5                   10                  15

Arg Cys Cys Asp Gly Gln Cys Gly Cys Asn Arg Gly Thr Gly Arg Cys
```

```
                    20                  25                  30

Phe Cys Arg
        35

<210> SEQ ID NO 178
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Ser Arg Arg Gly Cys Phe Arg Glu Gly Arg Trp Cys Pro Arg Ser
1               5                  10                  15

Ala Pro Cys Cys Ala Pro Leu Arg Cys Arg Gly Pro Ser Ile Arg Gln
            20                  25                  30

Gln Arg Cys Val Arg Glu
        35

<210> SEQ ID NO 179
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Ser Thr Val Arg Cys Gly Gly Cys Asn Arg Arg Cys Cys Ala Gly
1               5                  10                  15

Gly Cys Arg Ser Gly Arg Cys Ile Asn Gly Arg Cys Gln Cys Tyr Gly
            20                  25                  30

Arg

<210> SEQ ID NO 180
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Ser Glu Arg Arg Cys Glu Pro Ser Gly Arg Pro Cys Arg Pro Leu
1               5                  10                  15

Met Arg Ile Pro Cys Cys Gly Ser Cys Val Arg Gly Arg Cys Ala
            20                  25                  30

<210> SEQ ID NO 181
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Ser Arg Gly Gly Cys Leu Pro Arg Asn Arg Phe Cys Asn Pro Ser
1               5                  10                  15

Ser Gly Pro Arg Cys Cys Ser Gly Leu Thr Cys Arg Glu Leu Asn Ile
            20                  25                  30

Trp Ala Asn Arg Cys Leu
```

35

<210> SEQ ID NO 182
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Ser Cys Ala Arg Arg Arg Asn Trp Cys Gly Arg Asn Glu Asp Cys
1               5                   10                  15

Cys Cys Pro Met Arg Cys Ile Tyr Ala Trp Tyr Asn Gln Gln Gly Ser
            20                  25                  30

Cys Gln Thr Thr Ile Thr Gly Leu Phe Arg Arg Cys
        35                  40

<210> SEQ ID NO 183
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gly Ser Val Arg Ile Pro Val Ser Cys Arg His Ser Gly Gln Cys Leu
1               5                   10                  15

Arg Pro Cys Arg Asp Ala Gly Met Arg Thr Gly Arg Cys Met Asn Gly
            20                  25                  30

Arg Cys Asp Cys Thr Pro Arg
        35

<210> SEQ ID NO 184
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Ser Gln Lys Ile Leu Ser Asn Arg Cys Asn Ser Ser Glu Cys
1               5                   10                  15

Ile Pro His Cys Ile Arg Ile Phe Gly Thr Arg Ala Ala Lys Cys Ile
            20                  25                  30

Asn Arg Lys Cys Tyr Cys Tyr Pro
        35                  40

<210> SEQ ID NO 185
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Ser Ala Val Cys Asn Leu Lys Arg Cys Gln Leu Ser Cys Arg Ser
1               5                   10                  15

Leu Gly Leu Leu Gly Lys Cys Ile Gly Asp Lys Cys Glu Cys Val Lys
            20                  25                  30

His Gly

<210> SEQ ID NO 186
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gly Ser Ile Ser Ile Gly Ile Arg Cys Ser Pro Ser Ile Asp Leu Cys
1               5                   10                  15

Glu Gly Gln Cys Arg Ile Arg Arg Tyr Phe Thr Gly Tyr Cys Ser Gly
            20                  25                  30

Asp Thr Cys His Cys Ser Gly
        35

<210> SEQ ID NO 187
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gly Ser Gly Asp Cys Leu Pro His Leu Arg Arg Cys Arg Glu Asn Asn
1               5                   10                  15

Asp Cys Cys Ser Arg Arg Cys Arg Arg Gly Ala Asn Pro Glu Arg
            20                  25                  30

Arg Cys Arg
        35

<210> SEQ ID NO 188
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Ser Ser Cys Glu Pro Gly Arg Thr Phe Arg Asp Arg Cys Asn Thr
1               5                   10                  15

Cys Lys Cys Gly Ala Asp Gly Arg Ser Ala Ala Cys Thr Leu Arg Ala
            20                  25                  30

Cys Pro Asn Gln
        35

<210> SEQ ID NO 189
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Ser Gly Asp Cys Leu Pro His Leu Lys Arg Cys Lys Ala Asp Asn
1               5                   10                  15

Asp Cys Cys Gly Lys Lys Cys Lys Arg Arg Gly Thr Asn Ala Glu Lys
            20                  25                  30

```
Arg Cys Arg
        35

<210> SEQ ID NO 190
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Thr Asn Pro Glu Lys
            20                  25                  30

Arg Cys Arg
        35

<210> SEQ ID NO 191
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Ser Lys Asp Cys Leu Lys Lys Leu Lys Leu Cys Lys Glu Asn Lys
1               5                   10                  15

Asp Cys Cys Ser Lys Ser Cys Lys Arg Arg Gly Thr Asn Ile Glu Lys
            20                  25                  30

Arg Cys Arg
        35

<210> SEQ ID NO 192
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Ala Asn Pro Glu Lys
            20                  25                  30

Arg Cys Arg
        35

<210> SEQ ID NO 193
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Ser Val Phe Ile Asn Val Lys Cys Arg Gly Ser Pro Glu Cys Leu
1               5                   10                  15

Pro Lys Cys Lys Glu Ala Ile Gly Lys Ser Ala Gly Lys Cys Met Asn
            20                  25                  30
```

```
Gly Lys Cys Lys Cys Tyr Pro
        35

<210> SEQ ID NO 194
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Ser Val Phe Ile Asn Ala Lys Cys Arg Gly Ser Pro Glu Cys Leu
1               5                   10                  15

Pro Lys Cys Lys Glu Ala Ile Gly Lys Ala Ala Gly Lys Cys Met Asn
            20                  25                  30

Gly Lys Cys Lys Cys Tyr Pro
        35

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gly Ser Val Ile Ile Asn Val Lys Cys Lys Ile Ser Arg Gln Cys Leu
1               5                   10                  15

Glu Pro Cys Lys Lys Ala Gly Met Arg Phe Gly Lys Cys Met Asn Gly
            20                  25                  30

Lys Cys His Cys Thr Pro
        35

<210> SEQ ID NO 196
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Ser Val Pro Thr Asp Val Lys Cys Arg Gly Ser Pro Gln Cys Ile
1               5                   10                  15

Gln Pro Cys Lys Asp Ala Gly Met Arg Phe Gly Lys Cys Met Asn Gly
            20                  25                  30

Lys Cys His Cys Thr Pro
        35

<210> SEQ ID NO 197
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gly Ser Val Arg Ile Pro Val Ser Cys Lys His Ser Gly Gln Cys Leu
1               5                   10                  15

Lys Pro Cys Lys Asp Ala Gly Met Arg Phe Gly Lys Cys Met Asn Gly
```

```
                20                  25                  30

Lys Cys Asp Cys Thr Pro
            35

<210> SEQ ID NO 198
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Ser Val Arg Ile Pro Val Ser Cys Arg His Ser Gly Gln Cys Leu
1               5                  10                  15

Arg Pro Cys Arg Asp Ala Gly Met Arg Phe Gly Arg Cys Met Asn Gly
            20                  25                  30

Arg Cys Asp Cys Thr Pro
            35

<210> SEQ ID NO 199
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gly Ser Thr Asn Val Ser Cys Thr Thr Ser Lys Glu Cys Trp Ser Val
1               5                  10                  15

Cys Gln Arg Leu His Asn Thr Ser Arg Gly Lys Cys Met Asn Lys Lys
            20                  25                  30

Cys Arg Cys
        35

<210> SEQ ID NO 200
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Ser Asn Val Lys Cys Thr Gly Ser Lys Gln Cys Leu Pro Ala Cys
1               5                  10                  15

Lys Ala Ala Val Gly Lys Ala Ala Gly Lys Cys Met Asn Gly Lys Cys
            20                  25                  30

Lys Cys

<210> SEQ ID NO 201
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Ser Gly Val Pro Ile Asn Val Arg Cys Arg Gly Ser Arg Asp Cys
1               5                  10                  15

Leu Asp Pro Cys Arg Gly Ala Gly Glu Arg His Gly Arg Cys Gly Asn
```

Ser Arg Cys His Cys Thr Pro
        35

<210> SEQ ID NO 202
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Ser Val Arg Ile Pro Val Ser Cys Arg His Ser Gly Gln Cys Leu
1               5                   10                  15

Arg Pro Cys Arg Asp Ala Gly Glu Arg His Gly Arg Cys Gly Gly Gly
            20                  25                  30

Arg Cys Asp Cys Thr Pro Arg
        35

<210> SEQ ID NO 203
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Ser Gln Val Gln Thr Asn Val Arg Cys Gln Gly Gly Ser Cys Gly
1               5                   10                  15

Ser Val Cys Arg Arg Glu Gly Gly Ala Gly Gly Gly Cys Gly Asn
            20                  25                  30

Gly Arg Cys Gly Cys Tyr Arg Asn
        35                  40

<210> SEQ ID NO 204
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Ser Ile Lys Cys Ser Glu Ser Tyr Gln Cys Phe Pro Val Cys Lys
1               5                   10                  15

Ser Arg Phe Gly Lys Thr Asn Gly Arg Cys Val Asn Gly Phe Cys Asp
            20                  25                  30

Cys Phe

<210> SEQ ID NO 205
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Ser Val Lys Cys Ser Ser Pro Gln Gln Cys Leu Lys Pro Cys Lys
1               5                   10                  15

Ala Ala Phe Gly Ile Ser Ala Gly Gly Lys Cys Ile Asn Gly Lys Cys

```
                    20                  25                  30

Lys Cys Tyr
        35

<210> SEQ ID NO 206
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Ser Val Ser Cys Ser Ala Ser Ser Gln Cys Trp Pro Val Cys Lys
1               5                   10                  15

Lys Leu Phe Gly Thr Tyr Arg Gly Lys Cys Met Asn Ser Lys Cys Arg
            20                  25                  30

Cys Tyr

<210> SEQ ID NO 207
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gly Ser Glu Ser Cys Thr Ala Ser Asn Gln Cys Trp Ser Ile Cys Lys
1               5                   10                  15

Arg Leu His Asn Thr Asn Arg Gly Lys Cys Met Asn Lys Lys Cys Arg
            20                  25                  30

Cys Tyr

<210> SEQ ID NO 208
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Ser Val Ser Cys Thr Thr Ser Lys Glu Cys Trp Ser Val Cys Glu
1               5                   10                  15

Lys Leu Tyr Asn Thr Ser Arg Gly Lys Cys Met Asn Lys Lys Cys Arg
            20                  25                  30

Cys Tyr

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gly Ser Met Arg Cys Lys Ser Ser Lys Glu Cys Leu Val Lys Cys Lys
1               5                   10                  15

Gln Ala Thr Gly Arg Pro Asn Gly Lys Cys Met Asn Arg Lys Cys Lys
            20                  25                  30
```

Cys Tyr

<210> SEQ ID NO 210
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gly Ser Ile Lys Cys Thr Leu Ser Lys Asp Cys Tyr Ser Pro Cys Lys
1               5                   10                  15

Lys Glu Thr Gly Cys Pro Arg Ala Lys Cys Ile Asn Arg Asn Cys Lys
            20                  25                  30

Cys Tyr

<210> SEQ ID NO 211
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gly Ser Ile Arg Cys Ser Gly Ser Arg Asp Cys Tyr Ser Pro Cys Met
1               5                   10                  15

Lys Gln Thr Gly Cys Pro Asn Ala Lys Cys Ile Asn Lys Ser Cys Lys
            20                  25                  30

Cys Tyr

<210> SEQ ID NO 212
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gly Ser Ile Arg Cys Ser Gly Thr Arg Glu Cys Tyr Ala Pro Cys Gln
1               5                   10                  15

Lys Leu Thr Gly Cys Leu Asn Ala Lys Cys Met Asn Lys Ala Cys Lys
            20                  25                  30

Cys Tyr

<210> SEQ ID NO 213
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Ser Ile Ser Cys Thr Asn Pro Lys Gln Cys Tyr Pro His Cys Lys
1               5                   10                  15

Lys Glu Thr Gly Tyr Pro Asn Ala Lys Cys Met Asn Arg Lys Cys Lys
            20                  25                  30

Cys Phe

```
<210> SEQ ID NO 214
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Ser Ala Ser Cys Arg Thr Pro Lys Asp Cys Ala Asp Pro Cys Arg
1               5                   10                  15

Lys Glu Thr Gly Cys Pro Tyr Gly Lys Cys Met Asn Arg Lys Cys Lys
            20                  25                  30

Cys Asn

<210> SEQ ID NO 215
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gly Ser Thr Ser Cys Ile Ser Pro Lys Gln Cys Thr Glu Pro Cys Arg
1               5                   10                  15

Ala Lys Gly Cys Lys His Gly Lys Cys Met Asn Arg Lys Cys His Cys
            20                  25                  30

Met

<210> SEQ ID NO 216
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gly Ser Lys Glu Cys Thr Gly Pro Gln His Cys Thr Asn Phe Cys Arg
1               5                   10                  15

Lys Asn Lys Cys Thr His Gly Lys Cys Met Asn Arg Lys Cys Lys Cys
            20                  25                  30

Phe

<210> SEQ ID NO 217
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gly Ser Ile Lys Cys Arg Thr Pro Lys Asp Cys Ala Asp Pro Cys Arg
1               5                   10                  15

Lys Gln Thr Gly Cys Pro His Ala Lys Cys Met Asn Lys Thr Cys Arg
            20                  25                  30

Cys His

<210> SEQ ID NO 218
<211> LENGTH: 34
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 218

Gly Ser Val Lys Cys Thr Thr Ser Lys Glu Cys Trp Pro Pro Cys Lys
1               5                   10                  15

Ala Ala Thr Gly Lys Ala Ala Gly Lys Cys Met Asn Lys Lys Cys Lys
            20                  25                  30

Cys Gln

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gly Ser Leu Glu Cys Gly Ala Ser Arg Glu Cys Tyr Asp Pro Cys Phe
1               5                   10                  15

Lys Ala Phe Gly Arg Ala His Gly Lys Cys Met Asn Asn Lys Cys Arg
            20                  25                  30

Cys Tyr

<210> SEQ ID NO 220
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gly Ser Glu Lys Cys Phe Ala Thr Ser Gln Cys Trp Thr Pro Cys Lys
1               5                   10                  15

Lys Ala Ile Gly Ser Leu Gln Ser Lys Cys Met Asn Gly Lys Cys Lys
            20                  25                  30

Cys Tyr

<210> SEQ ID NO 221
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gly Ser Val Arg Cys Tyr Ala Ser Arg Glu Cys Trp Glu Pro Cys Arg
1               5                   10                  15

Arg Val Thr Gly Ser Ala Gln Ala Lys Cys Gln Asn Asn Gln Cys Arg
            20                  25                  30

Cys Tyr

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 222

Gly Ser Val Lys Cys Ser Ala Ser Arg Glu Cys Trp Val Ala Cys Lys
1               5                   10                  15

Lys Val Thr Gly Ser Gly Gln Gly Lys Cys Gln Asn Asn Gln Cys Arg
            20                  25                  30

Cys Tyr

<210> SEQ ID NO 223
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Ser Val Lys Cys Ile Ser Ser Gln Glu Cys Trp Ile Ala Cys Lys
1               5                   10                  15

Lys Val Thr Gly Arg Phe Glu Gly Lys Cys Gln Asn Arg Gln Cys Arg
            20                  25                  30

Cys Tyr

<210> SEQ ID NO 224
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gly Ser Val Arg Cys Tyr Asp Ser Arg Gln Cys Trp Ile Ala Cys Lys
1               5                   10                  15

Lys Val Thr Gly Ser Thr Gln Gly Lys Cys Gln Asn Lys Gln Cys Arg
            20                  25                  30

Cys Tyr

<210> SEQ ID NO 225
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gly Ser Val Asp Cys Thr Val Ser Lys Glu Cys Trp Ala Pro Cys Lys
1               5                   10                  15

Ala Ala Phe Gly Val Asp Arg Gly Lys Cys Met Gly Lys Lys Cys Lys
            20                  25                  30

Cys Tyr

<210> SEQ ID NO 226
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

-continued

```
Gly Ser Ala Lys Cys Arg Gly Ser Pro Glu Cys Leu Pro Cys Lys
1               5                   10                  15

Glu Ala Ile Gly Lys Ala Ala Gly Lys Cys Met Asn Gly Lys Cys Lys
            20                  25                  30

Cys Tyr

<210> SEQ ID NO 227
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gly Ser Lys Lys Cys Gln Gly Gly Ser Cys Ala Ser Val Cys Arg Arg
1               5                   10                  15

Val Ile Gly Val Ala Ala Gly Lys Cys Ile Asn Gly Arg Cys Val Cys
            20                  25                  30

Tyr

<210> SEQ ID NO 228
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gly Ser Lys Lys Cys Ser Asn Thr Ser Gln Cys Tyr Lys Thr Cys Glu
1               5                   10                  15

Lys Val Val Gly Val Ala Ala Gly Lys Cys Met Asn Gly Lys Cys Ile
            20                  25                  30

Cys Tyr

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gly Ser Val Lys Cys Ser Gly Ser Ser Lys Cys Val Lys Ile Cys Ile
1               5                   10                  15

Asp Arg Tyr Asn Thr Arg Gly Ala Lys Cys Ile Asn Gly Arg Cys Thr
            20                  25                  30

Cys Tyr

<210> SEQ ID NO 230
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gly Ser Asn Arg Cys Asn Asn Ser Ser Glu Cys Ile Pro His Cys Ile
1               5                   10                  15
```

```
Arg Ile Phe Gly Thr Arg Ala Ala Lys Cys Ile Asn Arg Lys Cys Tyr
            20                  25                  30

Cys Tyr

<210> SEQ ID NO 231
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gly Ser Lys Glu Cys Asn Gly Ser Ser Glu Cys Tyr Ser His Cys Glu
1               5                   10                  15

Gly Ile Thr Gly Lys Arg Ser Gly Lys Cys Ile Asn Lys Lys Cys Tyr
            20                  25                  30

Cys Tyr

<210> SEQ ID NO 232
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gly Ser Ala Phe Cys Asn Leu Arg Arg Cys Glu Leu Ser Cys Arg Ser
1               5                   10                  15

Leu Gly Leu Leu Gly Lys Cys Ile Gly Glu Glu Cys Lys Cys Val
            20                  25                  30

<210> SEQ ID NO 233
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gly Ser Ala Val Cys Asn Leu Lys Arg Cys Gln Leu Ser Cys Arg Ser
1               5                   10                  15

Leu Gly Leu Leu Gly Lys Cys Ile Gly Asp Lys Cys Glu Cys Val
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gly Ser Ala Ala Cys Tyr Ser Ser Asp Cys Arg Val Lys Cys Val Ala
1               5                   10                  15

Met Gly Phe Ser Ser Gly Lys Cys Ile Asn Ser Lys Cys Lys Cys Tyr
            20                  25                  30

<210> SEQ ID NO 235
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Ser Ala Ile Cys Ala Thr Asp Ala Asp Cys Ser Arg Lys Cys Pro
1               5                   10                  15

Gly Asn Pro Pro Cys Arg Asn Gly Phe Cys Ala Cys Thr
            20                  25

<210> SEQ ID NO 236
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Ser Thr Glu Cys Gln Ile Lys Asn Asp Cys Gln Arg Tyr Cys Gln
1               5                   10                  15

Ser Val Lys Glu Cys Lys Tyr Gly Lys Cys Tyr Cys Asn
            20                  25

<210> SEQ ID NO 237
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Ser Thr Gln Cys Gln Ser Val Arg Asp Cys Gln Gln Tyr Cys Leu
1               5                   10                  15

Thr Pro Asp Arg Cys Ser Tyr Gly Thr Cys Tyr Cys Lys
            20                  25

<210> SEQ ID NO 238
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gly Ser Val Ser Cys Arg Tyr Gly Ser Asp Cys Ala Glu Pro Cys Lys
1               5                   10                  15

Arg Leu Lys Cys Leu Leu Pro Ser Lys Cys Ile Asn Gly Lys Cys Thr
            20                  25                  30

Cys Tyr

<210> SEQ ID NO 239
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gly Ser Ile Lys Cys Arg Tyr Pro Ala Asp Cys His Ile Met Cys Arg
```

```
1               5                   10                  15
Lys Val Thr Gly Arg Ala Glu Gly Lys Cys Met Asn Gly Lys Cys Thr
            20                  25                  30

Cys Tyr
```

<210> SEQ ID NO 240
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

```
Gly Ser Ile Lys Cys Ser Ser Ser Ser Cys Tyr Glu Pro Cys Arg
1               5                   10                  15

Gly Val Thr Gly Arg Ala His Gly Lys Cys Met Asn Gly Arg Cys Thr
            20                  25                  30

Cys Tyr
```

<210> SEQ ID NO 241
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

```
Gly Ser Val Lys Cys Thr Gly Ser Lys Gln Cys Leu Pro Ala Cys Lys
1               5                   10                  15

Ala Ala Val Gly Lys Ala Ala Gly Lys Cys Met Asn Gly Lys Cys Lys
            20                  25                  30

Cys Tyr
```

<210> SEQ ID NO 242
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Gly Ser Val Ser Cys Lys His Ser Gly Gln Cys Ile Lys Pro Cys Lys
1               5                   10                  15

Asp Ala Gly Met Arg Phe Gly Lys Cys Met Asn Arg Lys Cys Asp Cys
            20                  25                  30

Thr
```

<210> SEQ ID NO 243
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Gly Ser Val Lys Cys Arg Gly Ser Pro Gln Cys Ile Gln Pro Cys Arg
1               5                   10                  15

Asp Ala Gly Met Arg Phe Gly Lys Cys Met Asn Gly Lys Cys His Cys
```

```
                    20                  25                  30

Thr

<210> SEQ ID NO 244
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gly Ser Val Lys Cys Thr Ser Pro Lys Gln Cys Leu Pro Pro Cys Lys
1               5                   10                  15

Ala Gln Phe Gly Ile Arg Ala Gly Ala Lys Cys Met Asn Gly Lys Cys
            20                  25                  30

Lys Cys Tyr
        35

<210> SEQ ID NO 245
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gly Ser Val Lys Cys Thr Ser Pro Lys Gln Cys Ser Lys Pro Cys Lys
1               5                   10                  15

Glu Leu Tyr Gly Ser Ser Ala Gly Ala Lys Cys Met Asn Gly Lys Cys
            20                  25                  30

Lys Cys Tyr
        35

<210> SEQ ID NO 246
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gly Ser Val Lys Cys Thr Ser Pro Lys Gln Cys Leu Pro Pro Cys Lys
1               5                   10                  15

Glu Ile Tyr Gly Arg His Ala Gly Ala Lys Cys Met Asn Gly Lys Cys
            20                  25                  30

His Cys Ser
        35

<210> SEQ ID NO 247
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Ser Val Lys Cys Thr Gly Ser Lys Gln Cys Trp Pro Val Cys Lys
1               5                   10                  15

Gln Met Phe Gly Lys Pro Asn Gly Lys Cys Met Asn Gly Lys Cys Arg
```

-continued

```
                    20                  25                  30

Cys Tyr

<210> SEQ ID NO 248
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gly Ser Val Lys Cys Arg Gly Ser Arg Asp Cys Leu Asp Pro Cys Lys
1               5                   10                  15

Lys Ala Gly Met Arg Phe Gly Lys Cys Ile Asn Ser Lys Cys His Cys
            20                  25                  30

Thr

<210> SEQ ID NO 249
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Ser Val Arg Cys Val Thr Asp Asp Cys Phe Arg Lys Cys Pro
1               5                   10                  15

Gly Asn Pro Ser Cys Lys Arg Gly Phe Cys Ala Cys Lys
            20                  25

<210> SEQ ID NO 250
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gly Ser Val Pro Cys Asn Asn Ser Arg Pro Cys Val Pro Val Cys Ile
1               5                   10                  15

Arg Glu Val Asn Asn Lys Asn Gly Lys Cys Ser Asn Gly Lys Cys Leu
            20                  25                  30

Cys Tyr

<210> SEQ ID NO 251
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gly Ser Val Pro Ile Asn Val Lys Cys Arg Gly Ser Arg Asp Cys Leu
1               5                   10                  15

Asp Pro Cys Lys Lys Ala Gly Met Arg Phe Gly Lys Cys Ile Asn Ser
            20                  25                  30

Lys Cys His Cys Thr Pro
            35
```

<210> SEQ ID NO 252
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Ser Val Gln Thr Asn Val Lys Cys Gln Gly Gly Ser Cys Ala Ser
1               5                   10                  15

Val Cys Arg Arg Glu Ile Gly Val Ala Ala Gly Lys Cys Ile Asn Gly
                20                  25                  30

Lys Cys Val Cys Tyr Arg Asn
        35

<210> SEQ ID NO 253
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gly Ser Ala Glu Ile Ile Arg Cys Ser Gly Thr Arg Glu Cys Tyr Ala
1               5                   10                  15

Pro Cys Gln Lys Leu Thr Gly Cys Leu Asn Ala Lys Cys Met Asn Lys
                20                  25                  30

Ala Cys Lys Cys Tyr Gly Cys Val
        35                  40

<210> SEQ ID NO 254
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gly Ser Arg Pro Thr Asp Ile Lys Cys Ser Ala Ser Tyr Gln Cys Phe
1               5                   10                  15

Pro Val Cys Lys Ser Arg Phe Gly Lys Thr Asn Gly Arg Cys Val Asn
                20                  25                  30

Gly Leu Cys Asp Cys Phe
        35

<210> SEQ ID NO 255
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gly Ser Gln Phe Thr Asp Val Lys Cys Thr Gly Ser Lys Gln Cys Trp
1               5                   10                  15

Pro Val Cys Lys Gln Met Phe Gly Lys Pro Asn Gly Lys Cys Met Asn
                20                  25                  30

Gly Lys Cys Arg Cys Tyr Ser
        35

<210> SEQ ID NO 256
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Ser Val Gly Ile Asn Val Lys Cys Lys His Ser Arg Gln Cys Leu
1               5                   10                  15

Lys Pro Cys Lys Asp Ala Gly Met Arg Phe Gly Lys Cys Thr Asn Gly
            20                  25                  30

Lys Cys His Cys Thr Pro Lys
        35

<210> SEQ ID NO 257
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gly Ser Val Val Ile Gly Gln Arg Cys Tyr Arg Ser Pro Asp Cys Tyr
1               5                   10                  15

Ser Ala Cys Lys Lys Leu Val Gly Lys Ala Thr Gly Lys Cys Thr Asn
            20                  25                  30

Gly Arg Cys Asp Cys
        35

<210> SEQ ID NO 258
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gly Ser Asn Phe Lys Val Glu Gly Ala Cys Ser Lys Pro Cys Arg Lys
1               5                   10                  15

Tyr Cys Ile Asp Lys Gly Ala Arg Asn Gly Lys Cys Ile Asn Gly Arg
            20                  25                  30

Cys His Cys Tyr Tyr
        35

<210> SEQ ID NO 259
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gly Ser Gln Ile Asp Thr Asn Val Lys Cys Ser Gly Ser Ser Lys Cys
1               5                   10                  15

Val Lys Ile Cys Ile Asp Arg Tyr Asn Thr Arg Gly Ala Lys Cys Ile
            20                  25                  30

Asn Gly Arg Cys Thr Cys Tyr Pro 35                  40

<210> SEQ ID NO 260
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gly Ser Gly Val Pro Ile Ser Val Arg Cys Arg Gly Ser Arg Asp Cys
1               5                   10                  15

Leu Glu Pro Cys Arg Arg Ala Gly Thr Arg Phe Gly Arg Cys Ile Asn
            20                  25                  30

Gly Arg Cys His Cys Thr Pro
        35

<210> SEQ ID NO 261
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gly Ser Gly Val Pro Ile Ser Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

Ser Arg Cys His Cys Thr Pro
        35

<210> SEQ ID NO 262
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gly Ser Gly Val Pro Ile Ser Val Arg Cys Arg Gly Ser Arg Asp Cys
1               5                   10                  15

Leu Glu Pro Cys Arg Arg Ala Gly Thr Arg Phe Gly Arg Cys Ile Asn
            20                  25                  30

Arg Arg Cys His Cys Thr Pro
        35

<210> SEQ ID NO 263
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Asn
            20                  25                  30

Ser Arg Cys His Cys Thr Pro
        35

<210> SEQ ID NO 264
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

Ser Arg Cys His Cys Thr Pro
        35

<210> SEQ ID NO 265
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

Ser Arg Cys His Cys Tyr Pro
        35

<210> SEQ ID NO 266
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gly Ser Gly Val Pro Ile Asn Val Arg Cys Arg Gly Ser Arg Asp Cys
1               5                   10                  15

Tyr Glu Pro Cys Arg Arg Ala Gly Thr Arg Phe Gly Arg Cys Ile Gln
            20                  25                  30

Ser Arg Cys His Cys Thr Pro
        35

<210> SEQ ID NO 267
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

```
Ser Arg Cys Tyr Cys Thr Pro
        35

<210> SEQ ID NO 268
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gly Ser Gly Val Pro Ile Ser Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

Ser Arg Cys His Cys Tyr Pro
        35

<210> SEQ ID NO 269
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gly Ser Gly Val Pro Ile Ser Val Arg Cys Arg Gly Ser Arg Asp Cys
1               5                   10                  15

Tyr Glu Pro Cys Arg Arg Ala Gly Thr Arg Phe Gly Arg Cys Ile Gln
            20                  25                  30

Ser Arg Cys His Cys Thr Pro
        35

<210> SEQ ID NO 270
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gly Ser Gly Val Pro Ile Ser Val Arg Cys Arg Gly Ser Arg Asp Cys
1               5                   10                  15

Leu Glu Pro Cys Arg Arg Ala Gly Thr Arg Phe Gly Arg Cys Ile Gln
            20                  25                  30

Ser Arg Cys Tyr Cys Thr Pro
        35

<210> SEQ ID NO 271
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Ala
```

-continued

```
                    20                  25                  30

Ser Arg Cys His Cys Tyr Pro
            35

<210> SEQ ID NO 272
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Ser
            20                  25                  30

Ser Arg Cys His Cys Tyr Pro
            35

<210> SEQ ID NO 273
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Thr
            20                  25                  30

Ser Arg Cys His Cys Tyr Pro
            35

<210> SEQ ID NO 274
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gly Ser Gly Val Pro Ile Asn Val Arg Cys Arg Gly Ser Arg Asp Cys
1               5                   10                  15

Leu Glu Pro Cys Arg Arg Ala Gly Thr Arg Phe Gly Arg Cys Ile Asn
            20                  25                  30

Ser Arg Cys His Cys Tyr Pro
            35

<210> SEQ ID NO 275
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid, amino acid analogue or null
<220> FEATURE:
<221> NAME/KEY: MOD_RES
```

```
<222> LOCATION: (5)..(6)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (15)..(15)
<223> OTHER INFORMATION: Any amino acid, amino acid analogue or null
<220> FEATURE:
<221> NAME/KEY: MOD_RES
<222> LOCATION: (20)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (30)..(30)
<223> OTHER INFORMATION: Any amino acid, amino acid analogue or null
<220> FEATURE:
<221> NAME/KEY: MOD_RES
<222> LOCATION: (37)..(40)
<223> OTHER INFORMATION: Any amino acid, amino acid analogue or null

<400> SEQUENCE: 275

Gly Val Xaa Ile Xaa Xaa Lys Cys Xaa Gly Ser Lys Gln Cys Xaa Asp
1               5                   10                  15

Pro Cys Lys Xaa Xaa Xaa Gly Xaa Arg Xaa Gly Lys Cys Xaa Asn Lys
                20                  25                  30

Lys Cys Lys Cys Xaa Xaa Xaa Xaa
            35                  40

<210> SEQ ID NO 276
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: P or R
<220> FEATURE:
<221> NAME/KEY: MOD_RES
<222> LOCATION: (5)..(5)
<223> OTHER INFORMATION: P or N
<220> FEATURE:
<221> NAME/KEY: MOD_RES
<222> LOCATION: (6)..(6)
<223> OTHER INFORMATION: V or I
<220> FEATURE:
<221> NAME/KEY: MOD_RES
<222> LOCATION: (9)..(9)
<223> OTHER INFORMATION: S, T, R or K
<220> FEATURE:
<221> NAME/KEY: MOD_RES
<222> LOCATION: (15)..(15)
<223> OTHER INFORMATION: Y or L
<220> FEATURE:
<221> NAME/KEY: MOD_RES
<222> LOCATION: (20)..(20)
<223> OTHER INFORMATION: Q, R or K
<220> FEATURE:
<221> NAME/KEY: MOD_RES
<222> LOCATION: (21)..(21)
<223> OTHER INFORMATION: A, K or R
<220> FEATURE:
```

```
<221> NAME/KEY: MOD_RES
<222> LOCATION: (22)..(22)
<223> OTHER INFORMATION: T or A
<220> FEATURE:
<221> NAME/KEY: MOD_RES
<222> LOCATION: (24)..(24)
<223> OTHER INFORMATION: C or M
<220> FEATURE:
<221> NAME/KEY: MOD_RES
<222> LOCATION: (26)..(26)
<223> OTHER INFORMATION: F or N
<220> FEATURE:
<221> NAME/KEY: MOD_RES
<222> LOCATION: (30)..(30)
<223> OTHER INFORMATION: M or I
<220> FEATURE:
<221> NAME/KEY: MOD_RES
<222> LOCATION: (37)..(37)
<223> OTHER INFORMATION: Y or T
<220> FEATURE:
<221> NAME/KEY: MOD_RES
<222> LOCATION: (38)..(38)
<223> OTHER INFORMATION: G or P
<220> FEATURE:
<221> NAME/KEY: MISC_FEATURE
<222> LOCATION: (39)..(40)
<223> OTHER INFORMATION: May or may not be present

<400> SEQUENCE: 276

Gly Val Xaa Ile Xaa Xaa Lys Cys Xaa Gly Ser Lys Gln Cys Xaa Asp
1               5                   10                  15

Pro Cys Lys Xaa Xaa Xaa Gly Xaa Arg Xaa Gly Lys Cys Xaa Asn Lys
            20                  25                  30

Lys Cys Lys Cys Xaa Xaa Cys Gly
        35                  40

<210> SEQ ID NO 277
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(4)
<223> OTHER INFORMATION: Any amino acid, amino acid analogue or null
<220> FEATURE:
<221> NAME/KEY: MOD_RES
<222> LOCATION: (6)..(6)
<223> OTHER INFORMATION: Any amino acid, amino acid analogue or null
<220> FEATURE:
<221> NAME/KEY: MOD_RES
<222> LOCATION: (8)..(8)
<223> OTHER INFORMATION: Any amino acid, amino acid analogue or null
<220> FEATURE:
<221> NAME/KEY: MOD_RES
<222> LOCATION: (15)..(15)
<223> OTHER INFORMATION: Any amino acid, amino acid analogue or null
<220> FEATURE:
<221> NAME/KEY: MOD_RES
<222> LOCATION: (19)..(20)
<223> OTHER INFORMATION: Any amino acid, amino acid analogue or null
<220> FEATURE:
<221> NAME/KEY: MOD_RES
<222> LOCATION: (24)..(26)
<223> OTHER INFORMATION: Any amino acid, amino acid analogue or null
<220> FEATURE:
<221> NAME/KEY: MOD_RES
<222> LOCATION: (29)..(30)
<223> OTHER INFORMATION: Any amino acid, amino acid analogue or null
<220> FEATURE:
<221> NAME/KEY: MOD_RES
<222> LOCATION: (32)..(32)
<223> OTHER INFORMATION: Any amino acid, amino acid analogue or null
```

<400> SEQUENCE: 277

Xaa Xaa Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Xaa Lys Cys Xaa Xaa Lys Xaa
            20                  25                  30

Cys Lys Cys Tyr Gly Cys Gly
            35

<210> SEQ ID NO 278
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: E, G or null
<220> FEATURE:
<221> NAME/KEY: MOD_RES
<222> LOCATION: (4)..(4)
<223> OTHER INFORMATION: V, S or null
<220> FEATURE:
<221> NAME/KEY: MOD_RES
<222> LOCATION: (6)..(6)
<223> OTHER INFORMATION: R or S
<220> FEATURE:
<221> NAME/KEY: MOD_RES
<222> LOCATION: (8)..(8)
<223> OTHER INFORMATION: S or T
<220> FEATURE:
<221> NAME/KEY: MOD_RES
<222> LOCATION: (15)..(15)
<223> OTHER INFORMATION: G or D
<220> FEATURE:
<221> NAME/KEY: MOD_RES
<222> LOCATION: (19)..(19)
<223> OTHER INFORMATION: Q or R
<220> FEATURE:
<221> NAME/KEY: MOD_RES
<222> LOCATION: (20)..(20)
<223> OTHER INFORMATION: Q or K
<220> FEATURE:
<221> NAME/KEY: MOD_RES
<222> LOCATION: (24)..(24)
<223> OTHER INFORMATION: T or P
<220> FEATURE:
<221> NAME/KEY: MOD_RES
<222> LOCATION: (25)..(25)
<223> OTHER INFORMATION: N or Q
<220> FEATURE:
<221> NAME/KEY: MOD_RES
<222> LOCATION: (26)..(26)
<223> OTHER INFORMATION: S or A
<220> FEATURE:
<221> NAME/KEY: MOD_RES
<222> LOCATION: (29)..(29)
<223> OTHER INFORMATION: M or L
<220> FEATURE:
<221> NAME/KEY: MOD_RES
<222> LOCATION: (30)..(30)
<223> OTHER INFORMATION: N or Q
<220> FEATURE:
<221> NAME/KEY: MOD_RES
<222> LOCATION: (32)..(32)
<223> OTHER INFORMATION: V or S

<400> SEQUENCE: 278

-continued

```
Gly Ser Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Lys Cys Xaa Xaa Lys Xaa
            20                  25                  30

Cys Lys Cys Tyr Gly Cys Gly
        35
```

<210> SEQ ID NO 279
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid, amino acid analogue or null
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (11)..(12)
<223> OTHER INFORMATION: Any amino acid, amino acid analogue or null
<220> FEATURE:
<221> NAME/KEY: MOD_RES
<222> LOCATION: (14)..(15)
<223> OTHER INFORMATION: Any amino acid, amino acid analogue or null
<220> FEATURE:
<221> NAME/KEY: MOD_RES
<222> LOCATION: (18)..(18)
<223> OTHER INFORMATION: Any amino acid, amino acid analogue or null
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (31)..(31)
<223> OTHER INFORMATION: Any amino acid, amino acid analogue or null
<220> FEATURE:
<221> NAME/KEY: MOD_RES
<222> LOCATION: (33)..(33)
<223> OTHER INFORMATION: Any amino acid, amino acid analogue or null
<220> FEATURE:
<221> NAME/KEY: MOD_RES
<222> LOCATION: (36)..(36)
<223> OTHER INFORMATION: Any amino acid, amino acid analogue or null
<220> FEATURE:
<221> NAME/KEY: MOD_RES
<222> LOCATION: (40)..(40)
<223> OTHER INFORMATION: Any amino acid, amino acid analogue or null

<400> SEQUENCE: 279

```
Xaa Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30

Xaa Lys Cys Xaa Cys Thr Pro Xaa
        35                  40
```

<210> SEQ ID NO 280

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: G, S or null
<220> FEATURE:
<221> NAME/KEY: MOD_RES
<222> LOCATION: (3)..(3)
<223> OTHER INFORMATION: G, S or null
<220> FEATURE:
<221> NAME/KEY: MOD_RES
<222> LOCATION: (5)..(5)
<223> OTHER INFORMATION: P or R
<220> FEATURE:
<221> NAME/KEY: MOD_RES
<222> LOCATION: (7)..(7)
<223> OTHER INFORMATION: N or P
<220> FEATURE:
<221> NAME/KEY: MOD_RES
<222> LOCATION: (9)..(9)
<223> OTHER INFORMATION: K or S
<220> FEATURE:
<221> NAME/KEY: MOD_RES
<222> LOCATION: (11)..(11)
<223> OTHER INFORMATION: R or K
<220> FEATURE:
<221> NAME/KEY: MOD_RES
<222> LOCATION: (12)..(12)
<223> OTHER INFORMATION: G or H
<220> FEATURE:
<221> NAME/KEY: MOD_RES
<222> LOCATION: (14)..(14)
<223> OTHER INFORMATION: R or G
<220> FEATURE:
<221> NAME/KEY: MOD_RES
<222> LOCATION: (15)..(15)
<223> OTHER INFORMATION: D or Q
<220> FEATURE:
<221> NAME/KEY: MOD_RES
<222> LOCATION: (18)..(18)
<223> OTHER INFORMATION: D or K
<220> FEATURE:
<221> NAME/KEY: MOD_RES
<222> LOCATION: (22)..(22)
<223> OTHER INFORMATION: K or D
<220> FEATURE:
<221> NAME/KEY: MOD_RES
<222> LOCATION: (31)..(31)
<223> OTHER INFORMATION: I or M
<220> FEATURE:
<221> NAME/KEY: MOD_RES
<222> LOCATION: (33)..(33)
<223> OTHER INFORMATION: S or G
<220> FEATURE:
<221> NAME/KEY: MOD_RES
<222> LOCATION: (36)..(36)
<223> OTHER INFORMATION: H or D
<220> FEATURE:
<221> NAME/KEY: MISC_FEATURE
<222> LOCATION: (40)..(40)
<223> OTHER INFORMATION: May or may not be present

<400> SEQUENCE: 280

Gly Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30
```

Xaa Lys Cys Xaa Cys Thr Pro Lys
        35                  40

<210> SEQ ID NO 281
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<223> OTHER INFORMATION: See specification as filed for detailed
      description of substitutions and preferred embodiments

<400> SEQUENCE: 281

Xaa Val Xaa Val Lys Cys Xaa Gly Ser Lys Gln Cys Xaa Pro Cys Lys
1               5                   10                  15

Arg Xaa Gly Xaa Arg Xaa Gly Lys Cys Ile Asn Lys Lys Xaa Cys Lys
            20                  25                  30

Cys Tyr Xaa
        35

<210> SEQ ID NO 282
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:

<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<223> OTHER INFORMATION: See specification as filed for detailed
      description of substitutions and preferred embodiments

<400> SEQUENCE: 282

Xaa Gly Cys Val Xaa Lys Cys Arg Pro Gly Xaa Lys Xaa Cys Cys Xaa
1               5                   10                  15

Pro Xaa Lys Arg Cys Ser Arg Arg Phe Gly Xaa Lys Lys Cys Lys Xaa
            20                  25                  30

<210> SEQ ID NO 283
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid, amino acid analogue or null
<220> FEATURE:
<221> NAME/KEY: MOD_RES
<222> LOCATION: (3)..(5)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (15)..(16)
<223> OTHER INFORMATION: Any amino acid, amino acid analogue or null
<220> FEATURE:
<221> NAME/KEY: MOD_RES
<222> LOCATION: (21)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (34)..(34)
<223> OTHER INFORMATION: Any amino acid, amino acid analogue or null
<220> FEATURE:
<221> NAME/KEY: MOD_RES
<222> LOCATION: (39)..(41)
<223> OTHER INFORMATION: Any amino acid, amino acid analogue or null

<400> SEQUENCE: 283

Xaa Val Xaa Xaa Xaa Val Lys Cys Xaa Gly Ser Lys Gln Cys Xaa Xaa
1               5

```
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (15)..(15)
<223> OTHER INFORMATION: Any amino acid, amino acid analogue or null
<220> FEATURE:
<221> NAME/KEY: MOD_RES
<222> LOCATION: (20)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (30)..(30)
<223> OTHER INFORMATION: Any amino acid, amino acid analogue or null
<220> FEATURE:
<221> NAME/KEY: MOD_RES
<222> LOCATION: (37)..(40)
<223> OTHER INFORMATION: Any amino acid, amino acid analogue or null

<400> SEQUENCE: 285

Gly Val Xaa Ile Xaa Xaa Arg Cys Xaa Gly Ser Arg Gln Cys Xaa Asp
1               5                   10                  15

Pro Cys Arg Xaa Xaa Xaa Gly Xaa Arg Xaa Gly Arg Cys Xaa Asn Arg
            20                  25                  30

Arg Cys Arg Cys Xaa Xaa Xaa Xaa
        35                  40

<210> SEQ ID NO 286
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: P or R
<220> FEATURE:
<221> NAME/KEY: MOD_RES
<222> LOCATION: (5)..(5)
<223> OTHER INFORMATION: P or N
<220> FEATURE:
<221> NAME/KEY: MOD_RES
<222> LOCATION: (6)..(6)
<223> OTHER INFORMATION: V or I
<220> FEATURE:
<221> NAME/KEY: MOD_RES
<222> LOCATION: (9)..(9)
<223> OTHER INFORMATION: S, T, R or K
<220> FEATURE:
<221> NAME/KEY: MOD_RES
<222> LOCATION: (15)..(15)
<223> OTHER INFORMATION: Y or L
<220> FEATURE:
<221> NAME/KEY: MOD_RES
<222> LOCATION: (20)..(20)
<223> OTHER INFORMATION: Q, R or K
<220> FEATURE:
<221> NAME/KEY: MOD_RES
<222> LOCATION: (21)..(21)
<223> OTHER INFORMATION: A, K or R
<220> FEATURE:
<221> NAME/KEY: MOD_RES
```

```
<222> LOCATION: (22)..(22)
<223> OTHER INFORMATION: T or A
<220> FEATURE:
<221> NAME/KEY: MOD_RES
<222> LOCATION: (24)..(24)
<223> OTHER INFORMATION: C or M
<220> FEATURE:
<221> NAME/KEY: MOD_RES
<222> LOCATION: (26)..(26)
<223> OTHER INFORMATION: F or N
<220> FEATURE:
<221> NAME/KEY: MOD_RES
<222> LOCATION: (30)..(30)
<223> OTHER INFORMATION: M or I
<220> FEATURE:
<221> NAME/KEY: MOD_RES
<222> LOCATION: (37)..(37)
<223> OTHER INFORMATION: Y or T
<220> FEATURE:
<221> NAME/KEY: MOD_RES
<222> LOCATION: (38)..(38)
<223> OTHER INFORMATION: G or P
<220> FEATURE:
<221> NAME/KEY: MISC_FEATURE
<222> LOCATION: (39)..(40)
<223> OTHER INFORMATION: May or may not be present

<400> SEQUENCE: 286

Gly Val Xaa Ile Xaa Xaa Arg Cys Xaa Gly Ser Arg Gln Cys Xaa Asp
1               5                   10                  15

Pro Cys Arg Xaa Xaa Xaa Gly Xaa Arg Xaa Gly Arg Cys Xaa Asn Arg
            20                  25                  30

Arg Cys Arg Cys Xaa Xaa Cys Gly
        35                  40

<210> SEQ ID NO 287
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(4)
<223> OTHER INFORMATION: Any amino acid, amino acid analogue or null
<220> FEATURE:
<221> NAME/KEY: MOD_RES
<222> LOCATION: (6)..(6)
<223> OTHER INFORMATION: Any amino acid, amino acid analogue or null
<220> FEATURE:
<221> NAME/KEY: MOD_RES
<222> LOCATION: (8)..(8)
<223> OTHER INFORMATION: Any amino acid, amino acid analogue or null
<220> FEATURE:
<221> NAME/KEY: MOD_RES
<222> LOCATION: (15)..(15)
<223> OTHER INFORMATION: Any amino acid, amino acid analogue or null
<220> FEATURE:
<221> NAME/KEY: MOD_RES
<222> LOCATION: (19)..(20)
<223> OTHER INFORMATION: Any amino acid, amino acid analogue or null
<220> FEATURE:
<221> NAME/KEY: MOD_RES
<222> LOCATION: (24)..(26)
<223> OTHER INFORMATION: Any amino acid, amino acid analogue or null
<220> FEATURE:
<221> NAME/KEY: MOD_RES
<222> LOCATION: (29)..(30)
<223> OTHER INFORMATION: Any amino acid, amino acid analogue or null
<220> FEATURE:
<221> NAME/KEY: MOD_RES
<222> LOCATION: (32)..(32)
<223> OTHER INFORMATION: Any amino acid, amino acid analogue or null
```

<400> SEQUENCE: 287

Xaa Xaa Xaa Xaa Ile Xaa Cys Xaa Gly Ser Arg Gln Cys Tyr Xaa Pro
1               5                   10                  15

Cys Arg Xaa Xaa Thr Gly Cys Xaa Xaa Xaa Arg Cys Xaa Xaa Arg Xaa
            20                  25                  30

Cys Arg Cys Tyr Gly Cys Gly
        35

<210> SEQ ID NO 288
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: E, G or null
<220> FEATURE:
<221> NAME/KEY: MOD_RES
<222> LOCATION: (4)..(4)
<223> OTHER INFORMATION: V, S or null
<220> FEATURE:
<221> NAME/KEY: MOD_RES
<222> LOCATION: (6)..(6)
<223> OTHER INFORMATION: R or S
<220> FEATURE:
<221> NAME/KEY: MOD_RES
<222> LOCATION: (8)..(8)
<223> OTHER INFORMATION: S or T
<220> FEATURE:
<221> NAME/KEY: MOD_RES
<222> LOCATION: (15)..(15)
<223> OTHER INFORMATION: G or D
<220> FEATURE:
<221> NAME/KEY: MOD_RES
<222> LOCATION: (19)..(19)
<223> OTHER INFORMATION: Q or R
<220> FEATURE:
<221> NAME/KEY: MOD_RES
<222> LOCATION: (20)..(20)
<223> OTHER INFORMATION: Q, R or K
<220> FEATURE:
<221> NAME/KEY: MOD_RES
<222> LOCATION: (24)..(24)
<223> OTHER INFORMATION: T or P
<220> FEATURE:
<221> NAME/KEY: MOD_RES
<222> LOCATION: (25)..(25)
<223> OTHER INFORMATION: N or Q
<220> FEATURE:
<221> NAME/KEY: MOD_RES
<222> LOCATION: (26)..(26)
<223> OTHER INFORMATION: S or A
<220> FEATURE:
<221> NAME/KEY: MOD_RES
<222> LOCATION: (29)..(29)
<223> OTHER INFORMATION: M or L
<220> FEATURE:
<221> NAME/KEY: MOD_RES
<222> LOCATION: (30)..(30)
<223> OTHER INFORMATION: N or Q
<220> FEATURE:
<221> NAME/KEY: MOD_RES
<222> LOCATION: (32)..(32)
<223> OTHER INFORMATION: V or S

<400> SEQUENCE: 288

Gly Ser Xaa Xaa Ile Xaa Cys Xaa Gly Ser Arg Gln Cys Tyr Xaa Pro

```
1               5                   10                  15
Cys Arg Xaa Xaa Thr Gly Cys Xaa Xaa Xaa Arg Cys Xaa Xaa Arg Xaa
            20                  25                  30

Cys Arg Cys Tyr Gly Cys Gly
            35

<210> SEQ ID NO 289
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid, amino acid analogue or null
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (7)..(7)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (11)..(12)
<223> OTHER INFORMATION: Any amino acid, amino acid analogue or null
<220> FEATURE:
<221> NAME/KEY: MOD_RES
<222> LOCATION: (14)..(15)
<223> OTHER INFORMATION: Any amino acid, amino acid analogue or null
<220> FEATURE:
<221> NAME/KEY: MOD_RES
<222> LOCATION: (18)..(18)
<223> OTHER INFORMATION: Any amino acid, amino acid analogue or null
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (31)..(31)
<223> OTHER INFORMATION: Any amino acid, amino acid analogue or null
<220> FEATURE:
<221> NAME/KEY: MOD_RES
<222> LOCATION: (33)..(33)
<223> OTHER INFORMATION: Any amino acid, amino acid analogue or null
<220> FEATURE:
<221> NAME/KEY: MOD_RES
<222> LOCATION: (36)..(36)
<223> OTHER INFORMATION: Any amino acid, amino acid analogue or null
<220> FEATURE:
<221> NAME/KEY: MOD_RES
<222> LOCATION: (40)..(40)
<223> OTHER INFORMATION: Any amino acid, amino acid analogue or null

<400> SEQUENCE: 289

Xaa Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
            35                  40

<210> SEQ ID NO 290
<211> LENGTH: 40
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: G, S or null
<220> FEATURE:
<221> NAME/KEY: MOD_RES
<222> LOCATION: (3)..(3)
<223> OTHER INFORMATION: G, S or null
<220> FEATURE:
<221> NAME/KEY: MOD_RES
<222> LOCATION: (5)..(5)
<223> OTHER INFORMATION: P or R
<220> FEATURE:
<221> NAME/KEY: MOD_RES
<222> LOCATION: (7)..(7)
<223> OTHER INFORMATION: N or P
<220> FEATURE:
<221> NAME/KEY: MOD_RES
<222> LOCATION: (9)..(9)
<223> OTHER INFORMATION: R, K or S
<220> FEATURE:
<221> NAME/KEY: MOD_RES
<222> LOCATION: (11)..(11)
<223> OTHER INFORMATION: R or K
<220> FEATURE:
<221> NAME/KEY: MOD_RES
<222> LOCATION: (12)..(12)
<223> OTHER INFORMATION: G or H
<220> FEATURE:
<221> NAME/KEY: MOD_RES
<222> LOCATION: (14)..(14)
<223> OTHER INFORMATION: R or G
<220> FEATURE:
<221> NAME/KEY: MOD_RES
<222> LOCATION: (15)..(15)
<223> OTHER INFORMATION: D or Q
<220> FEATURE:
<221> NAME/KEY: MOD_RES
<222> LOCATION: (18)..(18)
<223> OTHER INFORMATION: D, R or K
<220> FEATURE:
<221> NAME/KEY: MOD_RES
<222> LOCATION: (22)..(22)
<223> OTHER INFORMATION: K, R or D
<220> FEATURE:
<221> NAME/KEY: MOD_RES
<222> LOCATION: (31)..(31)
<223> OTHER INFORMATION: I or M
<220> FEATURE:
<221> NAME/KEY: MOD_RES
<222> LOCATION: (33)..(33)
<223> OTHER INFORMATION: S or G
<220> FEATURE:
<221> NAME/KEY: MOD_RES
<222> LOCATION: (36)..(36)
<223> OTHER INFORMATION: H or D
<220> FEATURE:
<221> NAME/KEY: MOD_RES
<222> LOCATION: (40)..(40)
<223> OTHER INFORMATION: K, R or null

<400> SEQUENCE: 290

Gly Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
            35                  40
```

```
<210> SEQ ID NO 291
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<223> OTHER INFORMATION: See specification as filed for detailed
      description of substitutions and preferred embodiments

<400> SEQUENCE: 291

Xaa Val Xaa Val Arg Cys Xaa Gly Ser Arg Gln Cys Xaa Pro Cys Arg
1               5                   10                  15

Arg Xaa Gly Xaa Arg Xaa Gly Arg Cys Ile Asn Arg Arg Xaa Cys Arg
            20                  25                  30

Cys Tyr Xaa
        35

<210> SEQ ID NO 292
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
```

<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<223> OTHER INFORMATION: See specification as filed for detailed
      description of substitutions and preferred embodiments

<400> SEQUENCE: 292

Xaa Gly Cys Val Xaa Arg Cys Arg Pro Gly Xaa Arg Xaa Cys Cys Xaa
1               5                   10                  15

Pro Xaa Arg Arg Cys Ser Arg Arg Phe Gly Xaa Arg Arg Cys Arg Xaa
            20                  25                  30

<210> SEQ ID NO 293
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid analogue or null
<220> FEATURE:
<221> NAME/KEY: MOD_RES
<222> LOCATION: (3)..(5)
<223> OTHER INFORMATION: Any amino acid analogue or null
<220> FEATURE:
<221> NAME/KEY: MOD_RES
<222> LOCATION: (9)..(9)
<223> OTHER INFORMATION: Any amino acid analogue or null
<220> FEATURE:
<221> NAME/KEY: MOD_RES
<222> LOCATION: (15)..(16)
<223> OTHER INFORMATION: Any amino acid analogue or null
<220> FEATURE:
<221> NAME/KEY: MOD_RES
<222> LOCATION: (21)..(22)
<223> OTHER INFORMATION: Any amino acid analogue or null
<220> FEATURE:
<221> NAME/KEY: MOD_RES
<222> LOCATION: (24)..(24)
<223> OTHER INFORMATION: Any amino acid analogue or null
<220> FEATURE:
<221> NAME/KEY: MOD_RES
<222> LOCATION: (26)..(26)
<223> OTHER INFORMATION: Any amino acid analogue or null
<220> FEATURE:
<221> NAME/KEY: MOD_RES
<222> LOCATION: (34)..(34)
<223> OTHER INFORMATION: Any amino acid analogue or null
<220> FEATURE:
<221> NAME/KEY: MOD_RES
<222> LOCATION: (39)..(41)
<223> OTHER INFORMATION: Any amino acid analogue or null

<400> SEQUENCE: 293

Xaa Val Xaa Xaa Xaa Val Arg Cys Xaa Gly Ser Arg Gln Cys Xaa Xaa
1               5                   10                  15

Pro Cys Arg Arg Xaa Xaa Gly Xaa Arg Xaa Gly Arg Cys Ile Asn Arg
                20                  25                  30

Arg Xaa Cys Arg Cys Tyr Xaa Xaa Xaa
            35                  40

<210> SEQ ID NO 294
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid analogue or null
<220> FEATURE:
<221> NAME/KEY: MOD_RES
<222> LOCATION: (7)..(10)
<223> OTHER INFORMATION: Any amino acid analogue or null
<220> FEATURE:
<221> NAME/KEY: MOD_RES
<222> LOCATION: (16)..(16)
<223> OTHER INFORMATION: Any amino acid analogue or null
<220> FEATURE:
<221> NAME/KEY: MOD_RES
<222> LOCATION: (18)..(18)
<223> OTHER INFORMATION: Any amino acid analogue or null
<220> FEATURE:
<221> NAME/KEY: MOD_RES
<222> LOCATION: (21)..(21)
<223> OTHER INFORMATION: Any amino acid analogue or null
<220> FEATURE:
<221> NAME/KEY: MOD_RES
<222> LOCATION: (23)..(23)
<223> OTHER INFORMATION: Any amino acid analogue or null
<220> FEATURE:
<221> NAME/KEY: MOD_RES
<222> LOCATION: (32)..(35)
<223> OTHER INFORMATION: Any amino acid analogue or null
<220> FEATURE:
<221> NAME/KEY: MOD_RES
<222> LOCATION: (40)..(45)
<223> OTHER INFORMATION: Any amino acid analogue or null

<400> SEQUENCE: 294

Xaa Xaa Xaa Gly Cys Val Xaa Xaa Xaa Arg Cys Arg Pro Gly Xaa
1               5                   10                  15

Arg Xaa Cys Cys Xaa Pro Xaa Arg Arg Cys Ser Arg Arg Phe Gly Xaa
                20                  25                  30

Xaa Xaa Xaa Arg Arg Cys Arg Xaa Xaa Xaa Xaa Xaa
            35                  40                  45

<210> SEQ ID NO 295
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid, amino acid analogue or null
<220> FEATURE:
<221> NAME/KEY: MOD_RES
<222> LOCATION: (3)..(3)
<223> OTHER INFORMATION: Any amino acid, amino acid analogue or null -continued

```
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (9)..(9)
<223> OTHER INFORMATION: Any amino acid, amino acid analogue or null
<220> FEATURE:
<221> NAME/KEY: MOD_RES
<222> LOCATION: (12)..(12)
<223> OTHER INFORMATION: Any amino acid, amino acid analogue or null
<220> FEATURE:
<221> NAME/KEY: MOD_RES
<222> LOCATION: (16)..(16)
<223> OTHER INFORMATION: Any amino acid, amino acid analogue or null
<220> FEATURE:
<221> NAME/KEY: MOD_RES
<222> LOCATION: (20)..(20)
<223> OTHER INFORMATION: Any amino acid, amino acid analogue or null
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (35)..(35)
<223> OTHER INFORMATION: Any amino acid, amino acid analogue or null
<220> FEATURE:
<221> NAME/KEY: MOD_RES
<222> LOCATION: (37)..(37)
<223> OTHER INFORMATION: Any amino acid, amino acid analogue or null
<220> FEATURE:
<221> NAME/KEY: MOD_RES
<222> LOCATION: (39)..(40)
<223> OTHER INFORMATION: Any amino acid, amino acid analogue or null

<400> SEQUENCE: 295

Xaa Val Xaa Ile Xaa Val Lys Cys Xaa Gly Ser Xaa Gln Cys Leu Xaa
1               5                   10                  15

Pro Cys Lys Xaa Ala Xaa Gly Xaa Arg Xaa Gly Lys Cys Met Asn Gly
            20                  25                  30

Lys Cys Xaa Cys Xaa Pro Xaa Xaa
        35                  40

<210> SEQ ID NO 296
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid, amino acid analogue or null
<220> FEATURE:
<221> NAME/KEY: MOD_RES
<222> LOCATION: (3)..(3)
<223> OTHER INFORMATION: Any amino acid, amino acid analogue or null
<220> FEATURE:
<221> NAME/KEY: MOD_RES
<222> LOCATION: (5)..(5)
<223> OTHER INFORMATION: Any amino acid, amino acid analogue or null
<220> FEATURE:
<221> NAME/KEY: MOD_RES
<222> LOCATION: (9)..(9)
```

<223> OTHER INFORMATION: Any amino acid, amino acid analogue or null
<220> FEATURE:
<221> NAME/KEY: MOD_RES
<222> LOCATION: (12)..(12)
<223> OTHER INFORMATION: Any amino acid, amino acid analogue or null
<220> FEATURE:
<221> NAME/KEY: MOD_RES
<222> LOCATION: (16)..(16)
<223> OTHER INFORMATION: Any amino acid, amino acid analogue or null
<220> FEATURE:
<221> NAME/KEY: MOD_RES
<222> LOCATION: (20)..(20)
<223> OTHER INFORMATION: Any amino acid, amino acid analogue or null
<220> FEATURE:
<221> NAME/KEY: MOD_RES
<222> LOCATION: (22)..(22)
<223> OTHER INFORMATION: Any amino acid, amino acid analogue or null
<220> FEATURE:
<221> NAME/KEY: MOD_RES
<222> LOCATION: (24)..(24)
<223> OTHER INFORMATION: Any amino acid, amino acid analogue or null
<220> FEATURE:
<221> NAME/KEY: MOD_RES
<222> LOCATION: (26)..(26)
<223> OTHER INFORMATION: Any amino acid, amino acid analogue or null
<220> FEATURE:
<221> NAME/KEY: MOD_RES
<222> LOCATION: (35)..(35)
<223> OTHER INFORMATION: Any amino acid, amino acid analogue or null
<220> FEATURE:
<221> NAME/KEY: MOD_RES
<222> LOCATION: (37)..(37)
<223> OTHER INFORMATION: Any amino acid, amino acid analogue or null
<220> FEATURE:
<221> NAME/KEY: MOD_RES
<222> LOCATION: (39)..(40)
<223> OTHER INFORMATION: Any amino acid, amino acid analogue or null

<400> SEQUENCE: 296

Xaa Val Xaa Ile Xaa Val Arg Cys Xaa Gly Ser Xaa Gln Cys Leu Xaa
1               5                   10                  15

Pro Cys Arg Xaa Ala Xaa Gly Xaa Arg Xaa Gly Arg Cys Met Asn Gly
            20                  25                  30

Arg Cys Xaa Cys Xaa Pro Xaa Xaa
        35                  40

<210> SEQ ID NO 297
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: N, S or G
<220> FEATURE:
<221> NAME/KEY: MOD_RES
<222> LOCATION: (15)..(15)
<223> OTHER INFORMATION: L or Y
<220> FEATURE:
<221> NAME/KEY: MOD_RES
<222> LOCATION: (16)..(16)
<223> OTHER INFORMATION: D or E
<220> FEATURE:
<221> NAME/KEY: MOD_RES
<222> LOCATION: (23)..(23)
<223> OTHER INFORMATION: M or T
<220> FEATURE:
<221> NAME/KEY: MOD_RES
<222> LOCATION: (30)..(30)
<223> OTHER INFORMATION: N, Q, A, S, T or L
<220> FEATURE:
<221> NAME/KEY: MOD_RES

```
<222> LOCATION: (31)..(31)
<223> OTHER INFORMATION: S, G or R
<220> FEATURE:
<221> NAME/KEY: MOD_RES
<222> LOCATION: (34)..(34)
<223> OTHER INFORMATION: H or Y
<220> FEATURE:
<221> NAME/KEY: MOD_RES
<222> LOCATION: (36)..(36)
<223> OTHER INFORMATION: T or Y

<400> SEQUENCE: 297

Gly Val Pro Ile Xaa Val Arg Cys Arg Gly Ser Arg Asp Cys Xaa Xaa
1               5                   10                  15

Pro Cys Arg Arg Ala Gly Xaa Arg Phe Gly Arg Cys Ile Xaa Xaa Arg
            20                  25                  30

Cys Xaa Cys Xaa Pro
        35

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Lys Cys Ile Asn Lys Lys Cys Lys Cys
1               5                   10

<210> SEQ ID NO 299
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Lys Cys Ile Asn
1

<210> SEQ ID NO 300
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Lys Lys Cys Lys
1

<210> SEQ ID NO 301
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Pro Cys Lys Arg
1
```

```
<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Lys Arg Cys Ser Arg Arg
1               5

<210> SEQ ID NO 303
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Lys Gln Cys
1

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Arg Cys Ile Asn Arg Arg Cys Arg Cys
1               5                   10

<210> SEQ ID NO 305
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Arg Cys Ile Asn
1

<210> SEQ ID NO 306
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Arg Arg Cys Arg
1

<210> SEQ ID NO 307
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307
```

```
Pro Cys Arg Arg
1

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Arg Arg Cys Ser Arg Arg
1               5

<210> SEQ ID NO 309
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Arg Gln Cys
1

<210> SEQ ID NO 310
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Pro Cys Lys Lys
1

<210> SEQ ID NO 311
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Lys Lys Cys Ser Lys Lys
1               5

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Lys Cys Met Asn Gly Lys Cys
1               5

<210> SEQ ID NO 313
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 313

Gly Arg Cys Met Asn Gly Arg Cys
1               5

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gly Ile Val Cys Lys Val Cys Lys Ile Ile Cys Gly Met Gln Gly Lys
1               5                   10                  15

Lys Val Asn Ile Cys Lys Ala Pro Ile Lys Cys Lys Cys Lys Lys Gly
            20                  25                  30

<210> SEQ ID NO 315
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg
        35

<210> SEQ ID NO 316
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 317
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Gly Val Pro Ile Asn Val Lys Cys Arg Gly Ser Arg Asp Cys Leu Asp
1               5                   10                  15
```

```
Pro Cys Lys Lys Ala Gly Met Arg Phe Gly Lys Cys Ile Asn Ser Lys
            20                  25                  30

Cys His Cys Thr Pro
        35

<210> SEQ ID NO 318
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Ala Val Cys Val Tyr Arg Thr Cys Asp Lys Asp Cys Lys Arg Arg Gly
1               5                   10                  15

Tyr Arg Ser Gly Lys Cys Ile Asn Asn Ala Cys Lys Cys Tyr Pro Tyr
            20                  25                  30

Gly

<210> SEQ ID NO 319
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Ile Ser Cys Thr Gly Ser Lys Gln Cys Tyr Asp Pro Cys Lys Arg Lys
1               5                   10                  15

Thr Gly Cys Pro Asn Ala Lys Cys Met Asn Lys Ser Cys Lys Cys Tyr
            20                  25                  30

Gly Cys Gly
        35

<210> SEQ ID NO 320
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Gln Val Gln Thr Asn Val Lys Cys Gln Gly Gly Ser Cys Ala Ser Val
1               5                   10                  15

Cys Arg Arg Glu Ile Gly Val Ala Ala Gly Lys Cys Ile Asn Gly Lys
            20                  25                  30

Cys Val Cys Tyr Arg Asn
        35

<210> SEQ ID NO 321
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Glu Val Ile Arg Cys Ser Gly Ser Lys Gln Cys Tyr Gly Pro Cys Lys
1               5                   10                  15
```

```
Gln Gln Thr Gly Cys Thr Asn Ser Lys Cys Met Asn Lys Val Cys Lys
            20                  25                  30

Cys Tyr Gly Cys Gly
        35

<210> SEQ ID NO 322
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Ala Cys Lys Gly Val Phe Asp Ala Cys Thr Pro Gly Lys Asn Glu Cys
1               5                   10                  15

Cys Pro Asn Arg Val Cys Ser Asp Lys His Lys Trp Cys Lys Trp Lys
            20                  25                  30

Leu

<210> SEQ ID NO 323
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Ile Tyr Thr Ser Lys Glu Cys Asn Gly Ser Ser Glu Cys Tyr Ser
1               5                   10                  15

His Cys Glu Gly Ile Thr Gly Lys Arg Ser Gly Lys Cys Ile Asn Lys
            20                  25                  30

Lys Cys Tyr Cys Tyr Arg
        35

<210> SEQ ID NO 324
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Phe
            20                  25                  30

Ser Phe Gly
        35

<210> SEQ ID NO 325
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Cys Val Arg Phe Trp Gly Lys Cys Ser Gln Thr Ser Asp Cys Cys
1               5                   10                  15
```

Pro His Leu Ala Cys Lys Ser Lys Trp Pro Arg Asn Ile Cys Val Trp
                20                  25                  30

Asp Gly Ser Val Gly
        35

<210> SEQ ID NO 326
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gly Cys Phe Gly Tyr Lys Cys Asp Tyr Tyr Lys Gly Cys Cys Ser Gly
1               5                   10                  15

Tyr Val Cys Ser Pro Thr Trp Lys Trp Cys Val Arg Pro Gly Pro Gly
                20                  25                  30

Arg

<210> SEQ ID NO 327
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Asn Ala Lys Phe Ile Leu Leu Val Leu Thr Thr Met Met Leu
1               5                   10                  15

Leu Pro Asp Thr Lys Gly Ala Glu Val Ile Arg Cys Ser Gly Ser Lys
                20                  25                  30

Gln Cys Tyr Gly Pro Cys Lys Gln Gln Thr Gly Cys Thr Asn Ser Lys
            35                  40                  45

Cys Met Asn Lys Val Cys Lys Cys Tyr Gly Cys Gly
        50                  55                  60

<210> SEQ ID NO 328
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Met Asn Ala Lys Leu Ile Tyr Leu Leu Leu Val Val Thr Thr Met Thr
1               5                   10                  15

Leu Met Phe Asp Thr Ala Gln Ala Val Asp Ile Met Cys Ser Gly Pro
                20                  25                  30

Lys Gln Cys Tyr Gly Pro Cys Lys Lys Glu Thr Gly Cys Pro Asn Ala
            35                  40                  45

Lys Cys Met Asn Arg Arg Cys Lys Cys Tyr Gly Cys Val
        50                  55                  60

<210> SEQ ID NO 329
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 329

Met Asn Ala Lys Leu Ile Tyr Leu Leu Val Val Thr Thr Met Met
1               5                   10                  15

Leu Thr Phe Asp Thr Thr Gln Ala Gly Asp Ile Lys Cys Ser Gly Thr
            20                  25                  30

Arg Gln Cys Trp Gly Pro Cys Lys Lys Gln Thr Thr Cys Thr Asn Ser
        35                  40                  45

Lys Cys Met Asn Gly Lys Cys Lys Cys Tyr Gly Cys Val Gly
    50                  55                  60

<210> SEQ ID NO 330
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Met Asn Thr Lys Phe Ile Phe Leu Leu Val Val Thr Asn Thr Met
1               5                   10                  15

Met Leu Phe Asp Thr Lys Pro Val Glu Gly Ile Ser Cys Thr Gly Ser
            20                  25                  30

Lys Gln Cys Tyr Asp Pro Cys Lys Arg Lys Thr Gly Cys Pro Asn Ala
        35                  40                  45

Lys Cys Met Asn Lys Ser Cys Lys Cys Tyr Gly Cys Gly
    50                  55                  60

<210> SEQ ID NO 331
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gly Val Pro Ile Asn Val Lys Cys Ser Gly Ser Arg Asp Cys Leu Glu
1               5                   10                  15

Pro Cys Lys Lys Ala Gly Met Arg Phe Gly Lys Cys Ile Asn Arg Lys
            20                  25                  30

Cys His Cys Thr Pro Lys
        35

<210> SEQ ID NO 332
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Gly Val Pro Ile Asn Val Lys Cys Thr Gly Ser Pro Gln Cys Leu Lys
1               5                   10                  15

Pro Cys Lys Asp Ala Gly Met Arg Phe Gly Lys Cys Ile Asn Gly Lys
            20                  25                  30

Cys His Cys Thr Pro Lys
        35

```
<210> SEQ ID NO 333
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 334
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gly Val Pro Ile Asn Val Lys Cys Arg Gly Ser Pro Gln Cys Ile Gln
1               5                   10                  15

Pro Cys Arg Asp Ala Gly Met Arg Phe Gly Lys Cys Met Asn Gly Lys
            20                  25                  30

Cys His Cys Thr Pro Gln
        35

<210> SEQ ID NO 335
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gly Val Glu Ile Asn Val Lys Cys Thr Gly Ser His Gln Cys Ile Lys
1               5                   10                  15

Pro Cys Lys Asp Ala Gly Met Arg Phe Gly Lys Cys Ile Asn Arg Lys
            20                  25                  30

Cys His Cys Thr Pro Lys
        35

<210> SEQ ID NO 336
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35
```

```
<210> SEQ ID NO 337
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gly Val Pro Thr Asp Val Lys Cys Arg Gly Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 338
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gly Val Pro Ile Asn Val Ser Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 339
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gly Val Pro Ile Asn Val Pro Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 340
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Val Gly Ile Asn Val Lys Cys Lys His Ser Gly Gln Cys Leu Lys Pro
1               5                   10                  15

Cys Lys Asp Ala Gly Met Arg Phe Gly Lys Cys Ile Asn Gly Lys Cys
            20                  25                  30

Asp Cys Thr Pro Lys
```

```
                35

<210> SEQ ID NO 341
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Val Gly Ile Asn Val Lys Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 342
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Val Gly Ile Pro Val Ser Cys Lys His Ser Gly Gln Cys Ile Lys Pro
1               5                   10                  15

Cys Lys Asp Ala Gly Met Arg Phe Gly Lys Cys Met Asn Arg Lys Cys
            20                  25                  30

Asp Cys Thr Pro Lys
        35

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Arg Lys Gly Cys Phe Lys Glu Gly His Ser Cys Pro Lys Thr Ala Pro
1               5                   10                  15

Cys Cys Arg Pro Leu Val Cys Lys Gly Pro Ser Pro Asn Thr Lys Lys
            20                  25                  30

Cys Thr Arg Pro
        35

<210> SEQ ID NO 344
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Ser Phe Cys Ile Pro Phe Lys Pro Cys Lys Ser Asp Glu Asn Cys Cys
1               5                   10                  15

Lys Lys Phe Lys Cys Lys Thr Thr Gly Ile Val Lys Leu Cys Arg Trp
            20                  25                  30
```

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Leu Lys Gly Cys Leu Pro Arg Asn Arg Phe Cys Asn Ala Leu Ser Gly
1               5                   10                  15

Pro Arg Cys Cys Ser Gly Leu Arg Cys Lys Glu Leu Ser Ile Trp Ala
            20                  25                  30

Ser Lys Cys Leu
        35

<210> SEQ ID NO 346
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Gly Asn Tyr Cys Leu Arg Gly Arg Cys Leu Pro Gly Gly Arg Lys Cys
1               5                   10                  15

Cys Asn Gly Arg Pro Cys Glu Cys Phe Ala Lys Ile Cys Ser Cys Lys
            20                  25                  30

Pro Lys

<210> SEQ ID NO 347
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Thr Val Lys Cys Gly Gly Cys Asn Arg Lys Cys Cys Pro Gly Gly Cys
1               5                   10                  15

Arg Ser Gly Lys Cys Ile Asn Gly Lys Cys Gln Cys Tyr
            20                  25

<210> SEQ ID NO 348
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gly Cys Met Lys Glu Tyr Cys Ala Gly Gln Cys Arg Gly Lys Val Ser
1               5                   10                  15

Gln Asp Tyr Cys Leu Lys His Cys Lys Cys Ile Pro Arg
            20                  25

<210> SEQ ID NO 349
<211> LENGTH: 34
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 349

Ala Cys Leu Gly Phe Gly Glu Lys Cys Asn Pro Ser Asn Asp Lys Cys
1               5                   10                  15

Cys Lys Ser Ser Ser Leu Val Cys Ser Gln Lys His Lys Trp Cys Lys
            20                  25                  30

Tyr Gly

<210> SEQ ID NO 350
<211> LENGTH: 37
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 350

Arg Gly Gly Cys Leu Pro His Asn Arg Phe Cys Asn Ala Leu Ser Gly
1               5                   10                  15

Pro Arg Cys Cys Ser Gly Leu Arg Cys Lys Glu Leu Ser Ile Arg Asp
            20                  25                  30

Ser Arg Cys Leu Gly
        35

<210> SEQ ID NO 351
<211> LENGTH: 36
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 351

Arg Gly Gly Cys Leu Pro Arg Asn Lys Phe Cys Asn Pro Ser Ser Gly
1               5                   10                  15

Pro Arg Cys Cys Ser Gly Leu Thr Cys Lys Glu Leu Asn Ile Trp Ala
            20                  25                  30

Ser Lys Cys Leu
        35

<210> SEQ ID NO 352
<211> LENGTH: 33
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 352

Gln Arg Ser Cys Ala Lys Pro Gly Asp Met Cys Met Gly Ile Lys Cys
1               5                   10                  15

Cys Asp Gly Gln Cys Gly Cys Asn Arg Gly Thr Gly Arg Cys Phe Cys
            20                  25                  30

Lys

<210> SEQ ID NO 353
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 353

Ala Arg Gly Cys Ala Asp Ala Tyr Lys Ser Cys Asn His Pro Arg Thr
1               5                   10                  15

Cys Cys Asp Gly Tyr Asn Gly Tyr Lys Arg Ala Cys Ile Cys Ser Gly
            20                  25                  30

Ser Asn Cys Lys Cys Lys Lys Ser
        35                  40

<210> SEQ ID NO 354
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Arg Gly Gly Cys Leu Pro His Asn Arg Phe Cys Asn Ala Leu Ser Gly
1               5                   10                  15

Pro Arg Cys Cys Ser Gly Leu Arg Cys Lys Glu Leu Ser Ile Trp Asp
            20                  25                  30

Ser Arg Cys Leu Gly
        35

<210> SEQ ID NO 355
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Arg Gly Gly Cys Leu Pro His Asn Arg Phe Cys Asn Ala Leu Ser Gly
1               5                   10                  15

Pro Arg Cys Cys Ser Gly Leu Lys Cys Lys Glu Leu Ser Ile Tyr Asp
            20                  25                  30

Ser Arg Cys Leu Gly
        35

<210> SEQ ID NO 356
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Arg Gly Gly Cys Leu Pro His Asn Arg Phe Cys Asn Ala Leu Ser Gly
1               5                   10                  15

Pro Arg Cys Cys Ser Arg Leu Lys Cys Lys Glu Leu Ser Ile Trp Asp
            20                  25                  30

Ser Arg Cys Leu Gly
        35

<210> SEQ ID NO 357
<211> LENGTH: 37
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 357

Arg Gly Gly Cys Leu Pro His Asn Arg Phe Cys Asn Ala Leu Thr Gly
1               5                   10                  15

Pro Arg Cys Cys Ser Arg Leu Arg Cys Lys Glu Leu Ser Ile Trp Asp
            20                  25                  30

Ser Ile Cys Leu Gly
        35

<210> SEQ ID NO 358
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Ser Cys Ala Asp Ala Tyr Lys Ser Cys Asp Ser Leu Lys Cys Cys Asn
1               5                   10                  15

Asn Arg Thr Cys Met Cys Ser Met Ile Gly Thr Asn Cys Thr Cys Arg
            20                  25                  30

Lys Lys

<210> SEQ ID NO 359
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Glu Arg Arg Cys Leu Pro Ala Gly Lys Thr Cys Val Arg Gly Pro Met
1               5                   10                  15

Arg Val Pro Cys Cys Gly Ser Cys Ser Gln Asn Lys Cys Thr
            20                  25                  30

<210> SEQ ID NO 360
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Leu Cys Ser Arg Glu Gly Glu Phe Cys Tyr Lys Leu Arg Lys Cys Cys
1               5                   10                  15

Ala Gly Phe Tyr Cys Lys Ala Phe Val Leu His Cys Tyr Arg Asn
            20                  25                  30

<210> SEQ ID NO 361
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ala Cys Gly Ser Cys Arg Lys Lys Cys Lys Gly Ser Gly Lys Cys Ile
1               5                   10                  15

```
Asn Gly Arg Cys Lys Cys Tyr
            20

<210> SEQ ID NO 362
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala Cys Gly Ser Cys Arg Lys Lys Cys Lys Gly Pro Gly Lys Cys Ile
1               5                   10                  15

Asn Gly Arg Cys Lys Cys Tyr
            20

<210> SEQ ID NO 363
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Ala Cys Gln Gly Tyr Met Arg Lys Cys Gly Arg Asp Lys Pro Pro Cys
1               5                   10                  15

Cys Lys Lys Leu Glu Cys Ser Lys Thr Trp Arg Trp Cys Val Trp Asn
            20                  25                  30

<210> SEQ ID NO 364
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Gly Arg Tyr Cys Gln Lys Trp Met Trp Thr Cys Asp Ser Lys Arg Ala
1               5                   10                  15

Cys Cys Glu Gly Leu Arg Cys Lys Leu Trp Cys Arg Lys Ile
            20                  25                  30

<210> SEQ ID NO 365
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Asn Ala Lys Cys Arg Gly Ser Pro Glu Cys Leu Pro Lys Cys Lys Glu
1               5                   10                  15

Ala Ile Gly Lys Ala Ala Gly Lys Cys Met Asn Gly Lys Cys Lys Cys
            20                  25                  30

Tyr Pro

<210> SEQ ID NO 366
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 366

Asn Val Lys Cys Arg Gly Ser Lys Glu Cys Leu Pro Ala Cys Lys Ala
1               5                   10                  15

Ala Val Gly Lys Ala Ala Gly Lys Cys Met Asn Gly Lys Cys Lys Cys
            20                  25                  30

Tyr Pro

<210> SEQ ID NO 367
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Asn Val Lys Cys Arg Gly Ser Pro Glu Cys Leu Pro Lys Cys Lys Glu
1               5                   10                  15

Ala Ile Gly Lys Ser Ala Gly Lys Cys Met Asn Gly Lys Cys Lys Cys
            20                  25                  30

Tyr Pro

<210> SEQ ID NO 368
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Asn Ala Lys Cys Arg Gly Ser Pro Glu Cys Leu Pro Lys Cys Lys Gln
1               5                   10                  15

Ala Ile Gly Lys Ala Ala Gly Lys Cys Met Asn Gly Lys Cys Lys Cys
            20                  25                  30

Tyr Pro

<210> SEQ ID NO 369
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Arg Gly Tyr Cys Ala Glu Lys Gly Ile Lys Cys His Asn Ile His Cys
1               5                   10                  15

Cys Ser Gly Leu Thr Cys Lys Cys Lys Gly Ser Ser Cys Val Cys Arg
            20                  25                  30

Lys

<210> SEQ ID NO 370
<211> LENGTH: 31
<212> TYPE: PRT
<213> ORGANISM: Artificial Sequence
<220> FEATURE:
<223> OTHER INFORMATION: Description of Artificial Sequence: Synthetic
```

```
                         polypeptide

<400> SEQUENCE: 370

Glu Arg Gly Cys Lys Leu Thr Phe Trp Lys Cys Lys Asn Lys Glu
1               5                   10                  15

Cys Cys Gly Trp Asn Ala Cys Ala Leu Gly Ile Cys Met Pro Arg
            20                  25                  30

<210> SEQ ID NO 371
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Lys Lys Lys Cys Ile Ala Lys Asp Tyr Gly Arg Cys Lys Trp Gly Gly
1               5                   10                  15

Thr Pro Cys Cys Arg Gly Arg Gly Cys Ile Cys Ser Ile Met Gly Thr
            20                  25                  30

Asn Cys Glu Cys Lys Pro Arg
        35

<210> SEQ ID NO 372
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Cys Lys Leu Thr Phe Trp Lys Cys Lys Asn Lys Lys Glu Cys Cys
1               5                   10                  15

Gly Trp Asn Ala Cys Ala Leu Gly Ile Cys Met Pro Arg
            20                  25

<210> SEQ ID NO 373
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Ala Cys Lys Gly Leu Phe Val Thr Cys Thr Pro Gly Lys Asp Glu Cys
1               5                   10                  15

Cys Pro Asn His Val Cys Ser Ser Lys His Lys Trp Cys Lys Tyr Lys
            20                  25                  30

<210> SEQ ID NO 374
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Ile Ala Cys Ala Pro Arg Gly Leu Leu Cys Phe Arg Asp Lys Glu Cys
1               5                   10                  15

Cys Lys Gly Leu Thr Cys Lys Gly Arg Phe Val Asn Thr Trp Pro Thr
```

```
                20                  25                  30

Phe Cys Leu Val
        35

<210> SEQ ID NO 375
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Ala Cys Ala Gly Leu Tyr Lys Lys Cys Gly Lys Gly Val Asn Thr Cys
1               5                   10                  15

Cys Glu Asn Arg Pro Cys Lys Cys Asp Leu Ala Met Gly Asn Cys Ile
                20                  25                  30

Cys Lys Lys Lys
        35

<210> SEQ ID NO 376
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Phe Thr Cys Ala Ile Ser Cys Asp Ile Lys Val Asn Gly Lys Pro Cys
1               5                   10                  15

Lys Gly Ser Gly Glu Lys Lys Cys Ser Gly Gly Trp Ser Cys Lys Phe
                20                  25                  30

Asn Val Cys Val Lys Val
        35

<210> SEQ ID NO 377
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Gly Phe Cys Ala Gln Lys Gly Ile Lys Cys His Asp Ile His Cys Cys
1               5                   10                  15

Thr Asn Leu Lys Cys Val Arg Glu Gly Ser Asn Arg Val Cys Arg Lys
                20                  25                  30

Ala

<210> SEQ ID NO 378
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Cys Ala Lys Lys Arg Asn Trp Cys Gly Lys Asn Glu Asp Cys Cys Cys
1               5                   10                  15

Pro Met Lys Cys Ile Tyr Ala Trp Tyr Asn Gln Gln Gly Ser Cys Gln
```

```
                    20                  25                  30

Ser Thr Ile Thr Gly Leu Phe Lys Lys Cys
        35                  40

<210> SEQ ID NO 379
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile
            20                  25

<210> SEQ ID NO 380
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Arg Gly Gly Cys Leu Pro His Asn Lys Phe Cys Asn Ala Leu Ser Gly
1               5                   10                  15

Pro Arg Cys Cys Ser Gly Leu Cys Lys Glu Leu Thr Ile Trp Asn
            20                  25                  30

Thr Lys Cys Leu Glu
        35

<210> SEQ ID NO 381
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Asn Val Lys Cys Thr Gly Ser Lys Gln Cys Leu Pro Ala Cys Lys Ala
1               5                   10                  15

Ala Val Gly Lys Ala Ala Gly Lys Cys Met Asn Gly Lys Cys Lys Cys
            20                  25                  30

Tyr Thr

<210> SEQ ID NO 382
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Gln Arg Ser Cys Ala Lys Pro Gly Glu Met Cys Met Arg Ile Lys Cys
1               5                   10                  15

Cys Asp Gly Gln Cys Gly Cys Asn Arg Gly Thr Gly Arg Cys Phe Cys
            20                  25                  30

Lys
```

<210> SEQ ID NO 383
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Gly Cys Ile Pro Lys His Lys Arg Cys Thr Trp Ser Gly Pro Lys Cys
1               5                   10                  15

Cys Asn Asn Ile Ser Cys His Cys Asn Ile Ser Gly Thr Leu Cys Lys
                20                  25                  30

Cys Arg Pro Gly
        35

<210> SEQ ID NO 384
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Asn Tyr Cys Val Ala Lys Arg Cys Arg Pro Gly Gly Arg Gln Cys Cys
1               5                   10                  15

Ser Gly Lys Pro Cys Ala Cys Val Gly Lys Val Cys Lys Cys Pro Arg
                20                  25                  30

Asp

<210> SEQ ID NO 385
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Glu Arg Gly Cys Ser Gly Ala Tyr Lys Arg Cys Ser Ser Ser Gln Arg
1               5                   10                  15

Cys Cys Glu Gly Arg Pro Cys Val Cys Ser Ala Ile Asn Ser Asn Cys
                20                  25                  30

Lys Cys Arg Lys Thr
        35

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Arg Tyr Cys Pro Arg Asn Pro Glu Ala Cys Tyr Asn Tyr Cys Leu Arg
1               5                   10                  15

Thr Gly Arg Pro Gly Gly Tyr Cys Gly Gly Arg Ser Arg Ile Thr Cys
                20                  25                  30

Phe Cys Phe Arg
        35

<210> SEQ ID NO 387
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Gln Arg Ser Cys Ala Lys Pro Gly Glu Met Cys Met Gly Ile Lys Cys
1               5                   10                  15

Cys Asp Gly Gln Cys Gly Cys Asn Arg Gly Thr Gly Arg Cys Phe Cys
            20                  25                  30

Lys

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Arg Arg Gly Cys Phe Lys Glu Gly Lys Trp Cys Pro Lys Ser Ala Pro
1               5                   10                  15

Cys Cys Ala Pro Leu Lys Cys Lys Gly Pro Ser Ile Lys Gln Gln Lys
            20                  25                  30

Cys Val Arg Glu
        35

<210> SEQ ID NO 389
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Thr Val Lys Cys Gly Gly Cys Asn Arg Lys Cys Cys Ala Gly Gly Cys
1               5                   10                  15

Arg Ser Gly Lys Cys Ile Asn Gly Lys Cys Gln Cys Tyr Gly Arg
            20                  25                  30

<210> SEQ ID NO 390
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Glu Arg Arg Cys Glu Pro Ser Gly Lys Pro Cys Arg Pro Leu Met Arg
1               5                   10                  15

Ile Pro Cys Cys Gly Ser Cys Val Arg Gly Lys Cys Ala
            20                  25

<210> SEQ ID NO 391
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 391

Arg Gly Gly Cys Leu Pro Arg Asn Lys Phe Cys Asn Pro Ser Ser Gly
1               5                   10                  15

Pro Arg Cys Cys Ser Gly Leu Thr Cys Lys Glu Leu Asn Ile Trp Ala
            20                  25                  30

Asn Lys Cys Leu
        35

<210> SEQ ID NO 392
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Cys Ala Lys Lys Arg Asn Trp Cys Gly Lys Asn Glu Asp Cys Cys Cys
1               5                   10                  15

Pro Met Lys Cys Ile Tyr Ala Trp Tyr Asn Gln Gly Ser Cys Gln
            20                  25                  30

Thr Thr Ile Thr Gly Leu Phe Lys Lys Cys
        35                  40

<210> SEQ ID NO 393
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Val Arg Ile Pro Val Ser Cys Lys His Ser Gly Gln Cys Leu Lys Pro
1               5                   10                  15

Cys Lys Asp Ala Gly Met Arg Thr Gly Lys Cys Met Asn Gly Lys Cys
            20                  25                  30

Asp Cys Thr Pro Lys
        35

<210> SEQ ID NO 394
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Val Lys Cys Thr Thr Ser Lys Asp Cys Trp Pro Pro Cys Lys Lys Val
1               5                   10                  15

Thr Gly Arg Ala
            20

<210> SEQ ID NO 395
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 395

Gly Ile Val Cys Arg Val Cys Arg Ile Ile Cys Gly Met Gln Gly Arg
1               5                   10                  15

Arg Val Asn Ile Cys Arg Ala Pro Ile Arg Cys Arg Cys Arg Arg Gly
            20                  25                  30

<210> SEQ ID NO 396
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Ser Glu Arg Asp Cys Ile Arg His Leu Gln Arg Cys Arg Glu Asn Arg
1               5                   10                  15

Asp Cys Cys Ser Arg Arg Cys Ser Arg Arg Gly Thr Asn Pro Glu Arg
            20                  25                  30

Arg Cys Arg
        35

<210> SEQ ID NO 397
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Val Arg Ile Pro Val Ser Cys Arg His Ser Gly Gln Cys Leu Arg Pro
1               5                   10                  15

Cys Arg Asp Ala Gly Met Arg Phe Gly Arg Cys Met Asn Gly Arg Cys
            20                  25                  30

Asp Cys Thr Pro Arg
        35

<210> SEQ ID NO 398
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Gly Val Pro Ile Asn Val Arg Cys Arg Gly Ser Arg Asp Cys Leu Asp
1               5                   10                  15

Pro Cys Arg Arg Ala Gly Met Arg Phe Gly Arg Cys Ile Asn Ser Arg
            20                  25                  30

Cys His Cys Thr Pro
        35

<210> SEQ ID NO 399
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 399

Ala Val Cys Val Tyr Arg Thr Cys Asp Arg Asp Cys Arg Arg Gly
1               5                   10                  15

Tyr Arg Ser Gly Arg Cys Ile Asn Asn Ala Cys Arg Cys Tyr Pro Tyr
            20                  25                  30

Gly

<210> SEQ ID NO 400
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Ile Ser Cys Thr Gly Ser Arg Gln Cys Tyr Asp Pro Cys Arg Arg Arg
1               5                   10                  15

Thr Gly Cys Pro Asn Ala Arg Cys Met Asn Arg Ser Cys Arg Cys Tyr
            20                  25                  30

Gly Cys Gly
        35

<210> SEQ ID NO 401
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gln Val Gln Thr Asn Val Arg Cys Gln Gly Gly Ser Cys Ala Ser Val
1               5                   10                  15

Cys Arg Arg Glu Ile Gly Val Ala Ala Gly Arg Cys Ile Asn Gly Arg
            20                  25                  30

Cys Val Cys Tyr Arg Asn
        35

<210> SEQ ID NO 402
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Glu Val Ile Arg Cys Ser Gly Ser Arg Gln Cys Tyr Gly Pro Cys Arg
1               5                   10                  15

Gln Gln Thr Gly Cys Thr Asn Ser Arg Cys Met Asn Arg Val Cys Arg
            20                  25                  30

Cys Tyr Gly Cys Gly
        35

<210> SEQ ID NO 403
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 403

Ala Cys Arg Gly Val Phe Asp Ala Cys Thr Pro Gly Arg Asn Glu Cys
1               5                   10                  15

Cys Pro Asn Arg Val Cys Ser Asp Arg His Arg Trp Cys Arg Trp Arg
                20                  25                  30

Leu

<210> SEQ ID NO 404
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Gln Ile Tyr Thr Ser Arg Glu Cys Asn Gly Ser Ser Glu Cys Tyr Ser
1               5                   10                  15

His Cys Glu Gly Ile Thr Gly Arg Arg Ser Gly Arg Cys Ile Asn Arg
                20                  25                  30

Arg Cys Tyr Cys Tyr Arg
            35

<210> SEQ ID NO 405
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Gly Cys Leu Glu Phe Trp Trp Arg Cys Asn Pro Asn Asp Asp Arg Cys
1               5                   10                  15

Cys Arg Pro Arg Leu Arg Cys Ser Arg Leu Phe Arg Leu Cys Asn Phe
                20                  25                  30

Ser Phe Gly
        35

<210> SEQ ID NO 406
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Asp Cys Val Arg Phe Trp Gly Arg Cys Ser Gln Thr Ser Asp Cys Cys
1               5                   10                  15

Pro His Leu Ala Cys Arg Ser Arg Trp Pro Arg Asn Ile Cys Val Trp
                20                  25                  30

Asp Gly Ser Val Gly
        35

<210> SEQ ID NO 407
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 407

Gly Cys Phe Gly Tyr Arg Cys Asp Tyr Tyr Arg Gly Cys Cys Ser Gly
1               5                   10                  15

Tyr Val Cys Ser Pro Thr Trp Arg Trp Cys Val Arg Pro Gly Pro Gly
            20                  25                  30

Arg

<210> SEQ ID NO 408
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Met Asn Ala Arg Phe Ile Leu Leu Val Leu Thr Thr Met Met Leu
1               5                   10                  15

Leu Pro Asp Thr Arg Gly Ala Glu Val Ile Arg Cys Ser Gly Ser Arg
            20                  25                  30

Gln Cys Tyr Gly Pro Cys Arg Gln Gln Thr Gly Cys Thr Asn Ser Arg
        35                  40                  45

Cys Met Asn Arg Val Cys Arg Cys Tyr Gly Cys Gly
    50                  55                  60

<210> SEQ ID NO 409
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Met Asn Ala Arg Leu Ile Tyr Leu Leu Val Val Thr Thr Met Thr
1               5                   10                  15

Leu Met Phe Asp Thr Ala Gln Ala Val Asp Ile Met Cys Ser Gly Pro
            20                  25                  30

Arg Gln Cys Tyr Gly Pro Cys Arg Arg Glu Thr Gly Cys Pro Asn Ala
        35                  40                  45

Arg Cys Met Asn Arg Arg Cys Arg Cys Tyr Gly Cys Val
    50                  55                  60

<210> SEQ ID NO 410
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Met Asn Ala Arg Leu Ile Tyr Leu Leu Val Val Thr Thr Met Met
1               5                   10                  15

Leu Thr Phe Asp Thr Thr Gln Ala Gly Asp Ile Arg Cys Ser Gly Thr
            20                  25                  30

Arg Gln Cys Trp Gly Pro Cys Arg Arg Gln Thr Thr Cys Thr Asn Ser
        35                  40                  45

Arg Cys Met Asn Gly Arg Cys Arg Cys Tyr Gly Cys Val Gly
    50                  55                  60
```

```
<210> SEQ ID NO 411
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Met Asn Thr Arg Phe Ile Phe Leu Leu Leu Val Val Thr Asn Thr Met
1               5                   10                  15

Met Leu Phe Asp Thr Arg Pro Val Glu Gly Ile Ser Cys Thr Gly Ser
            20                  25                  30

Arg Gln Cys Tyr Asp Pro Cys Arg Arg Thr Gly Cys Pro Asn Ala
        35                  40                  45

Arg Cys Met Asn Arg Ser Cys Arg Cys Tyr Gly Cys Gly
    50                  55                  60

<210> SEQ ID NO 412
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Gly Val Pro Ile Asn Val Arg Cys Ser Gly Ser Arg Asp Cys Leu Glu
1               5                   10                  15

Pro Cys Arg Arg Ala Gly Met Arg Phe Gly Arg Cys Ile Asn Arg Arg
            20                  25                  30

Cys His Cys Thr Pro Arg
        35

<210> SEQ ID NO 413
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Gly Val Pro Ile Asn Val Arg Cys Thr Gly Ser Pro Gln Cys Leu Arg
1               5                   10                  15

Pro Cys Arg Asp Ala Gly Met Arg Phe Gly Arg Cys Ile Asn Gly Arg
            20                  25                  30

Cys His Cys Thr Pro Arg
        35

<210> SEQ ID NO 414
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Gly Val Ile Ile Asn Val Arg Cys Arg Ile Ser Arg Gln Cys Leu Glu
1               5                   10                  15

Pro Cys Arg Arg Ala Gly Met Arg Phe Gly Arg Cys Met Asn Gly Arg
            20                  25                  30
```

Cys His Cys Thr Pro Arg
        35

<210> SEQ ID NO 415
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Gly Val Pro Ile Asn Val Arg Cys Arg Gly Ser Pro Gln Cys Ile Gln
1               5                   10                  15

Pro Cys Arg Asp Ala Gly Met Arg Phe Gly Arg Cys Met Asn Gly Arg
            20                  25                  30

Cys His Cys Thr Pro Gln
        35

<210> SEQ ID NO 416
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Gly Val Glu Ile Asn Val Arg Cys Thr Gly Ser His Gln Cys Ile Arg
1               5                   10                  15

Pro Cys Arg Asp Ala Gly Met Arg Phe Gly Arg Cys Ile Asn Arg Arg
            20                  25                  30

Cys His Cys Thr Pro Arg
        35

<210> SEQ ID NO 417
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Gly Val Glu Ile Asn Val Arg Cys Ser Gly Ser Pro Gln Cys Leu Arg
1               5                   10                  15

Pro Cys Arg Asp Ala Gly Met Arg Phe Gly Arg Cys Met Asn Arg Arg
            20                  25                  30

Cys His Cys Thr Pro Arg
        35

<210> SEQ ID NO 418
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Gly Val Pro Thr Asp Val Arg Cys Arg Gly Ser Pro Gln Cys Ile Gln
1               5                   10                  15

Pro Cys Arg Asp Ala Gly Met Arg Phe Gly Arg Cys Met Asn Gly Arg

Cys His Cys Thr Pro Arg
        35

<210> SEQ ID NO 419
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Gly Val Pro Ile Asn Val Ser Cys Thr Gly Ser Pro Gln Cys Ile Arg
1               5                   10                  15

Pro Cys Arg Asp Ala Gly Met Arg Phe Gly Arg Cys Met Asn Arg Arg
            20                  25                  30

Cys His Cys Thr Pro Arg
        35

<210> SEQ ID NO 420
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Gly Val Pro Ile Asn Val Pro Cys Thr Gly Ser Pro Gln Cys Ile Arg
1               5                   10                  15

Pro Cys Arg Asp Ala Gly Met Arg Phe Gly Arg Cys Met Asn Arg Arg
            20                  25                  30

Cys His Cys Thr Pro Arg
        35

<210> SEQ ID NO 421
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Val Gly Ile Asn Val Arg Cys Arg His Ser Gly Gln Cys Leu Arg Pro
1               5                   10                  15

Cys Arg Asp Ala Gly Met Arg Phe Gly Arg Cys Ile Asn Gly Arg Cys
            20                  25                  30

Asp Cys Thr Pro Arg
        35

<210> SEQ ID NO 422
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Val Gly Ile Asn Val Arg Cys Arg His Ser Gly Gln Cys Leu Arg Pro
1               5                   10                  15

```
Cys Arg Asp Ala Gly Met Arg Phe Gly Arg Cys Met Asn Gly Arg Cys
            20                  25                  30

Asp Cys Thr Pro Arg
        35

<210> SEQ ID NO 423
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Val Gly Ile Pro Val Ser Cys Arg His Ser Gly Gln Cys Ile Arg Pro
1               5                   10                  15

Cys Arg Asp Ala Gly Met Arg Phe Gly Arg Cys Met Asn Arg Arg Cys
            20                  25                  30

Asp Cys Thr Pro Arg
        35

<210> SEQ ID NO 424
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Arg Arg Gly Cys Phe Arg Glu Gly His Ser Cys Pro Arg Thr Ala Pro
1               5                   10                  15

Cys Cys Arg Pro Leu Val Cys Arg Gly Pro Ser Pro Asn Thr Arg Arg
            20                  25                  30

Cys Thr Arg Pro
        35

<210> SEQ ID NO 425
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Ser Phe Cys Ile Pro Phe Arg Pro Cys Arg Ser Asp Glu Asn Cys Cys
1               5                   10                  15

Arg Arg Phe Arg Cys Arg Thr Thr Gly Ile Val Arg Leu Cys Arg Trp
            20                  25                  30

<210> SEQ ID NO 426
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Leu Arg Gly Cys Leu Pro Arg Asn Arg Phe Cys Asn Ala Leu Ser Gly
1               5                   10                  15

Pro Arg Cys Cys Ser Gly Leu Arg Cys Arg Glu Leu Ser Ile Trp Ala
            20                  25                  30
```

-continued

Ser Arg Cys Leu
        35

<210> SEQ ID NO 427
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Gly Asn Tyr Cys Leu Arg Gly Arg Cys Leu Pro Gly Gly Arg Cys
1               5                   10                  15

Cys Asn Gly Arg Pro Cys Glu Cys Phe Ala Arg Ile Cys Ser Cys Arg
            20                  25                  30

Pro Arg

<210> SEQ ID NO 428
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Thr Val Arg Cys Gly Gly Cys Asn Arg Arg Cys Cys Pro Gly Gly Cys
1               5                   10                  15

Arg Ser Gly Arg Cys Ile Asn Gly Arg Cys Gln Cys Tyr
            20                  25

<210> SEQ ID NO 429
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gly Cys Met Arg Glu Tyr Cys Ala Gly Gln Cys Arg Gly Arg Val Ser
1               5                   10                  15

Gln Asp Tyr Cys Leu Arg His Cys Arg Cys Ile Pro Arg
            20                  25

<210> SEQ ID NO 430
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Ala Cys Leu Gly Phe Gly Glu Arg Cys Asn Pro Ser Asn Asp Arg Cys
1               5                   10                  15

Cys Arg Ser Ser Ser Leu Val Cys Ser Gln Arg His Arg Trp Cys Arg
            20                  25                  30

Tyr Gly

<210> SEQ ID NO 431
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Arg Asp
                20                  25                  30

Ser Arg Cys Leu Gly
                35

<210> SEQ ID NO 432
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Arg Gly Gly Cys Leu Pro Arg Asn Arg Phe Cys Asn Pro Ser Ser Gly
1               5                   10                  15

Pro Arg Cys Cys Ser Gly Leu Thr Cys Arg Glu Leu Asn Ile Trp Ala
                20                  25                  30

Ser Arg Cys Leu
                35

<210> SEQ ID NO 433
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Gln Arg Ser Cys Ala Arg Pro Gly Asp Met Cys Met Gly Ile Arg Cys
1               5                   10                  15

Cys Asp Gly Gln Cys Gly Cys Asn Arg Gly Thr Gly Arg Cys Phe Cys
                20                  25                  30

Arg

<210> SEQ ID NO 434
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Ala Arg Gly Cys Ala Asp Ala Tyr Arg Ser Cys Asn His Pro Arg Thr
1               5                   10                  15

Cys Cys Asp Gly Tyr Asn Gly Tyr Arg Arg Ala Cys Ile Cys Ser Gly
                20                  25                  30

Ser Asn Cys Arg Cys Arg Arg Ser
                35                  40

<210> SEQ ID NO 435
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Trp Asp
            20                  25                  30

Ser Arg Cys Leu Gly
        35

<210> SEQ ID NO 436
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Tyr Asp
            20                  25                  30

Ser Arg Cys Leu Gly
        35

<210> SEQ ID NO 437
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Arg Gly Gly Cys Leu Pro His Asn Arg Phe Cys Asn Ala Leu Ser Gly
1               5                   10                  15

Pro Arg Cys Cys Ser Arg Leu Arg Cys Arg Glu Leu Ser Ile Trp Asp
            20                  25                  30

Ser Arg Cys Leu Gly
        35

<210> SEQ ID NO 438
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Arg Gly Gly Cys Leu Pro His Asn Arg Phe Cys Asn Ala Leu Thr Gly
1               5                   10                  15

Pro Arg Cys Cys Ser Arg Leu Arg Cys Arg Glu Leu Ser Ile Trp Asp
            20                  25                  30

Ser Ile Cys Leu Gly
        35

<210> SEQ ID NO 439
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Ser Cys Ala Asp Ala Tyr Lys Ser Cys Asp Ser Leu Arg Cys Cys Asn
1               5                   10                  15

Asn Arg Thr Cys Met Cys Ser Met Ile Gly Thr Asn Cys Thr Cys Arg
            20                  25                  30

Arg Arg

<210> SEQ ID NO 440
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Glu Arg Arg Cys Leu Pro Ala Gly Arg Thr Cys Val Arg Gly Pro Met
1               5                   10                  15

Arg Val Pro Cys Cys Gly Ser Cys Ser Gln Asn Arg Cys Thr
            20                  25                  30

<210> SEQ ID NO 441
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Leu Cys Ser Arg Glu Gly Glu Phe Cys Tyr Arg Leu Arg Cys Cys
1               5                   10                  15

Ala Gly Phe Tyr Cys Arg Ala Phe Val Leu His Cys Tyr Arg Asn
            20                  25                  30

<210> SEQ ID NO 442
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Ala Cys Gly Ser Cys Arg Arg Cys Arg Gly Ser Gly Arg Cys Ile
1               5                   10                  15

Asn Gly Arg Cys Arg Cys Tyr
            20

<210> SEQ ID NO 443
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443
```

```
Ala Cys Gly Ser Cys Arg Arg Arg Cys Arg Gly Pro Gly Arg Cys Ile
1               5                   10                  15

Asn Gly Arg Cys Arg Cys Tyr
            20
```

<210> SEQ ID NO 444
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

```
Ala Cys Gln Gly Tyr Met Arg Arg Cys Gly Arg Asp Arg Pro Pro Cys
1               5                   10                  15

Cys Arg Arg Leu Glu Cys Ser Arg Thr Trp Arg Trp Cys Val Trp Asn
                20                  25                  30
```

<210> SEQ ID NO 445
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

```
Gly Arg Tyr Cys Gln Arg Trp Met Trp Thr Cys Asp Ser Arg Arg Ala
1               5                   10                  15

Cys Cys Glu Gly Leu Arg Cys Arg Leu Trp Cys Arg Arg Ile
                20                  25                  30
```

<210> SEQ ID NO 446
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

```
Asn Ala Arg Cys Arg Gly Ser Pro Glu Cys Leu Pro Arg Cys Arg Glu
1               5                   10                  15

Ala Ile Gly Arg Ala Ala Gly Arg Cys Met Asn Gly Arg Cys Arg Cys
                20                  25                  30

Tyr Pro
```

<210> SEQ ID NO 447
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

```
Asn Val Arg Cys Arg Gly Ser Arg Glu Cys Leu Pro Ala Cys Arg Ala
1               5                   10                  15

Ala Val Gly Arg Ala Ala Gly Arg Cys Met Asn Gly Arg Cys Arg Cys
                20                  25                  30

Tyr Pro
```

-continued

```
<210> SEQ ID NO 448
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Asn Val Arg Cys Arg Gly Ser Pro Glu Cys Leu Pro Arg Cys Arg Glu
1               5                   10                  15

Ala Ile Gly Arg Ser Ala Gly Arg Cys Met Asn Gly Arg Cys Arg Cys
            20                  25                  30

Tyr Pro

<210> SEQ ID NO 449
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Asn Ala Arg Cys Arg Gly Ser Pro Glu Cys Leu Pro Arg Cys Arg Gln
1               5                   10                  15

Ala Ile Gly Arg Ala Ala Gly Arg Cys Met Asn Gly Arg Cys Arg Cys
            20                  25                  30

Tyr Pro

<210> SEQ ID NO 450
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Arg Gly Tyr Cys Ala Glu Arg Gly Ile Arg Cys His Asn Ile His Cys
1               5                   10                  15

Cys Ser Gly Leu Thr Cys Arg Cys Arg Gly Ser Ser Cys Val Cys Arg
            20                  25                  30

Arg

<210> SEQ ID NO 451
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Arg Gly Cys Arg Leu Thr Phe Trp Arg Cys Arg Asn Arg Arg Glu
1               5                   10                  15

Cys Cys Gly Trp Asn Ala Cys Ala Leu Gly Ile Cys Met Pro Arg
            20                  25                  30

<210> SEQ ID NO 452
<211> LENGTH: 39
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 452

Arg Arg Arg Cys Ile Ala Arg Asp Tyr Gly Arg Cys Arg Trp Gly Gly
1               5                   10                  15

Thr Pro Cys Cys Arg Gly Arg Gly Cys Ile Cys Ser Ile Met Gly Thr
            20                  25                  30

Asn Cys Glu Cys Arg Pro Arg
        35

<210> SEQ ID NO 453
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Cys Arg Leu Thr Phe Trp Arg Cys Arg Asn Arg Glu Cys Cys
1               5                   10                  15

Gly Trp Asn Ala Cys Ala Leu Gly Ile Cys Met Pro Arg
            20                  25

<210> SEQ ID NO 454
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Ala Cys Arg Gly Leu Phe Val Thr Cys Thr Pro Gly Arg Asp Glu Cys
1               5                   10                  15

Cys Pro Asn His Val Cys Ser Ser Arg His Arg Trp Cys Arg Tyr Arg
            20                  25                  30

<210> SEQ ID NO 455
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Ile Ala Cys Ala Pro Arg Gly Leu Leu Cys Phe Arg Asp Arg Glu Cys
1               5                   10                  15

Cys Arg Gly Leu Thr Cys Arg Gly Arg Phe Val Asn Thr Trp Pro Thr
            20                  25                  30

Phe Cys Leu Val
        35

<210> SEQ ID NO 456
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Ala Cys Ala Gly Leu Tyr Arg Arg Cys Gly Arg Gly Val Asn Thr Cys
1               5                   10                  15

Cys Glu Asn Arg Pro Cys Arg Cys Asp Leu Ala Met Gly Asn Cys Ile
                20                  25                  30

Cys Arg Arg Arg
        35

<210> SEQ ID NO 457
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Phe Thr Cys Ala Ile Ser Cys Asp Ile Arg Val Asn Gly Arg Pro Cys
1               5                   10                  15

Arg Gly Ser Gly Glu Arg Arg Cys Ser Gly Gly Trp Ser Cys Arg Phe
                20                  25                  30

Asn Val Cys Val Arg Val
        35

<210> SEQ ID NO 458
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Gly Phe Cys Ala Gln Arg Gly Ile Arg Cys His Asp Ile His Cys Cys
1               5                   10                  15

Thr Asn Leu Arg Cys Val Arg Glu Gly Ser Asn Arg Val Cys Arg Arg
                20                  25                  30

Ala

<210> SEQ ID NO 459
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Cys Ala Arg Arg Arg Asn Trp Cys Gly Arg Asn Glu Asp Cys Cys Cys
1               5                   10                  15

Pro Met Arg Cys Ile Tyr Ala Trp Tyr Asn Gln Gln Gly Ser Cys Gln
                20                  25                  30

Ser Thr Ile Thr Gly Leu Phe Arg Arg Cys
        35                  40

<210> SEQ ID NO 460
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Tyr Cys Gln Arg Trp Met Trp Thr Cys Asp Ser Ala Arg Arg Cys Cys
1               5                   10                  15

Glu Gly Leu Val Cys Arg Leu Trp Cys Arg Arg Ile
            20                  25

<210> SEQ ID NO 461
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Thr Ile Trp Asn
            20                  25                  30

Thr Arg Cys Leu Glu
        35

<210> SEQ ID NO 462
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Asn Val Arg Cys Thr Gly Ser Arg Gln Cys Leu Pro Ala Cys Arg Ala
1               5                   10                  15

Ala Val Gly Arg Ala Ala Gly Arg Cys Met Asn Gly Arg Cys Arg Cys
            20                  25                  30

Tyr Thr

<210> SEQ ID NO 463
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Gln Arg Ser Cys Ala Arg Pro Gly Glu Met Cys Met Arg Ile Arg Cys
1               5                   10                  15

Cys Asp Gly Gln Cys Gly Cys Asn Arg Gly Thr Gly Arg Cys Phe Cys
            20                  25                  30

Arg

<210> SEQ ID NO 464
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gly Cys Ile Pro Arg His Arg Arg Cys Thr Trp Ser Gly Pro Arg Cys
1               5                   10                  15

Cys Asn Asn Ile Ser Cys His Cys Asn Ile Ser Gly Thr Leu Cys Arg

```
                    20                  25                  30

Cys Arg Pro Gly
        35

<210> SEQ ID NO 465
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Asn Tyr Cys Val Ala Arg Arg Cys Arg Pro Gly Arg Gln Cys Cys
1               5                   10                  15

Ser Gly Arg Pro Cys Ala Cys Val Gly Arg Val Cys Arg Cys Pro Arg
            20                  25                  30

Asp

<210> SEQ ID NO 466
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Glu Arg Gly Cys Ser Gly Ala Tyr Arg Arg Cys Ser Ser Ser Gln Arg
1               5                   10                  15

Cys Cys Glu Gly Arg Pro Cys Val Cys Ser Ala Ile Asn Ser Asn Cys
            20                  25                  30

Arg Cys Arg Arg Thr
        35

<210> SEQ ID NO 467
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Gln Arg Ser Cys Ala Arg Pro Gly Glu Met Cys Met Gly Ile Arg Cys
1               5                   10                  15

Cys Asp Gly Gln Cys Gly Cys Asn Arg Gly Thr Gly Arg Cys Phe Cys
            20                  25                  30

Arg

<210> SEQ ID NO 468
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Arg Arg Gly Cys Phe Arg Glu Gly Arg Trp Cys Pro Arg Ser Ala Pro
1               5                   10                  15

Cys Cys Ala Pro Leu Arg Cys Arg Gly Pro Ser Ile Arg Gln Gln Arg
            20                  25                  30
```

```
Cys Val Arg Glu
        35

<210> SEQ ID NO 469
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Thr Val Arg Cys Gly Gly Cys Asn Arg Arg Cys Cys Ala Gly Gly Cys
1               5                   10                  15

Arg Ser Gly Arg Cys Ile Asn Gly Arg Cys Gln Cys Tyr Gly Arg
            20                  25                  30

<210> SEQ ID NO 470
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Glu Arg Arg Cys Glu Pro Ser Gly Arg Pro Cys Arg Pro Leu Met Arg
1               5                   10                  15

Ile Pro Cys Cys Gly Ser Cys Val Arg Gly Arg Cys Ala
            20                  25

<210> SEQ ID NO 471
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Arg Gly Gly Cys Leu Pro Arg Asn Arg Phe Cys Asn Pro Ser Ser Gly
1               5                   10                  15

Pro Arg Cys Cys Ser Gly Leu Thr Cys Arg Glu Leu Asn Ile Trp Ala
            20                  25                  30

Asn Arg Cys Leu
        35

<210> SEQ ID NO 472
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Cys Ala Arg Arg Arg Asn Trp Cys Gly Arg Asn Glu Asp Cys Cys Cys
1               5                   10                  15

Pro Met Arg Cys Ile Tyr Ala Trp Tyr Asn Gln Gln Gly Ser Cys Gln
            20                  25                  30

Thr Thr Ile Thr Gly Leu Phe Arg Arg Cys
        35                  40
```

```
<210> SEQ ID NO 473
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Val Arg Ile Pro Val Ser Cys Arg His Ser Gly Gln Cys Leu Arg Pro
1               5                   10                  15

Cys Arg Asp Ala Gly Met Arg Thr Gly Arg Cys Met Asn Gly Arg Cys
            20                  25                  30

Asp Cys Thr Pro Arg
        35

<210> SEQ ID NO 474
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gln Lys Ile Leu Ser Asn Arg Cys Asn Asn Ser Ser Glu Cys Ile Pro
1               5                   10                  15

His Cys Ile Arg Ile Phe Gly Thr Arg Ala Ala Lys Cys Ile Asn Arg
            20                  25                  30

Lys Cys Tyr Cys Tyr Pro
        35

<210> SEQ ID NO 475
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Ala Val Cys Asn Leu Lys Arg Cys Gln Leu Ser Cys Arg Ser Leu Gly
1               5                   10                  15

Leu Leu Gly Lys Cys Ile Gly Asp Lys Cys Glu Cys Val Lys His Gly
            20                  25                  30

<210> SEQ ID NO 476
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Ile Ser Ile Gly Ile Arg Cys Ser Pro Ser Ile Asp Leu Cys Glu Gly
1               5                   10                  15

Gln Cys Arg Ile Arg Arg Tyr Phe Thr Gly Tyr Cys Ser Gly Asp Thr
            20                  25                  30

Cys His Cys Ser Gly
        35

<210> SEQ ID NO 477
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Gly Asp Cys Leu Pro His Leu Arg Arg Cys Arg Glu Asn Asn Asp Cys
1               5                   10                  15

Cys Ser Arg Arg Cys Arg Arg Gly Ala Asn Pro Glu Arg Arg Cys
            20                  25                  30

Arg

<210> SEQ ID NO 478
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Ser Cys Glu Pro Gly Arg Thr Phe Arg Asp Arg Cys Asn Thr Cys Lys
1               5                   10                  15

Cys Gly Ala Asp Gly Arg Ser Ala Ala Cys Thr Leu Arg Ala Cys Pro
            20                  25                  30

Asn Gln

<210> SEQ ID NO 479
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg

<210> SEQ ID NO 480
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg

<210> SEQ ID NO 481
<211> LENGTH: 33
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 481

Lys Asp Cys Leu Lys Lys Leu Lys Leu Cys Lys Glu Asn Lys Asp Cys
1               5                   10                  15

Cys Ser Lys Ser Cys Lys Arg Arg Gly Thr Asn Ile Glu Lys Arg Cys
                20                  25                  30

Arg

<210> SEQ ID NO 482
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
                20                  25                  30

Arg

<210> SEQ ID NO 483
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Val Phe Ile Asn Val Lys Cys Arg Gly Ser Pro Glu Cys Leu Pro Lys
1               5                   10                  15

Cys Lys Glu Ala Ile Gly Lys Ser Ala Gly Lys Cys Met Asn Gly Lys
                20                  25                  30

Cys Lys Cys Tyr Pro
        35

<210> SEQ ID NO 484
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
                20                  25                  30

Cys Lys Cys Tyr Pro
        35

<210> SEQ ID NO 485
<211> LENGTH: 36
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 485

Val Ile Ile Asn Val Lys Cys Lys Ile Ser Arg Gln Cys Leu Glu Pro
1               5                   10                  15

Cys Lys Lys Ala Gly Met Arg Phe Gly Lys Cys Met Asn Gly Lys Cys
            20                  25                  30

His Cys Thr Pro
        35

<210> SEQ ID NO 486
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Val Pro Thr Asp Val Lys Cys Arg Gly Ser Pro Gln Cys Ile Gln Pro
1               5                   10                  15

Cys Lys Asp Ala Gly Met Arg Phe Gly Lys Cys Met Asn Gly Lys Cys
            20                  25                  30

His Cys Thr Pro
        35

<210> SEQ ID NO 487
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro
        35

<210> SEQ ID NO 488
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Val Arg Ile Pro Val Ser Cys Arg His Ser Gly Gln Cys Leu Arg Pro
1               5                   10                  15

Cys Arg Asp Ala Gly Met Arg Phe Gly Arg Cys Met Asn Gly Arg Cys
            20                  25                  30

Asp Cys Thr Pro
        35

<210> SEQ ID NO 489
<211> LENGTH: 33
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 489

Thr Asn Val Ser Cys Thr Thr Ser Lys Glu Cys Trp Ser Val Cys Gln
1               5                   10                  15

Arg Leu His Asn Thr Ser Arg Gly Lys Cys Met Asn Lys Lys Cys Arg
            20                  25                  30

Cys

<210> SEQ ID NO 490
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Asn Val Lys Cys Thr Gly Ser Lys Gln Cys Leu Pro Ala Cys Lys Ala
1               5                   10                  15

Ala Val Gly Lys Ala Ala Gly Lys Cys Met Asn Gly Lys Cys Lys Cys
            20                  25                  30

<210> SEQ ID NO 491
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Gly Val Pro Ile Asn Val Arg Cys Arg Gly Ser Arg Asp Cys Leu Asp
1               5                   10                  15

Pro Cys Arg Gly Ala Gly Glu Arg His Gly Arg Cys Gly Asn Ser Arg
            20                  25                  30

Cys His Cys Thr Pro
        35

<210> SEQ ID NO 492
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Val Arg Ile Pro Val Ser Cys Arg His Ser Gly Gln Cys Leu Arg Pro
1               5                   10                  15

Cys Arg Asp Ala Gly Glu Arg His Gly Arg Cys Gly Gly Gly Arg Cys
            20                  25                  30

Asp Cys Thr Pro Arg
        35

<210> SEQ ID NO 493
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 493

Gln Val Gln Thr Asn Val Arg Cys Gln Gly Gly Ser Cys Ser Val
1               5                   10                  15

Cys Arg Arg Glu Gly Gly Ala Gly Gly Cys Gly Asn Gly Arg
                20                  25                  30

Cys Gly Cys Tyr Arg Asn
            35

<210> SEQ ID NO 494
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Ile Lys Cys Ser Glu Ser Tyr Gln Cys Phe Pro Val Cys Lys Ser Arg
1               5                   10                  15

Phe Gly Lys Thr Asn Gly Arg Cys Val Asn Gly Phe Cys Asp Cys Phe
                20                  25                  30

<210> SEQ ID NO 495
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Val Lys Cys Ser Ser Pro Gln Gln Cys Leu Lys Pro Cys Lys Ala Ala
1               5                   10                  15

Phe Gly Ile Ser Ala Gly Gly Lys Cys Ile Asn Gly Lys Cys Lys Cys
                20                  25                  30

Tyr

<210> SEQ ID NO 496
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Val Ser Cys Ser Ala Ser Ser Gln Cys Trp Pro Val Cys Lys Lys Leu
1               5                   10                  15

Phe Gly Thr Tyr Arg Gly Lys Cys Met Asn Ser Lys Cys Arg Cys Tyr
                20                  25                  30

<210> SEQ ID NO 497
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Glu Ser Cys Thr Ala Ser Asn Gln Cys Trp Ser Ile Cys Lys Arg Leu
1               5                   10                  15

His Asn Thr Asn Arg Gly Lys Cys Met Asn Lys Lys Cys Arg Cys Tyr
```

20                  25                  30

<210> SEQ ID NO 498
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

Val Ser Cys Thr Thr Ser Lys Glu Cys Trp Ser Val Cys Glu Lys Leu
1               5                   10                  15

Tyr Asn Thr Ser Arg Gly Lys Cys Met Asn Lys Lys Cys Arg Cys Tyr
                20                  25                  30

<210> SEQ ID NO 499
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Met Arg Cys Lys Ser Ser Lys Glu Cys Leu Val Lys Cys Lys Gln Ala
1               5                   10                  15

Thr Gly Arg Pro Asn Gly Lys Cys Met Asn Arg Lys Cys Lys Cys Tyr
                20                  25                  30

<210> SEQ ID NO 500
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Ile Lys Cys Thr Leu Ser Lys Asp Cys Tyr Ser Pro Cys Lys Lys Glu
1               5                   10                  15

Thr Gly Cys Pro Arg Ala Lys Cys Ile Asn Arg Asn Cys Lys Cys Tyr
                20                  25                  30

<210> SEQ ID NO 501
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Ile Arg Cys Ser Gly Ser Arg Asp Cys Tyr Ser Pro Cys Met Lys Gln
1               5                   10                  15

Thr Gly Cys Pro Asn Ala Lys Cys Ile Asn Lys Ser Cys Lys Cys Tyr
                20                  25                  30

<210> SEQ ID NO 502
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 502

Ile Arg Cys Ser Gly Thr Arg Glu Cys Tyr Ala Pro Cys Gln Lys Leu
1               5                   10                  15

Thr Gly Cys Leu Asn Ala Lys Cys Met Asn Lys Ala Cys Lys Cys Tyr
            20                  25                  30

<210> SEQ ID NO 503
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Ile Ser Cys Thr Asn Pro Lys Gln Cys Tyr Pro His Cys Lys Lys Glu
1               5                   10                  15

Thr Gly Tyr Pro Asn Ala Lys Cys Met Asn Arg Lys Cys Lys Cys Phe
            20                  25                  30

<210> SEQ ID NO 504
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

<210> SEQ ID NO 505
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

Thr Ser Cys Ile Ser Pro Lys Gln Cys Thr Glu Pro Cys Arg Ala Lys
1               5                   10                  15

Gly Cys Lys His Gly Lys Cys Met Asn Arg Lys Cys His Cys Met
            20                  25                  30

<210> SEQ ID NO 506
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Lys Glu Cys Thr Gly Pro Gln His Cys Thr Asn Phe Cys Arg Lys Asn
1               5                   10                  15

Lys Cys Thr His Gly Lys Cys Met Asn Arg Lys Cys Lys Cys Phe
            20                  25                  30

<210> SEQ ID NO 507
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Ile Lys Cys Arg Thr Pro Lys Asp Cys Ala Asp Pro Cys Arg Lys Gln
1               5                   10                  15

Thr Gly Cys Pro His Ala Lys Cys Met Asn Lys Thr Cys Arg Cys His
            20                  25                  30

<210> SEQ ID NO 508
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Val Lys Cys Thr Thr Ser Lys Glu Cys Trp Pro Pro Cys Lys Ala Ala
1               5                   10                  15

Thr Gly Lys Ala Ala Gly Lys Cys Met Asn Lys Lys Cys Lys Cys Gln
            20                  25                  30

<210> SEQ ID NO 509
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Leu Glu Cys Gly Ala Ser Arg Glu Cys Tyr Asp Pro Cys Phe Lys Ala
1               5                   10                  15

Phe Gly Arg Ala His Gly Lys Cys Met Asn Asn Lys Cys Arg Cys Tyr
            20                  25                  30

<210> SEQ ID NO 510
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Glu Lys Cys Phe Ala Thr Ser Gln Cys Trp Thr Pro Cys Lys Lys Ala
1               5                   10                  15

Ile Gly Ser Leu Gln Ser Lys Cys Met Asn Gly Lys Cys Lys Cys Tyr
            20                  25                  30

<210> SEQ ID NO 511
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Val Arg Cys Tyr Ala Ser Arg Glu Cys Trp Glu Pro Cys Arg Arg Val
1               5                   10                  15
```

```
Thr Gly Ser Ala Gln Ala Lys Cys Gln Asn Asn Gln Cys Arg Cys Tyr
            20                  25                  30
```

<210> SEQ ID NO 512
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

```
Val Lys Cys Ser Ala Ser Arg Glu Cys Trp Val Ala Cys Lys Lys Val
1               5                   10                  15

Thr Gly Ser Gly Gln Gly Lys Cys Gln Asn Asn Gln Cys Arg Cys Tyr
            20                  25                  30
```

<210> SEQ ID NO 513
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

```
Val Lys Cys Ile Ser Ser Gln Glu Cys Trp Ile Ala Cys Lys Lys Val
1               5                   10                  15

Thr Gly Arg Phe Glu Gly Lys Cys Gln Asn Arg Gln Cys Arg Cys Tyr
            20                  25                  30
```

<210> SEQ ID NO 514
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

```
Val Arg Cys Tyr Asp Ser Arg Gln Cys Trp Ile Ala Cys Lys Lys Val
1               5                   10                  15

Thr Gly Ser Thr Gln Gly Lys Cys Gln Asn Lys Gln Cys Arg Cys Tyr
            20                  25                  30
```

<210> SEQ ID NO 515
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

```
Val Asp Cys Thr Val Ser Lys Glu Cys Trp Ala Pro Cys Lys Ala Ala
1               5                   10                  15

Phe Gly Val Asp Arg Gly Lys Cys Met Gly Lys Lys Cys Lys Cys Tyr
            20                  25                  30
```

<210> SEQ ID NO 516
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Ala Lys Cys Arg Gly Ser Pro Glu Cys Leu Pro Lys Cys Lys Glu Ala
1               5                   10                  15

Ile Gly Lys Ala Ala Gly Lys Cys Met Asn Gly Lys Cys Lys Cys Tyr
            20                  25                  30

<210> SEQ ID NO 517
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Lys Lys Cys Gln Gly Gly Ser Cys Ala Ser Val Cys Arg Arg Val Ile
1               5                   10                  15

Gly Val Ala Ala Gly Lys Cys Ile Asn Gly Arg Cys Val Cys Tyr
            20                  25                  30

<210> SEQ ID NO 518
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Lys Lys Cys Ser Asn Thr Ser Gln Cys Tyr Lys Thr Cys Glu Lys Val
1               5                   10                  15

Val Gly Val Ala Ala Gly Lys Cys Met Asn Gly Lys Cys Ile Cys Tyr
            20                  25                  30

<210> SEQ ID NO 519
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Val Lys Cys Ser Gly Ser Ser Lys Cys Val Lys Ile Cys Ile Asp Arg
1               5                   10                  15

Tyr Asn Thr Arg Gly Ala Lys Cys Ile Asn Gly Arg Cys Thr Cys Tyr
            20                  25                  30

<210> SEQ ID NO 520
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Asn Arg Cys Asn Asn Ser Ser Glu Cys Ile Pro His Cys Ile Arg Ile
1               5                   10                  15

Phe Gly Thr Arg Ala Ala Lys Cys Ile Asn Arg Lys Cys Tyr Cys Tyr
            20                  25                  30

<210> SEQ ID NO 521

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Lys Glu Cys Asn Gly Ser Ser Glu Cys Tyr Ser His Cys Glu Gly Ile
1               5                   10                  15

Thr Gly Lys Arg Ser Gly Lys Cys Ile Asn Lys Lys Cys Tyr Cys Tyr
            20                  25                  30

<210> SEQ ID NO 522
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val
            20                  25

<210> SEQ ID NO 523
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ala Val Cys Asn Leu Lys Arg Cys Gln Leu Ser Cys Arg Ser Leu Gly
1               5                   10                  15

Leu Leu Gly Lys Cys Ile Gly Asp Lys Cys Glu Cys Val
            20                  25

<210> SEQ ID NO 524
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Ala Ala Cys Tyr Ser Ser Asp Cys Arg Val Lys Cys Val Ala Met Gly
1               5                   10                  15

Phe Ser Ser Gly Lys Cys Ile Asn Ser Lys Cys Lys Cys Tyr
            20                  25                  30

<210> SEQ ID NO 525
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Ala Ile Cys Ala Thr Asp Ala Asp Cys Ser Arg Lys Cys Pro Gly Asn
1               5                   10                  15
```

```
Pro Pro Cys Arg Asn Gly Phe Cys Ala Cys Thr
            20                  25

<210> SEQ ID NO 526
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Thr Glu Cys Gln Ile Lys Asn Asp Cys Gln Arg Tyr Cys Gln Ser Val
1               5                   10                  15

Lys Glu Cys Lys Tyr Gly Lys Cys Tyr Cys Asn
            20                  25

<210> SEQ ID NO 527
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Thr Gln Cys Gln Ser Val Arg Asp Cys Gln Gln Tyr Cys Leu Thr Pro
1               5                   10                  15

Asp Arg Cys Ser Tyr Gly Thr Cys Tyr Cys Lys
            20                  25

<210> SEQ ID NO 528
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Val Ser Cys Arg Tyr Gly Ser Asp Cys Ala Glu Pro Cys Lys Arg Leu
1               5                   10                  15

Lys Cys Leu Leu Pro Ser Lys Cys Ile Asn Gly Lys Cys Thr Cys Tyr
            20                  25                  30

<210> SEQ ID NO 529
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Ile Lys Cys Arg Tyr Pro Ala Asp Cys His Ile Met Cys Arg Lys Val
1               5                   10                  15

Thr Gly Arg Ala Glu Gly Lys Cys Met Asn Gly Lys Cys Thr Cys Tyr
            20                  25                  30

<210> SEQ ID NO 530
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 530

Ile Lys Cys Ser Ser Ser Ser Cys Tyr Glu Pro Cys Arg Gly Val
1               5                   10                  15

Thr Gly Arg Ala His Gly Lys Cys Met Asn Gly Arg Cys Thr Cys Tyr
            20                  25                  30

<210> SEQ ID NO 531
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Val Lys Cys Thr Gly Ser Lys Gln Cys Leu Pro Ala Cys Lys Ala Ala
1               5                   10                  15

Val Gly Lys Ala Ala Gly Lys Cys Met Asn Gly Lys Cys Lys Cys Tyr
            20                  25                  30

<210> SEQ ID NO 532
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Val Ser Cys Lys His Ser Gly Gln Cys Ile Lys Pro Cys Lys Asp Ala
1               5                   10                  15

Gly Met Arg Phe Gly Lys Cys Met Asn Arg Lys Cys Asp Cys Thr
            20                  25                  30

<210> SEQ ID NO 533
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Val Lys Cys Arg Gly Ser Pro Gln Cys Ile Gln Pro Cys Arg Asp Ala
1               5                   10                  15

Gly Met Arg Phe Gly Lys Cys Met Asn Gly Lys Cys His Cys Thr
            20                  25                  30

<210> SEQ ID NO 534
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Val Lys Cys Thr Ser Pro Lys Gln Cys Leu Pro Pro Cys Lys Ala Gln
1               5                   10                  15

Phe Gly Ile Arg Ala Gly Ala Lys Cys Met Asn Gly Lys Cys Lys Cys
            20                  25                  30

Tyr

<210> SEQ ID NO 535
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Val Lys Cys Thr Ser Pro Lys Gln Cys Ser Pro Cys Lys Glu Leu
1               5                   10                  15

Tyr Gly Ser Ser Ala Gly Ala Lys Cys Met Asn Gly Lys Cys Lys Cys
            20                  25                  30

Tyr

<210> SEQ ID NO 536
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Val Lys Cys Thr Ser Pro Lys Gln Cys Leu Pro Pro Cys Lys Glu Ile
1               5                   10                  15

Tyr Gly Arg His Ala Gly Ala Lys Cys Met Asn Gly Lys Cys His Cys
            20                  25                  30

Ser

<210> SEQ ID NO 537
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Val Lys Cys Thr Gly Ser Lys Gln Cys Trp Pro Val Cys Lys Gln Met
1               5                   10                  15

Phe Gly Lys Pro Asn Gly Lys Cys Met Asn Gly Lys Cys Arg Cys Tyr
            20                  25                  30

<210> SEQ ID NO 538
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Val Lys Cys Arg Gly Ser Arg Asp Cys Leu Asp Pro Cys Lys Lys Ala
1               5                   10                  15

Gly Met Arg Phe Gly Lys Cys Ile Asn Ser Lys Cys His Cys Thr
            20                  25                  30

<210> SEQ ID NO 539
<211> LENGTH: 27
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 539

Val Arg Cys Val Thr Asp Asp Cys Phe Arg Lys Cys Pro Gly Asn
1               5                   10                  15

Pro Ser Cys Lys Arg Gly Phe Cys Ala Cys Lys
            20                  25

<210> SEQ ID NO 540
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 540

Val Pro Cys Asn Asn Ser Arg Pro Cys Val Pro Val Cys Ile Arg Glu
1               5                   10                  15

Val Asn Asn Lys Asn Gly Lys Cys Ser Asn Gly Lys Cys Leu Cys Tyr
            20                  25                  30

<210> SEQ ID NO 541
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 541

Val Pro Ile Asn Val Lys Cys Arg Gly Ser Arg Asp Cys Leu Asp Pro
1               5                   10                  15

Cys Lys Lys Ala Gly Met Arg Phe Gly Lys Cys Ile Asn Ser Lys Cys
            20                  25                  30

His Cys Thr Pro
        35

<210> SEQ ID NO 542
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 542

Val Gln Thr Asn Val Lys Cys Gln Gly Gly Ser Cys Ala Ser Val Cys
1               5                   10                  15

Arg Arg Glu Ile Gly Val Ala Ala Gly Lys Cys Ile Asn Gly Lys Cys
            20                  25                  30

Val Cys Tyr Arg Asn
        35

<210> SEQ ID NO 543
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 543

-continued

Ala Glu Ile Ile Arg Cys Ser Gly Thr Arg Glu Cys Tyr Ala Pro Cys
1               5                   10                  15

Gln Lys Leu Thr Gly Cys Leu Asn Ala Lys Cys Met Asn Lys Ala Cys
            20                  25                  30

Lys Cys Tyr Gly Cys Val
            35

<210> SEQ ID NO 544
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Arg Pro Thr Asp Ile Lys Cys Ser Ala Ser Tyr Gln Cys Phe Pro Val
1               5                   10                  15

Cys Lys Ser Arg Phe Gly Lys Thr Asn Gly Arg Cys Val Asn Gly Leu
            20                  25                  30

Cys Asp Cys Phe
            35

<210> SEQ ID NO 545
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Gln Phe Thr Asp Val Lys Cys Thr Gly Ser Lys Gln Cys Trp Pro Val
1               5                   10                  15

Cys Lys Gln Met Phe Gly Lys Pro Asn Gly Lys Cys Met Asn Gly Lys
            20                  25                  30

Cys Arg Cys Tyr Ser
            35

<210> SEQ ID NO 546
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Val Gly Ile Asn Val Lys Cys Lys His Ser Arg Gln Cys Leu Lys Pro
1               5                   10                  15

Cys Lys Asp Ala Gly Met Arg Phe Gly Lys Cys Thr Asn Gly Lys Cys
            20                  25                  30

His Cys Thr Pro Lys
            35

<210> SEQ ID NO 547
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

```
Val Val Ile Gly Gln Arg Cys Tyr Arg Ser Pro Asp Cys Tyr Ser Ala
1               5                   10                  15

Cys Lys Lys Leu Val Gly Lys Ala Thr Gly Lys Cys Thr Asn Gly Arg
            20                  25                  30

Cys Asp Cys
        35

<210> SEQ ID NO 548
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Asn Phe Lys Val Glu Gly Ala Cys Ser Lys Pro Cys Arg Lys Tyr Cys
1               5                   10                  15

Ile Asp Lys Gly Ala Arg Asn Gly Lys Cys Ile Asn Gly Arg Cys His
            20                  25                  30

Cys Tyr Tyr
        35

<210> SEQ ID NO 549
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Gln Ile Asp Thr Asn Val Lys Cys Ser Gly Ser Ser Lys Cys Val Lys
1               5                   10                  15

Ile Cys Ile Asp Arg Tyr Asn Thr Arg Gly Ala Lys Cys Ile Asn Gly
            20                  25                  30

Arg Cys Thr Cys Tyr Pro
        35

<210> SEQ ID NO 550
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Gly Val Pro Ile Ser Val Arg Cys Arg Gly Ser Arg Asp Cys Leu Glu
1               5                   10                  15

Pro Cys Arg Arg Ala Gly Thr Arg Phe Gly Arg Cys Ile Asn Gly Arg
            20                  25                  30

Cys His Cys Thr Pro
        35

<210> SEQ ID NO 551
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 551

Gly Val Pro Ile Ser Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys His Cys Thr Pro
            35

<210> SEQ ID NO 552
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

Gly Val Pro Ile Ser Val Arg Cys Arg Gly Ser Arg Asp Cys Leu Glu
1               5                   10                  15

Pro Cys Arg Arg Ala Gly Thr Arg Phe Gly Arg Cys Ile Asn Arg Arg
            20                  25                  30

Cys His Cys Thr Pro
            35

<210> SEQ ID NO 553
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Asn Ser Arg
            20                  25                  30

Cys His Cys Thr Pro
            35

<210> SEQ ID NO 554
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys His Cys Thr Pro
            35

<210> SEQ ID NO 555
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 555

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys His Cys Tyr Pro
        35

<210> SEQ ID NO 556
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Gly Val Pro Ile Asn Val Arg Cys Arg Gly Ser Arg Asp Cys Tyr Glu
1               5                   10                  15

Pro Cys Arg Arg Ala Gly Thr Arg Phe Gly Arg Cys Ile Gln Ser Arg
            20                  25                  30

Cys His Cys Thr Pro
        35

<210> SEQ ID NO 557
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys Tyr Cys Thr Pro
        35

<210> SEQ ID NO 558
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Gly Val Pro Ile Ser Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys His Cys Tyr Pro
        35

<210> SEQ ID NO 559
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
                                           polypeptide

<400> SEQUENCE: 559

Gly Val Pro Ile Ser Val Arg Cys Arg Gly Ser Arg Asp Cys Tyr Glu
1               5                   10                  15

Pro Cys Arg Arg Ala Gly Thr Arg Phe Gly Arg Cys Ile Gln Ser Arg
            20                  25                  30

Cys His Cys Thr Pro
        35

<210> SEQ ID NO 560
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

Gly Val Pro Ile Ser Val Arg Cys Arg Gly Ser Arg Asp Cys Leu Glu
1               5                   10                  15

Pro Cys Arg Arg Ala Gly Thr Arg Phe Gly Arg Cys Ile Gln Ser Arg
            20                  25                  30

Cys Tyr Cys Thr Pro
        35

<210> SEQ ID NO 561
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Ala Ser Arg
            20                  25                  30

Cys His Cys Tyr Pro
        35

<210> SEQ ID NO 562
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Ser Ser Arg
            20                  25                  30

Cys His Cys Tyr Pro
        35

<210> SEQ ID NO 563
<211> LENGTH: 37
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 563

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Thr Ser Arg
            20                  25                  30

Cys His Cys Tyr Pro
        35

<210> SEQ ID NO 564
<211> LENGTH: 37
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 564

Gly Val Pro Ile Asn Val Arg Cys Arg Gly Ser Arg Asp Cys Leu Glu
1               5                   10                  15

Pro Cys Arg Arg Ala Gly Thr Arg Phe Gly Arg Cys Ile Asn Ser Arg
            20                  25                  30

Cys His Cys Tyr Pro
        35

<210> SEQ ID NO 565
<211> LENGTH: 292
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 565

Met Glu Thr Asp Thr Leu Leu Leu Trp Val Leu Leu Leu Trp Val Pro
1               5                   10                  15

Gly Ser Thr Gly Gly Ser Gly Val Pro Ile Asn Val Arg Cys Arg Gly
            20                  25                  30

Ser Arg Asp Cys Leu Asp Pro Cys Arg Arg Ala Gly Met Arg Phe Gly
        35                  40                  45

Arg Cys Ile Asn Ser Arg Cys His Cys Thr Pro Gly Gly Ser Gly Gly
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln

```
                180                 185                 190
Val Tyr Thr Leu Pro Pro Ser Arg Asp Glu Leu Thr Lys Asn Gln Val
            195                 200                 205

Ser Leu Thr Cys Leu Val Lys Gly Phe Tyr Pro Ser Asp Ile Ala Val
        210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
        290

<210> SEQ ID NO 566
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Met Glu Thr Asp Thr Leu Leu Leu Trp Val Leu Leu Leu Trp Val Pro
1               5                   10                  15

Gly Ser Thr Gly
        20

<210> SEQ ID NO 567
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 567

Gly Ser Gly Val Pro Ile Asn Val Arg Ser Arg Gly Ser Arg Asp Ser
1               5                   10                  15

Leu Asp Pro Ser Arg Arg Ala Gly Met Arg Phe Gly Arg Ser Ile Asn
            20                  25                  30

Ser Arg Ser His Ser Thr Pro
        35

<210> SEQ ID NO 568
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Ala Gly Ala
1

<210> SEQ ID NO 569
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 569

Asp Glu Val Asp
1

<210> SEQ ID NO 570
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Leu Glu His Asp
1
```

CARTILAGE-HOMING PEPTIDE CONJUGATES AND METHODS OF USE THEREOF

CROSS REFERENCE

This application is a U.S. National Phase Application under 35 U.S.C. § 371 of International Application No. PCT/US2018/023006, filed Mar. 16, 2018, which claims the benefit of U.S. Provisional Patent Application No. 62/472,485, filed Mar. 16, 2017, the entire disclosures of which are incorporated by reference.

SEQUENCE LISTING

The instant application contains a Sequence Listing which has been submitted electronically in ASCII format and is hereby incorporated by reference in its entirety. Said ASCII copy, created on Mar. 15, 2018, is named 45639-711_601_SL.txt and is 302,571 bytes in size.

BACKGROUND

Cartilage comprises chondrocytes, a specialized cell-type which produces components of the extracellular matrix, mainly including collagen, proteoglycans (e.g., aggrecan), and elastic fibers. The extracellular matrix proteins provide support, cushion, and durability to cartilage-rich portions of the body such as joints, ears, nose, and windpipe. Cartilage is one of few tissues in the body which does not contain blood vessels and is considered an avascular tissue. Unlike many cells in the body which rely on a combination of blood flow and diffusion, chondrocytes rely on diffusion. Because it does not have a direct blood supply, compared to other connective tissues, cartilage grows and repairs much more slowly. As a result, cartilage disorders are particularly difficult to treat.

SUMMARY

The present disclosure relates to compositions and methods for treatment of cartilage disorders. Described herein are peptides that home to, migrate to, accumulate in, bind to, are retained by, or are directed to, and/or bind in cartilage following administration in a subject. In some embodiments, the homing peptides of the present disclosure are used to deliver a detection agent to image and/or diagnose cartilage, injury, or disease. In some embodiments, compositions and methods for treatment of kidney disorders are described. In other embodiments, the homing peptides of the present disclosure are used to treat or deliver an active agent to a region, tissue, structure, or cell thereof.

In some aspects, a peptide active agent conjugate comprises: a) a peptide, wherein the peptide comprises a sequence that has at least 70% sequence identity with any one of SEQ ID NO: 24-SEQ ID NO: 274 and upon administration to a subject the peptide homes, targets, migrates to, accumulates in, binds to, is retained by, or is directed to a cartilage of the subject, and an active agent selected from an active agent class selected from TABLE 3 or TABLE 5; b) a peptide, wherein the peptide comprises a sequence that has at least 70% sequence identity with any one of SEQ ID NO: 24-SEQ ID NO: 274 and upon administration to a subject the peptide homes, targets, migrates to, accumulates in, binds to, is retained by, or is directed to a kidney of the subject, and an active agent selected from an active agent class selected from TABLE 4 or TABLE 5; c) a peptide, wherein the peptide comprises a sequence that has at least 70% sequence identity with any one of SEQ ID NO: 24-SEQ ID NO: 274 and upon administration to a subject the peptide homes, targets, migrates to, accumulates in, binds to, is retained by, or is directed to a cartilage or kidney of the subject, and an active agent selected from TABLE 3, TABLE 4, or TABLE 5; d) a peptide, wherein the peptide comprises a sequence that has at least 70% sequence identity with any one of SEQ ID NO: 314-SEQ ID NO: 564 and upon administration to a subject the peptide homes, targets, migrates to, accumulates in, binds to, is retained by, or is directed to a cartilage of the subject, and an active agent selected from TABLE 3 or TABLE 5; e) a peptide, wherein the peptide comprises a sequence that has at least 70% sequence identity with any one of SEQ ID NO: 314-SEQ ID NO: 564 and upon administration to a subject the peptide homes, targets, migrates to, accumulates in, binds to, is retained by, or is directed to a kidney of the subject, and an active agent selected from an active agent class selected from TABLE 4 or TABLE 5; f) a peptide, wherein the peptide comprises a sequence that has at least 70% sequence identity with any one of SEQ ID NO: 314-SEQ ID NO: 564 and upon administration to a subject the peptide homes, targets, migrates to, accumulates in, binds to, is retained by, or is directed to a cartilage or kidney of the subject, and an active agent selected from an active agent class selected from TABLE 3, TABLE 4, or TABLE 5; g) a peptide, wherein the peptide comprises a sequence that has at least 70% sequence identity with any one of SEQ ID NO: 260-SEQ ID NO: 274 and upon administration to a subject the peptide homes, targets, migrates to, accumulates in, binds to, is retained by, or is directed to a cartilage of the subject, and an active agent selected from TABLE 3, TABLE 5, or TABLE 6; h) a peptide, wherein the peptide comprises a sequence that has at least 70% sequence identity with any one of SEQ ID NO: 260-SEQ ID NO: 274 and upon administration to a subject the peptide homes, targets, migrates to, accumulates in, binds to, is retained by, or is directed to a kidney of the subject, and an active agent selected from TABLE 4, TABLE 5, or TABLE 6; i) a peptide, wherein the peptide comprises a sequence that has at least 70% sequence identity with any one of SEQ ID NO: 260-SEQ ID NO: 274 and upon administration to a subject the peptide homes, targets, migrates to, accumulates in, binds to, is retained by, or is directed to a cartilage or a kidney of the subject, and an active agent selected from TABLE 3, TABLE 4, TABLE 5, or TABLE 6; j) a peptide, wherein the peptide comprises a sequence that has at least 70% sequence identity with any one of SEQ ID NO: 550-SEQ ID NO: 564 and upon administration to a subject the peptide homes, targets, migrates to, accumulates in, binds to, is retained by, or is directed to a cartilage of the subject, and an active agent selected from TABLE 3, TABLE 5, or TABLE 6; k) a peptide, wherein the peptide comprises a sequence that has at least 70% sequence identity with any one of SEQ ID NO: 550-SEQ ID NO: 564 and upon administration to a subject the peptide homes, targets, migrates to, accumulates in, binds to, is retained by, or is directed to a kidney of the subject, and an active agent selected from TABLE 4, TABLE 5, or TABLE 6; or 1) a peptide, wherein the peptide comprises a sequence that has at least 70% sequence identity with any one of SEQ ID NO: 550-SEQ ID NO: 564 and upon administration to a subject the peptide homes, targets, migrates to, accumulates in, binds to, is retained by, or is directed to a cartilage or a kidney of the subject, and an active agent selected from TABLE 3, TABLE 4, TABLE 5, or TABLE 6. In some embodiments, the peptide comprises:

a) a sequence that has at least 75%, at least 80%, at least 85%, at least 90%, at least 95%, at least 97%, at least 99% or 100% sequence identity with any one of SEQ ID NO: 24-SEQ ID NO: 274 or a fragment thereof; b) a sequence that has at least 75%, at least 80%, at least 85%, at least 90%, at least 95%, at least 97%, at least 99% or 100% sequence identity with any one of SEQ ID NO: 260-SEQ ID NO: 274 or a fragment thereof; c) a sequence that has at least 75%, at least 80%, at least 85%, at least 90%, at least 95%, at least 97%, at least 99% or 100% sequence identity with any one of SEQ ID NO: 314-SEQ ID NO: 564 or a fragment thereof; or d) a sequence that has at least 75%, at least 80%, at least 85%, at least 90%, at least 95%, at least 97%, at least 99% or 100% sequence identity with any one of SEQ ID NO: 550-SEQ ID NO: 564 or a fragment thereof. In some embodiments, the peptide comprises: a) a sequence of any one of SEQ ID NO: 24-SEQ ID NO: 274 or a fragment thereof; b) a sequence of any one of SEQ ID NO: 260-SEQ ID NO: 274 or a fragment thereof; c) a sequence of any one of SEQ ID NO: 314-SEQ ID NO: 564 or a fragment thereof; or d) a sequence of any one of SEQ ID NO: 550-SEQ ID NO: 564 or a fragment thereof.

In some aspects, a peptide comprises a sequence that has at least 70%, at least 75%, at least 80%, at least 85%, at least 90%, at least 95%, at least 97%, at least 99%, or 100% sequence identity with any one of SEQ ID NO: 260-SEQ ID NO: 574 or at least 70%, at least 75%, at least 80%, at least 85%, at least 90%, at least 95%, at least 97%, at least 99%, or 100% sequence identity with any one of SEQ ID NO: 550-SEQ ID NO: 564.

In some embodiments, the peptide comprises: a) a sequence of any one of SEQ ID NO: 1-SEQ ID NO: 23 or a fragment thereof; b) a sequence of any one of SEQ ID NO: 275-SEQ ID NO: 297 or a fragment thereof; c) a sequence of any one of SEQ ID NO: 21-SEQ ID NO: 23 or a fragment thereof; or d) a sequence of any one of SEQ ID NO: 295-SEQ ID NO: 297 or a fragment thereof. In some embodiments, the peptide is at least 30%, at least 40%, at least 50%, at least 60%, at least 70%, at least 80%, at least 90%, at least 95%, at least, 97%, at least 98%, or at least 99% identical to any one of SEQ ID NO: 494-SEQ ID NO: 540 or at least 30%, at least 40%, at least 50%, at least 60%, at least 70%, at least 80%, at least 90%, at least 95%, at least 97%, at least 98%, or at least 99% identical to any one of SEQ ID NO: 204-SEQ ID NO: 250. In some embodiments, the peptide is at least 70%, at least 80%, at least 90%, at least 95%, at least 97%, or 100% identical to: a) SEQ ID NO: 111; b) SEQ ID NO: 401; c) SEQ ID NO: 24; d) SEQ ID NO: 314; e) SEQ ID NO: 27; f) SEQ ID NO: 317; g) SEQ ID NO: 185; h) SEQ ID NO: 475; i) SEQ ID NO: 30; j) SEQ ID NO: 320; k) SEQ ID NO: 108; l) SEQ ID NO: 398; m) SEQ ID NO: 36; n) SEQ ID NO: 326; o) SEQ ID NO: 199; p) SEQ ID NO: 478; q) SEQ ID NO: 25; r) SEQ ID NO: 315; s) SEQ ID NO: 106; t) SEQ ID NO: 396; u) SEQ ID NO: 26; v) SEQ ID NO: 316; w) SEQ ID NO: 187; x) SEQ ID NO: 477; y) SEQ ID NO: 107; or z) SEQ ID NO: 397. In some embodiments, the peptide is at least 70%, at least 80%, at least 90%, at least 95%, at least 97%, at least 99%, or 100% identical to: a) SEQ ID NO: 550; b) SEQ ID NO: 551; c) SEQ ID NO: 552; d) SEQ ID NO: 553; e) SEQ ID NO: 554; f) SEQ ID NO: 555; g) SEQ ID NO: 556; h) SEQ ID NO: 557; i) SEQ ID NO: 558; j) SEQ ID NO: 559; k) SEQ ID NO: 560; l) SEQ ID NO: 561; m) SEQ ID NO: 562; n) SEQ ID NO: 563; o) SEQ ID NO: 564; p) SEQ ID NO: 260; q) SEQ ID NO: 261; r) SEQ ID NO: 262; s) SEQ ID NO: 263; t) SEQ ID NO: 264; u) SEQ ID NO: 265; v) SEQ ID NO: 266; w) SEQ ID NO: 267; x) SEQ ID NO: 268; y) SEQ ID NO: 269; z) SEQ ID NO: 270; aa) SEQ ID NO: 271; bb) SEQ ID NO: 272; cc) SEQ ID NO: 273; or dd) SEQ ID NO: 274. In some embodiments, the peptide homes, targets, migrates to, accumulates in, binds to, is retained by, or is directed to cartilage, to kidney, or to cartilage and kidney. In some embodiments, the peptide homes, targets, migrates to, accumulates in, binds to, is retained by, or is directed to proximal tubules of the kidney. In some embodiments, the peptide is covalently conjugated to the active agent. In some embodiments, the peptide active agent conjugate homes, targets, migrates to, accumulates in, binds to, is retained by, or is directed to a cartilage or a kidney of the subject.

In some embodiments, the peptide comprises 4 or more cysteine residues. In some embodiments, the peptide comprises three or more disulfide bridges formed between cysteine residues, wherein one of the disulfide bridges passes through a loop formed by two other disulfide bridges. In some embodiments, the peptide comprises a plurality of disulfide bridges formed between cysteine residues. In some embodiments, the peptide comprises a disulfide through a disulfide knot. In some embodiments, at least one amino acid residue of the peptide is in an L configuration or, wherein at least one amino acid residue of the peptide is in a D configuration.

In some embodiments, the sequence comprises at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58 residues, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 residues.

In some embodiments, any one or more K residues are replaced by an R residue or wherein any one or more R residues are replaced by for a K residue In some embodiments, any one or more M residues are replaced by any one of the I, L, or V residues. In some embodiments, any one or more L residues are replaced by any one of the V, I, or M residues. In some embodiments, any one or more I residues are replaced by any of the M, L, or V residues. In some embodiments, any one or more V residues are replaced by any of the M, I, or L residues. In some embodiments, any one or more G residues are replaced by an A residue or wherein any one or more A residues are replaced by a G residue. In some embodiments, any one or more S residues are replaced by a T residue or wherein any one or more T residues are replaced by for an S residue. In some embodiments, any one or more Q residues are replaced by an N residue or wherein any one or more N residues are replaced by a Q residue. In some embodiments, any one or more D residues are replaced by an E residue or wherein any one or more E residues are replaced by a D residue.

In some embodiments, the peptide has a charge distribution comprising an acidic region and a basic region. In some embodiments, the acidic region is a nub. In some embodiments, the basic region is a patch. In some embodiments, the peptide comprises 5-12 basic residues. In some embodiments, the peptide comprises 0-5 acidic residues. In some embodiments, the peptide comprises 6 or more basic residues and 2 or fewer acidic residues. In some embodiments, the peptide comprises a 4-19 amino acid residue fragment containing at least 2 cysteine residues, and at least 2 positively charged amino acid residues. In some embodiments, the peptide comprises a 20-70 amino acid residue fragment containing at least 2 cysteine residues, no more than 2 basic residues and at least 2 positively charged amino acid residues. In some embodiments, the peptide comprises at least 3 positively charged amino acid residues. In some embodiments, the positively charged amino acid residues are selected from K, R, or a combination thereof.

In some embodiments, the peptide has a charge greater than 2 at physiological pH. In some embodiments, the peptide has a charge greater than 3.5 at physiological pH. In some embodiments, the peptide has a charge greater than 4.5 at physiological pH. In some embodiments, the peptide has a charge greater than 5.5 at physiological pH. In some embodiments, the peptide has a charge greater than 6.5 at physiological pH. In some embodiments, the peptide has a charge greater than 7.5 at physiological pH. In some embodiments, the peptide has a charge greater than 8.5 at physiological pH. In some embodiments, the peptide has a charge greater than 9.5 at physiological pH.

In some embodiments, the peptide is selected from a potassium channel agonist, a potassium channel antagonist, a portion of a potassium channel, a sodium channel agonist, a sodium channel antagonist, a calcium channel agonist, a calcium channel antagonist, a hadrucalcin, a theraphotoxin, a huwentoxin, a kaliotoxin, a cobatoxin, or a lectin. In some embodiments, the lectin is SHL-Ib2.

In some embodiments, the peptide is arranged in a multimeric structure with at least one other peptide.

In some embodiments, at least one residue of the peptide comprises a chemical modification. In some embodiments, the chemical modification is blocking the N-terminus of the peptide. In some embodiments, wherein the chemical modification is methylation, acetylation, or acylation. In some embodiments, the chemical modification is: methylation of one or more lysine residues or analogue thereof; methylation of the N-terminus; or methylation of one or more lysine residue or analogue thereof and methylation of the N-terminus. In some embodiments, the peptide is linked to an acyl adduct.

In some embodiments, the peptide is linked to an active agent. In some embodiments, the active agent is fused with the peptide at an N-terminus or a C-terminus of the peptide. In some embodiments, the active agent is another peptide. In some embodiments, the active agent is an antibody. In some embodiments, the active agent is an Fc domain, Fab domain, scFv, or Fv fragment. In some embodiments, the peptide fused with an Fc domain comprises a contiguous sequence. In some embodiments, 1, 2, 3, 4, 5, 6, 7, 8, 9, or 10 active agents are linked to the peptide. In some embodiments, the peptide is linked to the active agent at an N-terminus, at the epsilon amine of an internal lysine residue, at the carboxylic acid of an aspartic acid or glutamic acid residue, or a C-terminus of the peptide by a linker. In some embodiments, the peptide is linked to the active agent via a cleavable linker. In some embodiments, the peptide or peptide active agent conjugate further comprises a non-natural amino acid, wherein the non-natural amino acid is an insertion, appendage, or substitution for another amino acid.

In some embodiments, the peptide is linked to the active agent at the non-natural amino acid by a linker. In some embodiments, the linker comprises an amide bond, an ester bond, a carbamate bond, a carbonate bond, a hydrazone bond, an oxime bond, a disulfide bond, a thioester bond, a thioether bond, a triazole, a carbon-carbon bond, or a carbon-nitrogen bond. In some embodiments, the cleavable linker comprises a cleavage site for matrix metalloproteinases, thrombin, cathepsins, or beta-glucuronidase. In some embodiments, the linker is a hydrolytically labile linker. In some embodiments, the linker is pH sensitive, reducible, glutathione-sensitive, or protease cleavable. In some embodiments, the peptide is linked to the active agent via a stable linker. In some embodiments, the peptide has an isoelectric point of about 9.

In some embodiments, the peptide is linked to a detectable agent. In some embodiments, the detectable agent is fused with the peptide at an N-terminus or a C-terminus of the peptide. In some embodiments, 1, 2, 3, 4, 5, 6, 7, 8, 9, or 10 detectable agents are linked to the peptide. In some embodiments, the peptide is linked to the detectable agent via a cleavable linker. In some embodiments, the peptide is linked to the detectable agent at an N-terminus, at the epsilon amine of an internal lysine residue, or a C-terminus of the peptide by a linker. In some embodiments, the peptide active agent conjugate or peptide further comprises a non-natural amino acid, wherein the non-natural amino acid is an insertion, appendage, or substitution for another amino acid.

In some embodiments, the peptide is linked to the detectable agent at the non-natural amino acid by a linker In some embodiments, the linker comprises an amide bond, an ester bond, a carbamate bond, a hydrazone bond, an oxime bond, or a carbon-nitrogen bond. In some embodiments, the cleavable linker comprises a cleavage site for matrix metalloproteinases, thrombin, cathepsins, or beta-glucuronidase. In some embodiments, the peptide is linked to the detectable agent via a stable linker. In some embodiments, the detectable agent is a fluorophore, a near-infrared dye, a contrast agent, a nanoparticle, a metal-containing nanoparticle, a metal chelate, an X-ray contrast agent, a PET agent, a radioisotope, or a radionuclide chelator. In some embodiments, the detectable agent is a fluorescent dye.

In some aspects, a pharmaceutical composition comprises the peptide active agent conjugate of any embodiment as described herein or a salt thereof, or the peptide of any embodiment as described herein or a salt thereof, and a pharmaceutically acceptable carrier. In some embodiments, the pharmaceutical composition is formulated for administration to a subject. In some embodiments, the pharmaceutical composition is formulated for inhalation, intranasal administration, oral administration, topical administration, parenteral administration, intravenous administration, subcutaneous administration, intra-articular administration, intramuscular administration, intraperitoneal administration, dermal administration, transdermal administration, or a combination thereof.

In some aspects, a method of treating a condition in a subject in need thereof comprises administering to the subject the peptide active agent conjugate of any of embodiment as described herein, the peptide of any of any embodiment as described herein, or a pharmaceutical composition of any embodiment as described herein. In some embodiments, the peptide active agent conjugate, peptide, or pharmaceutical composition is administered by inhalation, intranasally, orally, topically, parenterally, intravenously, subcutaneously, intra-articularly, intramuscularly administration, intraperitoneally, dermally, transdermally, or a combination thereof. In some embodiments, the peptide active agent conjugate or the peptide homes, targets, or migrates to cartilage of the subject following administration. In some embodiments, the condition is associated with cartilage. In some embodiments, the condition is associated with a joint. In some embodiments, the condition is an inflammation, a cancer, a degradation, a growth disturbance, genetic, a tear, an infection, a disease, or an injury. In some embodiments, the condition is a chondrodystrophy. In some embodiments, the condition is a traumatic rupture or detachment. In some embodiments, the condition is a costochondritis. In some embodiments, the condition is a herniation. In some embodiments, the condition is a polychondritis. In some embodiments, the condition is a chordoma. In some embodiments, the condition is a type of arthritis. In some embodiments, the type of arthritis is rheumatoid arthritis. In some embodiments, the type of arthritis is osteoarthritis. In some embodiments, the condition is achondroplasia. In some embodiments, the condition is benign chondroma or malignant chondrosarcoma. In some embodiments, the condition is bursitis, tendinitis, gout, pseudogout, an arthropathy, psoriatic arthritis, ankylosing spondylitis, or an infection. In some embodiments, the peptide active agent conjugate, peptide, or pharmaceutical composition is administered to treat the injury, to repair a tissue damaged by the injury, or to treat a pain caused by the injury. In some embodiments, the peptide active agent conjugate, peptide, or pharmaceutical composition is administered to treat the tear or to repair a tissue damaged by the tear. In some embodiments, the peptide active agent conjugate, peptide, or pharmaceutical composition homes, targets, or migrates to a kidney of the subject following administration. In some embodiments, the condition is associated with a kidney. In some embodiments, the condition is lupus nephritis, acute kidney injury (AKI), chronic kidney disease (CKD), hypertensive kidney damage, diabetic nephropathy, or renal fibrosis.

In some aspects, a method of imaging an organ or body region of a subject comprises: administering to the subject the peptide active agent conjugate of any embodiment as described herein, the peptide of any embodiment as described herein, or the pharmaceutical composition of any embodiment as described herein; and imaging the subject. In some embodiments, the method further comprises detecting a cancer or diseased region, tissue, structure, or cell. In some embodiments, the method further comprises performing surgery on the subject. In some embodiments, the method further comprises treating the cancer. In some embodiments, the surgery comprises removing the cancer or the diseased region, tissue, structure or cell of the subject. In some embodiments, the method further comprises imaging the cancer or diseased region, tissue, structure, or cell of the subject after surgical removal. In some embodiments, the peptide active agent conjugate is expressed as a fusion protein.

INCORPORATION BY REFERENCE

All publications, patents, and patent applications mentioned, disclosed or referenced in this specification are herein incorporated by reference in their entirety and to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5 illustrates alignment of SEQ ID NO: 541 (SEQ ID NO: 541 is SEQ ID NO: 27, but without the first three amino acids "GSG" and is also SEQ ID NO: 317, but without the first amino acid "G") with SEQ ID NO: 316, SEQ ID NO: 541 with SEQ ID NO: 542 (SEQ ID NO: 542 is SEQ ID NO: 30, but without the first three amino acids "GSQ" and is SEQ ID NO: 320, but without the first amino acid "Q"), and SEQ ID NO: 541 with SEQ ID NO: 483. FIG. 5A illustrates the alignment of the peptide of SEQ ID NO: 541 with the peptide of SEQ ID NO: 316. Boxes delineate conserved positively charged residues. FIG. 5B illustrates the alignment of the peptide of SEQ ID NO: 541 with the peptide of SEQ ID NO: 542. Boxes delineate conserved positively charged residues. FIG. 5C illustrates the alignment of the peptide of SEQ ID NO: 541 with the peptide of SEQ ID NO: 483. Boxes delineate conserved positively charged residues.

FIG. 7 illustrates alignment of peptides within the pfam00451:toxin_2 structural class family of SEQ ID NO: 494-SEQ ID NO: 540. Boxed and bolded residues indicate relative conservation of sequence while non-boxed and non-bolded residues indicate areas of higher sequence variability.

FIG. 8 illustrates alignment of a peptide of SEQ ID NO: 494 from the pfam00451:toxin 2 structural class family with a cartilage homing peptide of this disclosure of SEQ ID NO: 27. Asterisks indicate positions with a single, fully conserved residue, a colon indicates conservation between groups of strongly similar properties (scoring>0.5 in the Gonnet point accepted mutation (PAM) 250 matrix), and a period indicates conservation between groups of weakly similar properties (scoring≤0.5 in the Gonnet PAM 250 matrix).

FIG. 10 shows white light images and corresponding whole body fluorescence images of a mouse administered 10 nmol of a peptide of SEQ ID NO: 108 conjugated to a Cy5.5 fluorophore (SEQ ID NO: 108A) at 24 hours post-administration.

FIG. 11 illustrates a multiple sequence alignment of SEQ ID NO: 316, SEQ ID NO: 317, SEQ ID NO: 321, SEQ ID NO: 333, SEQ ID NO: 337, SEQ ID NO: 338, SEQ ID NO: 340, SEQ ID NO: 398, SEQ ID NO: 474, SEQ ID NO: 483, SEQ ID NO: 486, and SEQ ID NO: 543-SEQ ID NO: 549 were used to predict enhanced peptide stability and immunogenicity. SEQ ID NO: 295 is a consensus sequence.

FIG. 13 shows IVIS fluorescence imaging of an isolated hind limb from a first mouse and an isolated hind limb from a second mouse after administration of 10 nmol SEQ ID NO: 108 peptide conjugated to a Cy5.5 fluorophore (SEQ ID NO: 108A). Areas of low signal intensity are shown in a thin solid line, areas of medium signal intensity are shown in a thick sold line, and areas of high signal intensity are shown in a thin dotted line. FIG. 13A shows the right hind limb with skin removed from a first mouse and from a second mouse 3 hours after peptide administration. FIG. 13B shows the right hind limb with muscle removed from a first mouse and from a second mouse 3 hours after peptide administration of 10 nmol SEQ ID NO: 108 peptide conjugated to a Cy5.5 fluorophore (SEQ ID NO: 108A). FIG. 13C shows the right hind limb with skin removed from a first mouse and from a second mouse 24 hours after peptide administration of 10 nmol SEQ ID NO: 108 peptide conjugated to a Cy5.5 fluorophore (SEQ ID NO: 108A). FIG. 13D shows the right hind limb with muscle removed from a first mouse and from a second mouse 24 hours after peptide administration of 10 nmol SEQ ID NO: 108 peptide conjugated to a Cy5.5 fluorophore (SEQ ID NO: 108A). FIG. 13E shows the right hind limb with skin removed from a first mouse and from a second mouse 48 hours after peptide administration of 10 nmol SEQ ID NO: 108 peptide conjugated to a Cy5.5 fluorophore (SEQ ID NO: 108A). FIG. 13F shows the right hind limb with muscle removed from a first mouse and from a second mouse 48 hours after peptide administration of 10 nmol SEQ ID NO: 108 peptide conjugated to a Cy5.5 fluorophore (SEQ ID NO: 108A). FIG. 13G shows the right hind limb with skin removed from a first mouse and from a second mouse 72 hours after peptide administration of 10 nmol SEQ ID NO: 108 peptide conjugated to a Cy5.5 fluorophore (SEQ ID NO: 108A). FIG. 13H shows the right hind limb with muscle removed from a first mouse and from a second mouse 72 hours after administration of 10 nmol SEQ ID NO: 108 peptide conjugated to a Cy5.5 fluorophore (SEQ ID NO: 108A).

FIG. 14 illustrates autoradiography images of frozen sections from a mouse, 3 hours after administration of 100 nmol of a radiolabeled peptide of SEQ ID NO: 108.

FIG. 15 illustrates autoradiography images of frozen sections from a mouse, 3 hours after administration of 100 nmol of a radiolabeled peptide of SEQ ID NO: 106.

FIG. 16 illustrates autoradiography images of frozen sections from a mouse, 3 hours after administration of 100 nmol of a radiolabeled peptide of SEQ ID NO: 187.

DETAILED DESCRIPTION

Figure 1:
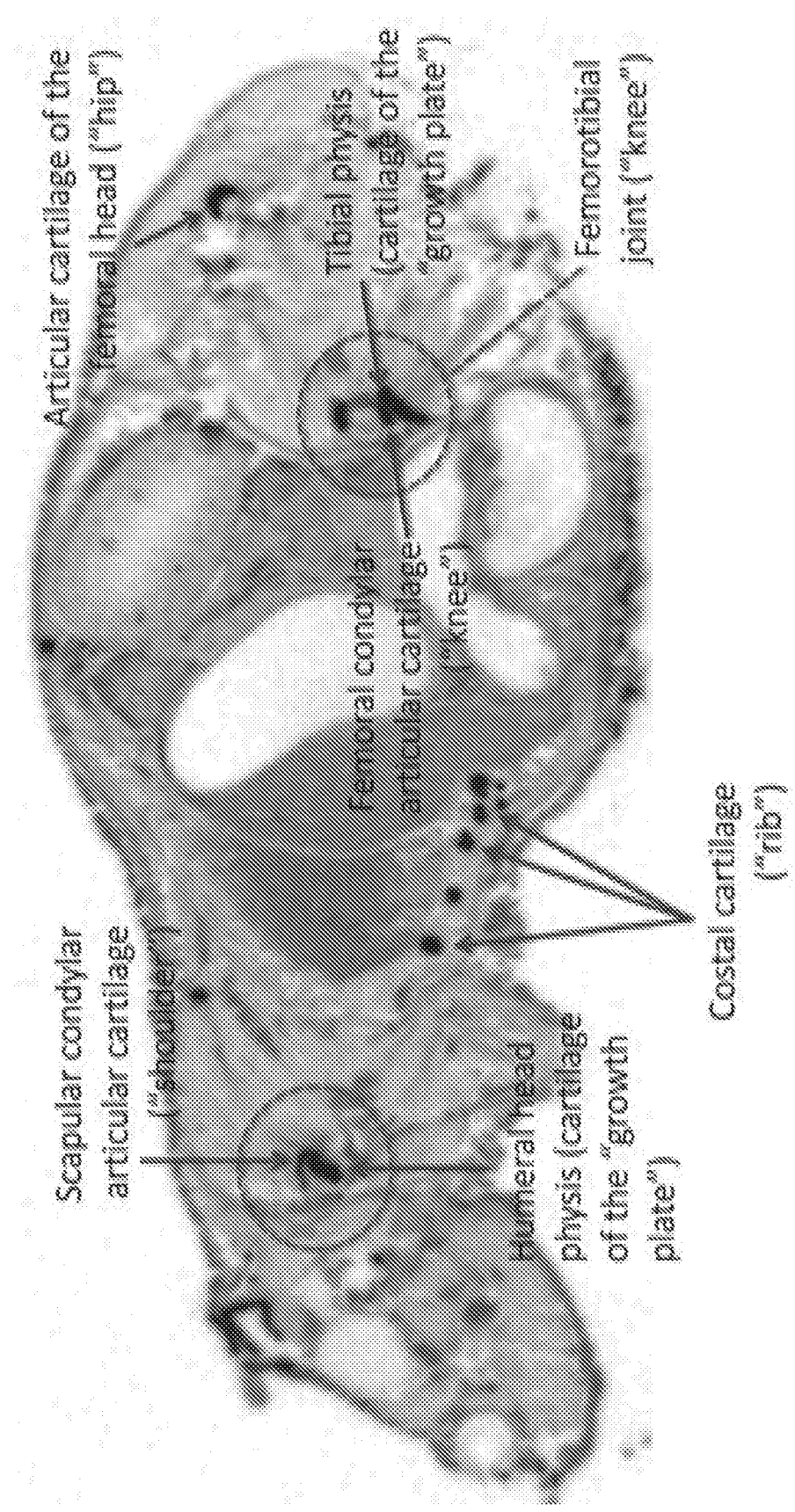
FIG. 1 illustrates the identification of the $^{14}C$ signal in the joint and other cartilage of an animal treated with the peptide of SEQ ID NO: 27.
Figure 2:
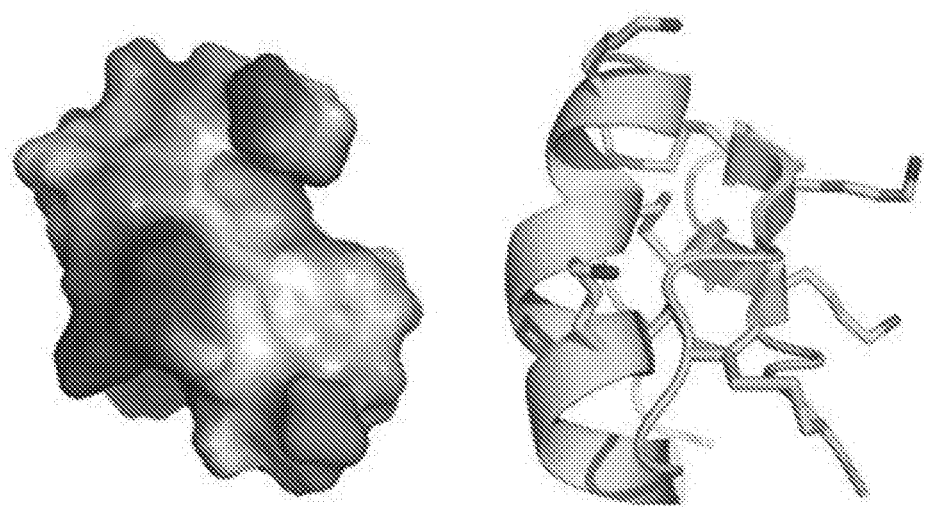
FIG. 2 illustrates a three-dimensional structure and a line structure of a peptide of SEQ ID NO: 31.

The present disclosure relates generally to compositions and methods for cartilage therapy. In some embodiments, the compositions and methods herein utilize peptides that home, target, are directed to, are retained by, accumulate in, migrate to, and/or bind to cartilage following administration to a subject. In some embodiments, the cartilage homing peptides of the present disclosure exert therapeutic effect in cartilage or tissue or cell thereof. In some embodiments, the cartilage homing peptides of the present disclosure are used to deliver an active agent to cartilage or tissue or cell thereof. The active agent can exert a therapeutic effect on cartilage or tissue or cell thereof. For example, in certain embodiments, the peptide itself or the active agent allows for localized delivery of an anti-inflammatory or other agent to cartilage or tissue or cell thereof. As another example, the active agent is a fluorophore that can be used for imaging of cartilage. In certain embodiments, the peptide itself induces therapeutic responses.

Cartilage disorders are particularly difficult to treat. A direct route for active agent administration can be parenterally (e.g., intravenously, subcutaneously, intramuscularly), intra-articularly, by inhalation, dermally, topically, or orally. However, cartilage can be avascular thus intravenous administration of drugs can fail to reach the cartilage in significant amounts. Drugs for cartilage diseases, such as osteoarthritis, can be injected directly locally into the affected area, for example, directly injected into the joint. Few drugs aimed at treating cartilage disorders have proved therapeutically viable with lack of access to target tissue being a primary reason for failure. The lack of access to the target tissue can also lead to administration of doses that are higher than would be necessary if a drug could home, target, or be directed to, is retained by, and/or binds to a target region, tissue, structure or cell. Thus, treatment of cartilage conditions often requires the use of high concentrations of non-specific drugs. In addition, a number of therapeutics are of interest in treating joint disorders, but are problematic because of the level of side effects caused by systemic administration of the drug (Dancevic and McCulloch, *Arthritis Res Ther.* 16:429 (2014)).

Specific and potent drugs that are capable of contacting the cartilage can counteract the non-specificity of many treatments by selectively targeting and delivering compounds to specific regions, tissues, cells and structures. Such drugs can also be useful to modulate ion channels, protein-protein interactions, extracellular matrix remodeling (i.e., protease inhibition), and the like. Such targeted therapy can allow for lower dosing, reduced side effects, improved patient compliance, and improvement in therapeutic outcomes, which would be advantageous not only in acute disease of the cartilage, but in chronic conditions as well.

The present disclosure provides peptides that can comprise or can be derived from cystine-dense peptides. As used herein, the term "cystine-dense peptide" can be interchangeable with the terms "knotted peptide," "knottin," and "optide," and cystine-dense peptides can also be abbreviated as "CDPs." Hitchins, amongst other disulfide-containing peptides, can also be considered "knotted peptides" or "cystine-dense peptides" for the purposes of this disclosure. Knottins, for example, are a class of cystine-dense peptides comprising from about 11 to about 80 amino acids in length that are often folded into a compact structure. Knottins and other cystine-dense peptides are typically assembled into a complex tertiary structure that is characterized by a number of intramolecular disulfide crosslinks and can contain beta strands, an alpha helix, and other secondary structures. The presence of the disulfide bonds can give cystine-dense peptides remarkable environmental stability, allowing them to withstand extremes of temperature and pH, to resist proteolytic enzymes in the blood stream or digestive tract, and can provide specific biodistribution, pharmacokinetic, binding interactions, cellular processing, or other properties of physiologic and therapeutic value. The peptides disclosed herein can be derived from certain cystine-dense peptides. The present disclosure describes a class of cystine-dense peptides that can effectively contact cartilage and be used either directly or as carriers of active drugs, peptides, or molecules to treat a cartilage condition. For instance, osteoarthritis is a cartilage condition that is associated with the thinning of cartilage covering the ends of bones resulting in bone directly contacting bone within the joint. Over time, the ends of the bones are subjected to increased levels of friction which ultimately causes erosion of the end of the bone. Individuals suffering from osteoarthritis experience reduced motion and increased pain. A therapeutic peptide that could contact the cartilage at the joint and ends of the bone to interact with the chondrocytes and induce increased expression of extracellular matrix proteins could be used in the treatment and prevention of osteoarthritis by increasing expression of collagen through, for example, the rate of production, amount of production, inhibition of proteins which degrade collagen, promote expression of other proteins which maintain the integrity of existing collagen proteins, or other mechanism. A peptide could also affect nearby tissues or cells such as the bone, ligaments, muscle, tendons, bursa, connective tissue, blood vessels, peripheral nerves, osteoclasts, osteoblasts, fibroblasts, synoviocytes, monocytes/macrophages, lymphocytes, plasma cells, adipocytes, endothelial cells, neurons, ligaments, muscle, tendons, and bursa. The peptides of the disclosure can be used to treat the symptoms of various conditions. The peptides of the disclosure can bind to, home to, migrate to, accumulate in, be retained by, or be directed to cartilage and its components, including chondrocytes, extracellular matrix, collagen, hyaluranon, aggrecan (also known as cartilage-specific proteoglycan core protein (CSPCP)), or other components of the extracellular matrix and the joint, or to other nearby components such as those described herein in joints and cartilaginous tissues as listed above.

Also described herein are peptides that selectively home, target, are directed to, migrate to, are retained by, or accumulate in and/or bind to specific regions, tissues, structures or cells of the cartilage that aid in managing, decreasing, ablating or reducing pain (e.g., joint pain) due to chronic disease or cartilage injury or other therapeutic indications as described herein. A peptide that homes, targets, migrates to, is directed to, is retained by, or accumulates in and/or binds to one or more specific regions, tissues, structures or cells of the cartilage can have fewer off-target and potentially negative effects, for example, side effects that often limit use and efficacy of pain drugs. In addition, such peptides can reduce dosage and increase the efficacy of existing drugs by directly targeting them to a specific region, tissue, structure or cell of the cartilage and helping the contact the cartilage or increasing the local concentration of agent. The peptide itself can modulate pain or it can be conjugated to an agent that modulates pain. Such pain modulation may operate by various mechanisms such as modulating inflammation, autoimmune responses, direct or indirect action on pain receptors, cell killing, or programmed cell death (whether via an apoptotic and/or non-apoptotic pathway of diseased cells or tissues, and the like (Tait et al., *J Cell Sci* 127(Pt 10):2135-44 (2014)).

Peptides of this disclosure that home, target, are directed to, migrate to, are retained by, accumulate in, or bind to specific regions, tissues, structures or cells of the cartilage can do so with different degrees of efficiency. Peptides can have a higher concentration in cartilage than in other locations, such as blood or muscle. Peptides can be recorded as having a signal in cartilage as a percentage of signal in blood. For example, a cartilage signal of 200% indicates that the signal in cartilage is twice as high as the signal in blood. In some embodiments, peptides that have cartilage homing properties can have a cartilage signal of >170% by radiographic densitometry measurements. In other embodiments, peptides that are cartilage homers can have a cartilage signal of >200% by radiographic densitometry measurements. In other embodiments, peptides that are more efficient cartilage homers can have a cartilage signal of >300% by radiographic densitometry measurements. In other embodiments, peptides that are more efficient cartilage homers can have a cartilage signal of >400% by radiographic densitometry measurements. In other embodiments, peptides that are strongest cartilage homers of highest interest can have a cartilage signal of >500% by radiographic densitometry measurements. In some embodiments, measurement of the ratio of peptide concentration in blood, muscle, or other tissues relative to the peptide concentration in cartilage can be performed using various methods including measuring the densitometry signal of peptides labeled with radioisotopes (as described above), or by using other assays.

Peptides that selectively home, target, are directed to, migrate to, are retained by, or accumulate in and/or bind to specific regions, tissues, structures or cells of the cartilage can occur after administration of the peptide to a subject. A subject can be a human or a non-human animal.

The peptides disclosed herein can be used as active agents, or conjugated to detection agents such a fluorophores, iodide-containing X-ray contrast agents, lanthanide chelates (e.g., gadolinium for MRI imaging), perfluorocarbons (for ultrasound), or PET tracers (e.g., 18F or 11C) for imaging and tracing the peptide, or conjugated to agents such as anti-inflammatory active agents or other active agents to the joint to treat inflammation or other disease.

The peptides disclosed herein can be used to bind cartilage explants ex vivo. Cartilage explants can be from any subject, such as a human or an animal. Assessment of peptide binding to cartilage explants can be used to screen peptides that may efficiently home to cartilage in vivo In some embodiments, peptides of this disclosure home, target, are directed to, migrate to, are retained by, accumulate in, or bind to specific regions, tissues, structures or cells of the kidneys. For example, in some embodiments, peptides of this disclosure home, target, are directed to, migrate to, are retained by, accumulate in, or bind to the proximal tubules of the kidneys, kidney nephrons, or podocytes. Peptides that selectively home, target, are directed to, migrate to, are retained by, or accumulate in and/or bind to specific regions, tissues, structures or cells of the kidney can occur after administration of the peptide to a subject. A subject can be a human or a non-human animal. The peptides disclosed herein can be used as active agents, or conjugated to detection agents such a fluorophores, iodide-containing X-ray contrast agents, lanthanide chelates (e.g., gadolinium for MRI imaging), perfluorocarbons (for ultrasound), or PET tracers (e.g., 18F or 11C) for imaging and tracing the peptide, or conjugated to agents such as anti-inflammatory agents or other agents to the kidney to treat renal cancer, chronic kidney failure or other kidney disease.

One roadblock in the advancement and wide spread use of peptides as a therapeutic is that peptides can be chemically and physically unstable. During the process of manufacturing of therapeutic peptides essential considerations can include storage conditions, sustained biochemical function, and in vivo delivery. Peptide degradation products can result in the formation of species that alter the safety profile, potency, and immunogenicity of the peptide. These peptide degradation products can form during manufacture and storage, as well as in vivo after delivery to a patient. Furthermore, peptide degradation may limit the shelf-life and increase production cost due to unstable peptides requiring refrigeration or shipment on dry ice. The latter can necessitate continual monitoring and validation of peptides as degradation products could have formed during the manufacturing process. Hence, there is an urgent need for the rationale design and production of therapeutic peptides that have enhanced stability, for example, in the ambient environment, during the process of manufacturing, in storage, and that prevent the likelihood of peptide degradation under a variety of conditions.

In some embodiments, the peptides and peptide-drug conjugates of the present disclosure have stability properties that minimize peptide or peptide-drug conjugate degradation to enable adequate storage. Long term, accelerated, and intermediate storage conditions for the peptides and peptide-drug conjugates of the present disclosure can include long term storage conditions of 25° C.±2° C./60% relative humidity (RH)±5% RH, or 30° C.±2° C./65% RH±5% RH for at least 6 months, at least 12 months, and up to 1 year, up to 2 years, up to 3 years, up to 4 years, or longer than 4 years. In addition, intermediate and short term storage conditions (e.g., during transport, distribution, manufacturing, or handling), or long term storage conditions for certain climates and infrastructures, can include storage conditions of 30° C.±2° C./65% RH±5% RH or 40° C.±2° C./75% RH±5% RH for up to 1 hour, for up to 8 hours, for up to 1 day, for up to 3 days, for up to 1 week, for up to 1 month, for up to 3 months, for up to 6 months or at least 6 months, up to 1 year, up to 2 years, up to 3 years, up to 4 years, or longer than 4 years). Moreover, the peptides and peptide-drug conjugates of the present disclosure can be refrigerated, for example between 5° C.±3° C. for at least 6 months, at least 12 months, and up to 1 year, up to 2 years, up to 3 years, up to 4 years, or longer than 4 years. In addition, intermediate and short term refrigeration conditions (e.g., during transport, distribution, manufacturing, or handling) can include 25° C.±2° C./60% RH±5% RH for up to 1 hour, for up to 8 hours, for up to 1 day, for up to 3 days, for up to 1 week, for up to 1 month, for up to 3 months, for up to 6 months or at least 6 months, and potentially longer (at least 12 months and up to 1 year, up to 2 years, up to 3 years, up to 4 years, or longer than 4 years). Such conditions for storage, whether based on ambient or refrigerated conditions can be adjusted based upon the four zones in the world (e.g., the International Council for Harmonisation of Technical Requirements for Pharmaceuticals for Human Use (ICH) stability Zone I, II, III, or IV) that are distinguished by their characteristic prevalent annual climatic conditions. In addition, formulation components can be principally chosen for their ability to preserve the native conformation and chemical structure of the peptides and peptide-drug conjugates of the present disclosure in storage by preventing denaturation due to hydrophobic interactions and aggregation, as well as by preventing chemical degradation, including truncation, oxidation, deamidation, cleavage, hydrolysis, isomerization, disulfide exchange, racemization, and beta elimination (Cleland, et al., *Crit Rev Ther Drug Carrier Syst* 10(4): 307-377 (1993); Shire et al., *J Pharm Sci* 93(6): 1390-1402 (2004); Wakankar and Borchardt, *J Pharm Sci* 95(11): 2321-2336 (2006)).

In some embodiments, the peptides and peptide-drug conjugates of the present disclosure have incorporated properties that minimize immunogenicity of the peptides and peptide-drug conjugates. Immunogenicity can be a major concern with the development of therapeutic peptides and proteins, and there is an urgent need for the rationale design and production of therapeutic peptides that have reduced immunogenicity and that increase their safety and efficacy. Immunogenicity can occur against a desired peptide sequence or a peptide degradation product. Immunogenicity can occur when a patient develops an immune response to the therapeutic peptide, protein, conjugate, or other drug, such as by producing antibodies that bind to and/or neutralize the therapeutic peptide, protein, conjugate, or other drug. The likelihood of immunogenicity can increase when drugs are administered more than once or chronically. Immunogenicity can reduce patient exposure to the drug, can reduce effectiveness of the drug, and can also result in safety risks for the patient, such as generating an immune response to self-proteins or other adverse responses related to increased immunogenicity to the therapeutic peptide, protein, conjugate, or other drug. Immunogenic responses can vary from patient to patient and also amongst different groups of HLA alleles, as well as over time. As such, minimizing risk of immunogenicity with a therapeutic peptide or protein can be important for developing a drug that can be effectively and safely used for treatment. Various methods exist for assessment of immunogenic potential, which can include in silico methods, in vitro testing, preclinical in vivo testing, and assessment during clinical dosing. Evaluation early in product design and development of the therapeutic peptides and peptide-drug conjugates of the present disclosure in the in vivo milieu in which they function (e.g., in inflammatory environments or at physiologic pH) can reveal susceptibilities to modifications (e.g., aggregation and deamidation) that can result in loss of efficacy or induction of immune responses. Such information can be used to facilitate product engineering to enhance the stability of the product under such in vivo conditions or reduce immunogenicity. Moreover, the therapeutic peptides and peptide-drug conjugates of the present disclosure can be designed to minimize protein aggregation. Strategies to minimize aggregate formation can be used early in drug development, for example, by using an appropriate cell substrate, selecting manufacturing conditions that minimize aggregate formation, employing a robust purification scheme that removes aggregates to the greatest extent possible, and choosing a formulation and container closure system that minimize aggregation during storage.

Additional aspects and advantages of the present disclosure will become apparent to those skilled in this art from the following detailed description, wherein illustrative embodiments of the present disclosure are shown and described. As will be realized, the present disclosure is capable of other and different embodiments, and its several details are capable of modifications in various respects, all without departing from the disclosure. Accordingly, the drawings and description are to be regarded as illustrative in nature, and not as restrictive.

As used herein, the abbreviations for the natural L-enantiomeric amino acids are conventional and are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Typically, Xaa can indicate any amino acid. In some embodiments, X can be asparagine (N), glutamine (Q), histidine (H), lysine (K), or arginine (R).

Some embodiments of the disclosure contemplate D-amino acid residues of any standard or non-standard amino acid or analogue thereof. When an amino acid sequence is represented as a series of three-letter or one-letter amino acid abbreviations, the left-hand direction is the amino terminal direction and the right-hand direction is the carboxyl terminal direction, in accordance with standard usage and convention.

Peptides

The cystine-dense peptides herein can bind targets with antibody-like affinity. The cystine-dense peptides can modulate the activity of a plurality of cartilage regions, tissues, structures or cells. For example, in some embodiments, the cystine-dense peptide conjugated to a bone-modifying drug homes to the cartilage of a diseased joint and releases the drug, creating a higher local concentration of drug in an area of eroded or damaged bone than would be achieved without the cartilage targeting function of the peptide. The cystine-dense peptide can be conjugated to a drug that can affect nearby tissues or cells such as the ligaments, muscle, tendons, bursa, connective tissue, blood vessels, peripheral nerves, osteoclasts, osteoblasts, fibroblasts, synoviocytes, monocytes/macrophages, lymphocytes, plasma cells, adipocytes, endothelial cells, neurons, ligaments, muscle, tendons, and bursa. The cystine-dense peptide conjugated to a drug can bind to, home to, migrate to, accumulate in, be retained by, or be directed to cartilage and its components, including chondrocytes, extracellular matrix, collagen of any type, hyaluranon, aggrecan (also known as cartilage-specific proteoglycan core protein (CSPCP)), proteoglycans, glycoasminoglycans, glycoproteins, decorin, biclycan, fibromodulin, or other components of the extracellular matrix and the joint, or to other nearby components such as those described herein in joints and cartilaginous tissues as listed above. Some of the cartilage regions, tissues, and structures that peptides and peptide-drug conjugates can target to treat a cartilage-associated disorder include: (a) elastic cartilage; (b) hyaline cartilage, such as articular cartilage and physeal cartilage; (c) fibrocartilage; and (d) any cells or cell types in (a)-(c) above. Some of the areas where the peptide and peptide-drug conjugates can target to treat a cartilage-associated disorder include: cartilage includes joints such as knees, hips, or digits, nasal cartilage, spinal cartilage, tracheal cartilage, and rib cartilage. In various aspects, cartilage components include aggrecan and type II collagen. Additionally, in some embodiments, cystine-dense peptides can penetrate into cells. In other embodiments, cystine-dense peptides do not enter cells. In other embodiments, cystine-dense peptides exhibit more rapid clearance and cellular uptake compared to other types of molecules.

The peptides of the present disclosure can comprise cysteine amino acid residues. In some cases, the peptide has at least 4 cysteine amino acid residues. In some cases, the peptide has at least 6 cysteine amino acid residues. In other cases, the peptide has at least 8 cysteine amino acid residues, at least 10 cysteine amino acid residues, at least 12 cysteine amino acid residues, at least 14 cysteine amino acid residues or at least 16 cysteine amino acid residues.

A cystine-dense peptide can comprise disulfide bridges. A cystine-dense can be a peptide wherein 5% or more of the residues are cysteines forming intramolecular disulfide bonds as cystines. A disulfide-linked peptide can be a drug scaffold. In some embodiments, the disulfide bridges form an inhibitor knot. A disulfide bridge can be formed between cysteine residues, for example, between cysteines 1 and 4, 2 and 5, or, 3 and 6. In some cases, one disulfide bridge passes through a loop formed by the other two disulfide bridges, for example, to form the inhibitor knot. In other cases, the disulfide bridges can be formed between any two cysteine residues.

The present disclosure further includes peptide scaffolds that, e.g., can be used as a starting point for generating additional peptides that can target and home to cartilage. In some embodiments, these scaffolds can be derived from a variety of cystine-dense peptides. In certain embodiments, cystine-dense peptides are assembled into a complex tertiary structure that is characterized by a number of intramolecular disulfide crosslinks, and optionally contain beta strands and other secondary structures such as an alpha helix. For example, cystine-dense peptides include, in some embodiments, small disulfide-rich proteins characterized by a disulfide through disulfide knot. This knot can be, e.g., obtained when one disulfide bridge crosses the macrocycle formed by two other disulfides and the interconnecting backbone. In some embodiments, the cystine-dense peptides can include growth factor cysteine knots or inhibitor cysteine knots. Other possible peptide structures can include peptide having two parallel helices linked by two disulfide bridges without β-sheets (e.g., hefutoxin).

A cystine-dense peptide can comprise at least one amino acid residue in an L configuration. A cystine-dense peptide can comprise at least one amino acid residue in a D configuration. In some embodiments, a cystine-dense peptide is 15-40 amino acid residues long. In other embodiments, a cystine-dense peptide is 11-57 amino acid residues long. In further embodiments, a cystine-dense peptide is at least 20 amino acid residues long.

In some embodiments, the peptides are members of the pfam00451:toxin_2 family. The pfam00451:toxin_2 structural class family can include a peptide of any one of SEQ ID NO: 494 SEQ ID NO: 540. A cartilage homing peptide of this disclosure can be a variant of any peptide members of the pfam00451:toxin_2 family. In some embodiments, an exemplary cartilage homing peptide of this disclosure that is a variant of the pfam00451:toxin_2 structural class family is a peptide of SEQ ID NO: 27. In other embodiments, an exemplary cartilage homing peptide of this disclosure that is a variant of the pfam00451:toxin_2 structural class family is a peptide of SEQ ID NO: 108. In other embodiments, the variant peptides are at least 30% identical to a peptide of the structural class pfam00451:toxin_2 family. In some embodiments, the variant peptides are 30%, 40%, 50%, 60%, 80%, 90% or 95% identical to a peptide of the structural class pfam00451:toxin_2 family. In some embodiments, the variant peptides are at least 30%, at least 40%, at least 50%, at least 60%, at least 80%, at least 90% or at least 95% identical to a peptide of the structural class pfam00451:toxin_2 family.

In some embodiments, cartilage homing peptides are family members the sequences

```
                                       (SEQ ID NO: 9)
GSXVXXXVKCXGSKQCXXPCKRXXGXRXGKCINKKXCKCYXXX
or (SEQ ID NO: 283)
XVXXXVKCXGSKQCXXPCKRXXGXRXGKCINKKXCKCYXXX
``` wherein X can be any amino acid or amino acid analogue or null, in which these sequences are based on the most common elements found in the following sequences: GSGVPINVKCRGSRDCLDPCKKA-GMRFGKCINSK-CHCTP-- (SEQ ID NO: 27), GS-VRIPVSCK-HSGQCLKPCKDA-GMRFGKCMNGK-CDCTPK- (SEQ ID NO: 26), GSQVQTNVKCQGGS-CASVCR-REIGVAAGKCINGK-CVCYRN- (SEQ ID NO: 30), GS-----ISCTGSKQCYDPCKRKTGCPNAKCMNKS-CK-CYGCG (SEQ ID NO: 29), GSEV---IRCSG-SKQCYGPCKQQTGCTNSKCMNKV-CKCYGCG (SEQ ID NO: 31), GSAVCVYRT------CDKDCKRR-GYRSGK-CINNA-CKCYPYG (SEQ ID NO: 28), GS----GIVC---KVCKIICGMQ-GKKVNICKAPIKCKCKKG- (SEQ ID NO: 24), and GSQIYTSKECNGSSECYSHCE-GITGKRSGKCINKK-CYCYR-- (SEQ ID NO: 33), where the following residues may be independently interchanged in the sequences: K and R; M, I, L, and V; G and A; S and T; Q and N; and X can independently be any number of any amino acid or no amino acid. The N-terminal GS sequence can be included or excluded between the peptides of the present disclosure.

In some embodiments, cartilage homing peptides are family members of the sequences

```
                                      (SEQ ID NO. 21)
GSXVXIXVKCXGSXQCLXPCKXAXGXRXGKCMNGKCXCXPXX
or (SEQ ID NO. 295)
XVXIXVKCXGSXQCLXPCKXAXGXRXGKCMNGKCXCXPXX,
``` wherein X can be any amino acid or amino acid analogue or null, in which these sequences are based on the most common elements found in the following sequences:

```
                                     (SEQ ID NO: 316)
-VRIPVSCKHSGQCLKPCKDA-GMRFGKCMNGKCDCTPK-, (SEQ ID NO: 317)
GVPINVKCRGSRDCLDPCKKA-GMRFGKCINSKCHCTP--, (SEQ ID NO: 321)
---EVIRCSGSKQCYGPCKQQTGCTNSKCMNKVCKCYGCG, (SEQ ID NO: 333)
GVIINVKCKISRQCLEPCKKA-GMRFGKCMNGKCHCTPK-, (SEQ ID NO: 337)
GVPTDVKCRGSPQCIQPCKDA-GMRFGKCMNGKCHCTPK-,
```

-continued

```
                                     (SEQ ID NO: 338)
GVPINVSCTGSPQCIKPCKDA-GMRFGKCMNRKCHCTPK-, (SEQ ID NO: 340)
-VGINVKCKHSGQCLKPCKDA-GMRFGKCINGKCDCTPK-, (SEQ ID NO: 398)
GVPINVRCRGSRDCLDPCRRA-GMRFGRCINSRCHCTP--, (SEQ ID NO: 474)
QKILSNRCNNSSECIPHCIRIFGTRAAKCINRKCYCYP--, (SEQ ID NO: 483)
-VFINVKCRGSPECLPKCKEAIGKSAGKCMNGKCKCYP--, (SEQ ID NO: 486)
-VPTDVKCRGSPQCIQPCKDA-GMRFGKCMNGKCHCTP--, (SEQ ID NO: 543)
--AEIIRCSGTRECYAPCQKLTGCLNAKCMNKACKCYGCV, (SEQ ID NO: 544)
-RPTDIKCSASYQCFPVCKSRFGKTNGRCVNGLCDCF---, (SEQ ID NO: 545)
-QFTDVKCTGSKQCWPVCKQMFGKPNGKCMNGKCRCYS--, (SEQ ID NO: 546)
-VGINVKCKHSRQCLKPCKDA-GMRFGKCTNGKCHCTPK-, (SEQ ID NO: 547)
-VVIGQRCYRSPDCYSACKKLVGKATGKCTNGRCDC----, (SEQ ID NO: 548)
--NFKVEGACSKPCRKYCIDK-GARNGKCINGRCHCYY--,
and (SEQ ID NO: 549)
QIDTNVKCSGSSKCVKICIDRYNTRGAKCINGRCTCYP--.
```

In some embodiments, the cartilage homing peptides are family members of the sequences GSXVXIXVRCXGSXQCLXPCRXAXGXRXGRCMN-GRCXCXPXX (SEQ ID NO: 22) or XVXIXVRCXGSXQCLXPCRXAXGXRXGRCMN-GRCXCXPXX (SEQ ID NO: 296) wherein X can be any amino acid or amino acid analogue or null, in which these sequences are based on the most common elements found in the following sequences and with K interchanged with R: SEQ ID NO: 316, SEQ ID NO: 317, SEQ ID NO: 321, SEQ ID NO: 333, SEQ ID NO: 337, SEQ ID NO: 338, SEQ ID NO: 340, SEQ ID NO: 398, SEQ ID NO: 483, SEQ ID NO: 486, or SEQ ID NO: 543-SEQ ID NO: 549.

In some embodiments, a peptide comprises the sequence GSGVPIX$^1$VRCRGSRDCX$^2$X$^3$PCRRAGX$^4$RFGRC-IX$^5$X$^6$RCX$^7$CX$^8$P (SEQ ID NO: 23) or GVPIX$^1$VRCRGSRDCX$^2$X$^3$PCRRAGX$^4$RFGRCIX$^5$X$^6$R-CX$^7$CX$^8$P (SEQ ID NO: 297), where the following residues where $X^1$ is selected from N, S, or G, wherein $X^2$ is selected from L or Y, wherein $X^3$ is selected from D or E, wherein $X^4$ is selected from M or T, wherein $X^5$ is selected from N, Q, A, S, T, or L, wherein $X^6$ is selected from S, G, or R, wherein $X^7$ is selected from H or Y, and wherein $X^8$ is selected from T or Y. In some embodiments, zero or one or more of the R residues in SEQ ID NO: 23 or SEQ ID NO: 297 can be replaced with K residues. In some embodiments, zero or one or more of the R residues in SEQ ID NO: 23 or SEQ ID NO: 297 can be replaced with A residues. In other embodiments, zero or one or more R residues in SEQ ID NO: 23 or SEQ ID NO: 297 can each be replaced with either a K or an A residue in any combination. In other embodiments, peptides are family members of the sequence GSXXXGCVXXXXKCRPGXKXCCXPXKRCSRRF- GXXXXXKKCKXXXXXX (SEQ ID NO: 10) or XXXGCVXXXXXKCRPGXKXCCXPXKRCSRRFGXX-XXKKCKXXXXXX (SEQ ID NO: 284), in which the sequence is based on the most common elements found in the following sequences: GS---ACKGVFDACTPGK-NECC-PNRVCSDK-H----KWCKWKL--- (SEQ ID NO: 32), GS---GCLEFWWKCNPNDDKC-CRPKLKCSKLF-----KLCNFSFG-- (SEQ ID NO: 34), GSSEKDCIKHLQRCR-ENKDCC--SKKCSRR-GTN-PEKRCR------ (SEQ ID NO: 25), and GS---GCFGY--KCDYY-KGCCSGYV-CSPTW------KWCVRPGPGR (SEQ ID NO: 36), where the following residues may be independently interchanged in the sequences: K and R; M, I, L, and V; G and A; S and T; Q and N; and X can independently be any number of any amino acid or no amino acid. The N-terminal GS sequence can be included or excluded between the peptides of the present disclosure.

In some embodiments, a peptide comprises the sequence GSGVX$^1$IX$^2$X$^3$KCX$^4$GSKQCX$^5$DPCKX$^6$X$^7$X$^8$GX$^9$-RX$^{10}$GKCX$^{11}$NKKCKCX$^{12}$X$^{13}$X$^{14}$X$^{15}$ (SEQ ID NO: 1) or GVX$^1$IX$^2$X$^3$KCX$^4$GSKQCX$^5$DPCKX$^6$X$^7$X$^8$GX$^9$RX$^{10}$-GKCX$^{11}$NKKCKCX$^{12}$X$^{13}$X$^{14}$X$^{15}$(SEQ ID NO: 275), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$ and X$^{15}$ are each individually any amino acid or amino acid analogue or null. In some cases, the peptide comprises the sequence GSGVX$^1$IX$^2$X$^3$KC-X$^4$GSKQCX$^5$DPCKX$^6$X$^7$X$^8$GX$^9$RX$^{10}$GKCX$^{11}$NKKC-KCX$^{12}$X$^{13}$X$^{14}$X$^{15}$ (SEQ ID NO: 2) or GVX$^1$IX$^2$X$^3$K-CX$^4$GSKQCX$^5$DPCKX$^6$X$^7$X$^8$GX$^9$RX$^{10}$GKCX$^{11}$NKK-CKCX$^{12}$X$^{13}$X$^{14}$X$^{15}$ (SEQ ID NO: 276), where X$^1$ is selected from P or R, wherein X$^2$ is selected from P or N, wherein X$^3$ is selected from V or I, wherein X$^4$ is selected from S, T, R or K, wherein X$^5$ is selected from Y or L, wherein X$^6$ is selected from Q, R or K, wherein X$^7$ is selected from A, K or R, wherein X$^8$ is selected from T or A, wherein X$^9$ is selected from C or M, wherein X$^{10}$ is selected from F or N, wherein X$^{11}$ is selected from M or I, wherein X$^{12}$ is selected from Y or T, wherein X$^{13}$ is selected from G or P, wherein X$^{14}$ is selected from C or null, and wherein X$^{15}$ is selected from G or null.

In some embodiments, a peptide comprises the sequence GSX$^1$X$^2$X$^3$X$^4$IX$^5$CX$^6$GSKQCYX$^7$PCKX$^8$X$^9$TGCX$^{10}$X$^{11}$-X$^{12}$KCX$^{13}$X$^{14}$X$^{15}$CKCYGCG (SEQ ID NO: 3) or X$^1$X$^2$X$^3$X$^4$IX$^5$CX$^6$GSKQCYX$^7$PCKX$^8$X$^9$TGCX$^{10}$X$^{11}$X$^{12}$KCX$^{13}$X$^{14}$KX$^{15}$CKCYGCG (SEQ ID NO: 277), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, and X$^{15}$ are each individually any amino acid or amino acid analogue or null. In some cases, the peptide comprises the sequence GSX$^1$X$^2$X$^3$X$^4$I-X$^5$CX$^6$GSKQCYX$^7$PCKX$^8$X$^9$TGCX$^{10}$X$^{11}$X$^{12}$KCX$^{13}$-X$^{14}$KX$^{15}$CKCYGCG (SEQ ID NO: 4) or X$^1$X$^2$X$^3$X$^4$I-X$^5$CX$^6$GSKQCYX$^7$PCKX$^8$X$^9$TGCX$^{10}$X$^{11}$X$^{12}$KCX$^{13}$-X$^{14}$KX$^{15}$CKCYGCG (SEQ ID NO: 278), where X$^1$ is selected from G or null, wherein X$^2$ is selected from S or null, wherein X$^3$ is selected from E, G or null, wherein X$^4$ is selected from V, S, or null, wherein X$^5$ is selected from R or S, wherein X$^6$ is selected from S or T, wherein X$^7$ is selected from G or D, wherein X$^8$ is selected from Q or R, wherein X$^9$ is selected from Q or K, wherein X$^{10}$ is selected from T or P, wherein X$^{11}$ is selected from N or Q, wherein X$^{12}$ is selected from S or A, wherein X$^{13}$ is selected from M or L, wherein X$^{14}$ is selected from N or Q, and wherein X$^{15}$ is selected from V or S.

In some embodiments, a peptide comprises the sequence GSX$^1$X$^2$X$^3$VX$^4$IX$^5$VX$^6$CX$^7$X$^8$SX$^9$X$^{10}$CLX$^{11}$PCKX$^{12}$A-GMRFGKCX$^{13}$NX$^{14}$KCX$^{15}$CTPX$^{16}$ (SEQ ID NO: 5) or X$^1$X$^2$X$^3$VX$^4$IX$^5$VX$^6$CX$^7$X$^8$SX$^9$X$^{10}$CLX$^{11}$PCKX$^{12}$AG-MRFGKCX$^{13}$NX$^{14}$KCX$^{15}$CTPX$^{16}$ (SEQ ID NO: 279), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$ are each individually any amino acid or amino acid analogue or null. In some cases, the peptide comprises the sequence GSX$^1$X$^2$X$^3$V-X$^4$IX$^5$VX$^6$CX$^7$X$^8$SX$^9$X$^{10}$CLX$^{11}$PCKX$^{12}$AGMRFGK-CX$^{13}$NX$^{14}$KCX$^{15}$CTPX$^{16}$ (SEQ ID NO: 6) or X$^1$X$^2$X$^3$V-X$^4$IX$^5$VX$^6$CX$^7$X$^8$SX$^9$X$^{10}$CLX$^{11}$PCKX$^{12}$AGMRFGK-CX$^{13}$NX$^{14}$KCX$^{15}$CTPX$^{16}$ (SEQ ID NO: 280), where X$^1$ is selected from G or null, wherein X$^2$ is selected from G, S or null, wherein X$^3$ is selected from G, S or null, wherein X$^4$ is selected from P or R, wherein X$^5$ is selected from N or P, wherein X$^6$ is selected from K or S, wherein X$^7$ is selected from R or K, wherein X$^8$ is selected from G or H, wherein X$^9$ is selected from R or G, wherein X$^{10}$ is selected from D or Q, wherein X$^{11}$ is selected from D or K, wherein X$^{12}$ is selected from K or D, wherein X$^{13}$ is selected from I or M, wherein X$^{14}$ is selected from S or G, wherein X$^{15}$ is selected from H or D, and wherein X$^{16}$ is selected from K or null.

In some embodiments, a peptide comprises the sequence GSXVXVKCXGSKQCXPCKRXGXRXGKCINKKXCK-CYX (SEQ ID NO: 7) or GSXGCVXKCRPGXKXCCXPXKRCSRRFGXKKCKX (SEQ ID NO: 8), wherein each letter is each individually any amino acid or amino acid analogue and where X is no amino acid or a 1-10 amino acid long peptide fragment wherein each amino acid within such peptide fragment can in each case be any amino acid or amino acid analogue. In some embodiments, a peptide comprises the sequence XVXVKCXGSKQCXPCKRXGXRXGKCINKKXCK-CYX (SEQ ID NO: 281) or XGCVXKCRPGXKXCCXPXKRCSRRFGXKKCKX (SEQ ID NO: 282), wherein each letter is each individually any amino acid or amino acid analogue and where X is no amino acid or a 1-10 amino acid long peptide fragment wherein each amino acid within such peptide fragment can in each case be any amino acid or amino acid analogue.

In some embodiments, a peptide comprises the sequence GSGVX$^1$IX$^2$X$^3$RCX$^4$GSRQCX$^5$DPCRX$^6$X$^7$X$^8$GX$^9$R-X$^{10}$GRCX$^{11}$NRRCRCX$^{12}$X$^{13}$X$^{14}$X$^{15}$ (SEQ ID NO: 11) or GVX$^1$IX$^2$X$^3$RCX$^4$GSRQCX$^5$DPCRX$^6$X$^7$X$^8$GX$^9$RX$^{10}$G-RCX$^{11}$NRRCRCX$^{12}$X$^{13}$X$^{14}$X$^{15}$ (SEQ ID NO: 285), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, and X$^{15}$ are each individually any amino acid or amino acid analogue or null. In some cases, the peptide comprises the sequence GSGVX$^1$IX$^2$X$^3$RCX$^4$GSRQCX$^5$DPCRX$^6$X$^7$X$^8$GX$^9$R-X$^{10}$GRCX$^{11}$NRRCRCX$^{12}$X$^{13}$X$^{14}$X$^{15}$ (SEQ ID NO: 12) or GVX$^1$IX$^2$X$^3$RCX$^4$GSRQCX$^5$DPCRX$^6$X$^7$X$^8$GX$^9$RX$^{10}$G-RCX$^{11}$NRRCRCX$^{12}$X$^{13}$X$^{14}$X$^{15}$ (SEQ ID NO: 286), where X$^1$ is selected from P or R, wherein X$^2$ is selected from P or N, wherein X$^3$ is selected from V or I, wherein X$^4$ is selected from S, T, R or K, wherein X$^5$ is selected from Y or L, wherein X$^6$ is selected from Q, R or K, wherein X$^7$ is selected from A, K or R, wherein X$^8$ is selected from T or A, wherein X$^9$ is selected from C or M, wherein X$^{10}$ is selected from F or N, wherein X$^{11}$ is selected from M or I, wherein X$^{12}$ is selected from Y or T, wherein X$^{13}$ is selected from G or P, wherein X$^{14}$ is selected from C or null, and wherein X$^{15}$ is selected from G or null.

In some embodiments, a peptide comprises the sequence GSX$^1$X$^2$X$^3$X$^4$IX$^5$CX$^6$GSRQCYX$^7$PCRX$^8$X$^9$TGCX$^{10}$-X$^{11}$X$^{12}$RCX$^{13}$X$^{14}$RX$^{15}$CRCYGCG (SEQ ID NO: 13) or X$^1$X$^2$X$^3$X$^4$IX$^5$CX$^6$GSRQCYX$^7$PCRX$^8$X$^9$TGCX$^{10}$X$^{11}$-X$^{12}$RCX$^{13}$X$^{14}$RX$^{15}$CRCYGCG (SEQ ID NO: 287), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, and X$^{15}$ are each individually any amino acid or amino acid analogue or null. In some cases, the peptide comprises the sequence GSX$^1$X$^2$X$^3$X$^4$IX$^5$CX$^6$GSRQCYX$^7$PCRX$^8$X$^9$TGC-X$^{10}$X$^{11}$X$^{12}$RCX$^{13}$X$^{14}$RX$^{15}$CRCYGCG, (SEQ ID NO: 14) or X$^1$X$^2$X$^3$X$^4$IX$^5$CX$^6$GSRQCYX$^7$P-CRX$^8$X$^9$TGCX$^{10}$X$^{11}$X$^{12}$RCX$^{13}$X$^{14}$RX$^{15}$CRCYGCG (SEQ ID NO: 288), where X$^1$ is selected from G or null, wherein X$^2$ is selected from S or null, wherein X$^3$ is selected from E, G or null, wherein X$^4$ is selected from V, S, or null, wherein X$^5$ is selected from R or S, wherein X$^6$ is selected from S or T, wherein X$^7$ is selected from G or D, wherein X$^8$ is selected from Q or R, wherein X$^9$ is selected from Q, R, or K, wherein X$^{10}$ is selected from T or P, wherein X$^{11}$ is selected from N or Q, wherein X$^{12}$ is selected from S or A, wherein X$^{13}$ is selected from M or L, wherein X$^{14}$ is selected from N or Q, and wherein X$^{15}$ is selected from V or S.

In some embodiments, a peptide comprises the sequence GSX$^1$X$^2$X$^3$VX$^4$IX$^5$VX$^6$CX$^7$X$^8$SX$^9$X$^{10}$CLX$^{11}$PCRX$^{12}$A-GMRFGRCX$^{13}$NX$^{14}$RCX$^{15}$CTPX$^{16}$ (SEQ ID NO: 15) or X$^1$X$^2$X$^3$VX$^4$IX$^5$VX$^6$CX$^7$X$^8$SX$^9$X$^{10}$CLX$^{11}$PCRX$^{12}$AG-MRFGRCX$^{13}$NX$^{14}$RCX$^{15}$CTPX$^{16}$ (SEQ ID NO: 289), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$ are each individually any amino acid or amino acid analogue or null. In some cases, the peptide comprises the sequence GSX$^1$X$^2$X$^3$VX$^4$IX$^5$VX$^6$CX$^7$X$^8$SX$^9$X$^{10}$CLX$^{11}$PCRX$^{12}$A-GMRFGRCX$^{13}$NX$^{14}$RCX$^{15}$CTPX$^{16}$ (SEQ ID NO: 16) or X$^1$X$^2$X$^3$VX$^4$IX$^5$VX$^6$CX$^7$X$^8$SX$^9$X$^{10}$CLX$^{11}$PCRX$^{12}$AGM-RFGRCX$^{13}$NX$^{14}$RCX$^{15}$CTPX$^{16}$ (SEQ ID NO: 290), where X$^1$ is selected from G or null, wherein X$^2$ is selected from G, S or null, wherein X$^3$ is selected from G, S or null, wherein X$^4$ is selected from P or R, wherein X$^5$ is selected from N or P, wherein X$^6$ is selected from R, K or S, wherein X$^7$ is selected from R or K, wherein X$^8$ is selected from G or H, wherein X$^9$ is selected from R or G, wherein X$^{10}$ is selected from D or Q, wherein X$^{11}$ is selected from D, R, or K, wherein X$^{12}$ is selected from K, R, or D, wherein X$^{13}$ is selected from I or M, wherein X$^{14}$ is selected from S or G, wherein X$^{15}$ is selected from H or D, and wherein X$^{16}$ is selected from K, R, or null.

In some embodiments, a peptide comprises the sequence GSXVXVRCXGSRQCXPCRRXGXRXGRCINRRX-CRCYX (SEQ ID NO: 17) or GSXGCVXR-CRPGXRXCCXPXRRCSRRFGXRRCRX (SEQ ID NO: 18), wherein each letter is each individually any amino acid or amino acid analogue and where X is no amino acid or a 1-10 amino acid long peptide fragment wherein each amino acid within such peptide fragment can in each case be any amino acid or amino acid analogue. In some embodiments, a peptide comprises the sequence XVXVRCXGSRQCXPCRRXGXRXGRCINRRXCRCYX (SEQ ID NO: 291) or XGCVXR-CRPGXRXCCXPXRRCSRRFGXRRCRX (SEQ ID NO: 292), wherein each letter is each individually any amino acid or amino acid analogue and where X is no amino acid or a 1-10 amino acid long peptide fragment wherein each amino acid within such peptide fragment can in each case be any amino acid or amino acid analogue.

In some embodiments, a peptide comprises the sequence GSXVXXXVRCXGSRQCXXPCRRXXGXRXGRCIN-RRXCRCYXXX (SEQ ID NO: 19), XVXXXVRCXGSRQCXXPCRRXXGXRXGRCINRRX-CRCYXXX (SEQ ID NO: 293), GSXXXGCVXXXXR-CRPGXRXCCXPXRRCSRRFGXXXXRRCRXXXXXX (SEQ ID NO: 20), or XXXGCVXXXXR-CRPGXRXCCXPXRRCSRRFGXXXXRRCRXXXXXX (SEQ ID NO: 294) wherein X is no amino acid or any amino acid analogue.

In some embodiments, a peptide comprises the one or more of the following peptide fragments: GKCMNGKC (SEQ ID NO: 312); GRCMNGRC (SEQ ID NO: 313); GKCINKKCKC (SEQ ID NO: 298); KCIN (SEQ ID NO: 299); KKCK (SEQ ID NO: 300); PCKR (SEQ ID NO: 301); KRCSRR (SEQ ID NO: 302); KQC (SEQ ID NO: 303); GRCINRRCRC (SEQ ID NO: 304); RCIN (SEQ ID NO: 305); RRCR (SEQ ID NO: 306); PCRR (SEQ ID NO: 307); RRCSRR (SEQ ID NO: 308); RQC (SEQ ID NO: 309); PCKK (SEQ ID NO: 310), and KKCSKK (SEQ ID NO: 311).

TABLE 1 lists some exemplary peptides according to the present disclosure.

TABLE 1

Exemplary Amino Acid Sequences

| SEQ ID NO: | Amino Acid Sequence |
|---|---|
| SEQ ID NO: 24 | GSGIVCKVCKIICGMQGKKVNICKAPIKCKCKKG |
| SEQ ID NO: 25 | GSSEKDCIKHLQRCRENKDCCSKKCSRRGTNPEKRCR |
| SEQ ID NO: 26 | GSVRIPVSCKHSGQCLKPCKDAGMRFGKCMNGKCDCTPK |
| SEQ ID NO: 27 | GSGVPINVKCRGSRDCLDPCKKAGMRFGKCINSKCHCTP |
| SEQ ID NO: 28 | GSAVCVYRTCDKDCKRRGYRSGKCINNACKCYPYG |
| SEQ ID NO: 29 | GSISCTGSKQCYDPCKRKTGCPNAKCMNKSCKCYGCG |
| SEQ ID NO: 30 | GSQVQTNVKCQGGSCASVCRREIGVAAGKCINGKCVCYRN |
| SEQ ID NO: 31 | GSEVIRCSGSKQCYGPCKQQTGCTNSKCMNKVCKCYGCG |
| SEQ ID NO: 32 | GSACKGVFDACTPGKNECCPNRVCSDKHKWCKWKL |
| SEQ ID NO: 33 | GSQIYTSKECNGSSECYSHCEGITGKRSGKCINKKCYCYR |
| SEQ ID NO: 34 | GSGCLEFWWKCNPNDDKCCRPKLKCSKLFKLCNFSFG |
| SEQ ID NO: 35 | GSDCVRFWGKCSQTSDCCPHLACKSKWPRNICVWDGSVG |

TABLE 1-continued

Exemplary Amino Acid Sequences

| SEQ ID NO: | Amino Acid Sequence |
| --- | --- |
| SEQ ID NO: 36 | GSGCFGYKCDYYKGCCSGYVCSPTWKWCVRPGPGR |
| SEQ ID NO: 37 | GSMNAKFILLLVLTTMMLLPDTKGAEVIRCSGSKQCYGPCKQQTGCTNSKCMNKVCKCYGCG |
| SEQ ID NO: 38 | GSMNAKLIYLLLVVTTMTLMFDTAQAVDIMCSGPKQCYGPCKKETGCPNAKCMNRRCKCYGCV |
| SEQ ID NO: 39 | GSMNAKLIYLLLVVTTMMLTFDTTQAGDIKCSGTRQCWGPCKKQTTCTNSKCMNGKCKCYGCVG |
| SEQ ID NO: 40 | GSMNTKFIFLLLVVTNTMMLFDTKPVEGISCTGSKQCYDPCKRKTGCPNAKCMNKSCKCYGCG |
| SEQ ID NO: 41 | GSGVPINVKCSGSRDCLEPCKKAGMRFGKCINRKCHCTPK |
| SEQ ID NO: 42 | GSGVPINVKCTGSPQCLKPCKDAGMRFGKCINGKCHCTPK |
| SEQ ID NO: 43 | GSGVIINVKCKISRQCLEPCKKAGMRFGKCMNGKCHCTPK |
| SEQ ID NO: 44 | GSGVPINVKCRGSPQCIQPCRDAGMRFGKCMNGKCHCTPQ |
| SEQ ID NO: 45 | GSGVEINVKCTGSHQCIKPCKDAGMRFGKCINRKCHCTPK |
| SEQ ID NO: 46 | GSGVEINVKCSGSPQCLKPCKDAGMRFGKCMNRKCHCTPK |
| SEQ ID NO: 47 | GSGVPTDVKCRGSPQCIQPCKDAGMRFGKCMNGKCHCTPK |
| SEQ ID NO: 48 | GSGVPINVSCTGSPQCIKPCKDAGMRFGKCMNRKCHCTPK |
| SEQ ID NO: 49 | GSGVPINVPCTGSPQCIKPCKDAGMRFGKCMNRKCHCTPK |
| SEQ ID NO: 50 | GSVGINVKCKHSGQCLKPCKDAGMRFGKCINGKCDCTPK |
| SEQ ID NO: 51 | GSVGINVKCKHSGQCLKPCKDAGMRFGKCMNGKCDCTPK |
| SEQ ID NO: 52 | GSVGIPVSCKHSGQCIKPCKDAGMRFGKCMNRKCDCTPK |
| SEQ ID NO: 53 | GSRKGCFKEGHSCPKTAPCCRPLVCKGPSPNTKKCTRP |
| SEQ ID NO: 54 | GSSFCIPFKPCKSDENCCKKFKCKTTGIVKLCRW |
| SEQ ID NO: 55 | GSLKGCLPRNRFCNALSGPRCCSGLRCKELSIWASKCL |
| SEQ ID NO: 56 | GSGNYCLRGRCLPGGRKCCNGRPCECFAKICSCKPK |
| SEQ ID NO: 57 | GSTVKCGGCNRKCCPGGCRSGKCINGKCQCY |
| SEQ ID NO: 58 | GSGCMKEYCAGQCRGKVSQDYCLKHCKCIPR |
| SEQ ID NO: 59 | GSACLGFGEKCNPSNDKCCKSSSLVCSQKHKWCKYG |
| SEQ ID NO: 60 | GSRGGCLPHNRFCNALSGPRCCSGLRCKELSIRDSRCLG |
| SEQ ID NO: 61 | GSRGGCLPRNKFCNPSSGPRCCSGLTCKELNIWASKCL |
| SEQ ID NO: 62 | GSQRSCAKPGDMCMGIKCCDGQCGCNRGTGRCFCK |
| SEQ ID NO: 63 | GSARGCADAYKSCNHPRTCCDGYNGYKRACICSGSNCKCKKS |
| SEQ ID NO: 64 | GSRGGCLPHNRFCNALSGPRCCSGLRCKELSIWDSRCLG |
| SEQ ID NO: 65 | GSRGGCLPHNRFCNALSGPRCCSGLKCKELSIYDSRCLG |
| SEQ ID NO: 66 | GSRGGCLPHNRFCNALSGPRCCSRLKCKELSIWDSRCLG |
| SEQ ID NO: 67 | GSRGGCLPHNRFCNALTGPRCCSRLRCKELSIWDSICLG |
| SEQ ID NO: 68 | GSSCADAYKSCDSLKCCNNRTCMCSMIGTNCTCRKK |
| SEQ ID NO: 69 | GSERRCLPAGKTCVRGPMRVPCCGSCSQNKCT |
| SEQ ID NO: 70 | GSLCSREGEFCYKLRKCCAGFYCKAFVLHCYRN |
| SEQ ID NO: 71 | GSACGSCRKKCKGSGKCINGRCKCY |

TABLE 1-continued

Exemplary Amino Acid Sequences

| SEQ ID NO: | Amino Acid Sequence |
|---|---|
| SEQ ID NO: 72 | GSACGSCRKKCKGPGKCINGRCKCY |
| SEQ ID NO: 73 | GSACQGYMRKCGRDKPPCCKKLECSKTWRWCVWN |
| SEQ ID NO: 74 | GSGRYCQKWMWTCDSKRACCEGLRCKLWCRKI |
| SEQ ID NO: 75 | GSNAKCRGSPECLPKCKEAIGKAAGKCMNGKCKCYP |
| SEQ ID NO: 76 | GSNVKCRGSKECLPACKAAVGKAAGKCMNGKCKCYP |
| SEQ ID NO: 77 | GSNVKCRGSPECLPKCKEAIGKSAGKCMNGKCKCYP |
| SEQ ID NO: 78 | GSNAKCRGSPECLPKCKQAIGKAAGKCMNGKCKCYP |
| SEQ ID NO: 79 | GSRGYCAEKGIKCHNIHCCSGLTCKCKGSSCVCRK |
| SEQ ID NO: 80 | GSERGCKLTFWKCKNKKECCGWNACALGICMPR |
| SEQ ID NO: 81 | GSKKKCIAKDYGRCKWGGTPCCRGRGCICSIMGTNCECKPR |
| SEQ ID NO: 82 | GSGCKLTFWKCKNKKECCGWNACALGICMPR |
| SEQ ID NO: 83 | GSACKGLFVTCTPGKDECCPNHVCSSKHKWCKYK |
| SEQ ID NO: 84 | GSIACAPRGLLCFRDKECCKGLTCKGRFVNTWPTFCLV |
| SEQ ID NO: 85 | GSACAGLYKKCGKGVNTCCENRPCKCDLAMGNCICKKK |
| SEQ ID NO: 86 | GSFTCAISCDIKVNGKPCKGSGEKKCSGGWSCKFNVCVKV |
| SEQ ID NO: 87 | GSGFCAQKGIKCHDIHCCTNLKCVREGSNRVCRKA |
| SEQ ID NO: 88 | GSCAKKRNWCGKNEDCCCPMKCIYAWYNQQGSCQSTITGLFKKC |
| SEQ ID NO: 89 | GSYCQKWMWTCDSARKCCEGLVCRLWCKKI |
| SEQ ID NO: 90 | GSRGGCLPHNKFCNALSGPRCCSGLKCKELTIWNTKCLE |
| SEQ ID NO: 91 | GSNVKCTGSKQCLPACKAAVGKAAGKCMNGKCKCYT |
| SEQ ID NO: 92 | GSQRSCAKPGEMCMRIKCCDGQCGCNRGTGRCFCK |
| SEQ ID NO: 93 | GSGCIPKHKRCTWSGPKCCNNISCHCNISGTLCKCRPG |
| SEQ ID NO: 94 | GSNYCVAKRCRPGGRQCCSGKPCACVGKVCKCPRD |
| SEQ ID NO: 95 | GSERGCSGAYKRCSSSQRCCEGRPCVCSAINSNCKCRKT |
| SEQ ID NO: 96 | GSRYCPRNPEACYNYCLRTGRPGGYCGGRSRITCFCFR |
| SEQ ID NO: 97 | GSQRSCAKPGEMCMGIKCCDGQCGCNRGTGRCFCK |
| SEQ ID NO: 98 | GSRRGCFKEGKWCPKSAPCCAPLKCKGPSIKQQKCVRE |
| SEQ ID NO: 99 | GSTVKCGGCNRKCCAGGCRSGKCINGKCQCYGR |
| SEQ ID NO: 100 | GSERRCEPSGKPCRPLMRIPCCGSCVRGKCA |
| SEQ ID NO: 101 | GSRGGCLPRNKFCNPSSGPRCCSGLTCKELNIWANKCL |
| SEQ ID NO: 102 | GSCAKKRNWCGKNEDCCCPMKCIYAWYNQQGSCQTTITGLFKKC |
| SEQ ID NO: 103 | GSVRIPVSCKHSGQCLKPCKDAGMRTGKCMNGKCDCTPK |
| SEQ ID NO: 104 | GSVKCTTSKDCWPPCKKVTGRA |
| SEQ ID NO: 105 | GSGIVCRVCRIICGMQGRRVNICRAPIRCRCRRG |
| SEQ ID NO: 106 | GSSERDCIRHLQRCRENRDCCSRRCSRRGTNPERRCR |
| SEQ ID NO: 107 | GSVRIPVSCRHSGQCLRPCRDAGMRFGRCMNGRCDCTPR |
| SEQ ID NO: 108 | GSGVPINVRCRGSRDCLDPCRRAGMRFGRCINSRCHCTP |
| SEQ ID NO: 109 | GSAVCVYRTCDRDCRRGYRSGRCINNACRCYPYG |

TABLE 1-continued

Exemplary Amino Acid Sequences

| SEQ ID NO: | Amino Acid Sequence |
|---|---|
| SEQ ID NO: 110 | GSISCTGSRQCYDPCRRTGCPNARCMNRSCRCYGCG |
| SEQ ID NO: 111 | GSQVQTNVRCQGGSCASVCRREIGVAAGRCINGRCVCYRN |
| SEQ ID NO: 112 | GSEVIRCSGSRQCYGPCRQQTGCTNSRCMNRVCRCYGCG |
| SEQ ID NO: 113 | GSACRGVFDACTPGRNECCPNRVCSDRHRWCRWRL |
| SEQ ID NO: 114 | GSQIYTSRECNGSSECYSHCEGITGRRSGRCINRRCYCYR |
| SEQ ID NO: 115 | GSGCLEFWWRCNPNDDRCCRPRLRCSRLFRLCNFSFG |
| SEQ ID NO: 116 | GSDCVRFWGRCSQTSDCCPHLACRSRWPRNICVWDGSVG |
| SEQ ID NO: 117 | GSGCFGYRCDYYRGCCSGYVCSPTWRWCVRPGPGR |
| SEQ ID NO: 118 | GSMNARFILLLVLTTMMLLPDTRGAEVIRCSGSRQCYGPCRQQTGCTNSRCMNRVCRCYGCG |
| SEQ ID NO: 119 | GSMNARLIYLLLVVTTMTLMFDTAQAVDIMCSGPRQCYGPCRRETGCPNARCMNRRCRCYGCV |
| SEQ ID NO: 120 | GSMNARLIYLLLVVTTMMLTFDTTQAGDIRCSGTRQCWGPCRRQTTCTNSRCMNGRCRCYGCVG |
| SEQ ID NO: 121 | GSMNTRFIFLLLVVTNTMMLFDTRPVEGISCTGSRQCYDPCRRTGCPNARCMNRSCRCYGCG |
| SEQ ID NO: 122 | GSGVPINVRCSGSRDCLEPCRRAGMRFGRCINRRCHCTPR |
| SEQ ID NO: 123 | GSGVPINVRCTGSPQCLRPCRDAGMRFGRCINGRCHCTPR |
| SEQ ID NO: 124 | GSGVIINVRCRISRQCLEPCRRAGMRFGRCMNGRCHCTPR |
| SEQ ID NO: 125 | GSGVPINVRCRGSPQCIQPCRDAGMRFGRCMNGRCHCTPQ |
| SEQ ID NO: 126 | GSGVEINVRCTGSHQCIRPCRDAGMRFGRCINRRCHCTPR |
| SEQ ID NO: 127 | GSGVEINVRCSGSPQCLRPCRDAGMRFGRCMNRRCHCTPR |
| SEQ ID NO: 128 | GSGVPTDVRCRGSPQCIQPCRDAGMRFGRCMNGRCHCTPR |
| SEQ ID NO: 129 | GSGVPINVSCTGSPQCIRPCRDAGMRFGRCMNRRCHCTPR |
| SEQ ID NO: 130 | GSGVPINVPCTGSPQCIRPCRDAGMRFGRCMNRRCHCTPR |
| SEQ ID NO: 131 | GSVGINVRCRHSGQCLRPCRDAGMRFGRCINGRCDCTPR |
| SEQ ID NO: 132 | GSVGINVRCRHSGQCLRPCRDAGMRFGRCMNGRCDCTPR |
| SEQ ID NO: 133 | GSVGIPVSCRHSGQCIRPCRDAGMRFGRCMNRRCDCTPR |
| SEQ ID NO: 134 | GSRRGCFREGHSCPRTAPCCRPLVCRGPSPNTRRCTRP |
| SEQ ID NO: 135 | GSSFCIPFRPCRSDENCCRRFRCRTTGIVRLCRW |
| SEQ ID NO: 136 | GSLRGCLPRNRFCNALSGPRCCSGLRCRELSIWASRCL |
| SEQ ID NO: 137 | GSGNYCLRGRCLPGGRRCCNGRPCECFARICSCRPR |
| SEQ ID NO: 138 | GSTVRCGGCNRRCCPGGCRSGRCINGRCQCY |
| SEQ ID NO: 139 | GSGCMREYCAGQCRGRVSQDYCLRHCRCIPR |
| SEQ ID NO: 140 | GSACLGFGERCNPSNDRCCRSSSLVCSQRHRWCRYG |
| SEQ ID NO: 141 | GSRGGCLPHNRFCNALSGPRCCSGLRCRELSIRDSRCLG |
| SEQ ID NO: 142 | GSRGGCLPRNRFCNPSSGPRCCSGLTCRELNIWASRCL |
| SEQ ID NO: 143 | GSQRSCARPGDMCMGIRCCDGQCGCNRGTGRCFCR |
| SEQ ID NO: 144 | GSARGCADAYRSCNHPRTCCDGYNGYRRACICSGSNCRCRRS |
| SEQ ID NO: 145 | GSRGGCLPHNRFCNALSGPRCCSGLRCRELSIWDSRCLG |

TABLE 1-continued

Exemplary Amino Acid Sequences

| SEQ ID NO: | Amino Acid Sequence |
|---|---|
| SEQ ID NO: 146 | GSRGGCLPHNRFCNALSGPRCCSGLRCRELSIYDSRCLG |
| SEQ ID NO: 147 | GSRGGCLPHNRFCNALSGPRCCSRLRCRELSIWDSRCLG |
| SEQ ID NO: 148 | GSRGGCLPHNRFCNALTGPRCCSRLRCRELSIWDSICLG |
| SEQ ID NO: 149 | GSSCADAYKSCDSLRCCNNRTCMCSMIGTNCTCRRR |
| SEQ ID NO: 150 | GSERRCLPAGRTCVRGPMRVPCCGSCSQNRCT |
| SEQ ID NO: 151 | GSLCSREGEFCYRLRRCCAGFYCRAFVLHCYRN |
| SEQ ID NO: 152 | GSACGSCRRRCRGSGRCINGRCRCY |
| SEQ ID NO: 153 | GSACGSCRRRCRGPGRCINGRCRCY |
| SEQ ID NO: 154 | GSACQGYMRRCGRDRPPCCRRLECSRTWRWCVWN |
| SEQ ID NO: 155 | GSGRYCQRWMWTCDSRRACCEGLRCRLWCRRI |
| SEQ ID NO: 156 | GSNARCRGSPECLPRCREAIGRAAGRCMNGRCRCYP |
| SEQ ID NO: 157 | GSNVRCRGSRECLPACRAAVGRAAGRCMNGRCRCYP |
| SEQ ID NO: 158 | GSNVRCRGSPECLPRCREAIGRSAGRCMNGRCRCYP |
| SEQ ID NO: 159 | GSNARCRGSPECLPRCRQAIGRAAGRCMNGRCRCYP |
| SEQ ID NO: 160 | GSRGYCAERGIRCHNIHCCSGLTCRCRGSSCVCRR |
| SEQ ID NO: 161 | GSERGCRLTFWRCRNRRECCGWNACALGICMPR |
| SEQ ID NO: 162 | GSRRRCIARDYGRCRWGGTPCCRGRGCICSIMGTNCECRPR |
| SEQ ID NO: 163 | GSGCRLTFWRCRNRRECCGWNACALGICMPR |
| SEQ ID NO: 164 | GSACRGLFVTCTPGRDECCPNHVCSSRHRWCRYR |
| SEQ ID NO: 165 | GSIACAPRGLLCFRDRECCRGLTCRGRFVNTWPTFCLV |
| SEQ ID NO: 166 | GSACAGLYRRCGRGVNTCCENRPCRCDLAMGNCICRRR |
| SEQ ID NO: 167 | GSFTCAISCDIRVNGRPCRGSGERRCSGGWSCRFNVCVRV |
| SEQ ID NO: 168 | GSGFCAQRGIRCHDIHCCTNLRCVREGSNRVCRRA |
| SEQ ID NO: 169 | GSCARRRNWCGRNEDCCCPMRCIYAWYNQQGSCQSTITGLFRRC |
| SEQ ID NO: 170 | GSYCQRWMWTCDSARRCCEGLVCRLWCRRI |
| SEQ ID NO: 171 | GSRGGCLPHNRFCNALSGPRCCSGLRCRELTIWNTRCLE |
| SEQ ID NO: 172 | GSNVRCTGSRQCLPACRAAVGRAAGRCMNGRCRCYT |
| SEQ ID NO: 173 | GSQRSCARPGEMCMRIRCCDGQCGCNRGTGRCFCR |
| SEQ ID NO: 174 | GSGCIPRHRRCTWSGPRCCNNISCHCNISGTLCRCRPG |
| SEQ ID NO: 175 | GSNYCVARRCRPGGRQCCSGRPCACVGRVCRCPRD |
| SEQ ID NO: 176 | GSERGCSGAYRRCSSSQRCCEGRPCVCSAINSNCRCRRT |
| SEQ ID NO: 177 | GSQRSCARPGEMCMGIRCCDGQCGCNRGTGRCFCR |
| SEQ ID NO: 178 | GSRRGCFREGRWCPRSAPCCAPLRCRGPSIRQQRCVRE |
| SEQ ID NO: 179 | GSTVRCGGCNRRCCAGGCRSGRCINGRCQCYGR |
| SEQ ID NO: 180 | GSERRCEPSGRPCRPLMRIPCCGSCVRGRCA |
| SEQ ID NO: 181 | GSRGGCLPRNRFCNPSSGPRCCSGLTCRELNIWANRCL |
| SEQ ID NO: 182 | GSCARRRNWCGRNEDCCCPMRCIYAWYNQQGSCQTTITGLFRRC |
| SEQ ID NO: 183 | GSVRIPVSCRHSGQCLRPCRDAGMRTGRCMNGRCDCTPR |

TABLE 1-continued

Exemplary Amino Acid Sequences

| SEQ ID NO: | Amino Acid Sequence |
|---|---|
| SEQ ID NO: 184 | GSQKILSNRCNNSSECIPHCIRIFGTRAAKCINRKCYCYP |
| SEQ ID NO: 185 | GSAVCNLKRCQLSCRSLGLLGKCIGDKCECVKHG |
| SEQ ID NO: 186 | GSISIGIRCSPSIDLCEGQCRIRRYFTGYCSGDTCHCSG |
| SEQ ID NO: 187 | GSGDCLPHLRRCRENNDCCSRRCRRRGANPERRCR |
| SEQ ID NO: 188 | GSSCEPGRTFRDRCNTCKCGADGRSAACTLRACPNQ |
| SEQ ID NO: 189 | GSGDCLPHLKRCKADNDCCGKKCKRRGTNAEKRCR |
| SEQ ID NO: 190 | GSGDCLPHLKRCKENNDCCSKKCKRRGTNPEKRCR |
| SEQ ID NO: 191 | GSKDCLKKLKLCKENKDCCSKSCKRRGTNIEKRCR |
| SEQ ID NO: 192 | GSGDCLPHLKRCKENNDCCSKKCKRRGANPEKRCR |
| SEQ ID NO: 193 | GSVFINVKCRGSPECLPKCKEAIGKSAGKCMNGKCKCYP |
| SEQ ID NO: 194 | GSVFINAKCRGSPECLPKCKEAIGKAAGKCMNGKCKCYP |
| SEQ ID NO: 195 | GSVIINVKCKISRQCLEPCKKAGMRFGKCMNGKCHCTP |
| SEQ ID NO: 196 | GSVPTDVKCRGSPQCIQPCKDAGMRFGKCMNGKCHCTP |
| SEQ ID NO: 197 | GSVRIPVSCKHSGQCLKPCKDAGMRFGKCMNGKCDCTP |
| SEQ ID NO: 198 | GSVRIPVSCRHSGQCLRPCRDAGMRFGRCMNGRCDCTP |
| SEQ ID NO: 199 | GSTNVSCTTSKECWSVCQRLHNTSRGKCMNKKCRC |
| SEQ ID NO: 200 | GSNVKCTGSKQCLPACKAAVGKAAGKCMNGKCKC |
| SEQ ID NO: 201 | GSGVPINVRCRGSRDCLDPCRGAGERHGRCGNSRCHCTP |
| SEQ ID NO: 202 | GSVRIPVSCRHSGQCLRPCRDAGERHGRCGGGRCDCTPR |
| SEQ ID NO: 203 | GSQVQTNVRCQGGSCGSVCRREGGGAGGGCGNGRCGCYRN |
| SEQ ID NO: 204 | GSIKCSESYQCFPVCKSRFGKTNGRCVNGFCDCF |
| SEQ ID NO: 205 | GSVKCSSPQQCLKPCKAAFGISAGGKCINGKCKCY |
| SEQ ID NO: 206 | GSVSCSASSQCWPVCKKLFGTYRGKCMNSKCRCY |
| SEQ ID NO: 207 | GSESCTASNQCWSICKRLHNTNRGKCMNKKCRCY |
| SEQ ID NO: 208 | GSVSCTTSKECWSVCEKLYNTSRGKCMNKKCRCY |
| SEQ ID NO: 209 | GSMRCKSSKECLVKCKQATGRPNGKCMNRKCKCY |
| SEQ ID NO: 210 | GSIKCTLSKDCYSPCKKETGCPRAKCINRNCKCY |
| SEQ ID NO: 211 | GSIRCSGSRDCYSPCMKQTGCPNAKCINKSCKCY |
| SEQ ID NO: 212 | GSIRCSGTRECYAPCQKLTGCLNAKCMNKACKCY |
| SEQ ID NO: 213 | GSISCTNPKQCYPHCKKETGYPNAKCMNRKCKCF |
| SEQ ID NO: 214 | GSASCRTPKDCADPCRKETGCPYGKCMNRKCKCN |
| SEQ ID NO: 215 | GSTSCISPKQCTEPCRAKGCKHGKCMNRKCHCM |
| SEQ ID NO: 216 | GSKECTGPQHCTNFCRKN-KCTHGKCMNRKCKCF |
| SEQ ID NO: 217 | GSIKCRTPKDCADPCRKQTGCPHAKCMNKTCRCH |
| SEQ ID NO: 218 | GSVKCTTSKECWPPCKAATGKAAGKCMNKKCKCQ |
| SEQ ID NO: 219 | GSLECGASRECYDPCFKAFGRAHGKCMNNKCRCY |
| SEQ ID NO: 220 | GSEKCFATSQCWTPCKKAIGSLQSKCMNGKCKCY |
| SEQ ID NO: 221 | GSVRCYASRECWEPCRRVTGSAQAKCQNNQCRCY |

TABLE 1-continued

Exemplary Amino Acid Sequences

| SEQ ID NO: | Amino Acid Sequence |
|---|---|
| SEQ ID NO: 222 | GSVKCSASRECWVACKKVTGSGQGKCQNNQCRCY |
| SEQ ID NO: 223 | GSVKCISSQECWIACKKVTGRFEGKCQNRQCRCY |
| SEQ ID NO: 224 | GSVRCYDSRQCWIACKKVTGSTQGKCQNKQCRCY |
| SEQ ID NO: 225 | GSVDCTVSKECWAPCKAAFGVDRGKCMGKKCKCY |
| SEQ ID NO: 226 | GSAKCRGSPECLPKCKEAIGKAAGKCMNGKCKCY |
| SEQ ID NO: 227 | GSKKCQGGSCASVCRRVIGVAAGKCINGRCVCY |
| SEQ ID NO: 228 | GSKKCSNTSQCYKTCEKVVGVAAGKCMNGKCICY |
| SEQ ID NO: 229 | GSVKCSGSSKCVKICIDRYNTRGAKCINGRCTCY |
| SEQ ID NO: 230 | GSNRCNNSSECIPHCIRIFGTRAAKCINRKCYCY |
| SEQ ID NO: 231 | GSKECNGSSECYSHCEGITGKRSGKCINKKCYCY |
| SEQ ID NO: 232 | GSAFCNLRRCELSCRSLGLLGKCIGEECKCV |
| SEQ ID NO: 233 | GSAVCNLKRCQLSCRSLGLLGKCIGDKCECV |
| SEQ ID NO: 234 | GSAACYSS-DCRVKCVAMGFSSGKCINSKCKCY |
| SEQ ID NO: 235 | GSAICATDADCSRKCPGNPPCRNGFCACT |
| SEQ ID NO: 236 | GSTECQIKNDCQRYCQSVKECKYGKCYCN |
| SEQ ID NO: 237 | GSTQCQSVRDCQQYCLTPDRCSYGTCYCK |
| SEQ ID NO: 238 | GSVSCRYGSDCAEPCKRLKCLLPSKCINGKCTCY |
| SEQ ID NO: 239 | GSIKCRYPADCHIMCRKVTGRAEGKCMNGKCTCY |
| SEQ ID NO: 240 | GSIKCSSSSSCYEPCRGVTGRAHGKCMNGRCTCY |
| SEQ ID NO: 241 | GSVKCTGSKQCLPACKAAVGKAAGKCMNGKCKCY |
| SEQ ID NO: 242 | GSVSCKHSGQCIKPCKDA-GMRFGKCMNRKCDCT |
| SEQ ID NO: 243 | GSVKCRGSPQCIQPCRDA-GMRFGKCMNGKCHCT |
| SEQ ID NO: 244 | GSVKCTSPKQCLPPCKAQFGIRAGAKCMNGKCKCY |
| SEQ ID NO: 245 | GSVKCTSPKQCSKPCKELYGSSAGAKCMNGKCKCY |
| SEQ ID NO: 246 | GSVKCTSPKQCLPPCKEIYGRHAGAKCMNGKCHCS |
| SEQ ID NO: 247 | GSVKCTGSKQCWPVCKQMFGKPNGKCMNGKCRCY |
| SEQ ID NO: 248 | GSVKCRGSRDCLDPCKKAGMRFGKCINSKCHCT |
| SEQ ID NO: 249 | GSVRCVTDDDCFRKCPGNPSCKRGFCACK |
| SEQ ID NO: 250 | GSVPCNNSRPCVPVCIREVNNKNGKCSNGKCLCY |
| SEQ ID NO: 251 | GSVPINVKCRGSRDCLDPCKKAGMRFGKCINSKCHCTP |
| SEQ ID NO: 252 | GSVQTNVKCQGGSCASVCRREIGVAAGKCINGKCVCYRN |
| SEQ ID NO: 253 | GSAEIIRCSGTRECYAPCQKLTGCLNAKCMNKACKCYGCV |
| SEQ ID NO: 254 | GSRPTDIKCSASYQCFPVCKSRFGKTNGRCVNGLCDCF |
| SEQ ID NO: 255 | GSQFTDVKCTGSKQCWPVCKQMFGKPNGKCMNGKCRCYS |
| SEQ ID NO: 256 | GSVGINVKCKHSRQCLKPCKDAGMRFGKCTNGKCHCTPK |
| SEQ ID NO: 257 | GSVVIGQRCYRSPDCYSACKKLVGKATGKCTNGRCDC |
| SEQ ID NO: 258 | GSNFKVEGACSKPCRKYCIDKGARNGKCINGRCHCYY |
| SEQ ID NO: 259 | GSQIDTNVKCSGSSKCVKICIDRYNTRGAKCINGRCTCYP |

TABLE 1-continued

Exemplary Amino Acid Sequences

| SEQ ID NO: | Amino Acid Sequence |
|---|---|
| SEQ ID NO: 260 | GSGVPISVRCRGSRDCLEPCRRAGTRFGRCINGRCHCTP |
| SEQ ID NO: 261 | GSGVPISVRCRGSRDCLEPCRRAGTRFGRCIQSRCHCTP |
| SEQ ID NO: 262 | GSGVPISVRCRGSRDCLEPCRRAGTRFGRCINRRCHCTP |
| SEQ ID NO: 263 | GSGVPINVRCRGSRDCLEPCRRAGTRFGRCINSRCHCTP |
| SEQ ID NO: 264 | GSGVPINVRCRGSRDCLEPCRRAGTRFGRCIQSRCHCTP |
| SEQ ID NO: 265 | GSGVPINVRCRGSRDCLEPCRRAGTRFGRCIQSRCHCYP |
| SEQ ID NO: 266 | GSGVPINVRCRGSRDCYEPCRRAGTRFGRCIQSRCHCTP |
| SEQ ID NO: 267 | GSGVPINVRCRGSRDCLEPCRRAGTRFGRCIQSRCYCTP |
| SEQ ID NO: 268 | GSGVPISVRCRGSRDCLEPCRRAGTRFGRCIQSRCHCYP |
| SEQ ID NO: 269 | GSGVPISVRCRGSRDCYEPCRRAGTRFGRCIQSRCHCTP |
| SEQ ID NO: 270 | GSGVPISVRCRGSRDCLEPCRRAGTRFGRCIQSRCYCTP |
| SEQ ID NO: 271 | GSGVPINVRCRGSRDCLEPCRRAGTRFGRCIASRCHCYP |
| SEQ ID NO: 272 | GSGVPINVRCRGSRDCLEPCRRAGTRFGRCISSRCHCYP |
| SEQ ID NO: 273 | GSGVPINVRCRGSRDCLEPCRRAGTRFGRCITSRCHCYP |
| SEQ ID NO: 274 | GSGVPINVRCRGSRDCLEPCRRAGTRFGRCINSRCHCYP |
| SEQ ID NO: 314 | GIVCKVCKIICGMQGKKVNICKAPIKCKCKKG |
| SEQ ID NO: 315 | SEKDCIKHLQRCRENKDCCSKKCSRRGTNPEKRCR |
| SEQ ID NO: 316 | VRIPVSCKHSGQCLKPCKDAGMRFGKCMNGKCDCTPK |
| SEQ ID NO: 317 | GVPINVKCRGSRDCLDPCKKAGMRFGKCINSKCHCTP |
| SEQ ID NO: 318 | AVCVYRTCDKDCKRRGYRSGKCINNACKCYPYG |
| SEQ ID NO: 319 | ISCTGSKQCYDPCKRKTGCPNAKCMNKSCKCYGCG |
| SEQ ID NO: 320 | QVQTNVKCQGGSCASVCRREIGVAAGKCINGKCVCYRN |
| SEQ ID NO: 321 | EVIRCSGSKQCYGPCKQQTGCTNSKCMNKVCKCYGCG |
| SEQ ID NO: 322 | ACKGVFDACTPGKNECCPNRVCSDKHKWCKWKL |
| SEQ ID NO: 323 | QIYTSKECNGSSECYSHCEGITGKRSGKCINKKCYCYR |
| SEQ ID NO: 324 | GCLEFWWKCNPNDDKCCRPKLKCSKLFKLCNFSFG |
| SEQ ID NO: 325 | DCVRFWGKCSQTSDCCPHLACKSKWPRNICVWDGSVG |
| SEQ ID NO: 326 | GCFGYKCDYYKGCCSGYVCSPTWKWCVRPGPGR |
| SEQ ID NO: 327 | MNAKFILLLVLTTMMLLPDTKGAEVIRCSGSKQCYGPCKQQTGCTNSKCMNKVCKCYGCG |
| SEQ ID NO: 328 | MNAKLIYLLLVVTTMTLMFDTAQAVDIMCSGPKQCYGPCKKETGCPNAKCMNRRCKCYGCV |
| SEQ ID NO: 329 | MNAKLIYLLLVVTTMMLTFDTTQAGDIKCSGTRQCWGPCKKQTTCTNSKCMNGKCKCYGCVG |
| SEQ ID NO: 330 | MNTKFIFLLLVVTNTMMLFDTKPVEGISCTGSKQCYDPCKRKTGCPNAKCMNKSCKCYGCG |
| SEQ ID NO: 331 | GVPINVKCSGSRDCLEPCKKAGMRFGKCINRKCHCTPK |
| SEQ ID NO: 332 | GVPINVKCTGSPQCLKPCKDAGMRFGKCINGKCHCTPK |
| SEQ ID NO: 333 | GVIINVKCKISRQCLEPCKKAGMRFGKCMNGKCHCTPK |
| SEQ ID NO: 334 | GVPINVKCRGSPQCIQPCRDAGMRFGKCMNGKCHCTPQ |

TABLE 1-continued

Exemplary Amino Acid Sequences

| SEQ ID NO: | Amino Acid Sequence |
|---|---|
| SEQ ID NO: 335 | GVEINVKCTGSHQCIKPCKDAGMRFGKCINRKCHCTPK |
| SEQ ID NO: 336 | GVEINVKCSGSPQCLKPCKDAGMRFGKCMNRKCHCTPK |
| SEQ ID NO: 337 | GVPTDVKCRGSPQCIQPCKDAGMRFGKCMNGKCHCTPK |
| SEQ ID NO: 338 | GVPINVSCTGSPQCIKPCKDAGMRFGKCMNRKCHCTPK |
| SEQ ID NO: 339 | GVPINVPCTGSPQCIKPCKDAGMRFGKCMNRKCHCTPK |
| SEQ ID NO: 340 | VGINVKCKHSGQCLKPCKDAGMRFGKCINGKCDCTPK |
| SEQ ID NO: 341 | VGINVKCKHSGQCLKPCKDAGMRFGKCMNGKCDCTPK |
| SEQ ID NO: 342 | VGIPVSCKHSGQCIKPCKDAGMRFGKCMNRKCDCTPK |
| SEQ ID NO: 343 | RKGCFKEGHSCPKTAPCCRPLVCKGPSPNTKKCTRP |
| SEQ ID NO: 344 | SFCIPFKPCKSDENCCKKFKCKTTGIVKLCRW |
| SEQ ID NO: 345 | LKGCLPRNRFCNALSGPRCCSGLRCKELSIWASKCL |
| SEQ ID NO: 346 | GNYCLRGRCLPGGRKCCNGRPCECFAKICSCKPK |
| SEQ ID NO: 347 | TVKCGGCNRKCCPGGCRSGKCINGKCQCY |
| SEQ ID NO: 348 | GCMKEYCAGQCRGKVSQDYCLKHCKCIPR |
| SEQ ID NO: 349 | ACLGFGEKCNPSNDKCCKSSSLVCSQKHKWCKYG |
| SEQ ID NO: 350 | RGGCLPHNRFCNALSGPRCCSGLRCKELSIRDSRCLG |
| SEQ ID NO: 351 | RGGCLPRNKFCNPSSGPRCCSGLTCKELNIWASKCL |
| SEQ ID NO: 352 | QRSCAKPGDMCMGIKCCDGQCGCNRGTGRCFCK |
| SEQ ID NO: 353 | ARGCADAYKSCNHPRTCCDGYNGYKRACICSGSNCKCKKS |
| SEQ ID NO: 354 | RGGCLPHNRFCNALSGPRCCSGLRCKELSIWDSRCLG |
| SEQ ID NO: 355 | RGGCLPHNRFCNALSGPRCCSGLKCKELSIYDSRCLG |
| SEQ ID NO: 356 | RGGCLPHNRFCNALSGPRCCSRLKCKELSIWDSRCLG |
| SEQ ID NO: 357 | RGGCLPHNRFCNALTGPRCCSRLRCKELSIWDSICLG |
| SEQ ID NO: 358 | SCADAYKSCDSLKCCNNRTCMCSMIGTNCTCRKK |
| SEQ ID NO: 359 | ERRCLPAGKTCVRGPMRVPCCGSCSQNKCT |
| SEQ ID NO: 360 | LCSREGEFCYKLRKCCAGFYCKAFVLHCYRN |
| SEQ ID NO: 361 | ACGSCRKKCKGSGKCINGRCKCY |
| SEQ ID NO: 362 | ACGSCRKKCKGPGKCINGRCKCY |
| SEQ ID NO: 363 | ACQGYMRKCGRDKPPCCKKLECSKTWRWCVWN |
| SEQ ID NO: 364 | GRYCQKWMWTCDSKRACCEGLRCKLWCRKI |
| SEQ ID NO: 365 | NAKCRGSPECLPKCKEAIGKAAGKCMNGKCKCYP |
| SEQ ID NO: 366 | NVKCRGSKECLPACKAAVGKAAGKCMNGKCKCYP |
| SEQ ID NO: 367 | NVKCRGSPECLPKCKEAIGKSAGKCMNGKCKCYP |
| SEQ ID NO: 368 | NAKCRGSPECLPKCKQAIGKAAGKCMNGKCKCYP |
| SEQ ID NO: 369 | RGYCAEKGIKCHNIHCCSGLTCKCKGSSCVCRK |
| SEQ ID NO: 370 | ERGCKLTFWKCKNKKECCGWNACALGICMPR |
| SEQ ID NO: 371 | KKKCIAKDYGRCKWGGTPCCRGRGCICSIMGTNCECKPR |
| SEQ ID NO: 372 | GCKLTFWKCKNKKECCGWNACALGICMPR |

TABLE 1-continued

Exemplary Amino Acid Sequences

| SEQ ID NO: | Amino Acid Sequence |
|---|---|
| SEQ ID NO: 373 | ACKGLFVTCTPGKDECCPNHVCSSKHKWCKYK |
| SEQ ID NO: 374 | IACAPRGLLCFRDKECCKGLTCKGRFVNTWPTFCLV |
| SEQ ID NO: 375 | ACAGLYKKCGKGVNTCCENRPCKCDLAMGNCICKKK |
| SEQ ID NO: 376 | FTCAISCDIKVNGKPCKGSGEKKCSGGWSCKFNVCVKV |
| SEQ ID NO: 377 | GFCAQKGIKCHDIHCCTNLKCVREGSNRVCRKA |
| SEQ ID NO: 378 | CAKKRNWCGKNEDCCCPMKCIYAWYNQQGSCQSTITGLFKKC |
| SEQ ID NO: 379 | YCQKWMWTCDSARKCCEGLVCRLWCKKI |
| SEQ ID NO: 380 | RGGCLPHNKFCNALSGPRCCSGLKCKELTIWNTKCLE |
| SEQ ID NO: 381 | NVKCTGSKQCLPACKAAVGKAAGKCMNGKCKCYT |
| SEQ ID NO: 382 | QRSCAKPGEMCMRIKCCDGQCGCNRGTGRCFCK |
| SEQ ID NO: 383 | GCIPKHKRCTWSGPKCCNNISCHCNISGTLCKCRPG |
| SEQ ID NO: 384 | NYCVAKRCRPGGRQCCSGKPCACVGKVCKCPRD |
| SEQ ID NO: 385 | ERGCSGAYKRCSSSQRCCEGRPCVCSAINSNCKCRKT |
| SEQ ID NO: 386 | RYCPRNPEACYNYCLRTGRPGGYCGGRSRITCFCFR |
| SEQ ID NO: 387 | QRSCAKPGEMCMGIKCCDGQCGCNRGTGRCFCK |
| SEQ ID NO: 388 | RRGCFKEGKWCPKSAPCCAPLKCKGPSIKQQKCVRE |
| SEQ ID NO: 389 | TVKCGGCNRKCCAGGCRSGKCINGKCQCYGR |
| SEQ ID NO: 390 | ERRCEPSGKPCRPLMRIPCCGSCVRGKCA |
| SEQ ID NO: 391 | RGGCLPRNKFCNPSSGPRCCSGLTCKELNIWANKCL |
| SEQ ID NO: 392 | CAKKRNWCGKNEDCCCPMKCIYAWYNQQGSCQTTITGLFKKC |
| SEQ ID NO: 393 | VRIPVSCKHSGQCLKPCKDAGMRTGKCMNGKCDCTPK |
| SEQ ID NO: 394 | VKCTTSKDCWPPCKKVTGRA |
| SEQ ID NO: 395 | GIVCRVCRIICGMQGRRVNICRAPIRCRCRRG |
| SEQ ID NO: 396 | SERDCIRHLQRCRENRDCCSRRCSRRGTNPERRCR |
| SEQ ID NO: 397 | VRIPVSCRHSGQCLRPCRDAGMRFGRCMNGRCDCTPR |
| SEQ ID NO: 398 | GVPINVRCRGSRDCLDPCRRAGMRFGRCINSRCHCTP |
| SEQ ID NO: 399 | AVCVYRTCDRDCRRGYRSGRCINNACRCYPYG |
| SEQ ID NO: 400 | ISCTGSRQCYDPCRRRTGCPNARCMNRSCRCYGCG |
| SEQ ID NO: 401 | QVQTNVRCQGGSCASVCRREIGVAAGRCINGRCVCYRN |
| SEQ ID NO: 402 | EVIRCSGSRQCYGPCRQQTGCTNSRCMNRVCRCYGCG |
| SEQ ID NO: 403 | ACRGVFDACTPGRNECCPNRVCSDRHRWCRWRL |
| SEQ ID NO: 404 | QIYTSRECNGSSECYSHCEGITGRRSGRCINRRCYCYR |
| SEQ ID NO: 405 | GCLEFWWRCNPNDDRCCRPRLRCSRLFRLCNFSFG |
| SEQ ID NO: 406 | DCVRFWGRCSQTSDCCPHLACRSRWPRNICVWDGSVG |
| SEQ ID NO: 407 | GCFGYRCDYYRGCCSGYVCSPTWRWCVRPGPGR |
| SEQ ID NO: 408 | MNARFILLLVLTTMMLLPDTRGAEVIRCSGSRQCYGPCRQQTGCTNSRCMNRVCRCYGCG |
| SEQ ID NO: 409 | MNARLIYLLLVVTTMTLMFDTAQAVDIMCSGPRQCYGPCRRETGCPNARCMNRRCRCYGCV |

TABLE 1-continued

Exemplary Amino Acid Sequences

| SEQ ID NO: | Amino Acid Sequence |
|---|---|
| SEQ ID NO: 410 | MNARLIYLLLVVTTMMLTFDTTQAGDIRCSGTRQCWGPCRRQTTCTNSRCMNGRCRCYGCVG |
| SEQ ID NO: 411 | MNTRFIFLLLVVTNTMMLFDTRPVEGISCTGSRQCYDPCRRRTGCPNARCMNRSCRCYGCG |
| SEQ ID NO: 412 | GVPINVRCSGSRDCLEPCRRAGMRFGRCINRRCHCTPR |
| SEQ ID NO: 413 | GVPINVRCTGSPQCLRPCRDAGMRFGRCINGRCHCTPR |
| SEQ ID NO: 414 | GVIINVRCISRQCLEPCRRAGMRFGRCMNGRCHCTPR |
| SEQ ID NO: 415 | GVPINVRCRGSPQCIQPCRDAGMRFGRCMNGRCHCTPQ |
| SEQ ID NO: 416 | GVEINVRCTGSHQCIRPCRDAGMRFGRCINRRCHCTPR |
| SEQ ID NO: 417 | GVEINVRCSGSPQCLRPCRDAGMRFGRCMNRRCHCTPR |
| SEQ ID NO: 418 | GVPTDVRCRGSPQCIQPCRDAGMRFGRCMNGRCHCTPR |
| SEQ ID NO: 419 | GVPINVSCTGSPQCIRPCRDAGMRFGRCMNRRCHCTPR |
| SEQ ID NO: 420 | GVPINVPCTGSPQCIRPCRDAGMRFGRCMNRRCHCTPR |
| SEQ ID NO: 421 | VGINVRCHSGQCLRPCRDAGMRFGRCINGRCDCTPR |
| SEQ ID NO: 422 | VGINVRCHSGQCLRPCRDAGMRFGRCMNGRCDCTPR |
| SEQ ID NO: 423 | VGIPVSCRHSGQCIRPCRDAGMRFGRCMNRRCDCTPR |
| SEQ ID NO: 424 | RRGCFREGHSCPRTAPCCRPLVCRGPSPNTRRCTRP |
| SEQ ID NO: 425 | SFCIPFRPCRSDENCCRRFRCRTTGIVRLCRW |
| SEQ ID NO: 426 | LRGCLPRNRFCNALSGPRCCSGLRCRELSIWASRCL |
| SEQ ID NO: 427 | GNYCLRGRCLPGGRRCCNGRPCECFARICSCRPR |
| SEQ ID NO: 428 | TVRCGGCNRRCCPGGCRSGRCINGRCQCY |
| SEQ ID NO: 429 | GCMREYCAGQCRGRVSQDYCLRHCRCIPR |
| SEQ ID NO: 430 | ACLGFGERCNPSNDRCCRSSSLVCSQRHRWCRYG |
| SEQ ID NO: 431 | RGGCLPHNRFCNALSGPRCCSGLRCRELSIRDSRCLG |
| SEQ ID NO: 432 | RGGCLPRNRFCNPSSGPRCCSGLTCRELNIWASRCL |
| SEQ ID NO: 433 | QRSCARPGDMCMGIRCCDGQCGCNRGTGRCFCR |
| SEQ ID NO: 434 | ARGCADAYRSCNHPRTCCDGYNGYRRACICSGSNCRCRRS |
| SEQ ID NO: 435 | RGGCLPHNRFCNALSGPRCCSGLRCRELSIWDSRCLG |
| SEQ ID NO: 436 | RGGCLPHNRFCNALSGPRCCSGLRCRELSIYDSRCLG |
| SEQ ID NO: 437 | RGGCLPHNRFCNALSGPRCCSRLRCRELSIWDSRCLG |
| SEQ ID NO: 438 | RGGCLPHNRFCNALTGPRCCSRLRCRELSIWDSICLG |
| SEQ ID NO: 439 | SCADAYKSCDSLRCCNNRTCMCSMIGTNCTCRRR |
| SEQ ID NO: 440 | ERRCLPAGRTCVRGPMRVPCCGSCSQNRCT |
| SEQ ID NO: 441 | LCSREGEFCYRLRRCCAGFYCRAFVLHCYRN |
| SEQ ID NO: 442 | ACGSCRRRCRGSGRCINGRCRCY |
| SEQ ID NO: 443 | ACGSCRRRCRGPGRCINGRCRCY |
| SEQ ID NO: 444 | ACQGYMRRCGRDRPPCCRRLECSRTWRWCVWN |
| SEQ ID NO: 445 | GRYCQRWMWTCDSRRACCEGLRCRLWCRRI |
| SEQ ID NO: 446 | NARCRGSPECLPRCREAIGRAAGRCMNGRCRCYP |

TABLE 1-continued

Exemplary Amino Acid Sequences

| SEQ ID NO: | Amino Acid Sequence |
| --- | --- |
| SEQ ID NO: 447 | NVRCRGSRECLPACRAAVGRAAGRCMNGRCRCYP |
| SEQ ID NO: 448 | NVRCRGSPECLPRCREAIGRSAGRCMNGRCRCYP |
| SEQ ID NO: 449 | NARCRGSPECLPRCRQAIGRAAGRCMNGRCRCYP |
| SEQ ID NO: 450 | RGYCAERGIRCHNIHCCSGLTCRCRGSSCVCRR |
| SEQ ID NO: 451 | ERGCRLTFWRCRNRRECCGWNACALGICMPR |
| SEQ ID NO: 452 | RRRCIARDYGRCRWGGTPCCRGRGCICSIMGTNCECRPR |
| SEQ ID NO: 453 | GCRLTFWRCRNRRECCGWNACALGICMPR |
| SEQ ID NO: 454 | ACRGLFVTCTPGRDECCPNHVCSSRHRWCRYR |
| SEQ ID NO: 455 | IACAPRGLLCFRDRECCRGLTCRGRFVNTWPTFCLV |
| SEQ ID NO: 456 | ACAGLYRRCGRGVNTCCENRPCRCDLAMGNCICRRR |
| SEQ ID NO: 457 | FTCAISCDIRVNGRPCRGSGERRCSGGWSCRFNVCVRV |
| SEQ ID NO: 458 | GFCAQRGIRCHDIHCCTNLRCVREGSNRVCRRA |
| SEQ ID NO: 459 | CARRRNWCGRNEDCCCPMRCIYAWYNQQGSCQSTITGLFRRC |
| SEQ ID NO: 460 | YCQRWMWTCDSARRCCEGLVCRLWCRRI |
| SEQ ID NO: 461 | RGGCLPHNRFCNALSGPRCCSGLRCRELTIWNTRCLE |
| SEQ ID NO: 462 | NVRCTGSRQCLPACRAAVGRAAGRCMNGRCRCYT |
| SEQ ID NO: 463 | QRSCARPGEMCMRIRCCDGQCGCNRGTGRCFCR |
| SEQ ID NO: 464 | GCIPRHRRCTWSGPRCCNNISCHCNISGTLCRCRPG |
| SEQ ID NO: 465 | NYCVARRCRPGGRQCCSGRPCACVGRVCRCPRD |
| SEQ ID NO: 466 | ERGCSGAYRRCSSSQRCCEGRPCVCSAINSNCRCRRT |
| SEQ ID NO: 467 | QRSCARPGEMCMGIRCCDGQCGCNRGTGRCFCR |
| SEQ ID NO: 468 | RRGCFREGRWCPRSAPCCAPLRCRGPSIRQQRCVRE |
| SEQ ID NO: 469 | TVRCGGCNRRCCAGGCRSGRCINGRCQCYGR |
| SEQ ID NO: 470 | ERRCEPSGRPCRPLMRIPCCGSCVRGRCA |
| SEQ ID NO: 471 | RGGCLPRNRFCNPSSGPRCCSGLTCRELNIWANRCL |
| SEQ ID NO: 472 | CARRRNWCGRNEDCCCPMRCIYAWYNQQGSCQTTITGLFRRC |
| SEQ ID NO: 473 | VRIPVSCRHSGQCLRPCRDAGMRTGRCMNGRCDCTPR |
| SEQ ID NO: 474 | QKILSNRCNNSSECIPHCIRIFGTRAAKCINRKCYCYP |
| SEQ ID NO: 475 | AVCNLKRCQLSCRSLGLLGKCIGDKCECVKHG |
| SEQ ID NO: 476 | ISIGIRCSPSIDLCEGQCRIRRYFTGYCSGDTCHCSG |
| SEQ ID NO: 477 | GDCLPHLRRCRENNDCCSRRCRRRGANPERRCR |
| SEQ ID NO: 478 | SCEPGRTFRDRCNTCKCGADGRSAACTLRACPNQ |
| SEQ ID NO: 479 | GDCLPHLRRCKADNDCCGKKCKRRGTNAEKRCR |
| SEQ ID NO: 480 | GDCLPHLKRCKENNDCCSKKCKRRGTNPEKRCR |
| SEQ ID NO: 481 | KDCLKKLKLCKENKDCCSKSCKRRGTNIEKRCR |
| SEQ ID NO: 482 | GDCLPHLKRCKENNDCCSKKCKRRGANPEKRCR |
| SEQ ID NO: 483 | VFINVKCRGSPECLPKCKEAIGKSAGKCMNGKCKCYP |
| SEQ ID NO: 484 | VFINAKCRGSPECLPKCKEAIGKAAGKCMNGKCKCYP |

TABLE 1-continued

Exemplary Amino Acid Sequences

| SEQ ID NO: | Amino Acid Sequence |
|---|---|
| SEQ ID NO: 485 | VIINVKCKISRQCLEPCKKAGMRFGKCMNGKCHCTP |
| SEQ ID NO: 486 | VPTDVKCRGSPQCIQPCKDAGMRFGKCMNGKCHCTP |
| SEQ ID NO: 487 | VRIPVSCKHSGQCLKPCKDAGMRFGKCMNGKCDCTP |
| SEQ ID NO: 488 | VRIPVSCRHSGQCLRPCRDAGMRFGRCMNGRCDCTP |
| SEQ ID NO: 489 | TNVSCTTSKECWSVCQRLHNTSRGKCMNKKCRC |
| SEQ ID NO: 490 | NVKCTGSKQCLPACKAAVGKAAGKCMNGKCKC |
| SEQ ID NO: 491 | GVPINVRCRGSRDCLDPCRGAGERHGRCGNSRCHCTP |
| SEQ ID NO: 492 | VRIPVSCRHSGQCLRPCRDAGERHGRCGGGRCDCTPR |
| SEQ ID NO: 493 | QVQTNVRCQGGSCGSVCRREGGGAGGGCGNGRCGCYRN |
| SEQ ID NO: 494 | IKCSESYQCFPVCKSRFGKTNGRCVNGFCDCF |
| SEQ ID NO: 495 | VKCSSPQQCLKPCKAAFGISAGgKCINGKCKCY |
| SEQ ID NO: 496 | VSCSASSQCWPVCKKLFGTYRGKCMNSKCRCY |
| SEQ ID NO: 497 | ESCTASNQCWSICKRLHNTNRGKCMNKKCRCY |
| SEQ ID NO: 498 | VSCTTSKECWSVCEKLYNTSRGKCMNKKCRCY |
| SEQ ID NO: 499 | MRCKSSKECLVKCKQATGRPNGKCMNRKCKCY |
| SEQ ID NO: 500 | IKCTLSKDCYSPCKKETGCPRAKCINRNCKCY |
| SEQ ID NO: 501 | IRCSGSRDCYSPCMKQTGCPNAKCINKSCKCY |
| SEQ ID NO: 502 | IRCSGTRECYAPCQKLTGCLNAKCMNKACKCY |
| SEQ ID NO: 503 | ISCTNPKQCYPHCKKETGYPNAKCMNRKCKCF |
| SEQ ID NO: 504 | ASCRTPKDCADPCRKETGCPYGKCMNRKCKCN |
| SEQ ID NO: 505 | TSCISPKQCTEPCRAKGCKHGKCMNRKCHCM |
| SEQ ID NO: 506 | KECTGPQHCTNFCRKN-KCTHGKCMNRKCKCF |
| SEQ ID NO: 507 | IKCRTPKDCADPCRKQTGCPHAKCMNKTCRCH |
| SEQ ID NO: 508 | VKCTTSKECWPPCKAATGKAAGKCMNKKCKCQ |
| SEQ ID NO: 509 | LECGASRECYDPCFKAFGRAHGKCMNNKCRCY |
| SEQ ID NO: 510 | EKCFATSQCWTPCKKAIGSLQSKCMNGKCKCY |
| SEQ ID NO: 511 | VRCYASRECWEPCRRVTGSAQAKCQNNQCRCY |
| SEQ ID NO: 512 | VKCSASRECWVACKKVTGSGQGKCQNNQCRCY |
| SEQ ID NO: 513 | VKCISSQECWIACKKVTGRFEGKCQNRQCRCY |
| SEQ ID NO: 514 | VRCYDSRQCWIACKKVTGSTQGKCQNKQCRCY |
| SEQ ID NO: 515 | VDCTVSKECWAPCKAAFGVDRGKCMGKKCKCY |
| SEQ ID NO: 516 | AKCRGSPECLPKCKEAIGKAAGKCMNGKCKCY |
| SEQ ID NO: 517 | KKCQGGSCASVCRRVIGVAAGKCINGRCVCY |
| SEQ ID NO: 518 | KKCSNTSQCYKTCEKVVGVAAGKCMNGKCICY |
| SEQ ID NO: 519 | VKCSGSSKCVKICIDRYNTRGAKCINGRCTCY |
| SEQ ID NO: 520 | NRCNNSSECIPHCIRIFGTRAAKCINRKCYCY |
| SEQ ID NO: 521 | KECNGSSECYSHCEGITGKRSGKCINKKCYCY |
| SEQ ID NO: 522 | AFCNLRRCELSCRSLGLLGKCIGEECKCV |

TABLE 1-continued

Exemplary Amino Acid Sequences

| SEQ ID NO: | Amino Acid Sequence |
|---|---|
| SEQ ID NO: 523 | AVCNLKRCQLSCRSLGLLGKCIGDKCECV |
| SEQ ID NO: 524 | AACYSS-DCRVKCVAMGFSSGKCINSKCKCY |
| SEQ ID NO: 525 | AICATDADCSRKCPGNPPCRNGFCACT |
| SEQ ID NO: 526 | TECQIKNDCQRYCQSVKECKYGKCYCN |
| SEQ ID NO: 527 | TQCQSVRDCQQYCLTPDRCSYGTCYCK |
| SEQ ID NO: 528 | VSCRYGSDCAEPCKRLKCLLPSKCINGKCTCY |
| SEQ ID NO: 529 | IKCRYPADCHIMCRKVTGRAEGKCMNGKCTCY |
| SEQ ID NO: 530 | IKCSSSSSCYEPCRGVTGRAHGKCMNGRCTCY |
| SEQ ID NO: 531 | VKCTGSKQCLPACKAAVGKAAGKCMNGKCKCY |
| SEQ ID NO: 532 | VSCKHSGQCIKPCKDA-GMRFGKCMNRKCDCT |
| SEQ ID NO: 533 | VKCRGSPQCIQPCRDA-GMRFGKCMNGKCHCT |
| SEQ ID NO: 534 | VKCTSPKQCLPPCKAQFGIRAGAKCMNGKCKCY |
| SEQ ID NO: 535 | VKCTSPKQCSKPCKELYGSSAGAKCMNGKCKCY |
| SEQ ID NO: 536 | VKCTSPKQCLPPCKEIYGRHAGAKCMNGKCHCS |
| SEQ ID NO: 537 | VKCTGSKQCWPVCKQMFGKPNGKCMNGKCRCY |
| SEQ ID NO: 538 | VKCRGSRDCLDPCKKAGMRFGKCINSKCHCT |
| SEQ ID NO: 539 | VRCVTDDDCFRKCPGNPSCKRGFCACK |
| SEQ ID NO: 540 | VPCNNSRPCVPVCIREVNNKNGKCSNGKCLCY |
| SEQ ID NO: 541 | VPINVKCRGSRDCLDPCKKAGMRFGKCINSKCHCTP |
| SEQ ID NO: 542 | VQTNVKCQGGSCASVCRREIGVAAGKCINGKCVCYRN |
| SEQ ID NO: 543 | AEIIRCSGTRECYAPCQKLTGCLNAKCMNKACKCYGCV |
| SEQ ID NO: 544 | RPTDIKCSASYQCFPVCKSRFGKTNGRCVNGLCDCF |
| SEQ ID NO: 545 | QFTDVKCTGSKQCWPVCKQMFGKPNGKCMNGKCRCYS |
| SEQ ID NO: 546 | VGINVKCKHSRQCLKPCKDAGMRFGKCTNGKCHCTPK |
| SEQ ID NO: 547 | VVIGQRCYRSPDCYSACKKLVGKATGKCTNGRCDC |
| SEQ ID NO: 548 | NFKVEGACSKPCRKYCIDKGARNGKCINGRCHCYY |
| SEQ ID NO: 549 | QIDTNVKCSGSSKCVKICIDRYNTRGAKCINGRCTCYP |
| SEQ ID NO: 550 | GVPISVRCRGSRDCLEPCRRAGTRFGRCINGRCHCTP |
| SEQ ID NO: 551 | GVPISVRCRGSRDCLEPCRRAGTRFGRCIQSRCHCTP |
| SEQ ID NO: 552 | GVPISVRCRGSRDCLEPCRRAGTRFGRCINRRCHCTP |
| SEQ ID NO: 553 | GVPINVRCRGSRDCLEPCRRAGTRFGRCINSRCHCTP |
| SEQ ID NO: 554 | GVPINVRCRGSRDCLEPCRRAGTRFGRCIQSRCHCTP |
| SEQ ID NO: 555 | GVPINVRCRGSRDCLEPCRRAGTRFGRCIQSRCHCYP |
| SEQ ID NO: 556 | GVPINVRCRGSRDCYEPCRRAGTRFGRCIQSRCHCTP |
| SEQ ID NO: 557 | GVPINVRCRGSRDCLEPCRRAGTRFGRCIQSRCYCTP |
| SEQ ID NO: 558 | GVPISVRCRGSRDCLEPCRRAGTRFGRCIQSRCHCYP |
| SEQ ID NO: 559 | GVPISVRCRGSRDCYEPCRRAGTRFGRCIQSRCHCTP |
| SEQ ID NO: 560 | GVPISVRCRGSRDCLEPCRRAGTRFGRCIQSRCYCTP |

TABLE 1-continued

Exemplary Amino Acid Sequences

| SEQ ID NO: | Amino Acid Sequence |
|---|---|
| SEQ ID NO: 561 | GVPINVRCRGSRDCLEPCRRAGTRFGRCIASRCHCYP |
| SEQ ID NO: 562 | GVPINVRCRGSRDCLEPCRRAGTRFGRCISSRCHCYP |
| SEQ ID NO: 563 | GVPINVRCRGSRDCLEPCRRAGTRFGRCITSRCHCYP |
| SEQ ID NO: 564 | GVPINVRCRGSRDCLEPCRRAGTRFGRCINSRCHCYP |

In any of SEQ ID NO: 1-SEQ ID NO: 564 or fragment thereof, any one or more K residues can be replaced by an R residue or an A residue, any one or more R residues can be replaced by a K residue or an A residue, any one or more A residues can be replaced by a K residue or an R residue, all K residues can be replaced by R residues or A residues, all but one K residue can be replaced by R or A residues, all but two K residues can be replaced by R residues or A residues, or in any combination thereof. In any of SEQ ID NO: 1-SEQ ID NO: 564 or any fragment thereof, any one or more M residues can be replaced by any one of I, L, or V residues, any one or more L residues can be replaced by any one of V, I, or M residues, any one or more I residues can be replaced by any one of M, L, or V residues, or any one or more V residues can be replaced by any one of I, L, or M residues. In any embodiment, at least one of the amino acids alone or in combination can be interchanged in the peptides or peptide fragments as follows: K/R, M/I/ L/V, G/A, S/T, Q/N, and D/E wherein each letter is each individually any amino acid or amino acid analogue. In some instances, the peptide can contain only one lysine residue, or no lysine residue. In any of SEQ ID NO: 1-SEQ ID NO: 564 or fragment thereof, any amino acid can be replaced with citrulline. In any of SEQ ID NO: 1-SEQ ID NO: 564 or any fragment thereof, X can independently be any number of any amino acid or no amino acid. In some cases, a peptide can include the first two N-terminal amino acids GS, as with peptides of SEQ ID NO: 1-SEQ ID NO: 274, or such N-terminal amino acids (GS) can be substituted by any other one or two amino acids. In other cases, a peptide does not include the first two N-terminal amino acids GS, as with peptides of SEQ ID NO: 275-SEQ ID NO: 564. In some cases, the N-terminus of the peptide is blocked, such as by an acetyl group; in other instances the C-terminus of the peptide is block, such as by an amide group.

In some instances, the peptide is any one of SEQ ID NO: 1-564 or a functional fragment thereof. In other embodiments, the peptide of the disclosure further comprises a peptide with 100%, 99%, 97%, 95%, 90%, 85%, or 80% homology to any one of SEQ ID NO: 1-SEQ ID NO: 564. In further embodiments, the peptide fragment comprises a contiguous fragment of any one of SEQ ID NO: 1-SEQ ID NO: 564 that is at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46 residues long, wherein the peptide fragment is selected from any portion of the peptide. In some embodiments, such peptide fragments contact the cartilage and exhibit properties of those described herein for peptide and peptide-active agent conjugates.

The peptides of the present disclosure can further comprise negative amino acid residues. In some cases, the peptide has 2 or fewer negative amino acid residues. In other cases, the peptide has 4 or fewer negative amino acid residues, 3 or fewer negative amino acid residues, or 1 or fewer negative amino acid residues. The negative amino acid residues can be selected from any negative charged amino acid residues. The negative amino acid residues can selected from either E or D, or a combination of both E and D.

The peptides of the present disclosure can further comprise basic amino acid residues. In some embodiments, basic residues are added to the peptide sequence to increase the charge at physiological pH. The added basic residues can be any basic amino acid. The added basic residues can be selected from K or R, or a combination of K or R.

In some embodiments, the peptide has a charge distribution comprising an acidic region and a basic region. An acidic region can be a nub. A nub is a portion of a peptide extending out of the peptide's three-dimensional structure. A basic region can be a patch. A patch is a portion of a peptide that does not designate any specific topology characteristic of the peptide's three-dimensional structure. In further embodiments, a cystine-dense peptide can be 6 or more basic residues and 2 or fewer acidic residues.

The peptides of the present disclosure can further comprise positively charged amino acid residues. In some cases, the peptide has at least 2 positively charged residues. In other cases, the peptide has at least 3 positively charged residues, at least 4 positively charged residues, at least 5 positively charged residues, at least 6 positively charged residues, at least 7 positively charged residues, at least 8 positively charged residues or at least 9 positively charged residues. The positively charged residues can be selected from any positively charged amino acid residues. The positively charged residues can be selected from either K or R, or a combination of K and R.

In addition, the peptides herein can comprise a 4-19 amino acid residue fragment of any of the above sequences containing at least 2 cysteine residues, and at least 2 or 3 positively charged amino acid residues (for example, arginine, lysine or histidine, or any combination of arginine, lysine or histidine). In other embodiments, the peptides herein is a 20-70 amino acid residue fragment of any of the above sequences containing at least 2 cysteine residues, no more than 2 basic residues, and at least 2 or 3 positively charged amino acid residues (for example, arginine, lysine or histidine, or any combination of arginine, lysine or histidine). In some embodiments, such peptide fragments contact the cartilage and exhibit properties of those described herein for peptide and peptide-active agent conjugates.

In some embodiments, the peptide contains one or more disulfide bonds and has a positive net charge at neutral pH.

At physiological pH, peptides can have a net charge, for example, of −5, −4, −3, −2, −1, 0, +1, +2, +3, +4, or +5. When the net charge is zero, the peptide can be uncharged or zwitterionic. In some instances, the peptide can have a positive charge at physiological pH. In some instances, the peptide can have a charge ≥+2 at physiological pH, ≥+3.5 at physiological pH, ≥+4.5 at physiological pH. In some embodiments, the peptide contains one or more disulfide bonds and has a positive net charge at neutral pH where the net charge can be +0.5 or less than +0.5, +1 or less than +1, +1.5 or less than +1.5, +2 or less than +2, +2.5 or less than +2.5, +3 or less than +3, +3.5 or less than +3.5, +4 or less than +4, +4.5 or less than +4.5, +5 or less than +5, +5.5 or less than +5.5, +6 or less than +6, +6.5 or less than +6.5, +7 or less than +7, +7.5 or less than +7.5, +8 or less than +8, +8.5 or less than +8.5, +9 or less than +9.5, +10 or less than +10. In some embodiments, the peptide has a negative net charge at physiological pH where the net charge can be −0.5 or less than −0.5, −1 or less than −1, −1.5 or less than −1.5, −2 or less than −2, −2.5 or less than −2.5, −3 or less than −3, −3.5 or less than −3.5, −4 or less than −4, −4.5 or less than −4.5, −5 or less than −5, −5.5 or less than −5.5, −6 or less than −6, −6.5 or less than −6.5, −7 or less than −7, −7.5 or less than −7.5, −8 or less than −8, −8.5 or less than −8.5, −9 or less than −9.5, −10 or less than −10. In some cases, the engineering of one or more mutations within a peptide yields a peptide with an altered isoelectric point, charge, surface charge, or rheology at physiological pH. Such engineering of a mutation to a peptide derived from a scorpion or spider can change the net charge of the complex, for example, by decreasing the net charge by 1, 2, 3, 4, or 5, or by increasing the net charge by 1, 2, 3, 4, or 5. In such cases, the engineered mutation may facilitate the ability of the peptide to contact the cartilage. Suitable amino acid modifications for improving the rheology and potency of a peptide can include conservative or non-conservative mutations. A peptide can comprises at most 1 amino acid mutation, at most 2 amino acid mutations, at most 3 amino acid mutations, at most 4 amino acid mutations, at most 5 amino acid mutations, at most 6 amino acid mutations, at most 7 amino acid mutations, at most 8 amino acid mutations, at most 9 amino acid mutations, at most 10 amino acid mutations, or another suitable number as compared to the sequence of the venom or toxin that the peptide is derived from. In other cases, a peptide, or a functional fragment thereof, comprises at least 1 amino acid mutation, at least 2 amino acid mutations, at least 3 amino acid mutations, at least 4 amino acid mutations, at least 5 amino acid mutations, at least 6 amino acid mutations, at least 7 amino acid mutations, at least 8 amino acid mutations, at least 9 amino acid mutations, at least 10 amino acid mutations, or another suitable number as compared to the sequence of the venom or toxin that the peptide is derived from. In some embodiments, mutations can be engineered within a peptide to provide a peptide that has a desired charge or stability at physiological pH.

Peptides can be mutated to add function or remove function. For example, peptides and peptide-conjugates of the present disclosure can be mutated to retain, remove, or add the ability to bind to ion channels, or to promote agonizing or antagonizing ion channels, such as potassium channel binding that may occur with the peptide or peptide-conjugates (e.g., the potassium channel hERG). In some instances, it can be advantageous to remove potassium channel binding from a peptide used for delivery of an active agent. Mutations can include one or more N to S, D to E, M to T, N to Q, N to A, N to S, N to T, N to L, S to G, and S to R amino acid substitutions, or one or more L to Y, H to Y, and T to Y amino acid substitutions, or any combination of thereof, depending on whether the variant is designed to retain function or to remove function of binding to the ion channel. In some embodiments the peptides and peptide-drug conjugates of the present disclosure are mutated to minimize ion channel binding in order to minimize side effects or enhance the safety either in the target tissue or systemically.

In some embodiments, charge can play a role in cartilage homing. The interaction of a peptide of this disclosure in solution and in vivo can be influenced by the isoelectric point (pI) of the peptide and/or the pH of the solution or the local environment it is in. The charge of a peptide in solution can impact the solubility of the protein as well as parameters such as biodistribution, bioavailability, and overall pharmacokinetics. Additionally, positively charged molecules can interact with negatively charged molecules. Positively charged molecules such as the peptides disclosed herein can interact and bind with negatively charged molecules such as the negatively charged extracellular matrix molecules in the cartilage including hyaluranon and aggrecan. Positively charged residues can also interact with specific regions of other proteins and molecules, such as negatively charged residues of receptors or electronegative regions of an ion channel pore on cell surfaces. As such, the pI of a peptide can influence whether a peptide of this disclosure can efficiently home to cartilage. Identifying a correlation between pI and cartilage homing can be an important strategy in identifying lead peptide candidates of the present disclosure. The pI of a peptide can be calculated using a number of different methods including the Expasy pI calculator and the Sillero method. The Expasy pI can be determined by calculating pKa values of amino acids as described in Bjellqvist et al., which were defined by examining polypeptide migration between pH 4.5 to pH 7.3 in an immobilized pH gradient gel environment with 9.2M and 9.8M urea at 15° C. or 25° C. (Bjellqvist et al. Electrophoresis. 14(10):1023-31 (1993)). The Sillero method of calculating pI can involve the solution of a polynomial equation and the individual pKas of each amino acid. This method does not use denaturing conditions (urea) (Sillero et al. 179(2): 319-35 (1989)) Using these pI calculation methods and quantifying the cartilage to blood ratio of peptide signal after administration to a subject can be a strategy for identifying a trend or correlation in charge and cartilage homing. In some embodiments, a peptide with a pI above biological pH (~pH 7.4) can exhibit efficient homing to cartilage. In some embodiments, a peptide with a pI of at least 8, at least 9, at least 10, or at least 11 can efficiently home to cartilage. In other embodiments, a peptide with a pI of 11-12 can home most efficiently to cartilage. In certain embodiments, a peptide can have a pI of about 9. In other embodiments, a peptide can have a pI of 8-10. In some embodiments, more basic peptides can home more efficiently to cartilage. In other embodiments, a high pI alone may not be sufficient to cause cartilage homing of a peptide.

In some embodiments, the tertiary structure and electrostatics of a peptide of the disclosure can impact cartilage homing. Structural analysis or analysis of charge distribution can be a strategy to predict residues important in biological function, such as cartilage homing. For example, several peptides of this disclosure that home to cartilage can be grouped into a structural class defined herein as "hitchins," and can share the properties of disulfide linkages between C1-C4, C2-C5, and C3-C6. The folding topologies of peptides linked through three disulfide linkages (C1-C4, C2-C5, and C3-C6), can be broken down into structural families based on the three-dimensional arrangement of the disulfides. Some cystine-dense peptides have the C3-C6 disulfide linkage passing through the macrocycle formed by the C1-C4 and C2-C5 disulfide linkages, hitchins have the C2-C5 disulfide linkage passing through the macrocycle formed by the C1-C4 and C3-C6 disulfide linkages, and yet other structural families have the C1-C4 disulfide linkage passing through the macrocycle formed by the C2-05 and C3-C6 disulfide linkages. Variants of "hitchin" class peptides with preserved disulfide linkages at these cysteine residues, primary sequence identity, and/or structural homology can be a method of identifying or predicting other potential peptide candidates that can home to cartilage. Additionally, members and related members of the calcin family of peptides can also home to cartilage, despite having a distinct tertiary structure from the "hitchin" class of peptides. Calcin peptides are structurally a subset of the cystine-dense peptides, with cystine-dense disulfide connectivity and topology, but are further classified on the basis of functioning to bind and activate ryanodine receptors (RyRs). These receptors are calcium channels that act to regulate the influx and efflux of calcium in muscle (Schwartz et al. Br J Pharmacol 157(3):392-403. (2009)). Variants of the calcin family of peptides with preserved key residues can be one way to predict promising candidates that can home to cartilage. In some embodiments, structural analysis of a peptide of this disclosure can be determined by evaluating peptides for resistance to degradation in buffers with various proteases or reducing agents. Structural analysis of the distribution of charge density on the surface of a peptide can also be a strategy for predicting promising candidates that can home to cartilage. Peptides with large patches of positive surface charge (when at pH 7.5) can home to cartilage.

The NMR solution structures, x-ray crystallography, or crystal structures of related structural homologs can be used to inform mutational strategies that can improve the folding, stability, and manufacturability, while maintaining the ability of a peptide to home to cartilage. They can be used to predict the 3D pharmacophore of a group of structurally homologous scaffolds, as well as to predict possible graft regions of related proteins to create chimeras with improved properties. For example, this strategy can be used to identify critical amino acid positions and loops that can be used to design drugs with improved properties or to correct deleterious mutations that complicate folding and manufacturability for the peptides. These key amino acid positions and loops can be retained while other residues in the peptide sequences can be mutated to improve, change, remove, or otherwise modify function, homing, and activity of the peptide.

Additionally, the comparison of the primary sequences and the tertiary sequences of two or more peptides can be used to reveal sequence and 3D folding patterns that can be leveraged to improve the peptides and parse out the biological activity of these peptides. For example, comparing two different peptide scaffolds that home to cartilage can lead to the identification of conserved pharmacophores that can guide engineering strategies, such as designing variants with improved folding properties. Important pharmacophore, for example, can comprise aromatic residues or basic residues, which can be important for binding.

Improved peptides can also be engineered based upon immunogenicity information, such as immunogenicity information predicted by TEPITOPE and TEPITOPEpan. TEPITOPE is a computational approach which uses position specific scoring matrix to provide prediction rules for whether a peptide will bind to 51 different HLA-DR alleles, and TEPITOPEpan is method that uses TEPITOPE to extrapolate from HLA-DR molecules with known binding specificities to HLA-DR molecules with unknown binding specificities based on pocket similarity. For example, TEPITOPE and TEPITOPEpan can be used to determine immunogenicity of peptides that home to cartilage. Immunogenicity information can also be predicted using the program NetMHCII version 2.3, which can determine the likelihood that a sequence might be presented as an immunogenic peptide via the major histocompatibility complex (MHC) presentation system of antigen presenting cells (APCs). (Nielson, M et al. *BMC Bioinformatics*, 8: 238 (2007); Nielsen, M. et al. *BMC Bioinformatics*, 10: 296 (2009)). This program can create an immunogenicity score by predicting the binding of a peptide to MHC alleles. Strong binding alleles and weak binding alleles in each major MHC allele group (DR, DQ, and DP) can be tallied separately. The number of peptides of a specific length within the sequence (e.g., a 'core' peptide that can be nine residues long) that are immunogenic can also be tallied. Comparison of peptides or 'core' peptides with high immunogenicity to peptides or 'core' peptides with low immunogenicity can guide engineering strategies for designing variants with decreased immunogenicity. Stronger binding peptides can be more likely to generate an immune response in patient carrying that given MHC alleles. Mutating stronger binding amino acids or peptides out of a peptide sequence can reduce the immunogenicity of the entire peptide. Another aspect of immunogenicity, in addition to whether a peptide binds to a patient's MHC allele, can be whether the patient's immune cells, such as a professional antigen presenting cells such as a macrophage, a B cell, or a dendritic cell, can process the peptide. A dendritic cell can take up a protein or peptide, and then can process a peptide, such as by cleaving to form a nine residue long peptide, which then can bind to the MHC and can be presented on the surface of the dendritic cell to the immune system's various T cells, including helper T cells and cytotoxic T cells, and thus can stimulate an immune response. The processing can involve peptide bond cleavage by enzymes and disulfide bond reduction, and thus a peptide or protein that is resistant to enzymatic cleavage and/or reduction can be resistant to processing and subsequent MHC presentation to the immune system. Therefore, having a peptide or protein that is resistant to enzymatic cleavage and/or reduction can reduce its immunogenic potential.

Furthermore, multiple sequence alignment can also be used to inform mutational strategies using previously identified sequences, and thus providing a guide to making changes that would eliminate labile residues and immunogenic regions of a peptide sequence. Peptides can be evaluated for residues of potential biochemical instability and regions of potential immunogenicity. Then, a residue that can allow for greater peptide stability at a certain location in a peptide can be identified from a multiple sequence alignment. For example, a specific residue can be identified from a multiple sequence alignment as providing greater stability for a peptide at position previously identified as a possible risk for a significant rate of deamidation, cleavage, degradation, oxidation, hydrolysis, isomerization, disulfide exchange, racemization, beta elimination, or aggregation. This information can then be used to create peptides with greater stability or reduced immunogenicity.

In addition to utilizing co-crystal x-ray structures, NMR solution structures, and mutagenesis studies, a multiple alignment of peptide sequences can be used to identify specific amino acids or regions of high conservation that indicate an important interaction with a target or receptor (e.g., binding to a potassium channel protein) or are important for folding and structure or other properties. Once the conserved amino acid or region is identified, then amino acids replacements can be determined that maintain the important properties of the peptide, such as maintenance of the structure, reduction in immunogenicity, reduction in binding to an ion channel protein, increased stability, or any combination of thereof.

The multiple sequence alignment can also identify possible locations to add a tyrosine or tryptophan residue for spectrophotometric reporting. Incorporation of aromatic amino acids such as Tyrosine or Tryptophan into a peptide such as SEQ ID NO: 108, which otherwise contains only amino acids of low UV absorbance at 280 nm, can be analytically advantageous. Tyrosine and Tryptophan amino acids contain aromatic ring structures. These residues have distinct absorption and emission wavelengths and good quantum yields, as shown in TABLE 2, not present in other amino acids. Both Tyrosine and Tryptophan can provide a good 'handle' for analytical detection of a peptide in solution since UV absorbance in the 250-300 nm range and peptide fluorescence is specific for these aromatic molecules. While detection of a peptide such as SEQ ID NO: 108 relies on the absorbance of the peptide bond at 220 nm, where many other materials including minor impurities in solvents also often contribute to signal, the absorbance and fluorescence properties of Tryptophan and Tyrosine containing peptides can provide for a significantly more selective and sensitive detection. Thus incorporating an aromatic amino acid can create peptides better suited for concentration and purity measurements, which can be useful during analytics, process development, manufacturing, and other drug development and drug manufacturing activities. Incorporation can be achieved either through substitutions of one or more amino acids in the peptide to Tyr and/or Trp, insertion of Tyr and/or Trp into the peptide, or via addition of Tyr and/or Trp to the N-terminus or C-terminus of the peptide.

TABLE 2

Absorbance and Fluorescence Characteristics of Tryptophan and Tyrosine.

| Amino Acid | Absorbance | | Fluorescence | |
|---|---|---|---|---|
| | Wavelength (nm) | Absorbtivity $(M*cm)^{-1}$ | Wavelength (nm) | Quantum Yield |
| Tryptophan | 280 | 5,600 | 348 | 0.20 |
| Tyrosine | 274 | 1,400 | 303 | 0.14 |

A peptide of this disclosure can bind to chloride, potassium, or sodium channels. The peptide can also bind to calcium channels. The peptide can block potassium channels and/or sodium channels. The peptide can block calcium channels. In some embodiments, the peptide can activate any one or more of such channels. In some embodiments, the peptide can block any one or more of such channels. In some embodiments, the peptide cannot interact with any of such channels or can be mutated to reduce or remove binding to any such channels. In still other embodiments, the peptide can be a potassium channel agonist, a potassium channel antagonist, a portion of a potassium channel, a sodium channel agonist, a sodium channel antagonist, a chloride channel agonist, a chloride channel antagonist, a calcium channel agonist, a calcium channel antagonist, a hadrucalcin, a theraphotoxin, a huwentoxin, a kaliotoxin, a cobatoxin or a lectin. In some embodiments, the lectin can be SHL-Ib2.

In some embodiments, the peptide can interact with, binds, inhibits, inactivates, or alters expression of ion channels or chloride channels. In some embodiments, the peptide can interact with an Nav1.7 ion channel. In some embodiments, the peptide can interact with a Kv 1.3 ion channel. In still other embodiments, the peptide interacts with proteases, matrix metalloproteinase, inhibits cancer cell migration or metastases, has antimicrobial activity, or has antitumor activity. In addition to acting on matrix metalloproteinases, the peptide can interact with other possible proteases (e.g., elastases). In some embodiments, a peptide of this disclosure can bind to multidrug resistance transporters. Peptide and peptide drug conjugate binding to and blocking multidrug resistance transporters can be used to treat bacterial infections or cancers of the joint and/or bone.

In some embodiments, the peptide has other therapeutic effects on the cartilage or structures thereof or nearby. Beta defensin expression in articular cartilage can be correlated with immunomodulatory functions as we well as osteoarthritis, autoimmune rheumatic disorders such as systemic lupus erythematosus and rheumatoid arthritis (Vordenbäumen and Schneider 2011, Varoga 2004 and Varoga 2005). In some embodiments, the peptides or their mutants inhibit beta defensins, supplement beta defensins, are competitive inhibitors of beta defensins, active or block activation of beta defensin targets, and are used as immune modulators, or to treat autoimmune, arthritis, infections, and other articular disorders.

The present disclosure can also encompass multimers of the various peptides described herein. Examples of multimers include dimers, trimers, tetramers, pentamers, hexamers, heptamers, and so on. A multimer can be a homomer formed from a plurality of identical subunits or a heteromer formed from a plurality of different subunits. In some embodiments, a peptide of the present disclosure is arranged in a multimeric structure with at least one other peptide, or two, three, four, five, six, seven, eight, nine, ten, or more other peptides. In certain embodiments, the peptides of a multimeric structure each have the same sequence. In alternative embodiments, some or all of the peptides of a multimeric structure have different sequences.

The present disclosure further includes peptide scaffolds that, e.g., can be used as a starting point for generating additional peptides. In some embodiments, these scaffolds can be derived from a variety of cystine-dense peptides. Some suitable peptides for scaffolds can include, but are not limited to, chlorotoxin, brazzein, circulin, stecrisp, hanatoxin, midkine, hefutoxin, potato carboxypeptidase inhibitor, bubble protein, attractin, α-GI, α-GID, μ-PIIIA, ω-MVIIA, ω-CVID, χ-MrIA, ρ-TIA, conantokin G, contulakin G, GsMTx4, margatoxin, shK, toxin K, chymotrypsin inhibitor (CTI), and EGF epiregulin core.

In some embodiments, the peptide sequences of the disclosure are flanked by additional amino acids. One or more additional amino acids can, for example, confer a desired in vivo charge, isoelectric point, chemical conjugation site, stability, or physiologic property to a peptide.

Identifying sequence homology can be important for determining key residues that preserve cartilage homing function. For example, in some embodiments identification of conserved positively charged residues can be important in preserving cartilage homing in any homologous variants that are made. In other embodiments, identification of basic or aromatic dyads, can be important in preserving interaction and activity with Kv ion channels in homologous variants.

Two or more peptides can share a degree of homology and share similar properties in vivo. For instance, a peptide can share a degree of homology with a peptide of the present disclosure. In some cases, a peptide of the disclosure can have up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology with a second peptide. In some cases, a peptide of the disclosure can have at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology with a second peptide. Various methods and software programs can be used to determine the homology between two or more peptides, such as NCBI BLAST, Clustal W, MAFFT, Clustal Omega, AlignMe, Praline, or another suitable method or algorithm.

In still other instances, the variant nucleic acid molecules of a peptide of any one of SEQ ID NO: 24-SEQ ID NO: 274 or SEQ ID NO: 314-SEQ ID NO: 564 can be identified by either a determination of the sequence identity or homology of the encoded peptide amino acid sequence with the amino acid sequence of any one of SEQ ID NO: 24-SEQ ID NO: 274, SEQ ID NO: 314-SEQ ID NO: 564, or by a nucleic acid hybridization assay. Such peptide variants can include nucleic acid molecules (1) that remain hybridized with a nucleic acid molecule having the nucleotide sequence of any one of SEQ ID NO: 24-SEQ ID NO: 274 or SEQ ID NO: 314-SEQ ID NO: 564 (or any complement of the previous sequences) under stringent washing conditions, in which the wash stringency is equivalent to 0.5×-2×SSC with 0.1% SDS at 55-65° C., and (2) that encode a peptide having at least 70%, at least 80%, at least 90%, at least 95% or greater than 95% sequence identity or homology to the amino acid sequence of any one SEQ ID NO: 24-SEQ ID NO: 274 or SEQ ID NO: 314-SEQ ID NO: 564. Alternatively, peptide variants of any one SEQ ID NO: 24-SEQ ID NO: 274 or SEQ ID NO: 314-SEQ ID NO: 564 can be characterized as nucleic acid molecules (1) that remain hybridized with a nucleic acid molecule having the nucleotide sequence of any one SEQ ID NO: 24-SEQ ID NO: 274 or SEQ ID NO: 314-SEQ ID NO: 564 (or any complement of the previous sequences) under highly stringent washing conditions, in which the wash stringency is equivalent to 0.1×-0.2×SSC with 0.1% SDS at 50-65° C., and (2) that encode a peptide having at least 70%, at least 80%, at least 90%, at least 95% or greater than 95% sequence identity or homology to the amino acid sequence of any one of SEQ ID NO: 24-SEQ ID NO: 274 or SEQ ID NO: 314-SEQ ID NO: 564.

Percent sequence identity or homology can be determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (Id.). The sequence identity or homology is then calculated as: ([Total number of identical matches]/[length of the longer sequence plus the number of gaps introduced into the longer sequence in order to align the two sequences])(100).

Additionally, there are many established algorithms available to align two amino acid sequences. For example, the "FASTA" similarity search algorithm of Pearson and Lipman is a suitable protein alignment method for examining the level of sequence identity or homology shared by an amino acid sequence of a peptide disclosed herein and the amino acid sequence of a peptide variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO: 1) and a test sequence that has either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, Siam J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity or homology of nucleic acid molecules using a ratio as disclosed above. For nucleotide sequence comparisons, the ktup value can range between one to six, preferably from three to six, most preferably three, with other parameters set as described above.

Some examples of common amino acids that are a "conservative amino acid substitution" are illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Determination of amino acid residues that are within regions or domains that are critical to maintaining structural integrity can be determined. Within these regions one can determine specific residues that can be more or less tolerant of change and maintain the overall tertiary structure of the molecule. Methods for analyzing sequence structure include, but are not limited to, alignment of multiple sequences with high amino acid or nucleotide identity or homology and computer analysis using available software (e.g., the Insight II® viewer and homology modeling tools; MSI, San Diego, Calif.), secondary structure propensities, binary patterns, complementary packing and buried polar interactions (Barton, G. J., *Current Opin. Struct. Biol.* 5:372-6 (1995) and Cordes, M. H. et al., *Current Opin. Struct. Biol.* 6:3-10 (1996)). In general, when designing modifications to molecules or identifying specific fragments determination of structure can typically be accompanied by evaluating activity of modified molecules.

Pairwise sequence alignment is used to identify regions of similarity that may indicate functional, structural and/or evolutionary relationships between two biological sequences (protein or nucleic acid). By contrast, multiple sequence alignment (MSA) is the alignment of three or more biological sequences. From the output of MSA applications, homology can be inferred and the evolutionary relationship between the sequences assessed. One of skill in the art would recognize as used herein, "sequence homology" and "sequence identity" and "percent (%) sequence identity" and "percent (%) sequence homology" have been used interchangeably to mean the sequence relatedness or variation, as appropriate, to a reference polynucleotide or amino acid sequence.

Chemical Modifications

A peptide can be chemically modified one or more of a variety of ways. In some embodiments, the peptide can be mutated to add function, delete function, or modify the in vivo behavior. One or more loops between the disulfide linkages can be modified or replaced to include active elements from other peptides (such as described in Moore and Cochran, Methods in Enzymology, 503, p. 223-251, 2012). Amino acids can also be mutated, such as to increase half-life or bioavailability, modify, add or delete binding behavior in vivo, add new targeting function, modify surface charge and hydrophobicity, or allow conjugation sites. N-methylation is one example of methylation that can occur in a peptide of the disclosure. In some embodiments, the peptide can be modified by methylation on free amines. For example, full methylation can be accomplished through the use of reductive methylation with formaldehyde and sodium cyanoborohydride.

A chemical modification can, for instance, extend the terminal half-life, the absorption half-life, the distribution half-life of a peptide, change the biodistribution or pharmacokinetic profile, or the modification itself can be useful to provide viscosupplementation to a joint. A chemical modification can comprise a polymer, a polyether, polyethylene glycol, a biopolymer, a polyamino acid, a fatty acid, a dendrimer, an Fc region, a simple saturated carbon chain such as palmitate or myristolate, sugars, hyaluronic acid, or albumin. The chemical modification of a peptide with an Fc region can be a fusion Fc-peptide. A polyamino acid can include, for example, a polyamino acid sequence with repeated single amino acids (e.g., polyglycine), and a polyamino acid sequence with mixed polyamino acid sequences (e.g., gly-ala-gly-ala (SEQ ID NO: 568)) that can or cannot follow a pattern, or any combination of the foregoing.

In some embodiments, the peptides of the present disclosure may be modified such that the modification increases the stability and/or the half-life of the peptides. In some embodiments, the attachment of a hydrophobic moiety, such as to the N-terminus, the C-terminus, or an internal amino acid, can be used to extend half-life of a peptide of the present disclosure. In other embodiments, the peptide of the present disclosure can include post-translational modifications (e.g., methylation and/or amidation), which can affect, e.g., serum half-life. In some embodiments, simple carbon chains (e.g., by myristoylation and/or palmitylation) can be conjugated to the peptides. In some embodiments, for example, the simple carbon chains may render conjugated peptides easily separable from unconjugated material. For example, methods that may be used to separate the desired peptides of the invention from unconjugated material include, but are not limited to, solvent extraction and reverse phase chromatography. In some embodiments, lipophilic moieties can be conjugated to the peptide and can extend half-life through reversible binding to serum albumin. Moreover, the conjugated moieties can be lipophilic moieties that extend half-life of the peptides through reversible binding to serum albumin. In some embodiments, the lipophilic moiety can be cholesterol or a cholesterol derivative including cholestenes, cholestanes, cholestadienes and oxysterols. In some embodiments, the peptides can be conjugated to myristic acid (tetradecanoic acid) or a derivative thereof. In other embodiments, the peptides of the present disclosure are coupled (e.g., conjugated) to a half-life modifying agent. Examples of half-life modifying agents include but are not limited to: a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, antibodies, or a molecule that binds to albumin.

In some embodiments, the first two N-terminal amino acids (GS) of SEQ ID NO: 1-SEQ ID NO: 274 can serve as a spacer or linker in order to facilitate conjugation or fusion to another molecule, as well as to facilitate cleavage of the peptide from such conjugated or fused molecules. In some embodiments, the peptides of the present disclosure can be conjugated to other moieties that can modify or effect changes to the properties of the peptides.

Active Agent Conjugates

Peptides according to the present disclosure can be conjugated or fused to a peptide biological agent or other agent comprising amino acids (e.g., an antibody or antibody fragment, receptor or receptor fragment, ligand or ligand fragment, hormone or hormone fragment, growth factors and growth factor fragments, biological toxins and fragments thereof, or other active portion of a peptide), a protein, a peptide, or to a small molecule, RNA, DNA, or other active agent molecular structure for use in the treatment of cartilage diseases, disorders, or injuries. A peptide active agent conjugate can be a peptide conjugated to an active agent by any mechanism described herein. For example, a peptide can be covalently conjugated to an active agent to form a peptide active agent conjugate. A peptide can be chemically conjugated to an active agent to form a peptide active agent conjugate. A peptide and active agent can be expressed as a fusion protein to form a peptide active agent conjugate. For example, an antibody or fragment thereof and a peptide can be expressed as a fusion protein to form a peptide active agent conjugate. For example, in certain embodiments, a peptide as described herein can be fused to another molecule, such as an active agent that provides a functional capability. A peptide can be conjugated with an active agent through expression of a vector containing the sequence of the peptide with the sequence of the active agent. In various embodiments, the sequence of the peptide and the sequence of the active agent are expressed from the same Open Reading Frame (ORF). In various embodiments, the sequence of the peptide and the sequence of the active agent can comprise a contiguous sequence. Various vectors and recombinant systems known in the art can be employed to make such fusion peptides. The peptide and the active agent can each retain similar functional capabilities in the fusion peptide compared with their functional capabilities when expressed separately.

Furthermore, for example, in certain embodiments, the peptides described herein are attached to another molecule, such as an active agent that provides a functional capability. In some embodiments, 1, 2, 3, 4, 5, 6, 7, 8, 9, or 10 active agents can be linked to a peptide. Multiple active agents can be attached by methods such as conjugating to multiple lysine residues and/or the N-terminus, or by linking the multiple active agents to a scaffold, such as a polymer or dendrimer and then attaching that agent-scaffold to the peptide (such as described in Yurkovetskiy, A. V., *Cancer Res* 75(16): 3365-72 (2015).

Described herein are active agents that can be conjugated to the peptides of the present invention for use in either cartilage disorders or kidney disorders, or both. In some embodiments, certain compounds or drugs are appropriate for use in either cartilage or kidney disorders, certain drug classes may be preferred for specific treatment depending on the indication or disorder. As described herein, it is understood that certain active agents are described in a non-limiting exemplary manner for use in treatments of cartilage and/or kidney indications. One or more of such active agents can be conjugated to a peptide of the present invention alone or in combination with one or more detectable agents described herein. In some embodiments, active agents that can be conjugated to any peptide of this disclosure can be classified by mechanism. For example, active agents can belong to the class of anti-inflammatory drugs, immunosuppressive (immune suppression) drugs, analgesics/pain relief drugs, disease modifying osteoarthritic drugs (DMOADs), cell depleting agents/apoptosis modifiers, bone resorptive agents and viscosupplementing agents, and tissue normalization (disease modifying) drugs.

Anti-inflammatory active agents can include, but are not limited to, corticosteroids, glucocorticoids, nonsteroidal anti-inflammatory drugs (NSAIDs), biologics, and other small molecules. Examples of corticosteroid active agents that can be conjugated to any peptide of this disclosure for delivery to the joints and kidneys include triamcinolone dexamethasone, budesonide, and triamcinolone acetonide. Examples of NSAID active agents that can be conjugated to any peptide of this disclosure for delivery to the joints and kidneys include naproxen and ibuprofen. Other active agents include acetylsalicylic acid and acetaminophen. NSAID active agents can be further classified into COX2 inhibitors. An example of a COX2 inhibitor active agent directed to a prostaglandin pathway that can be conjugated to any peptide of this disclosure for delivery to the joint includes celecoxib. An example of a COX2 inhibitor active agent with anti-leukotriene receptor antagonist that can be conjugated to any peptide of this disclosure for delivery to the joint includes montelukast. An example of a COX2 inhibitor active agent that can be conjugated to any peptide of this disclosure for delivery to the kidneys includes iguratimod. Biologic active agents can be further classified into active agents that are IL-1 family inhibitors, IL-17 or IL-23 pathway inhibitors, IL-6 family inhibitors, interferon receptor inhibitors, tumor necrosis factor (TNF) inhibitors, RANK pathway inhibitors, B cell inhibitors, anti-IgE active agents, and co-stimulation inhibitors. An example of an IL-1 family inhibitor active agent that can be conjugated to any peptide of this disclosure for delivery to the joints includes anakinra. An example of an IL-17/IL-23 pathway inhibitor active agent that can be conjugated to any peptide of this disclosure for delivery to the joints includes secukinumab. An example of an IL-6 family inhibitor active agent that can be conjugated to any peptide of this disclosure for delivery to the kidneys includes sirukumab. An example of an interferon receptor inhibitor active agent that can be conjugated to any peptide of this disclosure for delivery to the kidneys includes anifrolumab. An example of a TNF inhibitor active agent that can be conjugated to any peptide of this disclosure for delivery to the joints includes infliximab or etanercept. An example of a RANK pathway inhibitor active agent that can be conjugated to any peptide of this disclosure for delivery to the joints includes denosumab. An example of a B cell inhibitor active agent that can be conjugated to any peptide of this disclosure for delivery to the joints and kidneys includes rituximab. An example of an anti-IgE active agent that can be conjugated to any peptide of this disclosure for delivery to the kidneys includes omalizumab. An example of a co-stimulation inhibitor active agent that can be conjugated to any peptide of this disclosure for delivery to the joints includes abatacept.

Pain relief active agents can include, but are not limited to analgesics, counter-irritants, and pain receptor blocking drugs. Analgesics can be further classified into non-narcotic agents and narcotic agents. An example of a non-narcotic active agent that can be conjugated to any peptide of this disclosure for delivery to the joints includes acetaminophen. An example of a narcotic active agent that can be conjugated to any peptide of this disclosure for delivery to joints includes oxycodone. Counter-irritant active agents can be further classified as natural products. An example of a natural product that can be conjugated to any peptide of this disclosure for delivery to the joints includes capsaicin. Pain receptor blocking active agents can be further classified as TRPV4 inhibitors. An example of a TRPV4 inhibitor active agent that can be conjugated to any peptide of this disclosure for delivery to the joints includes GSK2193874.

Apoptosis modifier active agents can include, but are not limited to, biologics and small molecules. Biologic apoptosis modifier active agents can be further classified as Fas/

FasL inhibitors, TNF/TNFR inhibitors, TRAIL/TRAILR inhibitors, TWEAK/Fn14 inhibitors, IL-1 inhibitors, IL-1 receptor antagonists, growth factors, and sclerostin inhibitors. An example of a TNF/TNFR inhibitor active agent that can be conjugated to any peptide of this disclosure for delivery to the joints includes infliximab. An example of a TRAIL/TRAILR inhibitor active agent that can be conjugated to any peptide of this disclosure for delivery to the joints includes osteoprotegrin. An example of a TWEAK/Fn14 inhibitor active agent that can be conjugated to any peptide of this disclosure for delivery to the kidneys includes BIIB023. An example of an IL-1 receptor antagonist that can be conjugated to any peptide of this disclosure for delivery to the joints includes anakinra. An example of a growth factor active agent that can be conjugated to any peptide of this disclosure for delivery to the joints includes IGF-1. An example of a growth factor active agent that can be conjugated to any peptide of this disclosure for delivery to the kidneys includes EGF. An example of a sclerostin inhibitor active agent that can be conjugated to any peptide of this disclosure for delivery to the joints includes romosozumab. Small molecule apoptosis modifier active agents can be further classified as caspase inhibitors, iNOS inhibitors, surfactants, and bisphosphonates. An example of a caspase inhibitor active agent that can be conjugated to any peptide of this disclosure for delivery to the joints includes ZVAD-fmk. An example of an iNOS inhibitor active agent that can be conjugated to any peptide of this disclosure for delivery to the joints include S-methylisothiourea. An example of a surfactant active agent that can be conjugated to any peptide of this disclosure for delivery to the joints include P188. An example of a bisphosphonate active agent that can be conjugated to any peptide of this disclosure for delivery to the joints includes alendronate. Moreover, the known class of drugs called senotherapeutics, also referred to as senolytics or senolytic drugs or senolytic compounds, refers to small molecules that can selectively induce death of senescent cells and for example by directly or indirectly inducing apoptosis in senescent cells. In addition, senolytics may also act via non-apoptotic mechanisms of cell death including by necroptis, autophagic cell death, pyroptis and caspase-independent cell death (Journal of Cell Science 127; 2135-2144 (2014)). Such drugs can attenuate age-related deterioration of tissues or organs. Examples of drugs that can be conjugated to any peptide of this disclosure to induce apoptosis or induce cell death via non-apoptotic mechanisms include quercetin, dasatinib, bortezomib, carfilzomib, and navitoclax amongst other compounds disclosed herein. Additional active agents are described in the following references: Zhu, Y et al., *Aging Cell* 14(4):644-58 (2015); Kirkland, J L, Exp Gerontol. 48(1): 1-5 (2013); Kirkland J L and Tchkonia T, Exp Gereontol. 68: 19-25 (2015) Tchkonia, T et al., J Clin Invest., 123(3): 966-72 (2013); WO2016118859; Sugumar, D et al., Pharmagenomics Pers Med. 8: 23-33 (2015); Jiafa, R et al., Sci Rep. 6: 23968 (2016); Swanson, C D et al., Nat Rev Rheumatol., 5(6): 317-324 (2009); Oh, C J et al., PLoS One, 7(10):e45870 (2012); and Adebajo, A and Boehncke, W, Psoriatic Arthritis and Psoriasis: Pathology and Clinical Aspects, Springer (2016).

Tissue normalization (disease modifying) active agents can include, but are not limited to, biologics and small molecules. Biologic active agents can be further classified as chemokines (e.g., for stem cell recruitment) and growth factors. An example of a tissue normalization chemokine active agent that can be conjugated to any peptide of this disclosure for delivery to the joints includes MIP-3a. An example of a tissue normalization growth factor active agent that can be conjugated to any peptide of this disclosure for delivery to the joints includes BMP-2. Small molecule active agents can be further classified as flavonoids, ACE inhibitors, and anti-proliferative active agents. An example of a tissue normalization flavonoid active agent that can be conjugated to any peptide of this disclosure for delivery to the joints includes icariin. An example of a tissue normalization ACE inhibitor active agent that can be conjugated to any peptide of this disclosure for delivery to the kidneys includes captopril. An example of a tissue normalization anti-proliferative active agent that can be conjugated to any peptide of this disclosure for delivery to the joints includes methotrexate.

TABLE 3 describes active agents for treatment of a cartilage disorder that can be conjugated to any peptide of the present disclosure to form peptide-drug conjugates.

TABLE 3

Exemplary Active Agents for Cartilage Disorders

| Active Agent Class | Active Agent |
| --- | --- |
| Gold compound | Gold |
| Gold compound | Auranofin |
| Gold compound | Gold Sodium Thiomalate |
| Gold compound | Gold Thioglucose |
| Gold compound | Thiomalic Acid |
| Gold compound | Gold Thiosulphate |
| Analgesics | Tramadol (e.g., Ultram, Ultracet) and derivatives |
| Analgesics | Oxycodone (e.g., Percocet, Oxycontin) and derivatives |
| Analgesics | Hydrocodone (e.g., Norco, Vicoprofen) |
| Analgesics | Morphine |
| Analgesics | Fentanyl |
| Analgesics | Oxymorphone |
| Analgesics | Hydromorphone |
| Analgesics | Meperidine |
| Analgesics | Buprenorphine |
| Analgesics | Methadone |
| Bisphosphonate | Alendronate |
| Bisphosphonate | Ibandronate |
| Bisphosphonate | Risedronate |
| Bisphosphonate | Pamidronate |
| Bisphosphonate | Zoledronate |
| Non-Nitrogen Containing First Generation Bisphosphonate | Clodronate |
| Non-Nitrogen Containing First Generation Bisphosphonate | Etidronate |
| Non-Nitrogen Containing First Generation Bisphosphonate | Tiludronate |
| Apoptosis Inhibitors | Osteoprotegerin (OPG) |
| Sclerostin Antagonist Apoptosis Inhibitors | AMG785 (Romosozumab) |
| Caspase-1 ICE Inhibitors | VX-740 (Pralnacasan) |
| Counter-irritants | Menthol |
| Counter-irritants | Capsaicin |
| RANKL Targeting Agents | Denosumab |
| Cathepsin K Targeting Agents | Odanacatib |
| TNF-α Antagonists | CDP571 |
| TNF-α Antagonists | ISIS 104838 |
| Anti-Pain Drugs | Duloxetine |
| Polymers | Low Molecular Weight Chitosan |
| Matrix Drugs | Chondroitin sulfate glucosamine |
| Cytokines/Growth Factors | TGF-beta |
| Matrix | Laminin |
| Matrix | Fibronectin |
| Matrix | Lubricin |
| Matrix | Hyaluronic acid injections |
| Matrix | Glucosamine |
| Immunosuppressants | Rapamycin |
| HIF-1α Modulators | |
| HIF-2α Modulators | |
| Corticosteroid | Tixocortol pivalate |
| Glucocorticoid Corticosteroid | Hydrocortisone Acetate |
| Glucocorticoid Corticosteroid | Hydrocortisone t-Butyl Acetate |

TABLE 3-continued

Exemplary Active Agents for Cartilage Disorders

| Active Agent Class | Active Agent |
|---|---|
| Glucocorticoid Corticosteroid | Prednisolone Acetate |
| Glucocorticoid Corticosteroid | Prednisolone t-Butyl Acetate |
| Corticosteroid | Dexamethasone Acetate |
| Corticosteroid | Dexamethasone t-Butyl Acetate |
| Glucocorticoid Corticosteroid | Triamcinolone Diacetate |

TABLE 4 describes active agents for treatment of a kidney disorder that can be conjugated to any peptide of the present disclosure to form peptide-drug conjugates.

TABLE 4

Exemplary Active Agents for Kidney Disorders

| Active Agent Class | Active Agent |
|---|---|
| ACE Inhibitors | Captopril |
| Angiotensin receptor blockers | Angiotensin receptor blocker losartan (Cozaar) |
| Hormones | Adrenocorticotropic hormone |
| Hormones | corticotropin-releasing hormone amphotericin B digitalis glycosides potassium-depleting diuretics Coumarine anticoagulants |
| NLRP3 Inflammosome Targeted Drugs | MCC950 |
| NLRP3 Inflammosome Targeted Drugs | BHB |
| NLRP3 Inflammosome Targeted Drugs | Type I interferon |
| NLRP3 Inflammosome Targeted Drugs | IFN-beta |
| NLRP3 Inflammosome Targeted Drugs | Resveratrol |
| NLRP3 Inflammosome Targeted Drugs | Arglabin |
| NLRP3 Inflammosome Targeted Drugs | CB2R agonist |
| NLRP3 Inflammosome Targeted Drugs | MicroRNA-223 |

TABLE 5 describes active agents for treatment of a cartilage disorder and a kidney disorder that can be conjugated to any peptide of the present disclosure to form peptide-drug conjugates.

TABLE 5

Exemplary Active Agents for Cartilage Disorders and Kidney Disorders

| Active Agent Class | Active Agent |
|---|---|
| IL-6 Receptor Modulators | Tocilizumab |
| IL-6 Receptor Modulators | Sarilumab |
| IL-6 Receptor Modulators | ALX-0061 |
| IL-6 Receptor Modulators | Sirukumab |
| IL-6 Receptor Modulators | Clazakizumab |
| IL-6 Receptor Modulators | Olokizumab |
| IL-6 Receptor Modulators | MEDI5117 |
| IL-17 Antagonists | Secukinumab |
| IL-17 Antagonists | Brodalumab |
| IL-17 Antagonists | Ixekizumab |
| Antagonists of p40 Subunit of IL-12/IL-23 | Ustekinumab |
| Antagonists of p40 Subunit of IL-12/IL-23 | Briakinumab |
| Antagonists of p19 Subunit of IL-23 | Tildrakizumab |
| Antagonists of p19 Subunit of IL-23 | Guselkumab |
| IL-23 Antagonists | Soluble IL-23 (or cytokine-binding homology region of soluble IL-23) |
| IL-1 Antagonists | Canakinumab |
| IL-1 Antagonists | Rilonacept |
| IL-1 Antagonists | Gevokizumab |
| IL-1 Antagonists | LY2189102 |
| IL-1 Antagonists | Lentiviral-mediated RNAi |
| IL-12 Antagonists | |
| IL-1 Receptor Antagonists | Anakinra |
| IL-1 Receptor Antagonists | MEDI-8968 |
| IL-1 Receptor Antagonists | AMG-108 |
| IL-1 Receptor | Kineret |
| Interleukins/Pro-Inflammatory Cytokines | Pro-inflammatory IL-1α or IL-1β |
| Interleukins | IL-8 |
| Interleukins | IL-15 |
| Interleukins | IL-18 |
| Interleukins | IL-4 |
| Interleukins | IL-10 |
| Interleukins | IL-13 |
| Interleukins | IL-22 |
| Interleukins | IL-17 |
| p38 Inhibitors | VX-745 |
| p38 Inhibitors | BIRB 796 |
| p38 Inhibitors | SCIO-469 |
| p38 Inhibitors | VX-702 |
| p38 Inhibitors | Pamapimod |
| p38 Inhibitors | ARRY-797 |
| Corticosteroids | 17-monopropionate |
| Corticosteroids | Desciclesonide |
| Corticosteroids | Flunisolide |
| Corticosteroids | Mometasone furoate |
| Corticosteroids | 22-hydroxy intermediate budesonide derivative |
| Corticosteroids | 6β-hydroxy budesonide derivative |
| Corticosteroids | Δ6-budesonide derivative |
| Corticosteroids | 23-hydroxy budesonide derivative |
| Corticosteroids | 16α-butryloxyprednisolone budesonide derivative |
| Corticosteroids | 16α-hydroxyprednisolone budesonide derivative |
| Corticosteroid (Beclomethasone) | QVAR inhalation |
| Corticosteroid (Budesonide) | pulmicort respules |
| Corticosteroid | Flovent HFA 44 |
| Corticosteroid (Mometasone) | Asmanex HFA |
| Corticosteroid (Mometasone) | Budesonide symbicort |
| Corticosteroid | Dexamethasone sodium phosphate |
| Corticosteroid | Tixocortol pivalate |
| Corticosteroid | Ciclesonide |
| Glucocorticoids | 21-nortriamcincolone acetonide |
| Glucocorticoids | Δ6-triamcinolone |
| Glucocorticoids | 6b-hydroxy triamcinolone acetonide |
| Glucocorticoids | 21-carboxy triamcinolone acetonide |
| Glucocorticoids | 6b-OH, 21-COOH triamcinolone acetonide |
| Glucocorticoids | 6α fluorocortisol |
| Glucocorticoids | 9α fluorocortisol |
| Glucocorticoids | Δ1-dehydro configuration in prednisolone |
| Glucocorticoids | 16-methylene dexamethasone derivative |
| Glucocorticoids | 16α-methyl dexamethasone derivative |
| Glucocorticoids | 16β-methyl betamethasone derivative |
| Glucocorticoids | Cyclophosphamide |
| Glucocorticoids | Mycophenolate |
| Glucocorticoids/Mineralocorticoids | Cortisol |
| Glucocorticoids/Mineralocorticoids | Hydrocortisone |
| Glucocorticoids/Mineralocorticoids | Prednisolone |
| Glucocorticoids/Mineralocorticoids | Betamethasone |
| Glucocorticoid | Fluticasone |
| Glucocorticoid | Fluticasone propionate |
| Steroid (flunisolide) | Aerobid |
| Steroid (flunisolide) | Aerobid-M |

TABLE 5-continued

Exemplary Active Agents for Cartilage Disorders and Kidney Disorders

| Active Agent Class | Active Agent |
|---|---|
| Steroid (flunisolide) | Aerospan |
| Steroid (Flunisolide) | Fluticasone Furoate |
| Steroid (Fluticasone) | Flovent HFA 110 |
| Steroid (Fluticasone) | Flovent HFA 220 |
| Steroid (Fluticasone) | Flovent Diskus 50 |
| Steroid (Fluticasone) | Asmanex |
| Steroid | Betamethasone acetate |
| Steroid | Betamethasone sodium phosphate |
| Steroid | Betamethasone valerate |
| Steroid | Beclomethasone dipropionate |
| Local Anesthetic | procaine hydrochloride |
| Local Anesthetic | Novacain |
| Anesthetic | bupivacaine hydrochloride |
| Anesthetic | lidocaine hydrochloride |
| Local Anesthetic | ropivacaine hydrochloride |
| Analgesics | Morphine |
| Analgesics | Fentanyl |
| Quinazolines | Feitinib/Iressa |
| Quinazolines | Sorafenib/Nexavar |
| Quinazolines | Lapatinib ditosylate/Tykerb/Tyverb |
| Quinazolines | Sunitinib/Sutent |
| Quinazolines | Bortezomib/Velcade/Cytomib |
| Quinazolines | Everolimus/Temsirolimus |
| Quinazolines | Inhibitors of IAPS |
| Quinazolines | Activators of caspase pathway |
| Quinazolines | Activators of AKT pathway |
| Quinazolines | Propylpeptidase inhibitors |
| Quinazolines | Activators of p53 |
| Quinazolines | Inhibitors of anti-apoptotic protein inhibitors |
| Prolyl Hydroxylase (PHD) Inhibitors | Desferrioxamine |
| Prolyl Hydroxylase (PHD) Inhibitors | Dimethyloxalylglycine (DMOG) |
| Prolyl Hydroxylase (PHD) Inhibitors | L-mimosine (L-mim) |
| Aptamers | Peptide aptamers |
| Aptamers | RNA aptamer A-p50 |
| Aptamers | Peptide A aptamer TrxLef1D |
| Aptamers | Aptamer E07 |
| Aptamers | Aptamer gemcitabine polymers |
| Aptamers | RAGE |
| Aptamers | Pegaptanib |
| Proteosome Inhibitors | Bortezomib |
| Proteosome Inhibitors | Carfilzomib |
| Second Generation Proteosome Inhibitors | Ixazomib |
| Second Generation Proteosome Inhibitors | Delanzomib |
| Second Generation Proteosome Inhibitors | Oprozomib |
| Second Generation Proteosome Inhibitors | Marizomib |
| Apoptosis Inhibitors | FLIP agonist |
| Apoptosis Inhibitors | nitric oxide synthase inhibitors |
| Apoptosis Inhibitors | caspase-3 inhibitors (Z-DEVD-fmk (SEQ ID NO: 569)) |
| Apoptosis Inhibitors | caspase-9 inhibitors (Z-LEHD-fmk (SEQ ID NO: 570)) |
| Apoptosis Inhibitors | Sclerostin antagonists |
| Apoptosis Inhibitors/Growth Factor | IGF-1 |
| BCL-2 Agonist Apoptosis Inhibitors | Oblimersen |
| BCL-2 Agonist Apoptosis Inhibitors | Obatoclax |
| BCL-2 Agonist Apoptosis Inhibitors | Navitoclax |
| BCL-2 Agonist Apoptosis Inhibitors | Venetoclax (ABT-199) |
| BCL-2 Agonist Apoptosis Inhibitors | Navotoclax (ABT-263) |
| BCL-2 Agonist Apoptosis Inhibitors | GX01 series of compounds |
| BCL-2 Agonist Apoptosis Inhibitors | BCL-2 small molecule antagonists |
| BCL-2 Agonist Apoptosis Inhibitors | Tetracarcin-A derivatives |
| BCL-2 Agonist Apoptosis Inhibitors | Chelerythrine |
| BCL-2 Agonist Apoptosis Inhibitors | Antimycin A derivatives |
| BCL-2 Agonist Apoptosis Inhibitors | HA14-1 |
| BCL-2 Agonist Apoptosis Inhibitors | Synthetic compound antagonist of BH3 |
| BCL-2 Agonist Apoptosis Inhibitors | Genasense |
| BCL-2 Agonist Apoptosis Inhibitors | ISIS 22783 |
| BCL-2/BCL-XL Agonist Apoptosis Inhibitors | Bispecific Antisense |
| Proapoptotic BCL-2 Targeting Drugs | Bax, Bak, Bid, Bad-derived BH3 Peptides |
| Proapoptotic BCL-2 Targeting Drugs | SAHBs |
| Proapoptotic BCL-2 Targeting Drugs | BH3Is |
| BCL-2/BCL-XL Agonist Apoptosis Inhibitors | ABT-737 |
| BCL-X Inhibitors | |
| Apoptosis Modifiers | Caspase-1 Inhibitors |
| Apoptosis Modifiers | Caspase-8 Inhibitors |
| Pan-caspase Caspase Inhibitor | IDN-6556 |
| Pan-caspase Caspase Inhibitor | IDN-6734 |
| Pan-caspase Caspase Inhibitor | VX-799 |
| Pan-caspase Caspase Inhibitor | MX1013 |
| Pan-caspase Caspase Inhibitor | M-920 |
| Pan-caspase Caspase Activator | MX-2060 derivatives |
| Pan-caspase Caspase Activators | Small-molecule compounds |
| Pan-caspase Caspase Activators | RGD peptides |
| Pan-caspase inhibitors | ZVAD-fmk |
| Caspase-1 ICE Inhibitors | IDN-11104 |
| Caspase-1 ICE Inhibitors | VX-756 |
| Caspase-3 Inhibitors | M-826 |
| Caspase-3 Inhibitors | M-791 |
| Caspase-3 Inhibitors | Immunocasp-3 |
| Caspase-3 Inhibitors | Ad-G/iCasp3 |
| Caspase-3 Inhibitors | PEF-F8-CP3 |
| Caspase-6 Inhibitors | Immunocasp-6 |
| Caspase-9 Inhibitors | FKBP12/caspase-9 fusion protein |
| IAP Antagonists | BIR3 antagonists |
| XIAP Antagonists | Capped tripeptide XIAP Antagonists |
| XIAP Antagonists | Smac-mimetic compounds |
| XIAP Antagonists | AEG35156/GEM ®640 |
| XIAP Inhibitors | Embelin |
| XIAP Inhibitors | XIAP antisense and RNA constructs |
| XIAP/cIAP-1/cIAP-2 Inhibitors | Small molecule SMAC mimetics |
| IAP/Caspase Inhibitors | HIV-Tat/polyarginine-conjugated SMAC peptides |
| BIR2/Caspase-3 Inhibitors | TWX024 |
| BIR2 Inhibitors | Polyphenylurea derivatives |
| Survivin Targeting Drugs | LY2181308 |
| Survivin Targeting Drugs | Ad-Survivin T34A |
| Anti-TWEAK Apoptosis Modifiers | BIIB023 |
| Xanthine Oxidase Inhibitors | Allopurinol |
| Xanthine Oxidase Inhibitors | Febuxostat |
| Xanthine Oxidase Inhibitors | Zyloprin |
| Growth Factor | bFGF |
| Growth Factor | IGF |
| Growth Factor | TFG-beta |
| Growth Factor | BMP-2 |
| Growth Factor | BMP-9 |
| Growth Factor | BMP-13 |
| Growth Factor | BMP-7 |
| Growth Factor | BMP-3 inhibitors |
| Growth Factor | TFG-β1 |
| Growth Factor | OP-1 |
| Growth Factor | PDGF |
| Growth Factor | PTH |
| Growth Factor | PTHrP |
| Growth Factor | MIP-3α |
| Growth Factor | EPO |
| Growth Factor | FGF |
| Growth Factor | FGF-2 |
| Growth Factor | FGF-18 |
| Growth Factor | TGF-β3 |
| Growth Factor | VEGF |
| Growth Factor | Wnt proteins |
| Growth Factor | EGF |
| Growth Factor | GM-CSF |
| Flavonoid | Icariin |
| Flavonoid | Quercetin |
| Tyrosine Kinase Inhibitor (Lck/Btk Inhibitor) | Dasatinib |
| TRPV4 Activators | G5K1016790A |

TABLE 5-continued

Exemplary Active Agents for Cartilage Disorders and Kidney Disorders

| Active Agent Class | Active Agent |
|---|---|
| TRPV4 Activators | 4alpha-PDD |
| TRPV4 Inhibitors | HC-067047 |
| TRPV4 Inhibitors | GSK2193874 |
| NSAID | Ampion |
| NSAID | Phenylbutazone |
| NSAID | Naproxen lysozyme conjugate |
| NSAID | Acetal salicylic acid |
| DMARDs | Sulfasalazine |
| DMARDs | Leflunomide |
| DMARDs | Hydroxychloroquine (Plaquenil) |
| Disease-Modifying Osteoarthritis Drugs (DMOADs) | FGF-18 |
| Uricosurics | Sulfinpyrazone |
| MSC Matrix | Collagen |
| MSC Matrix | Fibrin |
| MSC Matrix | Polylactatous |
| Surfactant | P188 and other surfactants |
| Molecules for Bone Marrow Niches | Angiopoetin |
| Molecules for Bone Marrow Niches | Bone morphogenitic proteins |
| Molecules for Bone Marrow Niches | Epinephrine |
| Molecules for Bone Marrow Niches | Norepinephrine |
| Molecules for Bone Marrow Niches | GDF5 |
| Molecules for Bone Marrow Niches | ICAN1 |
| Molecules for Bone Marrow Niches | Jagged1 |
| Molecules for Bone Marrow Niches | Osteopontin |
| Molecules for Bone Marrow Niches | parathyoid hormone |
| Molecules for Bone Marrow Niches | Calcitonin |
| Molecules for Bone Marrow Niches | steel factor |
| Molecules for Bone Marrow Niches | Thrombopoetin |
| Molecules for Bone Marrow Niches | vascular cell adhesion molecule 1 |
| Chemokine Molecules for Bone Marrow Niches | CXCL12 |
| B Cell Targeting Agents | Rituximab |
| B Cell Targeting Agents | BLys |
| B Cell Targeting Agents | TACI |
| T Cell Co-stimulation Antagonists | Abatacept |
| JAK Targeting Agents | Tofacitinib |
| Calcineurin Inhibitors | Tacrolimus |
| Calcineurin Inhibitors | Cyclosporin |
| Calcineurin Inhibitors | Voclosporin |
| COX-2 Inhibitors | Iguratimod |
| COX-2 Inhibitors | Montelukast |
| COX-2 Inhibitors | Rofecoxib |
| COX-2 Inhibitors | Valdecoxib |
| Interferon Receptor Inhibitors | Anifrolumab |
| IFN-α Inhibitors | Sifalimumab |
| Anti-IgE Agents | Omalizumab |
| iNOS Inhibitors | S-methylisothiourea |
| CD20 Antagonists/B Cell Inhibitors | Ocrelizumab |
| BAFF Antagonists/B Cell Inhibitors | Belimumab |
| TNF Superfamily BAFF and APRIL Antagonists/B cell Inhibitors | Atacicept |
| TNF-α Antagonists | Thalidomide |
| TNF-α Antagonists | Lenalidomide |
| TNF-α Antagonists | Pomalidomide |
| TNF-α Antagonists | Pentocifylline |
| TNF-α Antagonists | Bupropion |
| TNF Antagonists | Lentiviral-mediated RNAi |
| TNF Agonists | Recombinant TNF-α |
| TRAIL Receptor Agonists | HGS-ETR1 |
| TRAIL Receptor Agonists | HGS-ETR2 |
| TRAIL Receptor Agonists | HGS-TR2J |
| TRAIL Receptor Agonists | PRO1762 |
| TRAIL Receptor Agonists | TRA-8 |
| CD95/Fas Agonists | CD95-Fc |
| Marine Bioactive Compounds | TRAIL-Resistance Overcoming Marine Bioactive Compounds |
| Marine Bioactive Compounds | mazamine A |
| Marine Bioactive Compounds | marine-derived chroomycins |
| Marine Bioactive Compounds | Carotenoids |
| Marine Bioactive Compounds | Aplysin |
| Marine Bioactive Compounds | Aplidin |
| Marine Bioactive Compounds | Siphonaxanthin |
| Marine Bioactive Compounds | pectinotoxin-2 |
| Anti-Complement Drugs | Eculizumab |
| PAR-2 Modulators | Pepducin P2pal-18 |
| miR-2013 Blockers | Anti-sense oligonucleotides |
| Nrf2 Activator | Dimethyl fumarate |
| p53 Targeting Drugs | INGN201 |
| p53 Targeting Drugs | SCH58500 |
| p53 Targeting Drugs | ONYX-015 |
| p53 Targeting Drugs | C-terminal p53 peptides |
| p53 Targeting Drugs | CDB3 |
| p53 Targeting Drugs | CP31398 |
| p53 Targeting Drugs | Prima-1 |
| p53 Targeting Drugs | HPV E6-binding peptide aptamers |
| p53 Targeting Drugs | Nutlins |
| p53 Targeting Drugs | Chalcones |
| p53 Targeting Drugs | Small peptides |
| p53 Targeting Drugs | Pifithrin-α |
| p53 Targeting Drugs/Apoptosis Modifiers (T cells) | QP1-1002 |
| Apaf-1 Targeting Drugs/Apoptosis Modifiers (T cells) | QM56 |
| Apaf-1 Targeting Drugs/Apoptosis Modifiers (T cells) | SVT016426 |
| Ferrostatin | 16/86 |
| BASP1 Targeting Drugs/Apoptosis Modifiers (T cells) | BASP siRNA |
| Anti-Inflammatory Drugs | CCX140 |
| Anti-Inflammatory Drugs | CXA-10 |
| Anti-Inflammatory Drugs/Anti-Fibrotic Drugs | Alkaline phosphatase |
| Anti-Fibrotic Drugs | Dnmt1 inhibitors |
| Anti-Inflammatory Drugs/Apoptosis Modifiers (T cells) | THR-184 |
| Immunosuppressants | Lithium |
| β2-Adrenergic Agonists | Formoterol |
| Anti-Inflammatory Drugs | CRMD-001 |
| Endothelin-1 Targeting Drugs | Astrasentan |
| Vasopressin Receptor Antagonists | Tolvaptan |
| Vasopressin Receptor Antagonists | RWJ-676070 |
| Immunosuppressants | Azathioprine |
| Immunosuppressants | Mycophenolic acid |
| Immunosuppressants | Cyclosporine |
| Immune Modulators | Laquinimod |
| Slow-acting antirheumatic drugs (SAARDs) | |
| | Colcrys |
| Hormones | parathyroid hormone |
| Hormones | growth hormone |
| | 11-beta hydroxysteroid dehydrogenases |
| | Mineralocorticoid |
| | Proopiomelanocortin |
| | fludrocortisonesoxycorticosterone acetate |
| | vaccines from live attenuated viruses |
| | Aspirin |
| | Insulin |
| | Isonizaid |
| | Oral hypoglycemic agents |
| | Antacids |
| | Carbamazepine |
| | Cholestyramine |
| | Colestipol |
| | Ephedrine |
| | Erythromycin |
| | Mitotane |
| | oral contraceptives |
| | Phenobarbital |
| | Phenytoin |
| | Rifampin |
| | Troleandomycin |
| | Non-selective caspase inhibitor |
| | okadaic acid |
| | Camptothetic |
| | Staurosporine |
| | HFA |
| | Alvesco inhalation |
| | Breo Ellipta |

TABLE 5-continued

Exemplary Active Agents for Cartilage Disorders and Kidney Disorders

| Active Agent Class | Active Agent |
|---|---|
| | Advair |
| | Mometasone |
| | Dulera |
| | Umeclidinium |
| | Anoro |
| Reactive Oxygen Species Targeting Drugs | |
| Cytokines/Growth Factors | TGF-beta |
| NOD-like receptor protein 3-dependent caspase 1 Targeting Drugs | |
| NSAID | Etoricoxib |
| Apoptosis Modifiers | MCL1 inhibitors |
| | Teriparatide |
| | BH3 mimetics |
| | AZD 4320 |
| Carrier Proteins | Low molecular weight human serum albumin |
| Ceramide Targeting Drugs | |
| DMARDs | Penicillamine |
| Chondrogenic factors | |
| Anti-oxidative factors | |
| A(1)AR agonist | |
| S1P(2)R antagonist | |
| Antimalarials | |
| BAX/BAK activating drugs | |
| Selective GR Activators (SEGRAs) | |
| Rap1 Targeted Drugs | |
| Senolytic | Ephrin Ligand (EFN) B1 blockers |
| Senolytic | Cyclin-dependent kinase inhibitor 1A (p21) phosphatidylinositol-4,5-bishophate 3-kinase delta catlyatic subunit (PI3KCD) blockers |
| Senolytic | Plasminogen-activated inhibitor-2 (PAI-2) blockers |
| Senesce-associated secretory phenotype (SASP) inhibitors | |
| Hormone | Tetracosactide |

TABLE 6 describes additional active agents for treatment of a cartilage disorder and a kidney disorder that can be conjugated to any peptide of the present disclosure to form peptide-drug conjugates.

TABLE 6

Exemplary Active Agents for Cartilage Disorders and Kidney Disorders

| Active Agent Class | Active Agent |
|---|---|
| Peptide | Oligopeptide |
| Peptide | Polypeptide |
| Peptide | Peptidomimetic |
| Nucleic Acid | Polynucleotide |
| Nucleic Acid | Polyribonucleotide |
| Nucleic Acid | Oligonucleotide |
| Nucleic Acid | DNA |
| Nucleic Acid | cDNA |
| Nucleic Acid | ssDNA |
| Nucleic Acid | RNA |
| Nucleic Acid | dsRNA |
| Nucleic Acid | micro RNA |
| Nucleic Acid | Interfering RNA |
| Nucleic Acid | Aptamer |
| Antibody | single chain variable Fragment (scFv) |
| Antibody | Antibody Fragment |
| Antibody | Aptamer |
| Antibody | Fc domains |
| Antibody | Fc regions |
| Antibody | Fc active fragments or modifications thereof |
| Cytokine | |
| Cytokine antagonists | Mavrilimumab |
| Cytokine antagonists | Ixekizumab |
| Cytokine antagonists | Tocilizumab |
| Cytokine antagonists | Anakinra |
| Cytokine antagonists | Ustekinumab |
| Cytokine antagonists | Secukinumab |
| Interferon | |
| Hormone | |
| Enzymes | |
| Growth Factor | |
| Checkpoint Inhibitor | |
| CD Antigen | |
| Chemokines | |
| Neurotransmitters | |
| Ion Channel Inhibitors | |
| G-protein coupled receptor inhibitors | |
| G-protein coupled receptor activators | |
| Tumor necrosis factor inhibitors | |
| Chemical Agents | |
| Radiosensitizers | |
| Radioprotectants | |
| Radionuclide | |
| Therapeutic Small Molecules | |
| Steroids | |
| Corticosteroids | |
| Anti-inflammatory Agents | |
| Immune Modulators | Abatacept |
| Immune Modulators | Rituximab |
| Complement Fixing Peptides or Proteins | |
| Tumor Necrosis Factor Family Inhibitors | Tumor Necrosis Factor (TNF) soluble receptor or antibody |
| Tumor Necrosis Factor Family Activators | |
| Tumor Necrosis Factor (TNF) soluble receptor or antibody | |
| Caspase protease inhibitors or activators | |
| NF-kB, RIPK1 and/or RIPK3 Inhibitors | |
| NF-kB, RIPK1 and/or RIPK3 Activators | |
| Death-receptor ligand activator or inhibitor | |
| Tumor Necrosis Factor Family Agonists | TNFR1 |
| Tumor Necrosis Factor Family Agonists | TNFR2 |
| Tumor Necrosis Factor Family Agonists | CD27/TNFRSF7 |
| Tumor Necrosis Factor Family Agonists | CD30/TNFRSF8 |
| Tumor Necrosis Factor Family Agonists | OX40/TNFRSF4 |
| Tumor Necrosis Factor Family Agonists | CD40/TNFRSF5 |
| Tumor Necrosis Factor Family Agonists | 4-1BB/TNFRSF9 |
| Tumor Necrosis Factor Family Agonists | RANK (receptor activator of NF-kappa B/TNFRSF11A) |
| Tumor Necrosis Factor Family Agonists | TWEAK receptor/TNFRSF12A |
| Tumor Necrosis Factor Family Agonists | TAC1/TNFRSF13B |
| Tumor Necrosis Factor Family Agonists | BAFF-R (BAFF receptor/TNFRSF13C) |
| Tumor Necrosis Factor Family Agonists | HVEM (herpes virus entry mediator/TNFRSF14) |
| Tumor Necrosis Factor Family Agonists | RELT/TNFRSF19L |

TABLE 6-continued

Exemplary Active Agents for Cartilage Disorders and Kidney Disorders

| Active Agent Class | Active Agent |
|---|---|
| Tumor Necrosis Factor Family Agonists | ectodysplasin A2 isoform receptor/TNFRS27 |
| Tumor Necrosis Factor Family Agonists | ectodysplasin A1 |
| TNF Family Member | Anhidrotic Receptor |
| Tumor Necrosis Factor Family Antagonists | Decoy Receptor 3/TNFRSF6B |
| Tumor Necrosis Factor Family Antagonists | Decoy Receptor 1/TNFRSF10C |
| Tumor Necrosis Factor Family Antagonists | Decoy Receptor 2/TNFRSF10D |
| Tumor Necrosis Factor Family Antagonists | DR3 (death receptor 3/ TNFRSF25) |
| Tumor Necrosis Factor Family Antagonists | DR4 (death receptor 4/ TNFRSF10A) |
| Tumor Necrosis Factor Family Antagonists | DR5 (death receptor 5/ TNFRSF10B) |
| Tumor Necrosis Factor Family Antagonists | DR6 (death receptor 6/ TNFRSF21) |
| Tumor Necrosis Factor Family Antagonists | Fas/TNFRSF6 |
| Tumor Necrosis Factor Family Antagonists | Lymphotoxin b receptor/ TNFRS3 |
| Tumor Necrosis Factor Family Antagonists | OPG (osteoprotegerin/ TNFRSF11B) |
| Tumor Necrosis Factor Family Antagonists | Nerve Growth Factor Receptor/TNFRSF16 |
| Tumor Necrosis Factor Family Antagonists | BCMA (B Cell Maturation Antigen/TNFRSF17) |
| Tumor Necrosis Factor Family Antagonists | GITR (Glucocorticoid-Induced TNF Receptor/TNFRSF18) |
| Tumor Necrosis Factor Family Antagonists | TAJ (Toxicity and JNK Inducer/TNFRSF19) |
| Tumor Necrosis Factor Family Antagonists | TNFRSF22 |
| Tumor Necrosis Factor Family Antagonists | TNFRSF23 |
| TNF Receptor Superfamily Ligands | TNF alpha |
| TNF Receptor Superfamily Ligands | Lymphotoxin-a |
| TNF Receptor Superfamily Ligands | Tumor Necrosis Factor Membrane Form |
| TNF Receptor Superfamily Ligands | Tumor Necrosis Factor Shed Form |
| TNF Receptor Superfamily Ligands | LIGHT |
| TNF Receptor Superfamily Ligands | Lymphotoxin b2a1 heterotrimer |
| TNF Receptor Superfamily Ligands | OX-40 Ligand |
| TNF Receptor Superfamily Ligands | Compound 1 [PMID: 24930776] |
| TNF Receptor Superfamily Ligands | CD40 Ligand |
| TNF Receptor Superfamily Ligands | Fas Ligand |
| TNF Receptor Superfamily Ligands | TL1A |
| TNF Receptor Superfamily Ligands | CD70 |
| TNF Receptor Superfamily Ligands | CD30 Ligand |
| TNF Receptor Superfamily Ligands | TRAF1 |
| TNF Receptor Superfamily Ligands | TRAF2 |
| TNF Receptor Superfamily Ligands | TRAF3 |
| TNF Receptor Superfamily Ligands | TRAIL |
| TNF Receptor Superfamily Ligands | RANK Ligand |
| TNF Receptor Superfamily Ligands | APRIL |
| TNF Receptor Superfamily Ligands | BAFF |
| TNF Receptor Superfamily Ligands | B and T lymphocyte Attenuators |
| TNF Receptor Superfamily Ligands | NGF |
| TNF Receptor Superfamily Ligands | BDNF |
| TNF Receptor Superfamily Ligands | Neurotrophin-3 |
| TNF Receptor Superfamily Ligands | Neurotrophin-4 |
| TNF Receptor Superfamily Ligands | TL6 |
| TNF Receptor Superfamily Ligands | Ectodysplasin A2 |
| TNF Receptor Superfamily Ligands | Ectodysplasin A1 |
| TNF blockers | Remicade (infliximab) |
| TNF blockers | Enbrel (etanercept) |
| TNF blockers | Humira (adalimumab) |
| TNF blockers | Cimzia (certolizumab pegol) |
| TNF blockers | Simponi (golimumab) |
| Tumor Necrosis Factor Receptor Family Agonists | |
| Toll Like Receptors Agonist | |

TABLE 6-continued

Exemplary Active Agents for Cartilage Disorders and Kidney Disorders

| Active Agent Class | Active Agent |
|---|---|
| TIMP-3 Inhibitors | |
| BCL-2 Family Inhibitors | |
| IAP Disruptors | |
| Protease Inhibitors | |
| Amino Sugars | |
| Chemotherapeutic Cytotoxic chemical Toxins | |
| Tyrosine Kinase inhibitors | Imatinib Mesylate |
| Protons | |
| Antivascular Agents | Bevacizumab |
| EGFR Inhibitors | Erlotinib |
| Anti-Infective Agents | |
| Antibiotics | |
| Anti-Viral Agents | |
| Anti-Fungal Agents | |
| Aminoglycoside | |
| Statins | |
| Nanoparticles | |
| Liposomes | |
| Polymers | Biopolymers |
| Polysaccharide | |
| Proteoglycan | |
| Glycosaminoglycans | |
| Polyethylene glycol | |
| Lipids | |
| Dendrimers | |
| Fatty Acids | |
| Glucocorticoid | |
| Corticosteroid | |
| Collagenase Inhibitor | |
| Matrix Metalloprotease Inhibitors | MMP-13 inhibitor |
| Vitamins | Vitamin D |
| Antibiotics | |
| Antiviral | |
| Antifungal | |
| Statins | |
| Immune Modulators | |
| Radioisotopes | |
| Toxins | |
| Enzymes | |
| Sensitizing drugs | |
| Anti-Angiogenic Agents | Cisplatin |
| Anti-Angiogenic Agents | Anti-Metabolites |
| Anti-Angiogenic Agents | Mitotic Inhibitors |
| Anti-Angiogenic Agents | Growth Factor Inhibitors |
| Chemotherapeutic Agent | Paclitaxel |
| Chemotherapeutic Agent | Temozolomide |
| Chemotherapeutic Agent | Topotecan |
| Chemotherapeutic Agent | Fluorouracil |
| Chemotherapeutic Agent | Vincristine |
| Chemotherapeutic Agent | Vinblastine |
| Chemotherapeutic Agent | Procarbazine |
| Chemotherapeutic Agent | Decarbazine |
| Chemotherapeutic Agent | Altretamine |
| Chemotherapeutic Agent | Methotrexate |
| Chemotherapeutic Agent | Mercaptopurine |
| Chemotherapeutic Agent | Thioguanine |
| Chemotherapeutic Agent | Fludarabine Phosphate |
| Chemotherapeutic Agent | Cladribine |
| Chemotherapeutic Agent | Pentostatin |
| Chemotherapeutic Agent | Cytarabine |
| Chemotherapeutic Agent | Azacitidine |
| Chemotherapeutic Agent | Etoposide |
| Chemotherapeutic Agent | Teniposide |
| Chemotherapeutic Agent | Irinotecan |
| Chemotherapeutic Agent | Docetaxel |
| Chemotherapeutic Agent | Doxorubicin |
| Chemotherapeutic Agent | Daunorubicin |
| Chemotherapeutic Agent | Dactinomycin |
| Chemotherapeutic Agent | Idarubicin |
| Chemotherapeutic Agent | Plicamycin |
| Chemotherapeutic Agent | Mitomycin |
| Chemotherapeutic Agent | Bleomycin |
| Chemotherapeutic Agent | Tamoxifen |
| Chemotherapeutic Agent | Flutamide |

TABLE 6-continued

Exemplary Active Agents for Cartilage Disorders and Kidney Disorders

| Active Agent Class | Active Agent |
|---|---|
| Chemotherapeutic Agent | Leuprolide |
| Chemotherapeutic Agent | Goserelin |
| Chemotherapeutic Agent | Aminogluthimide |
| Chemotherapeutic Agent | Anastrozole |
| Chemotherapeutic Agent | Amsacrine |
| Chemotherapeutic Agent | Asparaginase |
| Chemotherapeutic Agent | Mitoxantrone |
| Chemotherapeutic Agent | Mitotane |
| Chemotherapeutic Agent | Amifostine |
| Apoptotic Agents | |
| Cell Death or Cell Killing Agents | Caspases |
| Apoptosis Activators | |
| Apoptosis Inhibitors | XBP-1 |
| Apoptosis Inhibitors | Bcl-2 |
| Apoptosis Inhibitors | Bcl-Xl |
| Apoptosis Inhibitors | Bcl-w |
| Nonsteroidal Anti-Inflammatory Drugs (NSAID) | COX-2 Inhibitors |
| Nonsteroidal Anti-Inflammatory Drugs (NSAID) | Ketorolac |
| Nonsteroidal Anti-Inflammatory Drugs (NSAID) | Indomethacin |
| Nonsteroidal Anti-Inflammatory Drugs (NSAID) | Etodolac |
| Nonsteroidal Anti-Inflammatory Drugs (NSAID) | Tolemetin |
| Nonsteroidal Anti-Inflammatory Drugs (NSAID) | Naproxen |
| Nonsteroidal Anti-Inflammatory Drugs (NSAID) | Enolic Acid Derivatives |
| Nonsteroidal Anti-Inflammatory Drugs (NSAID) | Anthranilic Acid Derivatives |
| Nonsteroidal Anti-Inflammatory Drugs (NSAID) | Celecoxib |
| Nonsteroidal Anti-Inflammatory Drugs (NSAID) | Sulfonanilides |
| Nonsteroidal Anti-Inflammatory Drugs (NSAID) | Salicylates |
| Nonsteroidal Anti-Inflammatory Drugs (NSAID) | Aceclofenac |
| Nonsteroidal Anti-Inflammatory Drugs (NSAID) | Nabumetone |
| Nonsteroidal Anti-Inflammatory Drugs (NSAID) | Sulindac |
| Nonsteroidal Anti-Inflammatory Drugs (NSAID) | Diclofenac |
| Nonsteroidal Anti-Inflammatory Drugs (NSAID) | Ibuprofen |
| Steroids | Dexamethasone |
| Steroids | Budesonide |
| Steroids | Triamcinolone |
| Steroids | Triamcinolone acetonide |
| Steroids | Cortisone |
| Steroids | Prednisone |
| Steroids | Prednisolone |
| Steroids | Triamcinolone Hexacetonide |
| Steroids | Methylprednisolone |
| Pain Reliever | Acetaminophen |
| Opioids | |
| Local Anesthetics | |
| Anti-Depressants | |
| Glutamate Receptor Antagonists | |
| | Adenosine |
| Neuropeptides | |
| Uricase | |
| Elastase | |

Further examples of active agents include but are not limited to: a peptide, an oligopeptide, a polypeptide, a peptidomimetic, a polynucleotide, a polyribonucleotide, a DNA, a cDNA, a ssDNA, a RNA, a dsRNA, a micro RNA, an RNAi, an oligonucleotide, an antibody, a single chain variable fragment (scFv), an antibody fragment, an aptamer, a cytokine, an interferon, a hormone, an enzyme, a growth factor, a checkpoint inhibitor, a PD-1 inhibitor, a PD-L1 inhibitor, a CTLA4 inhibitor, a CD antigen, aa chemokine, a neurotransmitter, an ion channel inhibitor, a G-protein coupled receptor inhibitor, a G-protein coupled receptor activator, a chemical agent, a radiosensitizer, a radioprotectant, a radionuclide, a therapeutic small molecule, a steroid, a corticosteroid, an anti-inflammatory agent, an immune modulator, a complement fixing peptide or protein, a tumor necrosis factor inhibitor, a tumor necrosis factor activator, a tumor necrosis factor receptor family agonist, a tumor necrosis receptor antagonist, a tumor necrosis factor (TNF) soluble receptor or antibody, caspase protease activator or inhibitor, an NF-κB a RIPK1 and/or RIPK3 inhibitor or activator (e.g., through Toll-like receptors (TLRs) TLR-3 and/or TLR-4, or T-cell receptor (TCR) and the like), a death-receptor ligand (e.g., Fas ligand) activator or inhibitor, TNF receptor family (e.g., TNFR1, TNFR2, lymphotoxin β receptor/TNFRS3, OX40/TNFRSF4, CD40/TNFRSF5, Fas/TNFRSF6, decoy receptor 3/TNFRSF6B, CD27/TNFRSF7, CD30/TNFRSF8, 4-1BB/TNFRSF9, DR4 (death receptor 4/TNFRS10A), DR5 (death receptor 5/TNFRSF10B), decoy receptor 1/TNFRSF10C, decoy receptor 2/TNFRSF10D, RANK (receptor activator of NF-kappa B/TNFRSF11A), OPG (osteoprotegerin/TNFRSF11B), DR3 (death receptor 3/TNFRSF25), TWEAK receptor/TNFRSF12A, TACl/TNFRSF13B, BAFF-R (BAFF receptor/TNFRSF13C), HVEM (herpes virus entry mediator/TNFRSF14), nerve growth factor receptor/TNFRSF16, BCMA (B cell maturation antigen/TNFRSF17), GITR (glucocorticoid-induced TNF receptor/TNFRSF18), TAJ (toxicity and JNK inducer/TNFRSF19), RELT/TNFRSF19L, DR6 (death receptor 6/TNFRSF21), TNFRSF22, TNFRSF23, ectodysplasin A2 isoform receptor/TNFRS27, ectodysplasin 1, and anhidrotic receptor, a TNF receptor superfamily ligand including—TNF alpha, lymphotoxin-α, tumor necrosis factor membrane form, tumor necrosis factor shed form, LIGHT, lymphotoxin $\beta_2\alpha_1$ heterotrimer, OX-40 ligand, compound 1 [PMID: 24930776], CD40 ligand, Fas ligand, TL1A, CD70, CD30 ligand, TRAF1, TRAF2, TRAF3, TRAIL, RANK ligand, APRIL, BAFF, B and T lymphocyte attenuator, NGF, BDNF, neurotrophin-3, neurotrophin-4, TL6, ectodysplasin A2, ectodysplasin A1-a TIMP-3 inhibitor, a BCL-2 family inhibitor, navitoclax (Aging Cell. 15(3): 428-435. (2016)) an IAP disruptor, a protease inhibitor, an amino sugar, a chemotherapeutic (whether acting through an apoptotic or non-apoptotic pathway) (Ricci et al. Oncologist 11(4):342-57 (2006)), a cytotoxic chemical, a toxin, a tyrosine kinase inhibitor (e.g., imatinib mesylate), protons, bevacuzimab (antivascular agent), erlotinib (EGFR inhibitor), an anti-infective agent, an antibiotic, an anti-viral agent, an anti-fungal agent, an aminoglycoside, a nonsteroidal anti-inflammatory drug (NSAID), a statin, a nanoparticle, a liposome, a polymer, a biopolymer, a polysaccharide, a proteoglycan, a glycosaminoglycan, polyethylene glycol, a lipid, a dendrimer, a fatty acid, or an Fc domain or an Fc region, or an active fragment or a modification thereof. Any combination of the above active agents can be co-delivered with peptides or peptide conjugates of this disclosure. Additionally, in some embodiments, other co-therapies such as proton therapy or ablative radiotherapy can be administered to a subject in need thereof along with peptides or peptide conjugates of this disclosure. In some embodiments, the peptide is covalently or non-covalently linked to an active agent, e.g., directly or via a linker. TNF blockers suppress the immune system by blocking the activity of TNF, a substance in the body that can cause inflammation and lead to immune-system diseases, such as Crohn's disease, ulcerative colitis, rheumatoid arthritis, ankylo sing spondylitis, psoriatic arthritis and plaque psoriasis. The drugs in this class include Remicade (infliximab), Enbrel (etanercept), Humira (adalimumab), Cimzia (certolizumab pegol) and Simponi (golimumab). The peptide disclosed herein can be used to home, distribute to, target, directed to, is retained by, accumulate in, migrate to, and/or bind to cartilage, and thus also be used for localizing the attached or fused active agent. Furthermore, cystine-dense chlorotoxin peptide can be internalized in cells (Wiranowska, M., *Cancer Cell Int.*, 11: 27 (2011)). Therefore, cellular internalization, subcellular localization, and intracellular trafficking after internalization of the peptide itself, or an active agent peptide conjugate or fusion peptide can be important factors in the efficacy of an active agent conjugate or fusion. (Ducry, L., *Antibody Drug Conjugates* (2013); and Singh, S. K., *Pharm Res.*, 32(11): 3541-3571 (2015)). Exemplary linkers suitable for use with the embodiments herein are discussed in further detail below.

The peptides or peptide-active agent fusions of the present disclosure can also be conjugated to other moieties that can serve other roles, such as providing an affinity handle (e.g., biotin) for retrieval of the peptides from tissues or fluids. For example, peptides or peptide-active agent fusions of the present disclosure can also be conjugated to biotin. In addition to extension of half-life, biotin could also act as an affinity handle for retrieval of peptides or peptide-active agent fusions from tissues or other locations. In some embodiments, fluorescent biotin conjugates that can act both as a detectable label and an affinity handle can be used. Non limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexa fluor 488 biocytin, Alexa flour 546, Alexa Fluor 549, lucifer yellow cadaverine biotin-X, Lucifer yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels. In some embodiments, the peptide-active agent fusions described herein can be attached to another molecule. For example, the peptide sequence also can be attached to another active agent (e.g., small molecule, peptide, polypeptide, polynucleotide, antibody, aptamer, cytokine, growth factor, neurotransmitter, an active fragment or modification of any of the preceding, fluorophore, radioisotope, radionuclide chelator, acyl adduct, chemical linker, or sugar, etc.). In some embodiments, the peptide can be fused with, or covalently or non-covalently linked to an active agent.

Additionally, more than one peptide sequence can be present on or fused with a particular peptide. A peptide can be incorporated into a biomolecule by various techniques, for example by a chemical transformation, such as the formation of a covalent bond, such as an amide bond, or by solid phase or solution phase peptide synthesis, or by preparing a nucleic acid sequence encoding the biomolecule, wherein the nucleic acid sequence includes a subsequence that encodes the peptide. The subsequence can be in addition to the sequence that encodes the biomolecule, or can substitute for a subsequence of the sequence that encodes the biomolecule.

Detectable Agent Conjugates

Described herein are agents that can be conjugated to the peptides of the present invention for use in detection and tracing either cartilage disorders or kidney disorders, or both. As described herein, it is understood that certain active agents are described in a non-limiting exemplary manner for use in diagnostics, aiding surgery and treatment, prognosis and tracking of progress or remission of cartilage and/or kidney disorders, diseases or injury. One or more of such detectable agents can be conjugated to a peptide of the present invention alone or in combination with one or more active agents described herein. Moreover some detectable agents (e.g., radionuclides, radioisotopes, radiosensitizers and photosensitizers amongst others) may also exert therapeutic activity as well. A peptide can be conjugated to an agent used in imaging, research, therapeutics, theranostics, pharmaceuticals, chemotherapy, chelation therapy, targeted drug delivery, and radiotherapy. The agent can be a detectable agent. In some embodiments, a peptide of the present invention is conjugated to detectable agents, such as a metal, a radioisotope, a dye, fluorophore, or another suitable material that can be used in imaging. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212. In some embodiments, the fluorophore is a fluorescent agent emitting electromagnetic radiation at a wavelength between 650 nm and 4000 nm, such emissions being used to detect such agent. In some embodiments the fluorophore is a fluorescent agent is selected from the group consisting of non-limiting examples of fluorescent dyes that could be used as a conjugating molecule (or as applied to each class of molecules) in the present disclosure include DyLight-680, DyLight-750, VivoTag-750, DyLight-800, IRDye-800, VivoTag-680, Cy5.5, or indocyanine green (ICG class of dyes). In some embodiments, near infrared dyes include cyanine dyes. Additional non-limiting examples of fluorescent dyes for use as a conjugating molecule in the present disclosure include acradine orange or yellow, Alexa Fluors and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as for example mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, mercocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR and any derivative thereof, synaptopHluorin, tetraphenyl butadiene, tetrasodium tris, Texas Red, Titan Yellow, TSQ, umbelliferone, violanthrone, yellow fluorescent protein and YOYO-1. Other Suitable fluorescent dyes include, but are not limited to, fluorescein and fluorescein dyes (e.g., fluorescein isothiocyanine or FITC, naphthofluorescein, 4', 5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), indocyanine green dyes and the like. For each of the above listed fluorescent dyes various activated forms can be used for conjugation. Additional suitable detectable agents are described in PCT/US14/56177. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212.

Other embodiments of the present disclosure provide peptides conjugated to a radiosensitizer or photo sensitizer. Examples of radiosensitizers include but are not limited to: ABT-263, ABT-199, WEHI-539, paclitaxel, carboplatin, cisplatin, oxaliplatin, gemcitabine, etanidazole, misonidazole, tirapazamine, and nucleic acid base derivatives (e.g., halogenated purines or pyrimidines, such as 5-fluorodeoxyuridine). Examples of photosensitizers include but are not limited to: fluorescent molecules or beads that generate heat when illuminated, porphyrins and porphyrin derivatives (e.g., chlorins, bacteriochlorins, isobacteriochlorins, phthalocyanines, and naphthalocyanines), metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid. Advantageously, this approach allows for highly specific targeting of diseased cells (e.g., cancer cells) using both a therapeutic agent (e.g., drug) and electromagnetic energy (e.g., radiation or light) concurrently. In some embodiments, the peptide is covalently or non-covalently linked to the agent, e.g., directly or via a linker. Exemplary linkers suitable for use with the embodiments herein are discussed in further detail below.

Linkers

Peptides according to the present disclosure that home, target, migrate to, are retained by, accumulate in, and/or bind to, or are directed to the cartilage can be attached to another moiety (e.g., an active agent), such as a small molecule, a second peptide, a protein, an antibody, an antibody fragment, an aptamer, polypeptide, polynucleotide, a fluorophore, a radioisotope, a radionuclide chelator, a polymer, a biopolymer, a fatty acid, an acyl adduct, a chemical linker, or sugar or other active agent described herein through a linker, or directly in the absence of a linker.

A peptide can be directly attached to another molecule by a covalent attachment. For example, the peptide is attached to a terminus of the amino acid sequence of a larger polypeptide or peptide molecule, or is attached to a side chain, such as the side chain of a lysine, serine, threonine, cysteine, tyrosine, aspartic acid, a non-natural amino acid residue, or glutamic acid residue. The attachment can be via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond. In some embodiments, similar regions of the disclosed peptide(s) itself (such as a terminus of the amino acid sequence, an amino acid side chain, such as the side chain of a lysine, serine, threonine, cysteine, tyrosine, aspartic acid, a non-natural amino acid residue, or glutamic acid residue, via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond, or linker as described herein) can be used to link other molecules.

Attachment via a linker can involve incorporation of a linker moiety between the other molecule and the peptide. The peptide and the other molecule can both be covalently attached to the linker. The linker can be cleavable, labile, non-cleavable, stable self-immolating, hydrophilic, or hydrophobic. As used herein, the term "non-cleavable" (such as used in association with an amide, cyclic, or carbamate linker or as otherwise as described herein) is often used by a skilled artisan to distinguish a relatively stable structure from one that is more labile or "cleavable" (e.g., as used in association with cleavable linkers that may be dissociated or cleaved structurally by enzymes, proteases, self-immolation, pH, reduction, hydrolysis, certain physiologic conditions, or as otherwise described herein). It is understood that "non-cleavable" linkers offer stability against cleavage or other dissociation as compared to "cleavable" linkers, and the term is not intended to be considered an absolute non-cleavable or non-dissociative structure under any conditions. Consequently, as used herein, a "non-cleavable" linker is also referred to as a "stable" linker. The linker can have at least two functional groups with one bonded to the peptide, the other bonded to the other molecule, and a linking portion between the two functional groups.

Non-limiting examples of the functional groups for attachment can include functional groups capable of forming an amide bond, an ester bond, an ether bond, a carbonate bond, a carbamate bond, or a thioether bond. Non-limiting examples of functional groups capable of forming such bonds can include amino groups; carboxyl groups; hydroxyl groups; aldehyde groups; azide groups; alkyne and alkene groups; ketones; hydrazides; acid halides such as acid fluorides, chlorides, bromides, and iodides; acid anhydrides, including symmetrical, mixed, and cyclic anhydrides; carbonates; carbonyl functionalities bonded to leaving groups such as cyano, succinimidyl, and N-hydroxysuccinimidyl; hydroxyl groups; sulfhydryl groups; and molecules possessing, for example, alkyl, alkenyl, alkynyl, allylic, or benzylic leaving groups, such as halides, mesylates, tosylates, triflates, epoxides, phosphate esters, sulfate esters, and besylates.

Non-limiting examples of the linking portion can include alkylene, alkenylene, alkynylene, polyether, such as polyethylene glycol (PEG), hydroxy carboxylic acids, polyester, polyamide, polyamino acids, polypeptides, cleavable peptides, valine-citrulline, aminobenzylcarbamates, D-amino acids, and polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, epoxides, and ester groups.

A peptide and drug conjugated via a linker is described with the formula Peptide-A-B-C-Drug, wherein the linker is A-B-C. A can be a stable amide link, is an amine on the peptide and the linker and can be achieved via a tetrafluorophenyl (TFP) ester or an NHS ester. B can be (—CH2-)$_x$- or a short PEG (—CH$_2$CH$_2$O—)$_x$ (x is 1-10), and C can be the ester bond to the hydroxyl or carboxylic acid on the drug. In some embodiments, C can refer to the "cleavable" or "stable" part of the linker. In other embodiments, A can also be the "cleavable" part. In some embodiments, A can be amide, carbamate, thioether via maleimide or bromoacetamide, triazole, oxime, or oxacarboline. The cleaved active agent or drug can retain the chemical structure of the active agent before cleavage, or can be modified as a result of cleavage. Moreover, depending on the desired therapeutic properties of the peptide-drug conjugate, such active agent can be active while linked to the peptide, remain active after cleavage or become inactivated, be inactive while linked to the peptide, or it can be activated upon cleavage.

In some embodiments, peptide conjugates have stable linkers. A peptide of the disclosure can be expressed recombinantly or chemically synthesized. The peptide can be conjugated to a detectable agent or an active agent via a stable linker, such as an amide linkage or a carbamate linkage. The peptide can be conjugated to a detectable agent or an active agent via a stable linker, such as an amide bond using standard 1-ethyl-3-(3-dimethylaminopropyl)carbodiimide (EDC) or dicylcohexylcarbodiimide (DCC) based chemistry or thionyl chloride or phosphorous chloride-based bioconjugation chemistries. A stable linker may or may not be cleaved in buffer over extended periods of time (e.g., hours, days, or weeks). A stable linker may or may not be cleaved in body fluids such as plasma or synovial fluid over extended periods of time (e.g., hours, days, or weeks). A stable linker, may or may not be cleaved after exposure to enzymes, reactive oxygen species, other chemicals or enzymes that can be present in cells (e.g., macrophages), cellular compartments (e.g., endosomes and lysosomes), inflamed areas of the body (e.g., inflamed joints), tissues or body compartments. A stable linker may be cleaved by unknown mechanisms. A stable linker may or may not be cleaved in vivo but remains an active agent after peptide conjugation.

A peptide and drug conjugated via a linker can be described with the formula Peptide-A-B-C-Drug, wherein the linker is A-B-C. A can be a stable amide link such as that formed by reacting an amine on the peptide with a linker containing a tetrafluorophenyl (TFP) ester or an NHS ester. A can also be a stable carbamate linker such as that formed by reacting an amine on the peptide with an imidazole carbamate active intermediate formed by reaction of CDI with a hydroxyl on the linker. A can also be a stable secondary amine linkage such as that formed by reductive alkylation of the amine on the peptide with an aldehyde or ketone group on the linker. A can also be a stable thioether linker formed using a maleimide or bromoacetamide in the linker with a thiol in the peptide, a triazole linker, a stable oxime linker, or a oxacarboline linker. B can be (—CH2-)$_x$- or a short PEG (—CH$_2$CH$_2$O—)$_x$ (x is 0-20) or other spacers or no spacer. C can be an amide bond formed with an amine or a carboxylic acid on the drug, a thioether formed between a maleimide on the linker and a sulfhydroyl on the drug, a secondary or tertiary amine, a carbamate, or other stable bonds. Any linker chemistry described in "Current ADC Linker Chemistry," Jain et al., Pharm Res, 2015 DOI 10.1007/s11095-015-1657-7 can be used.

The resulting peptide conjugates can be administered to a human or animal subcutaneously, intravenously, orally, or injected directly into a joint to treat disease. The peptide is not specifically cleaved from the detectable agent or active agent via a targeted mechanism. The peptide can be degraded by mechanisms such as catabolism, releasing a drug that is modified or not modified form its native form (Antibody-Drug Conjugates: Design, Formulation, and Physicochemical Stability, Singh, Luisi, and Pak. Pharm Res (2015) 32:3541-3571). The peptide drug conjugate exerts its pharmacological activity while still intact, or while partially or fully degraded, metabolized, or catabolized.

In some embodiments, peptide conjugates can have cleavable linkers. In some embodiments, a peptide and drug can be conjugated via a linker and can be described with the formula Peptide-A-B-C-Drug, wherein the linker is A-B-C. In some embodiments, A can be a stable amide link such as that formed by reacting an amine on the peptide with a linker containing a tetrafluorophenyl (TFP) ester or an NHS ester. In certain embodiments, A can also be a stable carbamate linker that is formed by an amine reaction on the peptide with an imidazole carbamate active intermediate formed by reaction of CDI with a hydroxyl on the linker. In other embodiments, A can also be a stable secondary amine linkage such as that formed by reductive alkylation of the amine on the peptide with an aldehyde or ketone group on the linker. In some embodiments, A can also be a stable thioether linker formed using a maleimide or bromoacetamide in the linker with a thiol in the peptide, a triazole linker, a stable oxime linker, or an oxacarboline linker. B can be (—CH2-)$_x$- or a short PEG (—CH$_2$CH$_2$O—)$_x$ (x is 0-20) or other spacers or no spacer. C can be an ester bond to the hydroxyl or carboxylic acid on the drug, or a carbonate, hydrazone, or acylhydrazone, designed for hydrolytic cleavage. The hydrolytic rate of cleavage can be varied by varying the local environment around the bond, including carbon length (—CH2-)x, steric hindrance (including adjacent side groups such as methyl, ethyl, cyclic), hydrophilicity or hydrophobicity. In some embodiments, peptide conjugates can have a linear or cyclic ester linkage, which can include or do not include side chains such as methyl or ethyl groups. A linear ester linkage can be more susceptible to cleavage (such as by hydrolysis, an enzyme such as esterase, or other chemical reaction) than a cyclic ester due to steric hindrance or hydrophobicity/hydrophilicity effects. Likewise, side chains such as methyl or ethyl groups on the linear ester linkage can optionally make the linkage less susceptible to cleavage than without the side chains. In some embodiments, hydrolysis rate can be affected by local pH, such as lower pH in certain compartments of the body or of the cell such as endosomes and lysosomes or diseased tissues. In some embodiments, C can also be a pH sensitive group such as a hydrazone or oxime linkage. In other embodiments, C can be a disulfide bond designed to be released by reduction, such as by glutathione. In other embodiments, (or A-B-C) can be a peptidic linkage design for cleavable by enzymes. Optionally, a self-immolating group such as pABC can be included to cause release of a free unmodified drug upon cleavage (Antibody-Drug Conjugates: Design, Formulation, and Physicochemical Stability, Singh, Luisi, and Pak. Pharm Res (2015) 32:3541-3571). The linker can be cleaved by enzymes such as esterases, matrix metalloproteinases, cathepsins such as cathepsin B, glucuronidases, a protease, or thrombin. Alternatively, the bond designed for cleavage can be at A, rather than C, and C can be a stable bond or a cleavable bond. An alternative design can be to have stable linkers (such as amide or carbamate) at A and C and have a cleavable linker in B, such as a disulfide bond. The rate of reduction can be modulated by local effects such as steric hindrance from methyl or ethyl groups or modulating hydrophobicity/hydrophilicity. In some embodiments, peptide conjugates can have an ester carbonyl linkage, a long hydrocarbon linker, or carbamate linker, each of which can include hydrophilic groups, such as alcohols, acids, or ethers, or include a hydrocarbon side chain or other moiety that tunes the rate of cleavage. For example, the rate of hydrolysis can be faster with hydrophilic groups, such as alcohols, acids, or ethers, near an ester carbonyl. In another example, hydrophobic groups present as side chains or as a longer hydrocarbon linker can slow the cleavage rate of the ester. Likewise, cleavage of a carbamate group can also be tuned by hindrance, hydrophobicity, and the like. In another example, using a less labile linking group, such as a carbamate rather than an ester, can slow the cleavage rate of the linker.

Non-limiting examples of linkers include:

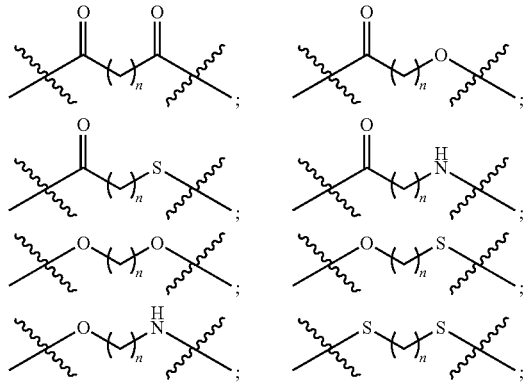

-continued

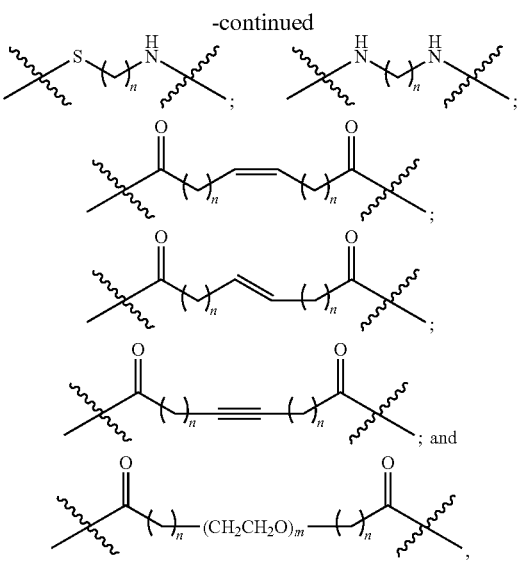

wherein each n is independently 0 to about 1,000; 1 to about 1,000; 0 to about 500; 1 to about 500; 0 to about 250; 1 to about 250; 0 to about 200; 1 to about 200; 0 to about 150; 1 to about 150; 0 to about 100; 1 to about 100; 0 to about 50; 1 to about 50; 0 to about 40; 1 to about 40; 0 to about 30; 1 to about 30; 0 to about 25; 1 to about 25; 0 to about 20; 1 to about 20; 0 to about 15; 1 to about 15; 0 to about 10; 1 to about 10; 0 to about 5; or 1 to about 5. In some embodiments, each n is independently 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50. In some embodiments, m is 1 to about 1,000; 1 to about 500; 1 to about 250; 1 to about 200; 1 to about 150; 1 to about 100; 1 to about 50; 1 to about 40; 1 to about 30; 1 to about 25; 1 to about 20; 1 to about 15; 1 to about 10; or 1 to about 5. In some embodiments, m is 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50.

In some cases a linker can be a succinic linker, and a drug can be attached to a peptide via an ester bond or an amide bond with two methylene carbons in between. In other cases, a linker can be any linker with both a hydroxyl group and a carboxylic acid, such as hydroxy hexanoic acid or lactic acid.

The linker can be a cleavable or a stable linker. The use of a cleavable linker permits release of the conjugated moiety (e.g., a therapeutic agent) from the peptide, e.g., after targeting to the cartilage. In some cases the linker is enzyme cleavable, e.g., a valine-citrulline linker. In some embodiments, the linker contains a self-immolating portion. In other embodiments, the linker includes one or more cleavage sites for a specific protease, such as a cleavage site for matrix metalloproteases (MMPs), thrombin, or cathepsin. Alternatively or in combination, the linker is cleavable by other mechanisms, such as via pH, reduction, or hydrolysis. A hydrolytically labile linker, (amongst other cleavable linkers described herein) can be advantageous in terms of releasing active agents from the peptide. For example, an active agent in a conjugate form with the peptide may not be active, but upon release from the conjugate after targeting to the cartilage, the active agent is active.

The rate of hydrolysis of the linker can be tuned. For example, the rate of hydrolysis of linkers with unhindered esters is faster compared to the hydrolysis of linkers with bulky groups next an ester carbonyl. A bulky group can be a methyl group, an ethyl group, a phenyl group, a ring, or an isopropyl group, or any group that provides steric bulk. In some cases, the steric bulk can be provided by the drug itself, such as by ketorolac when conjugated via its carboxylic acid. The rate of hydrolysis of the linker can be tuned according to the residency time of the conjugate in the cartilage. For example, when a peptide is cleared from the cartilage relatively quickly, the linker can be tuned to rapidly hydrolyze. In contrast, for example, when a peptide has a longer residence time in the cartilage, a slower hydrolysis rate can allow for extended delivery of an active agent. This can be important when the peptide is used to deliver a drug to the cartilage. "Programmed hydrolysis in designing paclitaxel prodrug for nanocarrier assembly" Sci Rep 2015, 5, 12023 Fu et al., provides an example of modified hydrolysis rates.

Peptide Stability

A peptide of the present disclosure can be stable in various biological conditions, as well as during manufacturing, handling, storage, and other conditions in either a liquid or a dried state. Additionally, a peptide of the present disclosure can be resistant to enzymatic cleavage needed for peptide processing by the immune system. For example, any peptide of SEQ ID NO: 1-SEQ ID NO: 564 can exhibit resistance to reducing agents, proteases, oxidative conditions, or acidic conditions.

In some cases, biologic molecules (such as peptides and proteins) can provide therapeutic functions, but such therapeutic functions are decreased or impeded by instability caused by the in vivo environment. (Moroz et al., *Adv Drug Deliv Rev* 101:108-21 (2016), Mitragotri et al., *Nat Rev Drug Discov* 13(9):655-72 (2014), Bruno et al., *Ther Deliv* (11):1443-67 (2013), Sinha et al., *Crit Rev Ther Drug Carrier Syst.* 24(1):63-92 (2007), Hamman et al., *BioDrugs* 19(3):165-77 (2005)). Peptide degradation can be a result of a number of processes involving hydrolytic pathways, peptide oxidation such as oxidation of methionine (Met) residues, deamidation of asparagine (Asn) and glutamine (Gln) residues, and isomerization and hydrolysis of an adjacent asparagine (Asp) residue. (Manning et al., *Pharmaceutical Research*, Vol. 27 No. 4 (2010)). The amino acid immediately following the Asn or Gln residue can also affect the rate of deamidation, whereas: Asn-Gly, Asn-Ser, Asn-His, and Gln-Gly can be more likely to undergo deamidation. Additionally, the peptide bond adjacent to amino acids such as Asp can undergo hydrolysis with amino acid pairings such as Asp-Gly, Asp-Ser, Asp-Tyr, and Asp-Pro, which can be more likely to undergo hydrolysis. Oxidation of amino acid residues such as Met can form a sulfoxide species. The specific degradation reactions rates can vary for any given peptide or protein sequence.

Furthermore, the microenvironment within the molecular structure of the peptide, solvent accessibility, and conformational stability of each residue can impact the likelihood of peptide degradation. Therefore, by modifying a peptide sequence to reduce occurrence of such degradation events, a the modified peptide or peptide-conjugate can have increased beneficial properties over unmodified peptides or peptide-drug conjugates, such as improved therapeutic efficacy, an increased safety profile, and can be less expensive to manufacture and develop. Key formulaic considerations that can prevent peptide decay can include the use of excipients, formulation at a desired pH, and storage under specific conditions (e.g., temperature, oxygen, light exposure, solid or liquid state, and container excipient materials). To circumvent degradation, peptide residues can be substituted with amino acids that increase stability, which can result in more efficacious and durable therapeutic peptides.

With respect to in vivo stability, the GI tract can contain a region of low pH (e.g., pH~1), a reducing environment, or a protease-rich environment that can degrade peptides and proteins. Proteolytic activity in other areas of the body, such as the mouth, eye, lung, intranasal cavity, joint, skin, vaginal tract, mucous membranes, and serum, can also be an obstacle to the delivery of functionally active peptides and polypeptides. Additionally, the half-life of peptides in serum can be very short, in part due to proteases, such that the peptide can be degraded too quickly to have a lasting therapeutic effect when administering a therapeutic and safe dosing regimen. Likewise, proteolytic activity in cellular compartments, such as lysosomes, and reduction activity in lysosomes and the cytosol can degrade peptides and proteins such that they may be unable to provide a therapeutic function on intracellular targets. Therefore, peptides that are resistant to reducing agents, proteases, and low pH may be able to provide enhanced therapeutic effects or enhance the therapeutic efficacy of co-formulated or conjugated active agents in vivo.

Additionally, oral delivery of drugs can be desirable in order to target certain areas of the body (e.g., disease in the GI tract such as colon cancer, irritable bowel disorder, infections, metabolic disorders, and constipation) despite the obstacles to the delivery of functionally active peptides and polypeptides presented by this method of administration. For example, oral delivery of drugs can increase compliance by providing a dosage form that is more convenient for patients to take as compared to parenteral delivery. Oral delivery can be useful in treatment regimens that have a large therapeutic window. Therefore, peptides that are resistant to reducing agents, proteases, and low pH can allow for oral delivery of peptides without nullifying their therapeutic function.

Peptide Resistance to Reducing Agents.

Peptides of this disclosure can contain one or more cysteines, which can participate in disulfide bridges that can be integral to preserving the folded state of the peptide. Exposure of peptides to biological environments with reducing agents can result in unfolding of the peptide and loss of functionality and bioactivity. For example, glutathione (GSH) is a reducing agent that can be present in many areas of the body and in cells, and can reduce disulfide bonds. As another example, a peptide can become reduced upon cellular internalization during trafficking of a peptide across the gastrointestinal epithelium after oral administration a peptide can become reduced upon exposure to various parts of the GI tract. The GI tract can be a reducing environment, which can inhibit the ability of therapeutic molecules with disulfide bonds to have optimal therapeutic efficacy, due to reduction of the disulfide bonds. A peptide can also be reduced upon entry into a cell, such as after internalization by endosomes or lysosomes or into the cytosol, or other cellular compartments. Reduction of the disulfide bonds and unfolding of the peptide can lead to loss of functionality or affect key pharmacokinetic parameters such as bioavailability, peak plasma concentration, bioactivity, and half-life. Reduction of the disulfide bonds can also lead to increased susceptibility of the peptide to subsequent degradation by proteases, resulting in rapid loss of intact peptide after administration. In some embodiments, a peptide that is resistant to reduction can remain intact and can impart a functional activity for a longer period of time in various compartments of the body and in cells, as compared to a peptide that is more readily reduced.

In certain embodiments, the peptides of this disclosure can be analyzed for the characteristic of resistance to reducing agents to identify stable peptides. In some embodiments, the peptides of this disclosure can remain intact after being exposed to different molarities of reducing agents such as 0.00001M-0.0001M, 0.0001M-0.001M, 0.001M-0.01M, 0.01 M-0.05 M, 0.05 M-0.1 M, for greater 15 minutes or more. In some embodiments, the reducing agent used to determine peptide stability can be dithiothreitol (DTT), Tris (2-carboxyethyl) phosphine HCl (TCEP), 2-Mercaptoethanol, (reduced) glutathione (GSH), or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%400% of the peptide remains intact after exposure to a reducing agent.

Peptide Resistance to Proteases.

The stability of peptides of this disclosure can be determined by resistance to degradation by proteases. Proteases, also referred to as peptidases or proteinases, can be enzymes that can degrade peptides and proteins by breaking bonds between adjacent amino acids. Families of proteases with specificity for targeting specific amino acids can include serine proteases, cysteine proteases, threonine proteases, aspartic proteases, glutamic proteases, esterases, serum proteases, and asparagine proteases. Additionally, metalloproteases, matrix metalloproteases, elastase, carboxypeptidases, Cytochrome P450 enzymes, and cathepsins can also digest peptides and proteins. Proteases can be present at high concentration in blood, in mucous membranes, lungs, skin, the GI tract, the mouth, nose, eye, and in compartments of the cell. Misregulation of proteases can also be present in various diseases such as rheumatoid arthritis and other immune disorders. Degradation by proteases can reduce bioavailability, biodistribution, half-life, and bioactivity of therapeutic molecules such that they are unable to perform their therapeutic function. In some embodiments, peptides that are resistant to proteases can better provide therapeutic activity at reasonably tolerated concentrations in vivo.

In some embodiments, peptides of this disclosure can resist degradation by any class of protease. In certain embodiments, peptides of this disclosure resist degradation by pepsin (which can be found in the stomach), trypsin (which can be found in the duodenum), serum proteases, or any combination thereof. In certain embodiments, peptides of this disclosure can resist degradation by lung proteases (e.g., serine, cysteinyl, and aspartyl proteases, metalloproteases, neutrophil elastase, alpha-1 antitrypsin, secretory leucoprotease inhibitor, elafin), or any combination thereof. In some embodiments, the proteases used to determine peptide stability can be pepsin, trypsin, chymotrypsin, or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a protease. Peptides of SEQ ID NO: 199, SEQ ID NO: 27, and SEQ ID NO: 108 can have particular structural qualities, which make them more resistant to protease degradation. For example, peptide of SEQ ID NO: 27 and SEQ ID NO: 109 exhibit the "hitchin" topology as described previously, which can be associated with resistance to protease and chemical degradation.

Peptide Stability in Acidic Conditions.

Peptides of this disclosure can be administered in biological environments that are acidic. For example, after oral administration, peptides can experience acidic environmental conditions in the gastric fluids of the stomach and gastrointestinal (GI) tract. The pH of the stomach can range from ~1-4 and the pH of the GI tract ranges from acidic to normal physiological pH descending from the upper GI tract to the colon. In addition, the vagina, late endosomes, and lysosomes can also have acidic pH values, such as less than pH 7. These acidic conditions can lead to denaturation of peptides and proteins into unfolded states. Unfolding of peptides and proteins can lead to increased susceptibility to subsequent digestion by other enzymes as well as loss of biological activity of the peptide.

In certain embodiments, the peptides of this disclosure can resist denaturation and degradation in acidic conditions and in buffers, which simulate acidic conditions. In certain embodiments, peptides of this disclosure can resist denaturation or degradation in buffer with a pH less than 1, a pH less than 2, a pH less than 3, a pH less than 4, a pH less than 5, a pH less than 6, a pH less than 7, or a pH less than 8. In some embodiments, peptides of this disclosure remain intact at a pH of 1-3. In certain embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH less than 1, a pH less than 2, a pH less than 3, a pH less than 4, a pH less than 5, a pH less than 6, a pH less than 7, or a pH less than 8. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH of 1-3. In other embodiments, the peptides of this disclosure can be resistant to denaturation or degradation in simulated gastric fluid (pH 1-2). In some embodiments, at least 5-10%, at least 10%-20%, at least 20%-30%, at least 30%-40%, at least 40%-50%, at least 50%-60%, at least 60%-70%, at least 70%-80%, at least 80%-90%, or at least 90-100% of the peptide remains intact after exposure to simulated gastric fluid. In some embodiments, low pH solutions such as simulated gastric fluid or citrate buffers can be used to determine peptide stability.

Peptide Stability at High Temperatures.

Peptides of this disclosure can be administered in biological environments with high temperatures. For example, after oral administration, peptides can experience high temperatures in the body. Body temperature can range from 36° C. to 40° C. High temperatures can lead to denaturation of peptides and proteins into unfolded states. Unfolding of peptides and proteins can lead to increased susceptibility to subsequent digestion by other enzymes as well as loss of biological activity of the peptide. In some embodiments, a peptide of this disclosure can remain intact at temperatures from 25° C. to 100° C. High temperatures can lead to faster degradation of peptides. Stability at a higher temperature can allow for storage of the peptide in tropical environments or areas where access to refrigeration is limited. In certain embodiments, 5%-100% of the peptide can remain intact after exposure to 25° C. for 6 months to 5 years. 5%-100% of a peptide can remain intact after exposure to 70° C. for 15 minutes to 1 hour. 5%-100% of a peptide can remain intact after exposure to 100° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 25° C. for 6 months to 5 years. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 70° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 100° C. for 15 minutes to 1 hour.

In some embodiments, the peptide of the peptide active agent conjugate comprises a sequence that has at least 75%, at least 80%, at least 85%, at least 90%, at least 95%, at least 97%, at least 99% or 100% sequence identity with any one of SEQ ID NO: 24-SEQ ID NO: 274 or a fragment thereof. In some embodiments, the peptide of the peptide active agent conjugate comprises a sequence that has at least 75%, at least 80%, at least 85%, at least 90%, at least 95%, at least 97%, at least 99% or 100% sequence identity with any one of SEQ ID NO: 260-SEQ ID NO: 274 or a fragment thereof. In some embodiments, the peptide of the peptide active agent conjugate comprises a sequence that has at least 75%, at least 80%, at least 85%, at least 90%, at least 95%, at least 97%, at least 99% or 100% sequence identity with any one of SEQ ID NO: 314-SEQ ID NO: 564 or a fragment thereof. In some embodiments, the peptide of the peptide active agent conjugate comprises a sequence that has at least 75%, at least 80%, at least 85%, at least 90%, at least 95%, at least 97%, at least 99% or 100% sequence identity with any one of SEQ ID NO: 550-SEQ ID NO: 564 or a fragment thereof. In some embodiments, the peptide of the peptide active agent conjugate comprises a sequence of any one of SEQ ID NO: 24-SEQ ID NO: 274 or a fragment thereof. In some embodiments, the peptide of the peptide active agent conjugate comprises a sequence of any one of SEQ ID NO: 260-SEQ ID NO: 274 or a fragment thereof. In some embodiments, the peptide of the peptide active agent conjugate comprises a sequence of any one of SEQ ID NO: 314-SEQ ID NO: 564 or a fragment thereof. In some embodiments, the peptide of the peptide active agent conjugate comprises a sequence of any one of SEQ ID NO: 550-SEQ ID NO: 564 or a fragment thereof. In some embodiments, the peptide comprises a sequence that has at least 70%, at least 75%, at least 80%, at least 85%, at least 90%, at least 95%, at least 97%, at least 99%, or 100% sequence identity with any one of SEQ ID NO: 260-SEQ ID NO: 574. In some embodiments, the peptide comprises at least 70%, at least 75%, at least 80%, at least 85%, at least 90%, at least 95%, at least 97%, at least 99%, or 100% sequence identity with any one of SEQ ID NO: 550-SEQ ID NO: 564. In some embodiments, the peptide active agent conjugate or the peptide comprises a sequence of any one of SEQ ID NO: 1-SEQ ID NO: 23 or a fragment thereof. In some embodiments, the peptide active agent conjugate or the peptide comprises a sequence of any one of SEQ ID NO: 275-SEQ ID NO: 297 or a fragment thereof. In some embodiments, the peptide active agent conjugate or the peptide comprises a sequence of any one of SEQ ID NO: 21-SEQ ID NO: 23 or a fragment thereof. In some embodiments, the peptide active agent conjugate or the peptide comprises a sequence of any one of SEQ ID NO: 295-SEQ ID NO: 297 or a fragment thereof. In some embodiments, the peptide active agent conjugate or the peptide comprises a peptide with at least 30%, at least 40%, at least 50%, at least 60%, at least 70%, at least 80%, at least 90%, at least 95%, at least, 97%, at least 98%, or at least 99% identical to any one of SEQ ID NO: 494-SEQ ID NO: 540 or at least 30%, at least 40%, at least 50%, at least 60%, at least 70%, at least 80%, at least 90%, at least 95%, at least 97%, at least 98%, or at least 99% identical to any one of SEQ ID NO: 204-SEQ ID NO: 250.

Pharmacokinetics of Peptides

The pharmacokinetics of any of the peptides of this disclosure can be determined after administration of the peptide via different routes of administration. For example, the pharmacokinetic parameters of a peptide of this disclosure can be quantified after intravenous, subcutaneous, intramuscular, rectal, aerosol, parenteral, ophthalmic, pulmonary, transdermal, vaginal, optic, nasal, oral, sublingual, inhalation, dermal, intrathecal, intranasal, intra-articular, peritoneal, buccal, synovial, or topical administration. Peptides of the present disclosure can be analyzed by using tracking agents such as radiolabels or fluorophores. For example, a radiolabeled peptide of this disclosure can be administered via various routes of administration. Peptide concentration or dose recovery in various biological samples such as plasma, urine, feces, any organ, skin, muscle, and other tissues can be determined using a range of methods including HPLC, fluorescence detection techniques (TECAN quantification, flow cytometry, iVIS), or liquid scintillation counting.

The methods and compositions described herein can relate to pharmacokinetics of peptide administration via any route to a subject. Pharmacokinetics can be described using methods and models, for example, compartmental models or noncompartmental methods. Compartmental models include but are not limited to monocompartmental model, the two compartmental model, the multicompartmental model or the like. Models can be divided into different compartments and can be described by the corresponding scheme. For example, one scheme is the absorption, distribution, metabolism and excretion (ADME) scheme. For another example, another scheme is the liberation, absorption, distribution, metabolism and excretion (LADME) scheme. In some aspects, metabolism and excretion can be grouped into one compartment referred to as the elimination compartment. For example, liberation can include liberation of the active portion of the composition from the delivery system, absorption includes absorption of the active portion of the composition by the subject, distribution includes distribution of the composition through the blood plasma and to different tissues, metabolism, which includes metabolism or inactivation of the composition and finally excretion, which includes excretion or elimination of the composition or the products of metabolism of the composition. Compositions administered intravenously to a subject can be subject to multiphasic pharmacokinetic profiles, which can include but are not limited to aspects of tissue distribution and metabolism/excretion. As such, the decrease in plasma or serum concentration of the composition is often biphasic, including, for example an alpha phase and a beta phase, occasionally a gamma, delta or other phase is observed Pharmacokinetics includes determining at least one parameter associated with administration of a peptide to a subject. In some aspects, parameters include at least the dose (D), dosing interval (τ), area under curve (AUC), maximum concentration ($C_{max}$), minimum concentration reached before a subsequent dose is administered ($C_{min}$), minimum time ($T_{min}$), maximum time to reach Cmax ($T_{max}$), volume of distribution ($V_d$), steady-state volume of distribution ($V_{ss}$), back-extrapolated concentration at time 0 ($C_0$), steady state concentration ($C_{ss}$), elimination rate constant ($k_e$), infusion rate ($k_{in}$), clearance (CL), bioavailability (f), fluctuation (% PTF) and elimination half-life ($t_{1/2}$).

In certain embodiments, the peptides of any of SEQ ID NO: 1-SEQ ID NO 564 exhibit optimal pharmacokinetic parameters after oral administration. In other embodiments, the peptides of any of SEQ ID NO: 1-SEQ ID NO: 564 exhibit optimal pharmacokinetic parameters after any route of administration, such as oral administration, inhalation, intranasal administration, topical administration, parenteral administration, intravenous administration, subcutaneous administration, intra-articular administration, intramuscular administration, intraperitoneal administration, transdermal administration, dermal administration, or any combination thereof.

In some embodiments any peptide of SEQ ID NO: 1-SEQ ID NO: 564 exhibits an average $T_{max}$ of 0.5-12 hours, or 1-48 hours at which the $C_{max}$ is reached, an average bioavailability in serum of 0.1%-10% in the subject after administering the peptide to the subject by an oral route, an average bioavailability in serum of less than 0.1% after oral administration to a subject for delivery to the GI tract, an average bioavailability in serum of 10-100% after parenteral administration, an average $t_{1/2}$ of 0.1 hours-168 hours, or 0.25 hours-48 hours in a subject after administering the peptide to the subject, an average clearance (CL) of 0.5-100 L/hour or 0.5-50 L/hour of the peptide after administering the peptide to a subject, an average volume of distribution ($V_d$) of 200-20,000 mL in the subject after systemically administering the peptide to the subject, or optionally no systemic uptake, any combination thereof.

Methods of Manufacture

Various expression vector/host systems can be utilized for the production of the recombinant expression of peptides described herein. Non-limiting examples of such systems include microorganisms such as bacteria transformed with recombinant bacteriophage DNA, plasmid DNA or cosmid DNA expression vectors containing a nucleic acid sequence encoding peptides or peptide fusion proteins/chimeric proteins described herein, yeast transformed with recombinant yeast expression vectors containing the aforementioned nucleic acid sequence, insect cell systems infected with recombinant virus expression vectors (e.g., baculovirus) containing the aforementioned nucleic acid sequence, plant cell systems infected with recombinant virus expression vectors (e.g., cauliflower mosaic virus (CaMV), tobacco mosaic virus (TMV) or transformed with recombinant plasmid expression vectors (e.g., Ti plasmid) containing the aforementioned nucleic acid sequence, or animal cell systems infected with recombinant virus expression vectors (e.g., adenovirus, vaccinia virus) including cell lines engineered to contain multiple copies of the aforementioned nucleic acid sequence, either stably amplified (e.g., CHO/dhfr, CHO/glutamine synthetase) or unstably amplified in double-minute chromosomes (e.g., murine cell lines). Disulfide bond formation and folding of the peptide could occur during expression or after expression or both.

A host cell can be adapted to express one or more peptides described herein. The host cells can be prokaryotic, eukaryotic, or insect cells. In some cases, host cells are capable of modulating the expression of the inserted sequences, or modifying and processing the gene or protein product in the specific fashion desired. For example, expression from certain promoters can be elevated in the presence of certain inducers (e.g., zinc and cadmium ions for metallothionine promoters). In some cases, modifications (e.g., phosphorylation) and processing (e.g., cleavage) of peptide products can be important for the function of the peptide. Host cells can have characteristic and specific mechanisms for the post-translational processing and modification of a peptide. In some cases, the host cells used to express the peptides secretes minimal amounts of proteolytic enzymes.

In the case of cell- or viral-based samples, organisms can be treated prior to purification to preserve and/or release a target polypeptide. In some embodiments, the cells are fixed using a fixing agent. In some embodiments, the cells are lysed. The cellular material can be treated in a manner that does not disrupt a significant proportion of cells, but which removes proteins from the surface of the cellular material, and/or from the interstices between cells. For example, cellular material can be soaked in a liquid buffer or, in the case of plant material, can be subjected to a vacuum, in order to remove proteins located in the intercellular spaces and/or in the plant cell wall. If the cellular material is a microorganism, proteins can be extracted from the microorganism culture medium. Alternatively, the peptides can be packed in inclusion bodies. The inclusion bodies can further be separated from the cellular components in the medium. In some embodiments, the cells are not disrupted. A cellular or viral peptide that is presented by a cell or virus can be used for the attachment and/or purification of intact cells or viral particles. In addition to recombinant systems, Peptides can also be synthesized in a cell-free system using a variety of known techniques employed in protein and peptide synthesis.

In some cases, a host cell produces a peptide that has an attachment point for a drug. An attachment point could comprise a lysine residue, an N-terminus, a cysteine residue, a cysteine disulfide bond, or a non-natural amino acid. The peptide could also be produced synthetically, such as by solid-phase peptide synthesis, or solution-phase peptide synthesis. The peptide could be folded (formation of disulfide bonds) during synthesis or after synthesis or both. Peptide fragments could be produced synthetically or recombinantly and then joined together synthetically, recombinantly, or via an enzyme.

Figure 3:
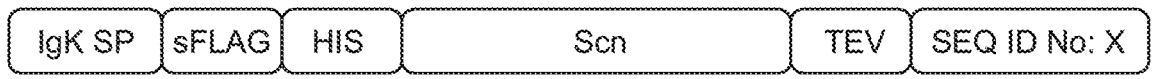
FIG. 3 illustrates an exemplary architecture of constructs expressing sequences of SEQ ID NO: X, where X can be any one of peptides of SEQ ID NO: 24-SEQ ID NO: 36.
Figure 4:
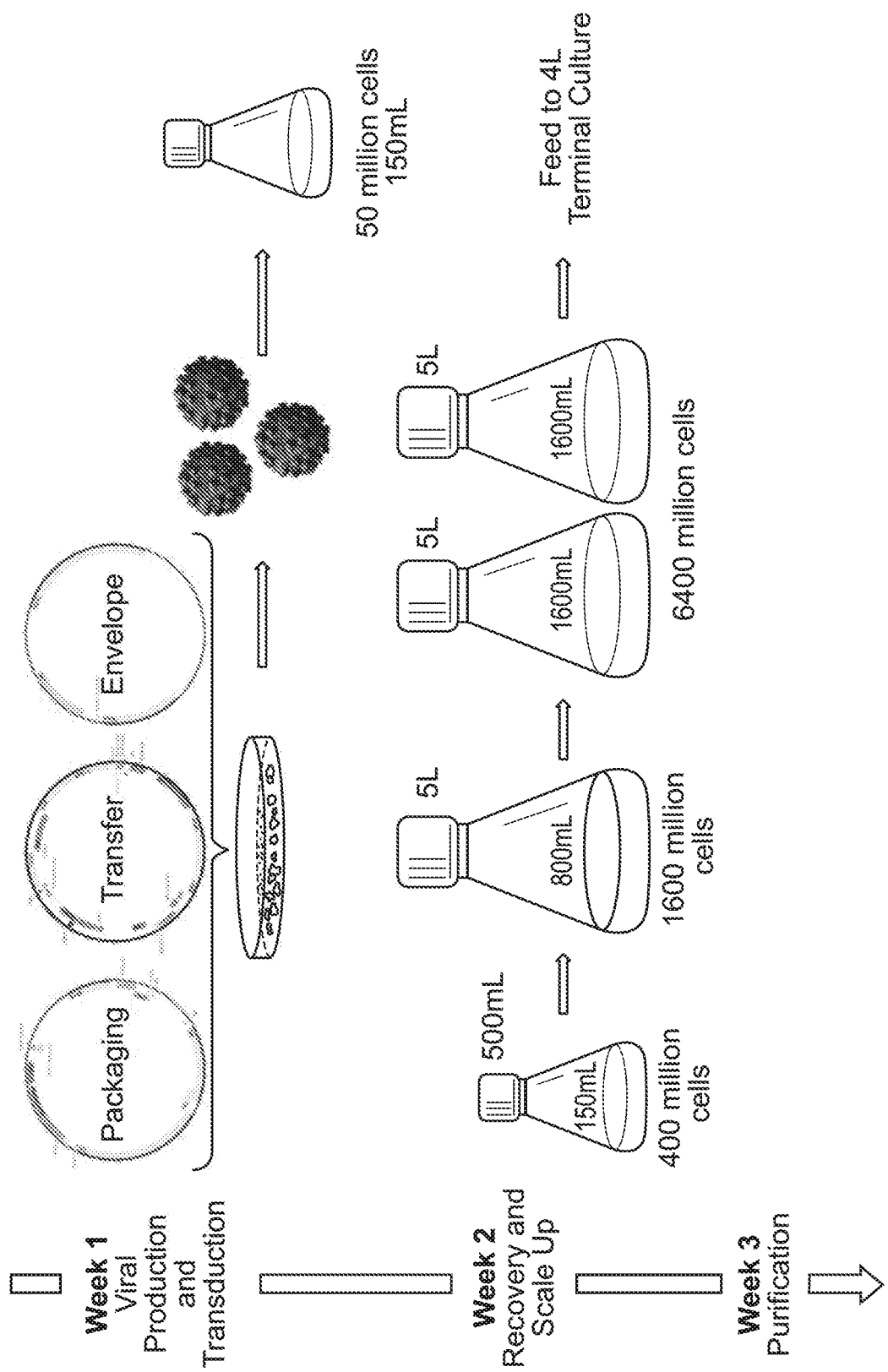
FIG. 4 illustrates a schematic of a method of manufacturing of a peptide of the disclosure.

FIG. 4 illustrates a schematic of a method of manufacturing a construct that expresses a peptide of the disclosure, such as the constructs illustrated in FIG. 3 and as described throughout the disclosure and in SEQ ID NO: 1-SEQ ID NO: 564 provided herein.

In other aspects, the peptides of the present disclosure can be prepared by conventional solid phase chemical synthesis techniques, for example according to the Fmoc solid phase peptide synthesis method ("Fmoc solid phase peptide synthesis, a practical approach," edited by W. C. Chan and P. D. White, Oxford University Press, 2000), Boc solid phase peptide synthesis, or solution phase peptide synthesis. The disulfide bonds can be formed after cleavage from the resin, such as by air oxidation or a buffer system with a set pH range such as from 7-10 and can contain a redox system such as glutathione/oxidized glutathione or cysteine/cystine. The disulfide bonds can also be formed by selective protection and deprotection of specific cysteine residues followed by oxidation, or on the resin. The peptide can be purified, such as by reversed-phase chromatography at any one or more steps during the production process. The peptide can be isolated by lyophilization and can be in various salt forms, such as TFA salt or ammonium and acetate salt.

Pharmaceutical Compositions of Peptides

A pharmaceutical composition of the disclosure can be a combination of any peptide described herein with other chemical components, such as carriers, stabilizers, diluents, dispersing agents, suspending agents, thickening agents, antioxidants, solubilizers, buffers, osmolytes, salts, surfactants, amino acids, encapsulating agents, bulking agents, cryoprotectants, and/or excipients. The pharmaceutical composition facilitates administration of a peptide described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, sublingual, inhalation, dermal, intrathecal, intranasal, intra-articular, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduce the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously.

A peptide of the disclosure can be applied directly to an organ, or an organ tissue or cells, such as brain or brain tissue or cancer cells, during a surgical procedure. The recombinant peptides described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the peptide described herein described herein can be administered in pharmaceutical compositions to a subject suffering from a condition that affects the immune system. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a peptide described herein can be manufactured, for example, by expressing the peptide in a recombinant system, purifying the peptide, lyophilizing the peptide, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of peptides described herein comprising the compounds described herein include formulating the peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Administration of Pharmaceutical Compositions

A pharmaceutical composition of the disclosure can be a combination of any peptide described herein with other chemical components, such as carriers, stabilizers, diluents, dispersing agents, suspending agents, thickening agents, and/or excipients. The pharmaceutical composition facilitates administration of a peptide described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, inhalation, dermal, intra-articular, intrathecal, intranasal, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water-soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduce the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously. A peptide described herein can be administered to a subject, home, target, migrates to, is retained by, and/or binds to, or be directed to an organ, e.g., the cartilage.

A peptide of the disclosure can be applied directly to an organ, or an organ tissue or cells, such as cartilage or cartilage tissue or cells, during a surgical procedure. The recombinant peptides described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the peptide described herein described herein are administered in pharmaceutical compositions to a subject suffering from a condition. In some instances the pharmaceutical composition will affect the physiology of the animal, such as the immune system, inflammatory response, or other physiologic affect. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a peptide described herein can be manufactured, for example, by expressing the peptide in a recombinant system, purifying the peptide, lyophilizing the peptide, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of peptides described herein comprising the compounds described herein include formulating the peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

Use of Peptide in Imaging and Surgical Methods

The present disclosure generally relates to peptides that home, target, migrate to, are retained by, accumulate in, and/or bind to, or are directed to specific regions, tissues, structures, or cells within the body and methods of using such peptides. These peptides have the ability to contact the cartilage, which makes them useful for a variety of applications. In particular, the peptides can have applications in site-specific modulation of biomolecules to which the peptides are directed to. End uses of such peptides can include, for example, imaging, research, therapeutics, theranostics, pharmaceuticals, chemotherapy, chelation therapy, targeted drug delivery, and radiotherapy. Some uses can include targeted drug delivery and imaging.

In some embodiments, the present disclosure provides a method for detecting a cancer, cancerous tissue, or tumor tissue, the method comprising the steps of contacting a tissue of interest with a peptide of the present disclosure, wherein the peptide is conjugated to a detectable agent and measuring the level of binding of the peptide, wherein an elevated level of binding, relative to normal tissue, is indicative that the tissue is a cancer, cancerous tissue or tumor tissue.

In some embodiments, the disclosure provides a method of imaging an organ or body region or region, tissue or structure of a subject, the method comprising administrating to the subject the peptide or a pharmaceutical composition disclosed herein and imaging the subject. In some embodiments such imaging is used to detect a condition associated with cartilage, or a function of the cartilage. In some cases the condition is an inflammation, a cancer, a degradation, a growth disturbance, genetic, a tear or an injury, or another suitable condition. In some cases the condition is a chondrodystrophy, a traumatic rupture or detachment, pain following surgery in regions of the body containing cartilage, costochondritis, herniation, polychondritis, arthritis, osteoarthritis, rheumatoid arthritis, ankylosing spondylitis (AS), Systemic Lupus Erythematosus (SLE or "Lupus"), Psoriatic Arthritis (PsA), gout, achondroplasia, or another suitable condition. In some case the condition is associated with a cancer or tumor of the cartilage. In some cases the condition is a type of chondroma or chondrosarcoma, whether metastatic or not, or another suitable condition. In some embodiments, such as those associated with cancers, the imaging may be associated with surgical removal of the diseased region, tissue, structure or cell of a subject.

Furthermore, the present disclosure provides methods for intraoperative imaging and resection of a diseased or inflamed tissue, cancer, cancerous tissue, or tumor tissue using a peptide of the present disclosure conjugated with a detectable agent. In some embodiments, the diseased or inflamed tissue, cancer, cancerous tissue, or tumor tissue is detectable by fluorescence imaging that allows for intraoperative visualization of the cancer, cancerous tissue, or tumor tissue using a peptide of the present disclosure. In some embodiments, the peptide of the present disclosure is conjugated to one or more detectable agents. In a further embodiment, the detectable agent comprises a fluorescent moiety coupled to the peptide. In another embodiment, the detectable agent comprises a radionuclide. In some embodiments, imaging is achieved during open surgery. In further embodiments, imaging is accomplished using endoscopy or other non-invasive surgical techniques.

Treatment of Cartilage Disorders

The term "effective amount," as used herein, can refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case can be determined using techniques, such as a dose escalation study.

The methods, compositions, and kits of this disclosure can comprise a method to prevent, treat, arrest, reverse, or ameliorate the symptoms of a condition. The treatment can comprise treating a subject (e.g., an individual, a domestic animal, a wild animal or a lab animal afflicted with a disease or condition) with a peptide of the disclosure. In treating a disease, the peptide can contact the cartilage of a subject. The subject can be a human. A subject can be a human; a non-human primate such as a chimpanzee, or other ape or monkey species; a farm animal such as a cattle, horse, sheep, goat, swine; a domestic animal such as a rabbit, dog, and cat; a laboratory animal including a rodent, such as a rat, mouse and guinea pig, or the like. A subject can be of any age. A subject can be, for example, an elderly adult, adult, adolescent, pre-adolescent, child, toddler, infant, or fetus in utero.

Treatment can be provided to the subject before clinical onset of disease. Treatment can be provided to the subject after clinical onset of disease. Treatment can be provided to the subject after 1 day, 1 week, 6 months, 12 months, or 2 years or more after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment can also include treating a human in a clinical trial. A treatment can comprise administering to a subject a pharmaceutical composition, such as one or more of the pharmaceutical compositions described throughout the disclosure. A treatment can comprise a once daily dosing. A treatment can comprise delivering a peptide of the disclosure to a subject, either parenterally, intravenously, subcutaneously, intramuscularly, by inhalation, dermally, intra-articular injection, orally, intrathecally, transdermally, intranasally, via a peritoneal route, or directly onto or into a joint, e.g., via topical, intra-articular injection route or injection route of application. A treatment can comprise administering a peptide-active agent complex to a subject, either parenterally, intravenously, subcutaneously, intramuscularly, by inhalation, dermally, intra-articular injection, orally, intrathecally, transdermally, intranasally, via a peritoneal route, or directly onto or into a joint or directly onto, near or into the cartilage, e.g., via topical, intra-articular injection route or injection route of application.

Types of cartilage diseases or conditions that can be treated with a peptide of the disclosure can include inflammation, pain management, anti-infective, pain relief, anti-cytokine, cancer, injury, degradation, genetic basis, remodeling, hyperplasia, surgical injury/trauma, or the like. Diseases or conditions of bone adjacent to cartilage can also be treated with a peptide of the disclosure. Examples of cartilage diseases or conditions that can be treated with a peptide of the disclosure include Costochondritis, Spinal disc herniation, Relapsing polychondritis, Injury to the articular cartilage, any manner of rheumatic disease (e.g., Rheumatoid Arthritis (RA), ankylosing spondylitis (AS), Systemic Lupus Erythematosus (SLE or "Lupus"), Psoriatic Arthritis (PsA), Osteoarthritis, Gout, and the like), Herniation, Achondroplasia, Benign or non-cancerous chondroma, Malignant or cancerous chondrosarcoma, Chondriodystrophies, Chondromalacia patella, Costochondritis, Halus rigidus, Hip labral tear, Osteochondritis dssecans, Osteochondrodysplasias, Torn meniscus, Pectus carinatum, Pectus excavatum, Chondropathy, Chondromalacia, Polychondritis, Relapsing Polychondritis, Slipped epiphysis, Osteochondritis Dissecans, Chondrodysplasia, Costochondritis, Perichondritis, Osteochondroma, Knee osteoarthritis, Finger osteoarthritis, Wrist osteoarthritis, Hip osteoarthritis, Spine osteoarthritis, Chondromalacia, Osteoarthritis Susceptibility, Ankle Osteoarthritis, Spondylosis, Secondary chondrosarcoma, Small and unstable nodules as seen in osteoarthritis, Osteochondroses, Primary chondrosarcoma, Cartilage disorders, scleroderma, collagen disorders, Chondrodysplasia, Tietze syndrome, Dermochondrocorneal dystrophy of Francois, Epiphyseal dysplasia multiple 1, Epiphyseal dysplasia multiple 2, Epiphyseal dysplasia multiple 3, Epiphyseal dysplasia multiple 4, Epiphyseal dysplasia multiple 5, Ossified Ear cartilages with Mental deficiency, Muscle Wasting and Bony Changes, Periosteal chondrosarcoma, Carpotarsal osteochondromatosis, Achondroplasia, Genochondromatosis II, Genochondromatosis, Chondrodysplasia—disorder of sex development, Chondroma, Chordoma, Atelosteogenesis, type 1, Atelosteogenesis Type III, Atelosteogenesis, type 2, Pyknoachondrogenesis, Osteoarthropathy of fingers familial, Dyschondrosteosis—nephritis, Coloboma of Alar-nasal cartilages with telecanthus, Alar cartilages hypoplasia—coloboma—telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Jequier-Kozlowski-skeletal dysplasia, Chondrodystrophy, Cranio osteoarthropathy, Tietze's syndrome, Hip dysplasia—ecchondromata, Bessel-Hagen disease, Chondromatosis (benign), Enchondromatosis (benign), Chondrocalcinosis due to apatite crystal deposition, Meyenburg-Altherr-Uehlinger syndrome, Enchondromatosis-dwarfism-deafness, premature growth plate closure (e.g., due to dwarfism, injury, therapy such as retinoid therapy for adolescent acne, or ACL repair), Astley-Kendall syndrome, Synovial osteochondromatosis, Severe achondroplasia with developmental delay and acanthosis nigricans, Chondrocalcinosis, Stanescu syndrome, Familial osteochondritis dissecans, Achondrogenesis type 1A, Achondrogenesis type 2, Achondrogenesis, Langer-Saldino Type, Achondrogenesis type 1B, Achondrogenesis type 1A and 1B, Type II Achondrogenesis-Hypochondrogenesis, Achondrogenesis, Achondrogenesis type 3, Achondrogenesis type 4, Chondrocalcinosis 1, Chondrocalcinosis 2, Chondrocalcinosis familial articular, Diastrophic dysplasia, Fibrochondrogenesis, Hypochondroplasia, Keutel syndrome, Maffucci Syndrome, Osteoarthritis Susceptibility 6, Osteoarthritis Susceptibility 5, Osteoarthritis Susceptibility 4, Osteoarthritis Susceptibility 3, Osteoarthritis Susceptibility 2, Osteoarthritis Susceptibility 1, Pseudoachondroplasia, Cauliflower ear, Costochondritis, Growth plate fractures, Pectus excavatum, septic arthritis, gout, pseudogout (calcium pyrophosphate deposition disease or CPPD), gouty arthritis, bacterial, viral, or fungal infections in or near the joint, bursitis, tendinitis, arthropathies, or a joint disease condition. Examples of bone diseases or conditions that can be treated with a peptide of the disclosure include osteopenia, post-menopausal bone loss, bone maintenance, bone fracture, arthroplasty recovery, osteoporosis, bone loss due to metastatic cancer, fractures due to bone loss (e.g., hip fractures in patients with osteoporosis), pathological fracture, or atypical fracture.

In some embodiments, a peptide or peptide conjugate of this disclosure can be administered to a subject in order to target, an arthritic joint. In other embodiments, a peptide or peptide conjugate of this disclosure can be administered to a subject in order to treat an arthritic joint.

In some embodiments, the present disclosure provides a method for treating a cancer, the method comprising administering to a subject in need thereof an effective amount of a peptide of the present disclosure.

In some embodiments, the present disclosure provides a method for treating a cancer, the method comprising administering to a patient in need thereof an effective amount of a pharmaceutical composition comprising a peptide of the present disclosure and a pharmaceutically acceptable carrier.

In some embodiments, the peptides of the present disclosure can be used to treat chondrosarcoma. Chondrosarcoma is a cancer of cartilage producing cells and is often found in bones and joints. It falls within the family of bone and soft-tissue sarcomas. In certain embodiments, administration of a peptide or peptide conjugate of the present disclosure can be used to image and diagnose or target and treat a subject with chondrosarcoma. The administration of a peptide or peptide conjugate of the present disclosure can be used in combination with ablative radiotherapy or proton therapy to treat chondrosarcoma. The subject can be a human or an animal.

In some embodiments, a peptide or peptide conjugate of this disclosure can be used to treat Chordoma. In certain embodiments, administration of a peptide or peptide conjugate of the present disclosure can be used to image and diagnose or target and treat a subject with chordoma. The administration of a peptide or peptide conjugate of the present disclosure can be used in combination with a tyrosine kinase inhibitor, such as imatinib mesylate, and ablative radiotherapy or proton therapy to treat chordoma. The administration of a peptide or peptide conjugate of the present disclosure can be used in combination with an antivascular agent such as bevacizumab and an epidermal growth factor receptor inhibitor such as erlotinib to treat chordoma. The subject can be a human or an animal.

In some embodiments, the present disclosure provides a method for inhibiting invasive activity of cells, the method comprising administering an effective amount of a peptide of the present disclosure to a subject.

In some embodiments, the peptides of the present disclosure are conjugated to one or more therapeutic agents. In further embodiments, the therapeutic agent is a chemotherapeutic, anti-cancer drug, or anti-cancer agent selected from, but are not limited to: anti-inflammatories, such as for example a glucocorticoid, a corticosteroid, a protease inhibitor, such as for example collagenase inhibitor or a matrix metalloprotease inhibitor (i.e., MMP-13 inhibitor), an amino sugar, vitamin (e.g., Vitamin D), and antibiotics, antiviral, or antifungal, a statin, an immune modulator, radioisotopes, toxins, enzymes, sensitizing drugs, nucleic acids, including interfering RNAs, antibodies, anti-angiogenic agents, cisplatin, anti-metabolites, mitotic inhibitors, growth factor inhibitors, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine, and their equivalents, as well as photo-ablation. Some of these active agents induce programmed cell death such as apoptosis in target cells and thereby improve symptoms or ameliorate disease. Apoptosis can be induced by many active agents, including, for example, chemotherapeutics, anti-inflammatories, corticosteroids, NSAIDS, tumor necrosis factor alpha (TNF-α) modulators, tumor necrosis factor receptor (TNFR) family modulators. In some embodiments, peptides of this disclosure can be used to target active agents to pathways of cell death or cell killing, such as caspases, apoptosis activators and inhibitors, XBP-1, Bcl-2, Bcl-Xl, Bcl-w, and other disclosed herein. In other embodiments, the therapeutic agent is any nonsteroidal anti-inflammatory drug (NSAID). The NSAID can be any heterocyclic acetic acid derivatives such as ketorolac, indomethacin, etodolac, or tolemetin, any propionic acid derivatives such as naproxen, any enolic acid derivatives, any anthranilic acid derivatives, any selective COX-2 inhibitors such as celecoxib, any sulfonanilides, any salicylates, aceclofenac, nabumetone, sulindac, diclofenac, or ibuprofen. In other embodiments, the therapeutic agent is any steroid, such as dexamethasone, budesonide, beclomethasone monopropionate, desciclesonide, triamcinolone, cortisone, prednisone, prednisolone, triamcinolone hexacetonide, or methylprednisolone. In other embodiments, the therapeutic agent is a pain reliever, such as acetaminophen, opioids, local anesthetics, antidepressants, glutamate receptor antagonists, adenosine, or neuropeptides. In some embodiments, a treatment consists of administering a combination of any of the above therapeutic agents and a peptide conjugate, such as a treatment in which both a dexamethasone-peptide conjugate and an NSAID are administered to a patient. Peptides of the current disclosure that target the cartilage can be used to treat the diseases conditions as described herein, for example, any diseases or conditions including tears, injuries (i.e., sports injuries), genetic factors, degradation, thinning, inflammation, cancer or any other disease or condition of the cartilage or to target therapeutically-active substances to treat these diseases amongst others. In other cases, a peptide of the disclosure can be used to treat traumatic rupture, detachment, chostochondritis, spinal disc herniation, relapsing and non-relapsing polychondritis, injury to the articular cartilage, osteoarthritis, arthritis or achondroplasia. In some cases, the peptide or peptide-active agent can be used to target cancer in the cartilage, for example benign chondroma or malignant chondrosarcoma, by contacting the cartilage by diffusion into chondrocytes and then having antitumor function, targeted toxicity, inhibiting metastases, etc. As well, such peptide or peptide-active agent can be used to label, detect, or image such cartilage lesions, including tumors and metastases amongst other lesions, which may be removed through various surgical techniques or by targeting with peptide-active agents that induce programmed cell death or kill cells.

Venom or toxin derived peptide(s), peptides, modified peptides, labeled peptides, peptide-active agent conjugates and pharmaceutical compositions described herein can be administered for prophylactic and/or therapeutic treatments. In therapeutic applications, the composition can be administered to a subject already suffering from a disease or condition, in an amount sufficient to cure or at least partially arrest the symptoms of the disease or condition, or to cure, heal, improve, or ameliorate the condition. Such peptides described herein can also be administered to prevent (either in whole or in part), lessen a likelihood of developing, contracting, or worsening a condition. Amounts effective for this use can vary based on the severity and course of the disease or condition, previous therapy, the subject's health status, weight, response to the drugs, and the judgment of the treating physician. Venom or toxin derived peptide(s), peptides, modified peptides, labeled peptides, peptide-active agent conjugates and pharmaceutical compositions described herein can allow for targeted homing of the peptide and local delivery of any conjugate. For example, a peptide conjugated to a steroid allows for local delivery of the steroid, which is significantly more effective and less toxic than traditional systemic steroids. A peptide conjugated to an NSAID is another example. In this case, the peptide conjugated to an NSAID allows for local delivery of the NSAID, which allows for administration of a lower NSAID dose and is subsequently less toxic. By delivering an active agent to the joint, pain relief can be more rapid, may be more long lasting, and can be obtained with a lower systemic dose and off-site undesired effects than with systemic dosing without targeting.

Peptides of the current disclosure that target the cartilage can be used to treat or manage pain associated with a cartilage injury or disorder, or any other cartilage or joint condition as described herein. The peptides can be used either directly or as carriers of active drugs, peptides, or molecules. For example, since ion channels can be associated with pain and can be activated in disease states such as arthritis, peptides that interact with ion channels can be used directly to reduce pain. In another embodiment, the peptide is conjugated to an active agent with anti-inflammatory activity, in which the peptide acts as a carrier for the local delivery of the active agent to reduce pain.

In some embodiments, the peptides described herein provide a method of treating a cartilage condition of a subject, the method comprising administering to the subject a therapeutically-effective amount of a peptide comprising the sequence SEQ ID NO: 1 or fragment thereof. In some embodiments, the peptides described herein provide a method of treating a cartilage condition of a subject, the method comprising administering to the subject a peptide of any one of SEQ ID NO: 2-SEQ ID NO: 564 or fragment thereof.

Treatment of Kidney Disorders

In some embodiments, peptides of this disclosure that home, target, are directed to, migrate to, are retained by, accumulate in, or bind to specific regions, tissues, structures or cells of the kidneys can be used to treat a kidney disorder. In other embodiments, peptides are used in peptide conjugates of the present disclosure to deliver an active agent for treatment of a kidney disorder.

In some embodiments, the peptides and peptide-conjugates of the present disclosure are used to treat a condition of the kidney, or a region, tissue, structure, or cell thereof. In certain embodiments, the condition is associated with kidney, or a function of a subject's kidneys. The present disclosure encompasses various acute and chronic renal diseases, including glomerular, tubule-interstitial, and microvascular diseases. Examples of conditions applicable to the present disclosure include but are not limited to: hypertensive kidney damage, acute kidney diseases and disorders (AKD), acute kidney injury (AKI) due to ischemia-reperfusion injury, drug treatment such as chemotherapy, cardiovascular surgery, surgery, medical interventions or treatment, radiocontrast nephropathy, or induced by cisplatin or carboplatin, which can be treated prophylactically, established AKI including ischemic renal injury, endotoxemia-induced AKI, endotoxemia/sepsis syndrome, or established nephrotoxic AKI (e.g., rhabdomyolysis, radiocontrast nephropathy, cisplatin/carboplatin AKI, aminoglycoside nephrotoxicity), end stage renal disease, acute and rapidly progressive glomerulonephritis, acute presentations of nephrotic syndrome, acute pyelonephritis, acute renal failure, chronic glomerulonephritis, chronic heart failure, chronic interstitial nephritis, graft versus host disease after renal transplant, chronic kidney disease (CKD) such as diabetic nephropathy, hypertensive nephrosclerosis, idiopathic chronic glomerulonephritis (e.g., focal glomerular sclerosis, membranous nephropathy, membranoproliferative glomerulonephritis, minimal change disease transition to chronic disease, anti-GBM disease, rapidly progressive cresentic glomerulonephritis, IgA nephropathy), secondary chronic glomerulonephritis (e.g., systemic lupus, polyarteritis nodosa, scleroderma, amyloidosis, endocarditis), hereditary nephropathy (e.g., polycystic kidney disease, Alport's syndrome), interstitial nephritis induced by drugs (e.g., Chinese herbs, NSAIDs), multiple myeloma or sarcoid, or renal transplantation such as donor kidney prophylaxis (treatment of donor kidney prior to transplantation), treatment post transplantation to treat delayed graft function, acute rejection, or chronic rejection, chronic liver disease, chronic pyelonephritis, diabetes, diabetic kidney disease, fibrosis, focal segmental glomerulosclerosis, Goodpasture's disease, hypertensive nephrosclerosis, IgG4-related renal disease, interstitial inflammation, lupus nephritis, nephritic syndrome, partial obstruction of the urinary tract, polycystic kidney disease, progressive renal disease, renal cell carcinoma, renal fibrosis, and vasculitis. For example, in certain embodiments, the peptides and peptide-conjugates of the present disclosure are used to reduce acute kidney injury in order to prevent it from progressing to chronic kidney disease.

Alternatively or in combination, in some embodiments, the peptide and peptide-conjugates of the present disclosure are used to elicit a protective response such as ischemic preconditioning and/or acquired cytoresistance in a kidney of the subject. In some embodiments, ischemic preconditioning and/or acquired cytoresistance is induced by administering an agent (e.g., a peptide or peptide-conjugate of the present disclosure) that upregulates the expression of protective stress proteins, such as antioxidants, anti-inflammatory proteins, or protease inhibitors. In certain embodiments, the induced response protects the kidney by preserving kidney function in whole or in part and/or by reducing injury to renal tissues and cells, e.g., relative to the situation where no protective response is induced. The peptides and peptide-conjugates of the present disclosure can provide certain benefits compared to other agents for inducing ischemic preconditioning and/or acquired cytoresistance, such as a well-defined chemical structure and avoidance of low pH precipitation.

In some embodiments, the protective response is induced in order to protect the kidney or tissues or cells thereof from an injury or insult that is predicted to occur (e.g., associated with a planned event such as a medical procedure, is likely to occur due to a condition in the subject) or has already occurred. In certain embodiments, the induced response prevents or reduces the extent of damage to the kidney or tissues or cells thereof caused by the injury or insult. For instance, in certain embodiments, the peptides and peptide-conjugates induce acquired cytoresistance by activating protective pathways and/or upregulating expression of protective stress proteins. Optionally, the peptides and peptide-conjugates are capable of inducing such protective responses while causing minimal or no injury to the kidney.

In various embodiments, the injury or insult is associated with one or more of: surgery, radiocontrast imaging, cardiopulmonary bypass, balloon angioplasty, induced cardiac or cerebral ischemic-reperfusion injury, organ transplantation, sepsis, shock, low blood pressure, high blood pressure, kidney hypoperfusion, chemotherapy, drug administration, nephrotoxic drug administration, blunt force trauma, puncture, poison, or smoking. For instance, in certain embodiments, the injury or insult is associated with a medical procedure that has been or will be performed on the subject, such as one or more of: surgery, radiocontrast imaging, cardiopulmonary bypass, balloon angioplasty, induced cardiac or cerebral ischemic-reperfusion injury, organ transplantation, chemotherapy, drug administration, or nephrotoxic drug administration.

In some embodiments, the peptide itself exhibits a renal therapeutic effect. For example, in certain embodiments, the cystine-dense peptide interacts with a renal ion channel, inhibits a protease, has antimicrobial activity, has anticancer activity, has anti-inflammatory activity, induces ischemic preconditioning or acquired cytoresistance, or produces a protective or therapeutic effect on a kidney of the subject, or a combination thereof. Optionally, the renal therapeutic effect exhibited by the peptide is a renal protective effect or renal prophylactic effect (e.g., ischemic preconditioning or acquired cytoresistance) that protects the kidney or a tissue or cell thereof from an upcoming injury or insult.

For example, in certain embodiments, a peptide of the present disclosure activates protective pathways and/or upregulates expression of protective stress proteins in the kidney or tissues or cells thereof. As another example, in certain embodiments, a peptide of the present disclosure accesses and suppresses intracellular injury pathways. In yet another example, in certain embodiments, a peptide of the present disclosure inhibits interstitial inflammation and prevents renal fibrosis. As a further example, in certain embodiments, a peptide of the present disclosure is administered prior to or currently with the administration of a nephrotoxic agent (e.g., aminoglycoside antibiotics such as gentamicin and minocycline, chemotherapeutics such as cisplatin, immunoglobulins or fragments thereof, mannitol, NSAIDs such as ketorolac or ibuprofen, cyclosporin, cyclophosphamide, radiocontrast dyes) in order to minimize its damaging effects, e.g., by blocking megalin-cubulin binding sites so that the nephrotoxic agent passes through the kidneys.

In some embodiments, the present disclosure provides that any peptide of the disclosure including SEQ ID NO: 24-SEQ ID NO: 274 or SEQ ID NO: 314-SEQ ID NO: 564 can as a peptide conjugate with an active agent for treatment of a kidney disorder. For example, a peptide of SEQ ID NO: 27, SEQ ID NO: 108, or SEQ ID NO: 199 can be conjugated to an active agent and administered to a subject in need thereof to treat a kidney disorder.

In some embodiments, homing of a peptide of this disclosure to cartilage or the kidneys can be assessed in an animal model such as those described in Alves et al. (Clin Rev Allergy Immunol. 2016 August; 51(1):27-47. doi: 10.1007/s12016-015-8522-7), Kuyinu et al. (J Orthop Surg Res. 2016 Feb. 2; 11:19. doi: 10. 1186/s13018-016-0346-5), Li et al. (Exp Biol Med (Maywood). 2015 August; 240(8): 1029-38. doi: 10. 1177/1535370215594583), and Mullins et al. (Dis Model Mech. 2016 Dec. 1; 9(12):1419-1433), all of which are incorporated herein by reference.

Multiple peptides described herein can be administered in any order or simultaneously. In some cases, multiple functional fragments of peptides derived from toxins or venom can be administered in any order or simultaneously. If simultaneously, the multiple peptides described herein can be provided in a single, unified form, such as an intravenous injection, or in multiple forms, such as subsequent intravenous dosages.

Peptides can be packaged as a kit. In some embodiments, a kit includes written instructions on the use or administration of the peptides.

EXAMPLES

The following examples are included to further describe some embodiments of the present disclosure, and should not be used to limit the scope of the disclosure.

Example 1

Manufacture of Peptides

The peptide sequence was reverse-translated into DNA, synthesized, and cloned in-frame with siderocalin using standard molecular biology techniques. (M. R. Green, Joseph Sambrook. Molecular Cloning. 2012 Cold Spring Harbor Press.). The resulting construct was packaged into a lentivirus, transfected into HEK293 cells, expanded, isolated by immobilized metal affinity chromatography (IMAC), cleaved with tobacco etch virus protease, and purified to homogeneity by reverse-phase chromatography. Following purification, each peptide was lyophilized and stored frozen.

Example 2

Radiolabeling of Peptide

This example describes radiolabeling of peptides with standard techniques. See J Biol Chem. 254(11):4359-65 (1979). The sequences were engineered to have the amino acids, "G" and "S" at the N terminus. See Methods in Enzymology V91:1983 p. 570 and Journal of Biological Chemistry 254(11):1979 p. 4359. An excess of formaldehyde was used to ensure complete methylation (dimethylation of every free amine). The labeled peptides were isolated via solid-phase extraction on Strata-X columns (Phenomenex 8B-S100-AAK), rinsed with water with 5% methanol, and recovered in methanol with 2% formic acid. Solvent was subsequently removed in a blowdown evaporator with gentle heat and a stream of nitrogen gas.

Example 3

Peptide Detectable Agent Conjugates

This example describes the dye labeling of peptides. A peptide of the disclosure is expressed recombinantly or chemically synthesized, and then the N-terminus of the peptide is conjugated to a detectable agent via an NHS ester using DCC or EDC to produce a peptide-detectable agent conjugate. The detectable agent is the fluorophore dye is a cyanine dye, such as Cy5.5 or an Alexa fluorophore, such as Alexa647.

The peptide detectable agent conjugates are administered to a subject. The subject can be a human or a non-human animal. After administration, the peptide detectable agent conjugates home to cartilage. The subject, or a biopsy from the subject, can be imaged to visualize localization of the peptide detectable agent conjugates to cartilage. In some aspects, visualization of the peptide detectable agent conjugates in cartilage after administration results in diagnosis of arthritis, cartilage damage, or any cartilage disorder.

Example 4

Method to Determine Improved Peptide Variants

This example shows a method for determining ways to improve peptide variants by comparing and analyzing the primary sequences and tertiary structures of scaffold peptides. FIG. 5A-FIG. 5C show sequences of SEQ ID NO: 541 aligned with SEQ ID NO: 316, SEQ ID NO: 541 aligned with SEQ ID NO: 542, and SEQ ID NO: 541 aligned with SEQ ID NO: 483. The sequence alignment of the two scaffolds was used to identify conserved positively charged residues (shown in boxes) that may be important for cartilage homing. A peptide of SEQ ID NO: 483 homes to cartilage and other peptides with positively charged residues in similar positions, or cysteines in similar positions, or other residues that are in similar positions are also predicted to home to cartilage.

Figure 6:
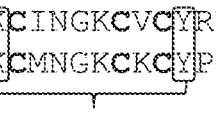
FIG. 6 illustrates the alignment of the peptide of SEQ ID NO: 320 with the peptide of SEQ ID NO: 484. Boxes delineate conserved positively charged residues.

FIG. 6 shows sequences of SEQ ID NO: 320 aligned with SEQ ID NO: 484. The sequence alignment of the two scaffolds was used to identify the basic/aromatic dyad that may be involved in the interaction with the Kv ion channel (K27 and Y36 of SEQ ID NO: 484). The mutation of K27 to alanine, arginine, or glutamic acid destroyed activity against the squid Kv1A ion channel. K27 and Y36 may be desirable to maintain or add to a cartilage homing peptide of this disclosure to maintain or improve homing, to maintain or improve residence time in cartilage, or to maintain or improve modulation of an ion channel such as Kv. In contrast, K27 and Y36 may be desirable to mutate out of a cartilage homing peptide to reduce interaction with an ion channel such as Kv. Disruption of either the basic or aromatic residue eliminates ion channel activity. In another example, D amino acids are expected to reduce or eliminate binding.

Example 5

Sequence Alignment to pFam00451:Toxin_2 Family to Identify Cartilage Homing Peptides This example describes a method for identifying new cartilage homing peptides by sequence alignment to the pFam00451:toxin_2 structural class family. The pFam00451:toxin_2 structural class is a family of peptides related by similarities in sequence identity. FIG. 7 illustrates alignment of peptides within the pfam00451:toxin_2 structural class family of SEQ ID NO: 494-SEQ ID NO: 540. Boxed and bolded residues indicate relative conservation of sequence while non-boxed and non-bolded residues indicate areas of higher sequence variability. SEQ ID NO: 494 was identified as a cartilage homing candidate peptide based on its structural similarities with the pFam00451:toxin_structural class family. FIG. 8 illustrates the sequence alignment of a peptide of SEQ ID NO: 494 from the pfam00451:toxin_2 structural class family with the sequence of SEQ ID NO: 27. Asterisks indicate positions with a single, fully conserved residue, a colon indicates conservation between groups of strongly similar properties (scoring>0.5 in the Gonnet point accepted mutation (PAM) 250 matrix), and a period indicates conservation between groups of weakly similar properties (scoring≤0.5 in the Gonnet PAM 250 matrix). SEQ ID NO: 108 was also identified as a cartilage homing candidate based on its structural similarities with the pfam00451:toxin_2 structural class family of peptides.

The pFam00451:toxin_2 structural class family is used as a scaffold to identify variant peptides that have cartilage homing properties. Any member of the pFam00451:toxin_2 structural class family is used to predict new cartilage homing peptides based on homology, preserved residues, or a preserved cysteine residue.

Example 6

Dosing of Peptide with Kidney Ligation

This example describes a dosing scheme for administering peptides to mice in conjunction with kidney ligation. Different dosages of the peptides were administered to Female Harlan athymic nude mice, weighing 20 g-25 g, via tail vein injection (n=2 mice per peptide). The sequence of thirteen cartilage homing peptides of SEQ ID NO: 24-SEQ ID NO: 36 are shown in TABLE 1. The experiment was done in duplicates. The kidneys were ligated to prevent renal filtration of the peptides. Each peptide was radiolabeled by methylating lysines and the N-terminus, so the actual binding agent may contain methyl or dimethyl lysine(s) and a methylated or dimethylated amino terminus.

A target dosage of 50-100 nmol of each peptide carrying 10-25 uCi of $^{14}C$ was administered to Female Harlan athymic nude mice while anesthetized. Each peptide was allowed to freely circulate within the animal before the animals were euthanized and sectioned.

Example 7

Peptide Homing with Kidney Ligation

This example illustrates peptide homing to cartilage of mice with kidneys that were ligated prior to peptide administration. At the end of the dosing period in EXAMPLE 6, mice were frozen in a hexane/dry ice bath and then frozen in a block of carboxymethylcellulose. Whole animal sagittal slices were prepared that resulted in thin frozen sections being available for imaging. Thin, frozen sections of animal including imaging of tissues such as brain, tumor, liver, kidney, lung, heart, spleen, pancreas, muscle, adipose, gall bladder, upper gastrointestinal tract, lower gastrointestinal tract, bone, bone marrow, reproductive track, eye, cartilage, stomach, skin, spinal cord, bladder, salivary gland, and other types of tissues were obtained with a microtome, allowed to desiccate in a freezer, and exposed to phosphoimager plates for about ten days.

Figure 12:
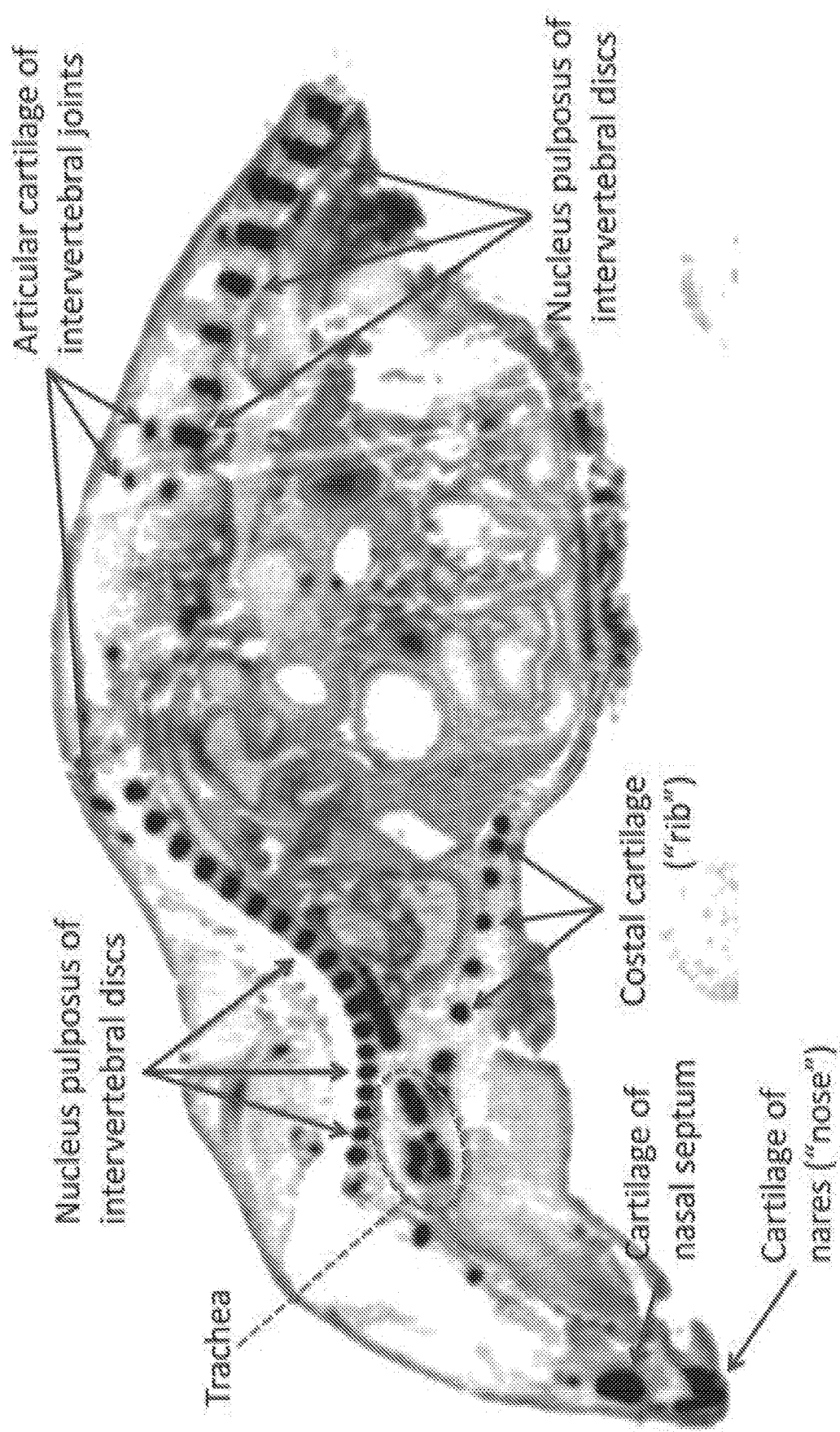
FIG. 12 illustrates the identification of locations the $^{14}C$ signal in the nasal, spinal, tracheal, and other cartilage of an animal treated with the peptide of SEQ ID NO: 27.

These plates were developed, and the signal (densitometry) from each organ was normalized to the signal found in the heart blood of each animal. A signal in tissue darker than the signal expected from blood in that tissue indicates peptide accumulation in a region, tissue, structure or cell. For instance, the cartilage is avascular and contains minute amounts of blood. A ratio of at least 170% signal in the cartilage versus heart ventricle was chosen as a reference level for significant targeting to cartilage, which also correlated with clear accumulation in cartilaginous tissues in the images of the slices. FIG. 1 identifies the locations of the SEQ ID NO: 27 peptide distribution in joint and other cartilage. FIG. 12 identifies the locations of the SEQ ID NO: 27 peptide distribution in nasal, spinal, tracheal, and other cartilage, including to hyaline cartilage such as articular cartilage and physeal cartilage, as well as fibrocartilage.

Figure 9:
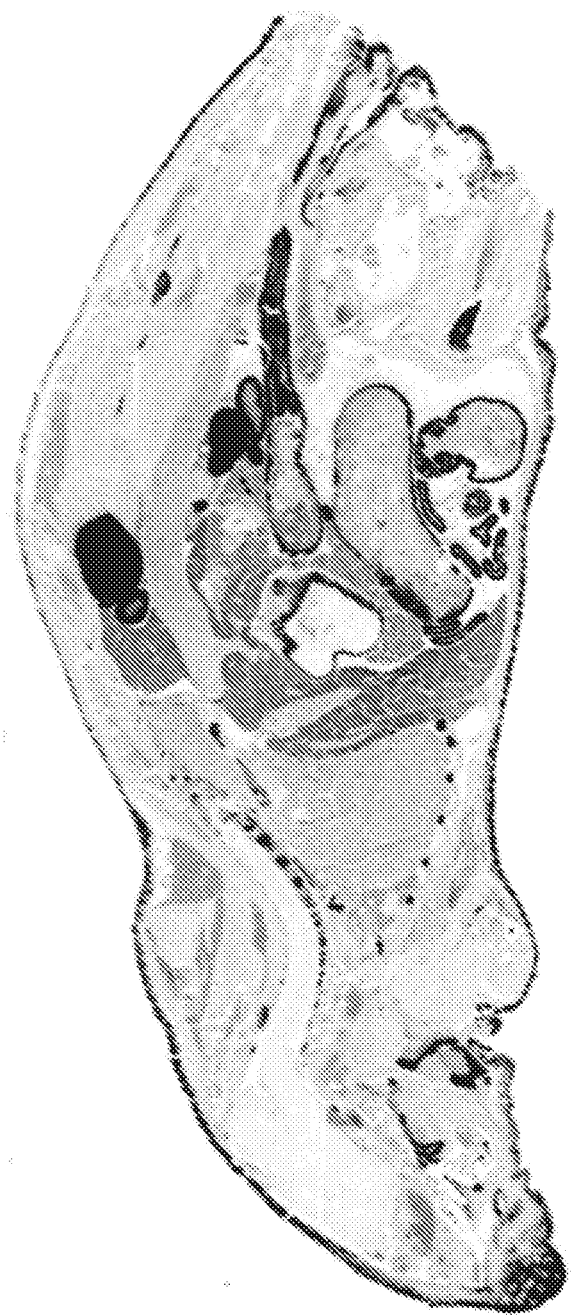
FIG. 9 illustrates the $^{14}C$ signal in the cartilage of an animal with intact kidneys 24 hours after treatment with a peptide of SEQ ID NO: 27.
Figure 10A:
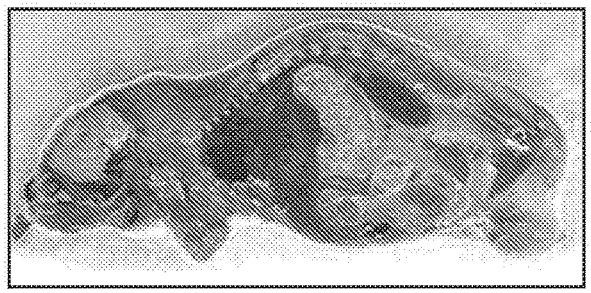
FIG. 10A illustrates an image of a frozen section of a mouse, 24 hours after administration of 10 nmol of a peptide of SEQ ID NO: 108 conjugated to a Cy5.5 fluorophore (SEQ ID NO: 108A).
Figure 10B:
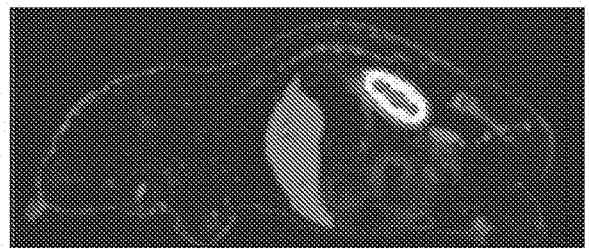
FIG. 10B illustrates the fluorescence signal in the mouse, corresponding to the section shown in FIG. 10A, 24 hours after administration of 10 nmol of a peptide of SEQ ID NO: 108 conjugated to a Cy5.5 fluorophore (SEQ ID NO: 108A).
Figure 10C:
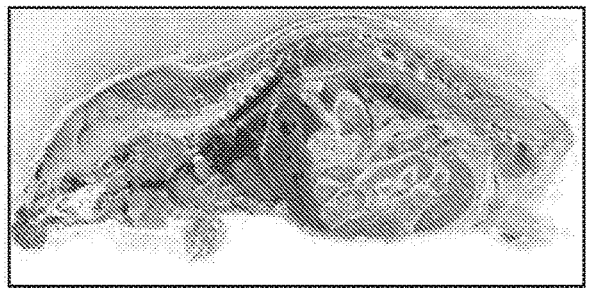
FIG. 10C illustrates an image of a different frozen section of the mouse, 24 hours after administration of 10 nmol of a peptide of SEQ ID NO: 108 conjugated to a Cy5.5 fluorophore (SEQ ID NO: 108A).
Figure 10D:
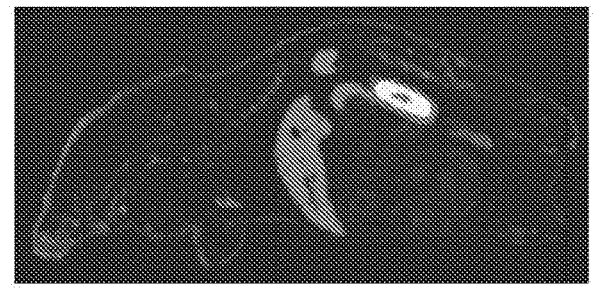
FIG. 10D illustrates the fluorescence signal in the mouse, corresponding to the section shown in FIG. 10C, 24 hours after administration of 10 nmol of a peptide of SEQ ID NO: 108 conjugated to a Cy5.5 fluorophore (SEQ ID NO: 108A).
Figure 10E:
FIG. 10E illustrates an image of a different frozen section of the mouse, 24 hours after administration of 10 nmol of a peptide of SEQ ID NO: 108 conjugated to a Cy5.5 fluorophore (SEQ ID NO: 108A).
Figure 10F:
FIG. 10F illustrates a fluorescence signal in the mouse, corresponding to the section shown in FIG. 10E, 24 hours after administration of 10 nmol of a peptide of SEQ ID NO: 108 conjugated to a Cy5.5 fluorophore (SEQ ID NO: 108A).

Additionally, the peptide can be retained in cartilage for hours after treatment. The SEQ ID NO: 27 peptide was radiolabeled as in EXAMPLE 6 and 100 nmol of peptide was injected into a mouse with intact kidneys. FIG. 9 illustrates the retention of and the tissue distribution in the cartilage of a peptide of SEQ ID NO: 27, 24 hours after administration.

Example 8

Dosing of Peptide without Kidney Ligation

This example describes a dosing scheme for administering peptides to mice without kidney ligation. The peptide administered had the sequence of SEQ ID NO: 27 as shown in TABLE 1. The peptide was radiolabeled by methylating lysines and the N-terminus, so the actual binding agent may contain methyl or dimethyl lysine(s) and a methylated or dimethylated amino terminus.

A target dosage of 100 nmol of each peptide carrying 10-25 µCi of $^{14}C$ was administered to Female Harlan athymic nude mice by a tail vein injection. Each peptide was allowed to freely circulate within the animal for either 4 hours or 24 hours before the animals were euthanized and sectioned.

Example 9

Peptide Homing with Intact Kidneys

This example illustrates peptide homing to cartilage in animals with intact kidneys. At the end of the 4 hour or 24 hour dosing periods in EXAMPLE 8, mice were frozen in a hexane/dry ice bath and then frozen in a block of carboxymethylcellulose. Whole animal sagittal slices were prepared that resulted in thin frozen sections being available for imaging. Thin, frozen sections of animal including imaging of tissues such as brain, tumor, liver, kidney, lung, heart, spleen, pancreas, muscle, adipose, gall bladder, upper gastrointestinal track, lower gastrointestinal track, bone, bone marrow, reproductive track, eye, cartilage, stomach, skin, spinal cord, bladder, salivary gland, and other types of tissues were obtained with a microtome, allowed to desiccate in a freezer, and exposed to phosphoimager plates for about ten days.

These plates were developed. A signal in tissue darker than the signal expected from blood in that tissue indicates peptide accumulation in a region, tissue, structure or cell. For instance, the cartilage is avascular and contains minute amounts of blood. High signal in the kidneys indicates presence and accumulation of the peptide in the kidneys. FIG. 1 identifies the locations of the SEQ ID NO: 27 peptide distribution in joint and other cartilage as well as kidneys.

Example 10

Peptide Homing with Therapeutic Agents

This example describes certain exemplary therapeutic agents that are conjugated to a peptide. A peptide of the disclosure is expressed recombinantly or chemically synthesized and then is conjugated to an exemplary drug, such as paclitaxel or triamcinolone acetonide or budesonide using techniques known in the art, such as those described in Bioconjugate Techniques by Greg Hermanson (Elsevier Inc., $3^{rd}$ Edition, 2013). One or more drugs is conjugated per peptide, or an average of less than one drug is conjugated per peptide.

Coupling of these drugs to a peptide of any of SEQ ID NO: 24-SEQ ID NO: 274 or SEQ ID NO: 314-SEQ ID NO: 564 targets the drug to the cartilage of the subject. One or more drug-peptide conjugates are administered to a human or animal.

Example 11

Peptide Homing to an Arthritic Joint

This example illustrates peptide homing to cartilage in humans or animals with arthritis. A peptide of the present disclosure is expressed recombinantly or chemically synthesized and is used directly, after radiolabeling, or after conjugation to a fluorophore or therapeutic compound. A peptide is selected from any one of the peptides of SEQ ID NO: 24-SEQ ID NO: 274 or SEQ ID NO: 314-SEQ ID NO: 564. The peptide or peptide conjugate is administered to a human or animal subcutaneously, intravenously, or orally, or is injected directly into a joint intraarticularly. The peptide or peptide conjugate homes to cartilage.

Example 12

Peptide Homing to Cartilage in Non-Human Animals

This example illustrates a peptide or peptide conjugate of this disclosure homing to cartilage in non-human animals. Non-human animals include but are not limited to guinea pigs, rabbits, dog, cats, horses, rats, mice, cows, pigs, non-human primates, and other non-human animals. A peptide of the present disclosure is recombinantly expressed or chemically synthesized and are used directly, after radiolabeling, or after conjugation to a fluorophore or therapeutic compound. The peptide is selected from any one of the peptides of SEQ ID NO: 24-SEQ ID NO: 274 or SEQ ID NO: 314-SEQ ID NO: 564. The resulting peptide or peptide conjugate is administered to a non-human animal subcutaneously, intravenously, or orally, or is injected directly into a joint intra-articularly. Biodistribution is assessed by LC/MS, autoradiography, positron emission tomography (PET), or fluorescence imaging. A peptide or peptide conjugate is homed to cartilage in non-human animals.

Example 13

Whole Body Fluorescence and Isolated Limb Fluorescence of Homing Peptides

This example illustrates whole body fluorescence and isolated limb fluorescence of peptide homers of this disclosure. Any peptide of the present disclosure is chemically conjugated to one molecule of a near infrared fluorophore, at the N-terminus of the peptide via an active NHS ester on the dye. A dose of 10 nmol of each peptide conjugated to a fluorophore is administered to Female Harlan athymic nude mice, weighing 20-25 g, and is administered via tail vein injection. Each experiment is done at least in duplicate (n=2 mice per group). The peptide fluorophore conjugate is allowed to freely circulate for the described time period before the mice were euthanized at various time points. Mice are evaluated for peptide distribution of the peptide fluorescence in whole body imaging and in isolated hind limb imaging.

For Whole body fluorescence (WBF), at the end of the dosing period, mice are frozen in a hexane/dry ice bath and then embedded in a frozen block of carboxymethylcellulose. Whole animal sagittal slices are prepared that resulted in thin frozen sections for imaging. Thin frozen sections are obtained using a microtome and allowed visualization of tissues. Sections are allowed to dessicate in a freezer prior to imaging. WBF is performed on fluorescent sections, which are scanned on a Li-Cor Odyssey scanner at a setting of 169 µm resolution, medium quality, 700 channel, L-2.0 intensity.

For isolated hind limb fluorescence studies, mice are euthanized by $CO_2$ asphyxiation at the end of the dosing period. The right hind limb is removed at the hip joint and imaged on a Sepctrum IVIS imager (ex/em: 675 nm. 720 nm) with a 1 second exposure length and a focal height of 0.5 cm. Limbs are imaged with skin removed and with muscle removed.

Example 14

Whole Body Autoradiography of Homing Peptides

This example illustrates whole body autoradiography of peptide homers of this disclosure. Peptides are radiolabeled by methylating lysines at the N-terminus as described in EXAMPLE 2. As such, the peptide may contain methyl or dimethyl lysines and a methylated or dimethlyated amino terminus. A dose of 100 nmol radiolabeled peptide is administered via tail vein injection in Female Harlan athymic nude mice, weighing 20-25 g. The experiment is done in at least duplicate (n=2 animals per group). In some animals, kidneys are ligated to prevent renal filtration of the radiolabled peptides and extend plasma half-life. Each radiolabeled peptide is allowed to freely circulate within the animal for the described time period before the animals were euthanized and sectioned.

Whole body autoradiography (WBA) sagittal sectioning is performed as follows. At the end of the dosing period, mice are frozen in a hexane/dry ice bath and then embedded in a frozen block of carboxymethylcellulose. Whole animal sagittal slices are prepared that resulted in thin frozen sections for imaging. Thin frozen sections are obtained using a microtome and allowed visualization of tissues such as brain, tumor, liver, kidney, lung, heart, spleen, pancreas, muscle, adipose, gall bladder, upper gastrointestinal tract, lower gastrointestinal tract, bone, bone marrow, reproductive tract, eye, cartilage, stomach, skin, spinal cord, bladder, salivary gland, and more. Sections are allowed to dessicate in a freezer prior to imaging.

For the autoradiography imaging, tape mounted thin sections are freeze dried and radioactive samples were exposed to phosphoimager plates for 7 days. These plates are developed and the signal (densitometry) from each organ was normalized to the signal found in the cardiac blood of each animal. A signal in tissue darker than the signal expected from blood in that tissue indicates accumulation in a region, tissue, structure, or cell.

Example 15

Peptide Localization in Chondrocytes

This example illustrates binding of peptides of this disclosure to chondrocytes within cartilage in animals with intact kidneys. In one embodiment, animals are dosed and are processed as described in EXAMPLE 13 and EXAMPLE 14. At the end of the dosing period, animals are euthanized and cartilage is optionally removed for use in staining and imaging procedures. Whole animal sagittal slices are prepared that result in thin frozen sections being available for staining and imaging. One or more of the following cartilage components are identified in thin frozen sections or live cartilage explants using standard staining techniques: collagen fibrils, glycosaminoglycans, or chondrocytes. A peptide of this disclosure is found to localize to chondrocytes in cartilage, localized intracellularly or extracellularly bound or both. Localization is visualized and confirmed by microscopy.

In another embodiment, peptides or peptide-drug conjugates of this disclosure are administered in humans and are localized on or in chondrocytes in cartilage.

Example 16

Peptide Localization in Cartilage Extracellular Matrix

This example illustrates localization of peptides of this disclosure in cartilage extracellular matrix. In one embodiment, animals are dosed and are processed as described in EXAMPLE 13 and EXAMPLE 14 in animals with intact kidneys. At the end of the dosing period, animals are euthanized and cartilage is optionally removed for use in staining and imaging procedures. Whole animal sagittal slices are prepared that result in thin frozen sections being available for staining and imaging. Thin frozen sections or live cartilage explants are acquired, stained, and visualized as described in EXAMPLE 15. A peptide of the present disclosure is found to localize to the extracellular matrix in cartilage. The peptide may be bound to one or more components of the extracellular matrix, such as proteoglycans, glycosaminoglycans, aggrecan, decorin, or collagen. Localization is visualized and confirmed by microscopy.

In another embodiment, peptides or peptide-drug conjugates of this disclosure are administered in humans and are localized in cartilage extracellular matrix.

Example 17

Peptide Binding to Cartilage Explants

This example illustrates a peptide or peptide conjugation of this disclosure homing, targeting, being directed to, migrating to, being retained by, accumulating in, or binding to human and animal cartilage explants in culture. A peptide is selected from any one of the peptides of SEQ ID NO: 24-SEQ ID NO: 274 or SEQ ID NO: 314-SEQ ID NO: 564. Peptides are recombinantly expressed or chemically synthesized and are used directly, after radiolabeling, or after conjugation to a fluorophore or therapeutic compound. A peptide of peptide conjugate of this disclosure is incubated with cartilage explants derived from humans or animals. Peptides of peptide conjugate are found to bind to cartilage explants. The interaction with cartilage is confirmed using various methods that include but are not limited to liquid scintillation counting, confocal microscopy, immunohistochemistry, HPLC, or LC/MS. The peptide shows a higher level of signal than a control peptide that is administered that is not a cartilage binding peptide.

Example 18

Effects of Peptide on Ion Channels

This example describes the interaction between peptides of the present disclosure and ion channels. Ion channels can be associated with pain and can be activated in disease states such as arthritis. A peptide of the disclosure is expressed and administered in a pharmaceutical composition to a patient to treat a joint condition or disease associated with an ion channel and treatable by binding, blocking, or interacting with the ion channel. Ion channels, such as Nav 1.7, are inhibited by peptides of the present disclosure. A given peptide is expressed recombinantly or chemically synthesized, wherein the peptide selected from SEQ ID NO: 24-SEQ ID NO: 274 or SEQ ID NO: 314-SEQ ID NO: 564. Following expression or synthesis, the peptide is used directly or conjugated to a therapeutic compound, such as those described herein. A peptide of the present disclosure selectively interacts with ion channels, or is mutated in order to interact with ion channels. For example, a peptide of this disclosure is bound to Nav 1.7 or Nav 1.7 is blocked by a peptide of this disclosure. When the peptide is administered to a human subject, Nav 1.7 signaling is reduced in the tissues in proximity to the joints, and pain relief is thereby provided.

Example 19

Peptide-Fc Protein Fusions

This example illustrates making and using peptide-Fc protein fusions. A peptide of SEQ ID NO: 108 was recombinantly expressed with the sequence for the human IgG1 Fc protein in HEK293 cells to yield a sequence of SEQ ID NO: 565

(METDTLLLWVLLLWVPGSTGGSGVPINVRCRGSRDCLDPCRRAGMRFG

RCINSRCHCTPGGSGGSDKTHTCPPCPAPELLGGPSVFLFPPKPKDTLM

ISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

K).

The sequence of any peptide of this disclosure is expressed as a fusion protein with either murine or human Fc by adding a secretion signal sequence to the N-terminus and an Fc sequence to the C-terminus. This creates a bivalent molecule with improved secretion properties. The larger peptide-Fc fusion is expressed in different mammalian or insect cell lines and is useful as a research reagent and a therapeutic.

Fc fusion to a peptide of SEQ ID NO: 108 to yield a sequence of SEQ ID NO: 565 extends half-life and improves biodistribution of the peptide to cartilage. Any peptide of this disclosure is co-expressed with Fc protein to yield Fc-fusion peptides with longer half-life and improved homing to cartilage. In SEQ ID NO: 565, the secretion signal sequence METDTLLLWVLLLWVPGSTG (SEQ ID NO: 566) is followed by the peptide of SEQ ID NO: 108, and is followed by the sequence for Fc protein. Cleaving can be imprecise, resulting in cleavage at position 20 or position 21 of SEQ ID NO: 565.

Example 20

Peptide Conjugate Hydrolysis

This example describes preparation of peptide conjugates having tunable hydrolysis rates. The peptide-drug conjugates described below are synthesized with the modification that instead of using succinic anhydride, other molecules are used to provide steric hindrance to hydrolysis or an altered local environment at the carbon adjacent to the final hydrolyzable ester. In one exemplary conjugate, the peptide-drug conjugate is synthesized with tetramethyl succinic anhydride to generate hindered esters, which causes a decreased rate of hydrolysis. In another exemplary conjugate, one methyl group is present at the adjacent carbon. In another exemplary conjugate, two methyl groups are present at the adjacent carbon. In another exemplary conjugate, one ethyl group is present at the adjacent carbon. In another exemplary conjugate, two ethyl groups are present at the adjacent carbon. In another exemplary conjugate, the carbon linker length is increased such as by using glutaric anhydride instead of succinic anhydride, increasing the local hydrophobicity and lowering the hydrolysis rate. In another exemplary conjugate, a hydroxyl group is located on the adjacent carbon, increasing the local hydrophilicity and increasing the hydrolysis rate. The rate of hydrolysis in these exemplary conjugates is therefore adjusted, preventing premature cleavage and ensuring that the majority of peptide-dexamethasone conjugates accumulate in cartilage prior to release of the drug by hydrolysis but that the dexamethasone is also released in the cartilage in a timely manner.

The resulting peptide conjugates are administered to a human or animal subcutaneously, intravenously, orally, or injected directly into a joint to treat disease.

Example 21

Peptide Conjugates with Stable Linkers

This example describes preparation of peptide conjugates with stable linkers. A peptide of the disclosure is expressed recombinantly or is chemically synthesized. The peptide is conjugated to a detectable agent or an active agent via a stable linker, such as an amide linkage or a carbamate linkage. The peptide is conjugated to a detectable agent or an active agent via a stable linker, such as an amide bond using standard 1-ethyl-3-(3-dimethylaminopropyl)carbodiimide (EDC) or dicylcohexylcarbodiimide (DCC) based chemistry or thionyl chloride or phosphorous chloride-based bioconjugation chemistries.

A peptide and drug conjugated via a linker are described with the formula Peptide-A-B-C-Drug, wherein the linker is A-B-C. A can be a stable amide link that is formed by reacting with an amine on the peptide with a linker containing a tetrafluorophenyl (TFP) ester or an NHS ester. A can also be a stable carbamate linker that is formed by reacting with an amine on the peptide imidazole carbamate active intermediate formed by the reaction of CDI with a hydroxyl on the linker. A can also be a stable secondary amine linkage that is formed by reductive alkylation of the amine on the peptide with an aldehyde or ketone group on the linker. A can also be a stable thioether linker formed using a maleimide or bromoacetamide in the linker with a thiol in the peptide, a triazole linker, a stable oxime linker, or an oxacarboline linker. B is ($-CH2-)_x-$, a short PEG ($-CH_2CH_2O-)_x$ (x is 0-20). Alternatively, spacers within the linker is optional and can be included or not at all. C is an amide bond formed with an amine or a carboxylic acid on the drug, a thioether formed between a maleimide on the linker and a sulfhydroyl on the drug, a secondary or tertiary amine, a carbamate, or other stable bonds. Any linker chemistry described in "Current ADC Linker Chemistry," Jain et al., *Pharm Res,* 2015 DOI 10. 1007/s11095-015-1657-7 can be used.

The resulting peptide conjugates are administered to a human or animal subcutaneously, intravenously, orally, or injected directly into a joint to treat disease. The peptide is not specifically cleaved from the detectable agent or active agent via a targeted mechanism. The peptide can be degraded by mechanisms such as catabolism, releasing a drug that is modified or not modified form its native form (Singh, Luisi, and Pak, *Pharm Res* 32:3541-3571 (2015)). The peptide drug conjugate exerts its pharmacological activity while still intact, or while partially or fully degraded, metabolized, or catabolized.

Example 22

Peptide Conjugates with Cleavable Linkers

This example describes preparation of peptide conjugates having cleavable linkers. A peptide of the disclosure is expressed recombinantly or chemically synthesized. A peptide and drug are conjugated via a linker and is described with the formula Peptide-A-B-C-Drug, wherein the linker is A-B-C. A is a stable amide link such as that formed by reacting an amine on the peptide with a linker containing a tetrafluorophenyl (TFP) ester or an NHS ester. A can also be a stable carbamate linker such as that formed by reacting an amine on the peptide with an imidazole carbamate active intermediate formed by reaction of CDI with a hydroxyl on the linker. A can also be a stable secondary amine linkage such as that formed by reductive alkylation of the amine on the peptide with an aldehyde or ketone group on the linker. A can also be a stable thioether linker formed using a maleimide or bromoacetamide in the linker with a thiol in the peptide, a triazole linker, a stable oxime linker, or a oxacarboline linker. B is ($-CH2-)_x-$ or a short PEG ($-CH_2CH_2O-)_x$ (x is 0-20) or other spacers or no spacer. C is an ester bond to the hydroxyl or carboxylic acid on the drug, or a carbonate, hydrazone, or acylhydrazone, designed for hydrolytic cleavage. The hydrolytic rate of cleavage is varied by varying the local environment around the ester, including carbon length ($-CH2-)x$, steric hindrance (including adjacent side groups such as methyl, ethyl, cyclic), hydrophilicity or hydrophobicity. Hydrolysis rate is affected by local pH, such as lower pH in certain compartments of the body or of the cell such as endosomes and lysosomes or diseased tissues. C is a pH sensitive group such as a hydrazone or oxime linkage. Alternatively C is a disulfide bond designed to be released by reduction, such as by glutathione. Alternatively C (or A-B-C) is a peptidic linkage design for cleavabe by enzymes. Optionally, a self-immolating group such as pABC is included to cause release of a free unmodified drug upon cleavage (Antibody-Drug Conjugates: Design, Formulation, and Physicochemical Stability, Singh, Luisi, and Pak. Pharm Res (2015) 32:3541-3571). The linker is cleaved by enzymes such as esterases, matrix metalloproteinases, cathepsins such as cathepsin B, glucuronidases, a protease, or thrombin. Alternatively, the bond designed for cleavage is at A, rather than C, and C could be a stable bond or a cleavable bond. An alternative design is to have stable linkers (such as amide or carbamate) at A and C and have a cleavable linker in B, such as a disulfide bond. The rate of reduction is modulated by local effects such as steric hindrance from methyl or ethyl groups or modulating hydrophobicity/hydrophilicity.

The resulting peptide conjugates are administered to a human or animal subcutaneously, intravenously, orally, or injected directly into a joint to treat disease.

Example 23

Acetylsalicylic Acid Peptide Conjugate

This example describes the conjugation of acetylsalicylic acid to a peptide using a lactic acid linker. A conjugate is produced from a mixture of (R,S)-acetylsalicylic acid, lactic acid, and a peptide:

The acetylsalicylic acid-lactic acid linker conjugate depicted above is then reacted with a lysine or the N-terminus of a cystine-dense peptide to create an acetylsalicylic acid-lactic acid-peptide conjugate. The cystine-dense peptide is selected from the peptides of SEQ ID NO: 24-SEQ ID NO: 274 or SEQ ID NO: 314-SEQ ID NO: 564.

Acetylsalicylic acid is currently dosed as an enantiomeric mixture, in which enantiomers with a single racemic stereocenter are very difficult to separate. As in the reaction scheme (I), a diastereomer with two chiral centers is created by the addition of a chiral linker such as L-lactic acid. Since diastereomers are easily separated, the active enantiomer of acetylsalicylic acid conjugated to the lactic acid linker can be purified prior to conjugation to a cystine-dense peptide. The chemical synthesis can use any conjugation techniques known in the art, such as described in Bioconjugate Techniques by Greg Hermanson and in "Ketorolac-dextran conjugates: synthesis, in vitro, and in vivo evaluation:" Acta Pharm. 57 (2007) 441-450, Vyas, Trivedi, and Chaturvedi. The conjugate can display anti-inflammatory activity, or free acetylsalicylic acid is released from the conjugate to provide anti-inflammatory activity. The free acetylsalicylic acid can result from hydrolysis that occurs after administration, such as hydrolysis at the ester bond. By dosing the conjugate containing the cartilage homing peptide, a higher AUC of acetylsalicylic acid delivery to the joint may be achieved than would be achieved by systemic dosing of acetylsalicylic acid alone.

Such peptide-drug conjugates can be made using either a cleavable or stable linker as described herein (e. g., EXAMPLES 21 and 22).

Example 24

Acetylsalicylic Acid Peptide Conjugate

This example describes the conjugation of acetylsalicylic acid to a peptide using a PEG linker. A conjugate is produced using acetylsalicylic acid and a PEG linker, which forms an ester bond that can hydrolyze as described in "In vitro and in vivo study of poly(ethylene glycol) conjugated ibuprofen to extend the duration of action," Scientia Pharmaceutica, 2011, 79:359-373, Nayak and Jain. Fischer esterification is used to conjugate ibuprofen with a short PEG, e.g., with triethylene glycol, to yield ibuprofen-ester-PEG-OH.

Following preparation of the PEG-ibuprofen conjugate as shown above, the hydroxyl moiety of PEG is activated with N,N'-disuccinimidyl carbonate (DSC) to form ibuprofenester-PEG-succinimidyl carbonate, which is then reacted with a lysine or the N-terminus of a cystine-dense peptide to form an ibuprofen-ester-PEG-peptide conjugate. The cystine-dense peptide is selected from any one of the peptides of sequence SEQ ID NO: 24-SEQ ID NO: 274 or SEQ ID NO: 314-SEQ ID NO: 564. The conjugate can display anti-inflammatory activity, or free ibuprofen is released from the conjugate to provide anti-inflammatory activity. The free ibuprofen can result from hydrolysis that occurs after administration, such as hydrolysis at the ester bond.

Ibuprofen-peptide conjugates are administered to a subject in need thereof. The subject can be a human or a non-human animal.

Such peptide-drug conjugates can be made using either a cleavable or stable linker as described herein (e.g., EXAMPLES 21 and 22).

Example 25

Dexamethasone Peptide Conjugate

This example describes different methods of conjugating dexamethasone with a peptide of this disclosure. A peptide of SEQ ID NO: 108 was recombinantly expressed. Dexamethasone was readily conjugated to a peptide of this disclosure using a dicarboxylic acid linker. The peptide-dexamethasone conjugate was made by first converting dexamethasone to a hemisuccinate by reacting it with succinic anhydride. The hemisuccinate was then converted to a succinate carboxylic acid containing an active ester, using dicyclohexyl carbodiimide (DCC) or 1-ethyl-3-(3-dimethylamninopropyl)carbodiimide (EDC) in the presence of N-hydroxy succinimide (NHS). This active ester was then reacted with a lysine or the N-terminus of a cystine-dense peptide to create a dexamethasone-carboxylic acid-peptide conjugate. Methods such as those described in "Functionalized derivatives of hyaluronic acid oligosaccharides: drug carriers and novel biomaterials" Bioconjugate Chemistry 1994, 5, 339-347, Pouyani and Prestwich, and Bioconjugate Techniques by Greg Hermanson can be used (Elsevier Inc., 3$^{rd}$ Edition, 2013).

Peptide-dexamethasone conjugates were prepared by coupling dexamethasone to the peptides of this disclosure using standard coupling-reagent chemistry. For example, dexamethasone conjugates were made by reacting dexamethasone hemigluterate with 1.05 molar equivalents of 1,1'-carbonyldiimidazole in anhydrous DMSO in an inert atmosphere. After 30 minutes, excess dexamethasone in anhydrous DMSO was added along with two molar equivalents of anhydrous trimethylamine. The N-hydroxysuccinimide ester of the peptide-dexamethasone conjugate was generated to form a shelf-stable intermediate for later reaction with an amine-containing carrier. The N-terminal dexamethasone-peptide conjugate (SEQ ID NO: 108B) was verified by electrospray mass spectrometry (ES-MS) within a 10 ppm error.

A peptide of any of the sequences of this disclosure including SEQ ID NO: 24-SEQ ID NO: 274 or SEQ ID NO: 314-SEQ ID NO: 564, are conjugated to dexamethasone using the methods described above.

Such peptide-drug conjugates can be made using either a cleavable or stable linker as described herein (e.g., EXAMPLES 21 and 22).

Example 26

Beclomethasone Monopropionate Peptide Conjugates

This example describes conjugation of a peptide of SEQ ID NO: 27 or SEQ ID NO: 108 of this disclosure to beclomethasone monopropionate. Beclomethasone monopropionate is readily conjugated to any peptide disclosed herein via a dicarboxylic acid linker. The dicarboxylic acid linker is a linear dicarboxylic acid, such as succinic acid, or a related cyclic anhydride, such as succinic anhydride. Reactions with anhydrides can proceed under simple conditions. For example, the reaction of beclomethasone monopropionate with five molar equivalents of glutaric anhydride is carried out in anhydrous pyridine at room temperature. Reactions with dicarboxylic acids can occur using standard carbodiimide coupling methods. For example, beclomethasone monopropionate is reacted with one molar equivalent dimethylsuccinic acid, one molar equivalent 1-ethyl-3-(3-dimethylaminopropyl)carbodiimide (or another carbodiimide), and 0.2 molar equivalents of 40-dimethylamino pyridine.

The same methods as described in EXAMPLE 20 are used to adjust the rate of hydrolysis of peptide-beclomethasone monopropionate conjugates, preventing premature cleavage and ensuring that the beclomethasone monopropionate of peptide-beclomethasone monopropionate conjugates accumulate in cartilage.

Peptide-beclomethasone monopropionate conjugates are prepared by coupling beclomethasone monopropionate to the peptides of this disclosure using standard coupling-reagent chemistry. The peptide-beclomethasone monopropionate conjugate was made by first converting beclomethasone monopropionate to a hemisuccinate by reacting it with succinic anhydride. The hemisuccinate was then converted to a succinate carboxylic acid containing an active ester, using dicyclohexyl carbodiimide (DCC) or 1-ethyl-3-(3-dimethylamninopropyl)carbodiimide (EDC) in the presence of N-hydroxy succinimide (NHS). This active ester was then reacted with a lysine or the N-terminus of a peptide to create a beclomethasone monopropionate-carboxylic acid-peptide conjugate. Methods such as those described in "Functionalized derivatives of hyaluronic acid oligosaccharides: drug carriers and novel biomaterials" Bioconjugate Chemistry 1994, 5, 339-347, Pouyani and Prestwich, and Bioconjugate Techniques by Greg Hermanson can be used (Elsevier Inc., 3$^{rd}$ Edition, 2013).

Peptide-beclomethasone monopropionate conjugates were prepared by coupling beclomethasone monopropionate to the peptides of this disclosure using standard coupling-reagent chemistry. For example, beclomethasone monopropionate conjugates were made by reacting beclomethasone monopropionate hemigluterate with 1.05 molar equivalents of 1,1'-carbonyldiimidazole in anhydrous DMSO in an inert atmosphere. After 30 minutes, excess beclomethasone monopropionate in anhydrous DMSO was added along with two molar equivalents of anhydrous trimethylamine. The N-hydroxysuccinimide ester of the peptide-beclomethasone monopropionate conjugate was generated to form a shelf-stable intermediate for later reaction with an amine-containing carrier.

Beclomethasone monopropionate is also readily conjugated to any peptide disclosed herein via a dicarboxylic acid linker. The dicarboxylic acid linker is a linear dicarboxylic acid, such as succinic acid, or a related cyclic anhydride, such as succinic anhydride. Reactions with anhydrides can proceed under simple conditions. For example, the reaction of beclomethasone monopropionate with five molar equivalents of glutaric anhydride is carried out in anhydrous pyridine at room temperature. Reactions with dicarboxylic acids can occur using standard carbodiimide coupling methods. For example, beclomethasone monopropionate is reacted with one molar equivalent dimethylsuccinic acid, one molar equivalent 1-ethyl-3-(3-dimethylaminopropyl) carbodiimide (or another carbodiimide), and 0.2 molar equivalents of 40-dimethylamino pyridine. The peptide-beclomethasone monopropionate conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration of the peptide-beclomethasone monopropionate conjugates, the cartilage and/or kidney inflammation is alleviated.

The peptide can also be a peptide of SEQ ID: NO: 33. The peptide can be any peptide with the sequence selected SEQ ID NO: 24-SEQ ID NO: 274 or SEQ ID NO: 314-SEQ ID NO: 564.

Such peptide-drug conjugates are made using either a cleavable or stable linker as described herein (e.g., EXAMPLES 21 and 22).

Example 27

Desciclesonide Peptide Conjugates

This example describes conjugation of a peptide of SEQ ID NO: 199 or SEQ ID NO: 187 of this disclosure to desciclesonide. Ciclesonide is a prodrug that is metabolized in vivo to the active metabolite desciclesonide. By conjugating desciclesonide to a peptide via an ester linker, upon hydrolysis the released drug would be desciclesonide, just as after systemic administration of ciclesonide the active metabolite desciclesonide is present and active. Desciclesonide is readily conjugated to any peptide disclosed herein via a dicarboxylic acid linker. The dicarboxylic acid linker is a linear dicarboxylic acid, such as succinic acid, or a related cyclic anhydride, such as succinic anhydride. Reactions with anhydrides can proceed under simple conditions. For example, the reaction of desciclesonide with five molar equivalents of glutaric anhydride is carried out in anhydrous pyridine at room temperature. Reactions with dicarboxylic acids can occur using standard carbodiimide coupling methods. For example, desciclesonide is reacted with one molar equivalent dimethylsuccinic acid, one molar equivalent 1-ethyl-3-(3-dimethylaminopropyl)carbodiimide (or another carbodiimide), and 0.2 molar equivalents of 40-dimethylamino pyridine.

The same methods as described in EXAMPLE 20 are used to adjust the rate of hydrolysis of peptide-desciclesonide conjugates, preventing premature cleavage and ensuring that the desciclesonide of peptide-desciclesonide conjugates accumulate in cartilage.

Desciclesonide is also readily conjugated to any peptide disclosed herein via a dicarboxylic acid linker. The dicarboxylic acid linker is a linear dicarboxylic acid, such as succinic acid, or a related cyclic anhydride, such as succinic anhydride. Reactions with anhydrides can proceed under simple conditions. For example, the reaction of desciclesonide with five molar equivalents of glutaric anhydride is carried out in anhydrous pyridine at room temperature. Reactions with dicarboxylic acids can occur using standard carbodiimide coupling methods. For example, desciclesonide is reacted with one molar equivalent dimethylsuccinic acid, one molar equivalent 1-ethyl-3-(3-dimethylaminopropyl)carbodiimide (or another carbodiimide), and 0.2 molar equivalents of 40-dimethylamino pyridine. The peptide-desciclesonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration of the peptide-desciclesonide conjugates, the cartilage and/or kidney inflammation is alleviated.

The peptide-desciclesonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration of the peptide-desciclesonide conjugates, the cartilage and/or kidney inflammation is alleviated.

The peptide can also be a peptide of SEQ ID: NO: 196. The peptide can be any peptide with the sequence selected from SEQ ID NO: 24-SEQ ID NO: 274 or SEQ ID NO: 314-SEQ ID NO: 564.

Such peptide-drug conjugates are made using either a cleavable or stable linker as described herein (e.g., EXAMPLES 21 and 22).

Example 28

Desciclesonide Peptide Conjugates

This example describes conjugation of a peptide of SEQ ID NO: 199 or SEQ ID NO: 187 of this disclosure to desciclesonide. Ciclesonide is a prodrug that is metabolized in vivo to the active metabolite desciclesonide. By conjugating desciclesonide to a peptide via an ester linker, upon hydrolysis the released drug would be desciclesonide, just as after systemic administration of ciclesonide the active metabolite desciclesonide is present and active. Desciclesonide is readily conjugated to any peptide disclosed herein via a stable linker.

The peptide-desciclesonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration of the peptide-desciclesonide conjugates, the cartilage and/or kidney inflammation is alleviated.

The peptide can also be a peptide of SEQ ID: NO: 196. The peptide can be any peptide with the sequence selected SEQ ID NO: 24-SEQ ID NO: 274 or SEQ ID NO: 314-SEQ ID NO: 564.

Such peptide-drug conjugates are made using either a cleavable or stable linker as described herein (e.g., EXAMPLES 21 and 22).

Example 29

Peptide-Ustekinumab Conjugates

This example describes conjugation of a peptide of SEQ ID NO: 106 this disclosure to ustekinumab. Ustekinumab is readily conjugated to any peptide disclosed herein via standard chemistries such as those described in, but not limited to, Bioconjugate Techniques by Greg Hermanson (Elsevier Inc., 3$^{rd}$ edition, 2013). Alternatively the peptide-active agent of this Example can be expressed as a fusion protein. From one to eight peptides are linked to ustekinumab.

The peptide-ustekinumab conjugates are administered to a subject in need thereof and home, target, are directed to, are retained by, accumulate in, migrate to, and/or bind to cartilage. The subject is a human or animal and has psoriatic arthritis. Upon administration of the peptide-ustekinumab conjugates, the psoriatic arthritis condition is alleviated.

The peptide can also be a peptide of SEQ ID NO: 36. The peptide can be any peptide with the sequence selected from SEQ ID NO: 24-SEQ ID NO: 274 or SEQ ID NO: 314-SEQ ID NO: 564.

Example 30

Peptide-Xeljanz Conjugates

This example describes conjugation of a peptide of SEQ ID NO: 187 this disclosure to xeljanz. Xeljanz is readily conjugated to any peptide disclosed herein via standard chemistries such as those described in, but not limited to, Bioconjugate Techniques by Greg Hermanson (Elsevier Inc., $3^{rd}$ edition, 2013). From one to eight peptides are linked to xeljanz.

The peptide-xeljanz conjugates are administered to a subject in need thereof and home, target, are directed to, are retained by, accumulate in, migrate to, and/or bind to cartilage. The subject is a human or animal and has rheumatoid arthritis. Upon administration and homing of peptide-xeljanz conjugates, the rheumatoid arthritis condition is alleviated.

The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 31

Peptide-IL-17 Inhibitor Conjugates

This example describes conjugation of a peptide of SEQ ID NO: 108 this disclosure to an IL-17 inhibitor. An IL-17 inhibitor is readily conjugated to any peptide disclosed herein via standard chemistries such as those described in, but not limited to, Bioconjugate Techniques by Greg Hermanson (Elsevier Inc., $3^{rd}$ edition, 2013).

The peptide-IL-17 inhibitor conjugates are administered to a subject in need thereof and home, target, are directed to, are retained by, accumulate in, migrate to, and/or bind to cartilage. The subject is a human or animal and has ankylosing spondylitis. Upon administration and homing of peptide-IL-17 inhibitor conjugates, the ankylosing spondylitis condition is alleviated.

The peptide can also be a peptide of SEQ ID NO: 111. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 32

Peptide-Iguratimod Conjugates

This example describes conjugation of a peptide of SEQ ID NO: 199 this disclosure to iguratimod. Iguratimod is readily conjugated to any peptide disclosed herein via standard chemistries such as those described in, but not limited to, Bioconjugate Techniques by Greg Hermanson (Elsevier Inc., $3^{rd}$ edition, 2013).

The peptide-iguratimod conjugates are administered to a subject in need thereof and home, target, are directed to, are retained by, accumulate in, migrate to, and/or bind to kidneys. The subject is a human or animal and has rheumatoid arthritis. Upon administration and homing of peptide-iguratimod conjugates, the rheumatoid arthritis condition is alleviated.

The peptide can also be a peptide of SEQ ID NO: 26. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 33

Peptide Mycophenolic Acid Conjugates

This example describes conjugation of a peptide of SEQ ID NO: 27 this disclosure to mycophenolic acid. Mycophenolic acid is readily conjugated to any peptide disclosed herein via standard chemistries such as those described in, but not limited to, Bioconjugate Techniques by Greg Hermanson (Elsevier Inc., $3^{rd}$ edition, 2013).

The peptide-mycophenolic acid conjugates are administered to a subject in need thereof and home, target, are directed to, are retained by, accumulate in, migrate to, and/or bind to kidneys. The subject is a human or animal and has organ transplantation, infection, cancer, or other kidney disorders. Upon administration and homing of peptide-mycophenolic acid conjugates, the organ transplantation, infection, cancer, other kidney disorders condition is alleviated.

The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 34

Peptide-Tacrolimus Conjugates

This example describes conjugation of a peptide of SEQ ID NO: 108 this disclosure to tacrolimus. Tacrolimus is readily conjugated to any peptide disclosed herein via standard chemistries such as those described in, but not limited to, Bioconjugate Techniques by Greg Hermanson (Elsevier Inc., $3^{rd}$ edition, 2013).

The peptide-tacrolimusconjugates are administered to a subject in need thereof and home, target, are directed to, are retained by, accumulate in, migrate to, and/or bind to kidneys. The subject is a human or animal and has organ transplantation, any other kidney disease. Upon administration and homing of peptide-tacrolimus conjugates, the organ transplantation, any other kidney disease condition is alleviated.

The peptide can also be a peptide of SEQ ID NO: 111. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 35

Peptide-Secukinumab Conjugates

This example describes conjugation of a peptide of SEQ ID NO: 106 this disclosure to secukinumab. Secukinumab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to secukinumab. Alternatively the peptide-active agent of this Example can be expressed as a fusion protein.

The peptide-secukinumab conjugates are administered to a subject in need thereof and home, target, are directed to, are retained by, accumulate in, migrate to, and/or bind to cartilage. The subject is a human or animal and has ankylosing spondylitis. Upon administration and homing of peptide-secukinumab acid conjugates, the ankylosing spondylitis condition is alleviated.

The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 36

Peptide-Sirukumab Conjugates

This example describes conjugation of a peptide of SEQ ID NO: 199 this disclosure to sirukumab. Sirukumab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to sirukumab. Alternatively the peptide-active agent of this Example can be expressed as a fusion protein.

The peptide-sirukumab conjugates are administered to a subject in need thereof and home, target, are directed to, are retained by, accumulate in, migrate to, and/or bind to kidneys. The subject is a human or animal and has rheumatoid arthritis, immune diseases of the kidneys. Upon administration and homing of peptide-sirukumab conjugates, the rheumatoid arthritis, immune diseases of the kidneys condition is alleviated.

The peptide can also be a peptide of SEQ ID NO: 36. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 37

Peptide-Anifrolumab Conjugates

This example describes conjugation of a peptide of SEQ ID NO: 27 this disclosure to anifrolumab. Anifrolumab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to anifrolumab. Alternatively the peptide-active agent of this Example can be expressed as a fusion protein.

The peptide-anifrolumab conjugates are administered to a subject in need thereof and home, target, are directed to, are retained by, accumulate in, migrate to, and/or bind to kidneys. The subject is a human or animal and has lupus nephritis. Upon administration and homing of peptide-anifrolumab conjugates, the lupus nephritis condition is alleviated.

The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 38

Peptide-Denosumab Conjugates

This example describes conjugation of a peptide of SEQ ID NO: 108 this disclosure to denosumab. Denosumab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to denosumab. Alternatively the peptide-active agent of this Example can be expressed as a fusion protein.

The peptide-denosumab conjugates are administered to a subject in need thereof and home, target, are directed to, are retained by, accumulate in, migrate to, and/or bind to cartilage. The subject is a human or animal and has osteoporosis. Upon administration and homing of peptide-denosumab conjugates, the osteoporosis condition is alleviated.

The peptide can also be a peptide of SEQ ID NO: 25. The peptide can be any peptide with the sequence selected SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 39

Peptide-Rituximab Conjugates

This example describes conjugation of a peptide of SEQ ID NO: 108 this disclosure to rituximab. Rituximab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to rituximab. Alternatively the peptide-active agent of this Example can be expressed as a fusion protein.

The peptide-rituximab conjugates are administered to a subject in need thereof and home, target, are directed to, are retained by, accumulate in, migrate to, and/or bind to cartilage or kidneys. The subject is a human or animal and has rheumatoid arthritis, kidney transplant. Upon administration and homing of peptide-rituximab conjugates, the rheumatoid arthritis, kidney transplant condition is alleviated.

The peptide can also be a peptide of SEQ ID NO: 26. The peptide can be any peptide with the sequence selected SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 40

Peptide-Omalizumab Conjugates

This example describes conjugation of a peptide of SEQ ID NO: 108 this disclosure to omalizumab. Omalizumab is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to omalizumab. Alternatively the peptide-active agent of this Example can be expressed as a fusion protein.

The peptide-omalizumab conjugates are administered to a subject in need thereof and home, target, are directed to, are retained by, accumulate in, migrate to, and/or bind to kidneys. The subject is a human or animal and has kidney inflammation. Upon administration and homing of peptide-omalizumab conjugates, the kidney inflammation condition is alleviated.

The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 41

Peptide-Abatacept Conjugates

This example describes conjugation of a peptide of SEQ ID NO: 199 this disclosure to abatacept. Abatacept is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to abatacept. Alternatively the peptide-active agent of this Example can be expressed as a fusion protein.

The peptide-abatacept conjugates are administered to a subject in need thereof and home, target, are directed to, are retained by, accumulate in, migrate to, and/or bind to kidneys. The subject is a human or animal and has rheumatoid arthritis, lupus nephritis, organ transplant, focal segmental glomerulosclerosis. Upon administration and homing of peptide-abatacept conjugates, the rheumatoid arthritis, lupus nephritis, organ transplant, focal segmental glomerulosclerosis condition is alleviated.

The peptide can also be a peptide of SEQ ID NO: 111. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 42

Peptide-Oxycodone Conjugates

This example describes conjugation of a peptide of SEQ ID NO: 187 this disclosure to oxycodone. Oxycodone is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-oxycodone conjugates are administered to a subject in need thereof and home, target, are directed to, are retained by, accumulate in, migrate to, and/or bind to cartilage. The subject is a human or animal and has cartilage or kidney-related pain. Upon administration and homing of peptide-oxycodone conjugates, the cartilage-related pain condition is alleviated.

The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 43

Peptide Capsaicin Conjugates

This example describes conjugation of a peptide of SEQ ID NO: 108 this disclosure to capsaicin. Capsaicin is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-capsaicin conjugates are administered to a subject in need thereof and home, target, are directed to, are retained by, accumulate in, migrate to, and/or bind to cartilage. The subject is a human or animal and has cartilage-related pain. Upon administration and homing of peptide-capsaicin conjugates, the cartilage or kidney-related pain condition is alleviated.

The peptide can also be a peptide of SEQ ID NO: 36. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 44

Peptide-GSK2193874 Conjugates

This example describes conjugation of a peptide of SEQ ID NO: 106 this disclosure to GSK2193874. GSK2193874 is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-GSK2193874 conjugates are administered to a subject in need thereof and home, target, are directed to, are retained by, accumulate in, migrate to, and/or bind to GSK2193874. The subject is a human or animal and has cartilage-related pain. Upon administration and homing of peptide-GSK2193874 conjugates, the cartilage-related pain condition is alleviated.

The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 45

Peptide BIIB023 Conjugates

This example describes conjugation of a peptide of SEQ ID NO: 199 this disclosure to BIIB023. BIIB023 is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to BIIB023. Alternatively the peptide-active agent of this Example can be expressed as a fusion protein.

The peptide-BIIB023 conjugates are administered to a subject in need thereof and home, target, are directed to, are retained by, accumulate in, migrate to, and/or bind to cartilage. The subject is a human or animal and has lupus nephritis or rheumatoid arthritis. Upon administration and homing of peptide-BIIB023 conjugates, the lupus nephritis or rheumatoid arthritis condition is alleviated.

The peptide can also be a peptide of SEQ ID NO: 25. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 46

Peptide-Anakinra Conjugates

This example describes conjugation or fusion of a peptide of SEQ ID NO: 187 or SEQ ID NO: 550-564 of this disclosure to anakinra. A linker is optionally used to conjugate the peptide to anakinra. Anakinra is readily conjugated to any peptide disclosed herein via standard chemistries such as those described in, but not limited to, Bioconjugate Techniques by Greg Hermanson (Elsevier Inc., $3^{rd}$ edition, 2013). From one to eight peptides are linked to anakinra. Alternatively the peptide-active agent of this Example can be expressed as a fusion protein.

The peptide-anakinra conjugates or fusions are administered to a subject in need thereof and home, target, are directed to, are retained by, accumulate in, migrate to, and/or bind to cartilage. The subject is a human or animal and has lupus nephritis or rheumatoid arthritis. Upon administration and homing of peptide-anakinra conjugates or fusions, the lupus nephritis or rheumatoid arthritis condition is alleviated.

The peptide can also be a peptide of SEQ ID NO: 26. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 47

Peptide-IGF-1 Conjugates

This example describes conjugation of a peptide of SEQ ID NO: 108 this disclosure to IGF-1. IGF-1 is readily conjugated to any peptide disclosed herein via standard chemistries such as those described in, but not limited to, Bioconjugate Techniques by Greg Hermanson (Elsevier Inc., $3^{rd}$ edition, 2013). From one to eight peptides are linked to IGF-1. Alternatively the peptide-active agent (where the active agent is the biologic of this Example) can be expressed as a fusion protein.

The peptide-IGF-1 conjugates are administered to a subject in need thereof and home, target, are directed to, are retained by, accumulate in, migrate to, and/or bind to cartilage. The subject is a human or animal and has renal cancer or arthritis. Upon administration and homing of peptide-IGF-1 conjugates, the renal cancer or arthritis condition is alleviated.

The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 48

Peptide-Romosozumab Conjugates

This example describes conjugation of a peptide of SEQ ID NO: 106 this disclosure to Romosozumab. Romosozumab is readily conjugated to any peptide disclosed herein via standard chemistries such as those described in, but not limited to, Bioconjugate Techniques by Greg Hermanson (Elsevier Inc., $3^{rd}$ edition, 2013). From one to eight peptides are linked to romosozumab. Alternatively the peptide-active agent of this Example can be expressed as a fusion protein.

The peptide-romosozumab conjugates are administered to a subject in need thereof and home, target, are directed to, are retained by, accumulate in, migrate to, and/or bind to cartilage. The subject is a human or animal and has osteoporosis. Upon administration and homing of peptide-romosozumab conjugates, the osteoporosis condition is alleviated.

The peptide can also be a peptide of SEQ ID NO: 111. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 49

Peptide-ZVAD-fmk Conjugates

This example describes conjugation of a peptide of SEQ ID NO: 187 this disclosure to ZVAD-fmk. ZVAD-fmk is readily conjugated to any peptide disclosed herein via standard chemistries such as those described in, but not limited to, Bioconjugate Techniques by Greg Hermanson (Elsevier Inc., $3^{rd}$ edition, 2013). From one to eight peptides are linked to ZVAD-fmk. The peptide-ZVAD-fmk conjugates are administered to a subject in need thereof and home, target, are directed to, are retained by, accumulate in, migrate to, and/or bind to cartilage. The subject is a human or animal and has cartilage grafting, arthritis, surgical intervention, surgery for cartilage repair. Upon administration and homing of peptide-ZVAD-fmk conjugates, the cartilage grafting, arthritis, surgical intervention, surgery for cartilage repair condition is alleviated.

The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 50

Peptide-S-Methylisothiourea Conjugates

This example describes conjugation of a peptide of SEQ ID NO: 108 this disclosure to S-methylisothiourea. S-methylisothiourea is readily conjugated to any peptide disclosed herein via standard chemistries such as those described in, but not limited to, Bioconjugate Techniques by Greg Hermanson (Elsevier Inc., $3^{rd}$ edition, 2013).

The peptide-S-methylisothiourea conjugates are administered to a subject in need thereof and home, target, are directed to, are retained by, accumulate in, migrate to, and/or bind to cartilage. The subject is a human or animal and has arthritis surgery, kidney iron overload, renal ischemia reperfusion injury, or acute kidney injury. Upon administration and homing of peptide-S-methylisothiourea conjugates, the arthritis surgery, kidney iron overload, renal ischemia reperfusion injury, or acute kidney injury condition is alleviated.

The peptide can also be a peptide of SEQ ID NO: 33. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 51

Peptide-P188 Conjugates

This example describes conjugation of a peptide of SEQ ID NO: 106 this disclosure to P188. P188 is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-P188 conjugates are administered to a subject in need thereof and home, target, are directed to, are retained by, accumulate in, migrate to, and/or bind to cartilage. The subject is a human or animal and has arthritis surgery. Upon administration and homing of peptide-P188 conjugates, the arthritis surgery condition is alleviated.

The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 52

Peptide-Alendronate Conjugates

This example describes conjugation of a peptide of SEQ ID NO: 187 this disclosure to alendronate. Alendronate is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-alendronate conjugates are administered to a subject in need thereof and home, target, are directed to, are retained by, accumulate in, migrate to, and/or bind to cartilage. The subject is a human or animal and has bone erosion. Upon administration and homing of peptide-alendronate conjugates, the bone erosion condition is alleviated.

The peptide can also be a peptide of SEQ ID NO: 22. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 53

Peptide-MIP-3α Conjugates

This example describes conjugation of a peptide of SEQ ID NO: 108 this disclosure to MIP-3a. MIP-3α is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to MIP-3α. Alternatively the peptide-active agent of this Example can be expressed as a fusion protein The peptide-MIP-3α conjugates are administered to a subject in need thereof and home, target, are directed to, are retained by, accumulate in, migrate to, and/or bind to cartilage. The subject is a human or animal and has Joint injury, repair and regeneration of cartilage and bone. Upon administration and homing of peptide-MIP-3α conjugates, the Joint injury, repair and regeneration of cartilage and bone condition is alleviated.

The peptide can also be a peptide of SEQ ID NO: 26. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 54

Peptide-BMP-2 Conjugates

This example describes conjugation of a peptide of SEQ ID NO: 106 this disclosure to BMP-2. BMP-2 is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to BMP-2. Alternatively the peptide-active agent of this Example can be expressed as a fusion protein.

The peptide-BMP-2 conjugates are administered to a subject in need thereof and home, target, are directed to, are retained by, accumulate in, migrate to, and/or bind to cartilage. The subject is a human or animal and has Joint repair. Upon administration and homing of peptide-BMP-2 conjugates, the Joint repair condition is alleviated.

The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 55

Peptide-Icariin Conjugates

This example describes conjugation of a peptide of SEQ ID NO: 187 this disclosure to icariin. Icariin is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-icariin conjugates are administered to a subject in need thereof and home, target, are directed to, are retained by, accumulate in, migrate to, and/or bind to cartilage. The subject is a human or animal and has Joint repair. Upon administration and homing of peptide-icariin conjugates, the Joint repair condition is alleviated.

The peptide can also be a peptide of SEQ ID NO: 108. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or a stable linker as described herein (e.g., EXAMPLES 21 and 22).

Example 56

Peptide-Captopril Conjugates

This example describes conjugation of a peptide of SEQ ID NO: 27 this disclosure to captopril. Captopril is readily conjugated to any peptide disclosed herein via standard chemistries such as those described in, but not limited to, Bioconjugate Techniques by Greg Hermanson (Elsevier Inc., 3$^{rd}$ edition, 2013).

The peptide-captopril conjugates are administered to a subject in need thereof and home, target, are directed to, are retained by, accumulate in, migrate to, and/or bind to kidneys. The subject is a human or animal and has diabetic nephropathy. Upon administration and homing of peptide-captopril conjugates, the diabetic nephropathy condition is alleviated.

The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 57

Peptide-Tofacitinib Conjugates

This example describes conjugation of a peptide of SEQ ID NO: 108 this disclosure to tofacitinib. Tofacitinib is readily conjugated to any peptide disclosed herein via standard chemistries such as those described in, but not limited to, Bioconjugate Techniques by Greg Hermanson (Elsevier Inc., 3$^{rd}$ edition, 2013). From one to eight peptides are linked to tofacitinib.

The peptide-tofacitinib conjugates are administered to a subject in need thereof and home, target, are directed to, are retained by, accumulate in, migrate to, and/or bind to cartilage. The subject is a human or animal and has rheumatoid arthritis and kidney transplant, ankyloses spondylitis. Upon administration and homing of peptide-tofacitinib conjugates, the rheumatoid arthritis and kidney transplant, ankyloses spondylitis condition is alleviated.

The peptide can also be a peptide of SEQ ID NO: 36. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 58

Peptide-Dimethyl Fumarate Conjugates

This example describes conjugation of a peptide of SEQ ID NO: 108 this disclosure to dimethyl fumarate. Dimethyl fumarate is readily conjugated to any peptide disclosed herein via standard chemistries such as those described in, but not limited to, Bioconjugate Techniques by Greg Hermanson (Elsevier Inc., 3$^{rd}$ edition, 2013). Alternatively, peptide-dimethyl fumarate conjugates can be synthesized by Michael addition of a thiol (on the peptide of linker) to dimethyl fumarate as described by Schmidt et al. (Bioorg Med Chem. 2007 Jan. 1; 15(1):333-42. Epub 2006 Sep. 29).

The peptide-dimethyl fumarate conjugates are administered to a subject in need thereof and home, target, are directed to, are retained by, accumulate in, migrate to, and/or bind to kidneys. The subject is a human or animal and has Kidney fibrosis, psoriatic arthritis, rheumatoid arthritis. Upon administration and homing of peptide-dimethyl fumarate conjugates, the Kidney fibrosis, psoriatic arthritis, rheumatoid arthritis condition is alleviated.

The peptide can also be a peptide of SEQ ID NO: 187. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 59

Intra-Articular Administration of Peptides and Peptide Conjugates

This example illustrates intra-articular administration of peptides or peptide conjugates of this disclosure. A peptide of this disclosure is expressed recombinantly or chemically synthesized. In some cases, the peptide is subsequently conjugated to a detectable agent or an active agent. The peptide or peptide conjugate is administered to a subject in need thereof via intra-articular administration. The cartilage is penetrated by the peptide or peptide conjugate due to the small size of the peptide or peptide conjugate, and due to binding of cartilage components by the peptide or peptide conjugate. The peptide or peptide conjugate is bound to cartilage and the residence time in the cartilage is longer due to this binding. Optionally, the injected material is aggregated, is crystallized, or complexes are formed, further extending the depot effect and contributing to longer residence time.

The peptide can be a peptide of SEQ ID NO: 108. The peptide can also be a peptide of SEQ ID NO: 24. The peptide can be any peptide with the sequence selected SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 60

Treatment of Osteoarthritis

This example describes a method for treating osteoarthritis using peptides of the present disclosure. This method is used as a treatment for acute and/or chronic symptoms associated with osteoarthritis. A peptide of the present disclosure is expressed recombinantly or chemically synthesized and then is used directly or conjugated to an anti-inflammatory compound, such as aspirin, desciclesonide, or secukinumab. The resulting peptide or peptide-drug conjugate is administered in a pharmaceutical composition subcutaneously, intravenously, or orally, or is injected directly into a joint of a patient and targeted to cartilage. The formulation can be modified physically or chemically to increase the time of exposure in the cartilage. One or more anti-inflammatory peptide conjugates are administered to a human or animal.

The peptide can be a peptide of SEQ ID NO: 106. The peptide can also be a peptide of SEQ ID NO: 33. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 61

Treatment of Cartilage Degradation

This example describes a method for treating and/or preventing cartilage degradation using a peptide of the present disclosure. This method is used as a treatment for acute and/or chronic symptoms associated with cartilage degradation. Progressive degradation or thinning of the cartilage is difficult to treat in part because molecules such as small molecule drugs and antibodies typically do not reach the avascular cartilage. A peptide of the present disclosure is used for its homing and/or native activity, or is mutated to generate activity such as MMP protease inhibition. It is expressed recombinantly or chemically synthesized and then is used directly or conjugated to an extracellular matrix targeting active agent, such as an inhibitor of MMP activity or an anti-apoptosis agent (e.g., osteoprotegrin, romosozumab, P188, ZVAD-fmk, quercetin, dasatinib, dimethyl fumarate, bortezomib, carilzomib, or navitoclax). The resulting peptide or peptide-drug conjugate is administered in a pharmaceutical composition subcutaneously, intravenously, or orally, or is injected directly into a joint of a patient and targeted to extracellular matrix. One or more extracellular matrix targeting conjugates are administered to a human or animal.

The peptide can be a peptide of SEQ ID NO: 187. The peptide can also be a peptide of SEQ ID NO: 27. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 62

Treatment of a Cartilage Injury

This example describes a method for treating a cartilage injury using a peptide of the present disclosure. A peptide of the present disclosure is expressed recombinantly or chemically synthesized and then is used directly or conjugated to a therapeutic compound, such as those described herein, including, but not limited to BMP-2, BMP-7, BMP-9, BMP-13, PDGF, PTH, PTHrP, IL-8, MIP-3α. The resulting peptide or peptide-drug conjugate is administered in a pharmaceutical composition to a patient and targeted to cartilage. One or more therapeutic compound-peptide conjugates are administered to a human or animal.

The peptide can be a peptide of SEQ ID NO: 108. The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 63

Treatment of Rheumatoid Arthritis

This example describes a method for treating rheumatoid arthritis. This method is used as a treatment for acute and/or chronic symptoms associated with rheumatoid arthritis. A peptide of the present disclosure is expressed recombinantly or chemically synthesized and then is used directly, or is conjugated to an anti-inflammatory compound, such as adalimumab, certolizumab, golimumab, thalidomide, lenalidomide, pomalidomide, pentocifylline, bupropion. When the peptide is used directly, the peptide can, for example, bind or inhibit ion channels such as Kv 1.3. The resulting peptide or peptide-drug conjugate is administered in a pharmaceutical composition to a patient and is targeted to cartilage. One or more anti-inflammatory compound-peptide conjugates are administered to a human or animal subcutaneously, intravenously, or orally, or is injected directly into a joint The peptide can be a peptide of SEQ ID NO: 106. The peptide can also be a peptide of SEQ ID NO: 25. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 64

Treatment of Gout

This example describes a method for treating gout using peptides of the present disclosure. This method is used as a treatment for acute and/or chronic symptoms associated with gout. A peptide of the present disclosure is expressed and administered in a pharmaceutical composition to a patient as a therapeutic for gout. A peptide of the disclosure is recombinantly or chemically synthesized and then is used directly or conjugated to pegloticase to treat a cartilage disorder. A peptide of the disclosure is recombinantly or chemically synthesized and then is used directly or conjugated to probenecid to treat a kidney disorder. The peptide is administered in a pharmaceutical composition to a patient and the peptide is targeted to the cartilage or kidney affected by gout. One or more peptides are administered to a human or animal subcutaneously, intravenously, or orally, or is injected directly into a joint.

The peptide can be a peptide of SEQ ID NO: 187. The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 65

Treatment or Management of Pain

This example describes a method for treating or managing pain associated with a cartilage injury or disorder. This method is used as a treatment for acute and/or chronic symptoms associated with a cartilage injury or disorder. A peptide of the disclosure is expressed and administered in a pharmaceutical composition to a patient as a therapeutic for pain as a result of injury or other cartilage or joint condition as described herein. The peptide of the present disclosure inhibits ion channels, such as Nav 1.7. The peptide is expressed recombinantly or chemically synthesized, wherein the peptide selected from SEQ ID NO: 24-SEQ ID NO: 274 or SEQ ID NO: 314-SEQ ID NO: 564. Alternatively, the peptides of SEQ ID NO: 24-SEQ ID NO: 274 or SEQ ID NO: 314-SEQ ID NO: 564 are mutated to maintain the cartilage homing function, but to add or increase ion channel inhibition, such as to Nav 1.7. Following expression or synthesis, the peptide is used directly or conjugated to a narcotic (e.g., oxycodone), a non-narcotic analgesic, a natural counter-irritant (capsaicin), or a pain receptor channel inhibitor (such as the TRPV4 inhibitor GSK2193874). Following administration of the peptide, the peptide targets to the cartilage affected by pain. One or more peptides are administered to a human or animal subcutaneously, intravenously, or orally, or is injected directly into a joint.

The peptide can be a peptide of SEQ ID NO: 108. The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 66

Treatment or Management of Pain with Peptides Only

This example describes a method for treating or managing pain associated with a cartilage injury or disorder. This method is used as a treatment for acute and/or chronic symptoms associated with a cartilage injury or disorder. A peptide of the disclosure is expressed and administered in a pharmaceutical composition to a patient as a therapeutic for pain as a result of injury or other cartilage or joint condition as described herein. The peptide of the present disclosure inhibits ion channels, such as Nav 1.7. The peptide is expressed recombinantly or chemically synthesized, wherein the peptide selected from SEQ ID NO: 24-SEQ ID NO: 274 or SEQ ID NO: 314-SEQ ID NO: 564. Alternatively, the peptides of SEQ ID NO: 24-SEQ ID NO: 274 or SEQ ID NO: 314-SEQ ID NO: 564 are mutated to maintain the cartilage homing function, but to add or increase ion channel inhibition, such as to Nav 1.7. Following expression or synthesis, the peptide is used directly. Following administration of the peptide, the peptide targets to the cartilage affected by pain. One or more peptides are administered to a human or animal subcutaneously, intravenously, or orally, or is injected directly into a joint.

The peptide can be a peptide of SEQ ID NO: 108. The peptide can also be a peptide of SEQ ID NO: 107. The peptide can be any peptide with the sequence selected from SEQ ID NO: 24-SEQ ID NO: 274 or SEQ ID NO: 314-SEQ ID NO: 564.

Example 67

Treatment of Chondrosarcoma

This example illustrates treatment of chondrosarcoma using peptides of the present disclosure. A peptide of the present disclosure is recombinantly expressed or chemically synthesized and are used directly, after radiolabeling, or after conjugation to a fluorophore or therapeutic compound, such as dasatinib. The peptide or peptide conjugate is administered in a pharmaceutical composition to a subject as a therapeutic for chondrosarcoma. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by chondrosarcoma.

The peptide can be a peptide of SEQ ID NO: 106. The peptide can also be a peptide of SEQ ID NO: 108. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 68

Treatment of Chordoma

This example illustrates treatment of chordoma using peptides of the present disclosure. A peptide of the present disclosure is recombinantly expressed or chemically synthesized and are used directly, after radiolabeling, or after conjugation to a fluorophore or therapeutic compound, such as dasatinib. The peptide or peptide conjugate is administered in a pharmaceutical composition to a subject as a therapeutic for chordoma. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by chordoma.

The peptide can be a peptide of SEQ ID NO: 187. The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 69

Treatment for Rapid Pain Relief

This example illustrates rapid pain relief in patients treated for rheumatoid arthritis or osteoarthritis with the peptides or peptide conjugates of this disclosure. A peptide of this disclosure is expressed recombinantly or chemically synthesized, and then the N-terminus of the peptide is conjugated to an active agent via an NHS ester to produce a peptide-active agent conjugate. In some aspects the active agent such as a kidney therapeutic from TABLE 4, TABLE 5, or TABLE 6. In some cases, the peptide alone is administered to the subject.

The peptide or peptide-active agent conjugate is administered to a subject in need thereof. The subject is a human or non-human animal. The subject in need thereof has rheumatoid arthritis or osteoarthritis. The peptide or peptide conjugate is delivered via intravenous administration. Upon administration, the peptide or peptide conjugate rapidly homes to cartilage. Rapid pain relief within five minutes to an hour is experienced by the subject, and pain relieve can last as long as over 3 hours.

The peptide can be a peptide of SEQ ID NO: 108. The peptide can also be a peptide of SEQ ID NO: 33. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 70

Treatment for Lupus Nephritis

This example illustrates treatment of lupus nephritis using peptides or peptide conjugates of this disclosure. A peptide of the present disclosure is recombinantly expressed or chemically synthesized and are used directly, after radiolabeling, or after conjugation to a fluorophore or therapeutic compound, such as abatacept or BIIB023.

The peptide or peptide conjugate is administered in a pharmaceutical composition to a subject as a therapeutic for lupus nephritis. The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly. The peptides or peptide conjugates target kidney affected by lupus nephritis.

The peptide can be a peptide of SEQ ID NO: 27. The peptide can also be a peptide of SEQ ID NO: 24. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 71

Treatment for Acute Kidney Injury (AKI)

This example illustrates treatment of acute kidney injury (AKI) using peptides or peptide conjugates of this disclosure. A peptide of the present disclosure is recombinantly expressed or chemically synthesized and are used directly, after radiolabeling, or after conjugation to a fluorophore or therapeutic compound, such as such as a kidney therapeutic from TABLE 4, TABLE 5, or TABLE 6.

The peptide or peptide conjugate is administered in a pharmaceutical composition to a subject as a therapeutic for acute kidney injury (AKI). The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by acute kidney injury (AKI).

The peptide can be a peptide of SEQ ID NO: 108. The peptide can also be a peptide of SEQ ID NO: 36. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 72

Treatment for Chronic Kidney Disease (CKD)

This example illustrates treatment of chronic kidney disease (CKD) using peptides or peptide conjugates of this disclosure. A peptide of the present disclosure is recombinantly expressed or chemically synthesized and are used directly, after radiolabeling, or after conjugation to a fluorophore or therapeutic compound, such as a kidney therapeutic from TABLE 4, TABLE 5, or TABLE 6.

The peptide or peptide conjugate is administered in a pharmaceutical composition to a subject as a therapeutic for chronic kidney disease (CKD). The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by chronic kidney disease (CKD).

The peptide can be a peptide of SEQ ID NO: 199. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 73

Treatment for Hypertensive Kidney Damage

This example illustrates treatment of hypertensive kidney damage using peptides or peptide conjugates of this disclosure. A peptide of the present disclosure is recombinantly expressed or chemically synthesized and are used directly, after radiolabeling, or after conjugation to a fluorophore or therapeutic compound, such as such as a kidney therapeutic from TABLE 4, TABLE 5, or TABLE 6.

The peptide or peptide conjugate is administered in a pharmaceutical composition to a subject as a therapeutic for hypertensive kidney damage. The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by hypertensive kidney damage.

The peptide can be a peptide of SEQ ID NO: 27. The peptide can also be a peptide of SEQ ID NO: 185. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 74

Treatment for Diabetic Nephropathy

This example illustrates treatment of diabetic nephropathy using peptides or peptide conjugates of this disclosure. A peptide of the present disclosure is recombinantly expressed or chemically synthesized and are used directly, after radiolabeling, or after conjugation to a fluorophore or therapeutic compound, such as such as a kidney therapeutic from TABLE 4, TABLE 5, or TABLE 6.

The peptide or peptide conjugate is administered in a pharmaceutical composition to a subject as a therapeutic for diabetic nephropathy. The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by diabetic nephropathy.

The peptide can be a peptide of SEQ ID NO: 108. The peptide can also be a peptide of SEQ ID NO: 22. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 75

Treatment for Renal Fibrosis

This example illustrates treatment of renal fibrosis using peptides or peptide conjugates of this disclosure. A peptide of the present disclosure is recombinantly expressed or chemically synthesized and are used directly, after radiolabeling, or after conjugation to a fluorophore or therapeutic compound, such as such as a kidney therapeutic from TABLE 4, TABLE 5, or TABLE 6.

The peptide or peptide conjugate is administered in a pharmaceutical composition to a subject as a therapeutic for renal fibrosis. The peptide is selected from any one of the peptides of SEQ ID NO: 24-SEQ ID NO: 274 or SEQ ID NO: 314-SEQ ID NO: 564. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by renal fibrosis.

The peptide can be a peptide of SEQ ID NO: 199. The peptide can also be a peptide of SEQ ID NO: 26. The peptide can be any peptide with the sequence selected from SEQ ID NO: 24-SEQ ID NO: 274 or SEQ ID NO: 314-SEQ ID NO: 564. Such peptide-drug conjugates can be made using either a cleavable or stable linker as described herein (e.g., EXAMPLES 21 and 22).

Example 76

Peptide Variants Based on Multiple Sequence Alignment

This example illustrates using multiple sequence alignment to design peptide variants with increased stability and decreased immunogenicity. An alignment was generated using R language and an "msa" software package, which codes for R language specific for multiple alignments (Bodenhofer, U et al. *Bioinformatics*, 31 (24): 3997-3999 (2015)). FIG. 11 illustrates a multiple sequence alignment of SEQ ID NO: 316, SEQ ID NO: 317, SEQ ID NO: 321, SEQ ID NO: 333, SEQ ID NO: 337, SEQ ID NO: 338, SEQ ID NO: 340, SEQ ID NO: 398, SEQ ID NO: 474, SEQ ID NO: 483, SEQ ID NO: 486, and SEQ ID NO: 543-SEQ ID NO: 549. The alignment identified permissive or preferred amino acids at a given location, and provided a guide for discovery of novel peptide variants that could be generated and that could retain essential properties such as structure, function, peptide folding, biodistribution, or stability. SEQ ID NO: 21 and SEQ ID NO: 295 are consensus sequences based on the above multiple sequence alignment. SEQ ID NO: 21 is the same sequence as SEQ ID NO: 295 but with an N-terminal "GS." Furthermore, based on the ability to substitute K residues to R residues, the multiple sequence alignment identified peptides of the family of sequences of SEQ ID NO: 22 and SEQ ID NO: 296 as potential peptide variants that could be generated and that could retain essential properties such as structure, function, peptide folding, biodistribution, or stability. Additionally, the multiple sequence alignment identified SEQ ID NO: 312 as a conserved region within the sequences of the alignment, which may, at least in part, be important for maintaining the essential properties such as structure, function, peptide folding, biodistribution, binding, accumulation, retention, or stability.

Example 77

Peptide Immunogenicity

This example illustrates the testing of the immunogenicity of a peptide. NetMHC II version 2.3 prediction software was used to identify immunogenic peptides based on a neural network alignment algorithm that predicts peptide binding to MHC Class II molecules. The NetMHC II prediction software was utilized to determine the putative peptide binding capability to DR, DQ, and DP MHC II alleles and the strength of the interaction between peptide and MHC II molecules. TABLE 7 shows the resulting immunogenicity score of select peptides. The numbers of strong versus weak peptides were tallied into each major MHC allele group (DR, DQ, and DP). Additionally, the numbers of 'unique strong' and 'unique weak core' peptides were also tallied. These data were used to predict which peptides are less likely to induce an immunogenic response in patients. For example, the stronger a peptide binds to an allele, the more likely it is to be presented in a MHC/peptide combination on an antigen presenting cell, thus triggering an immune response, and a peptide that is predicted to bind to fewer alleles is more likely to have weaker binding to given alleles and should be less immunogenic.

TABLE 7

Immunogenicity Scores of Peptides

| SEQ ID NO: | Strong Binding Alleles (DR + DQ + DP) | Unique Strong Core Peptides | Weak Binding Alleles (DR + DQ + DP) | Unique Weak Core Peptides |
|---|---|---|---|---|
| 108 | 1 + 0 + 0 | 1 + 0 + 0 | 7 + 1 + 0 | 7 + 2 + 0 |
| 260 | 0 + 0 + 0 | 0 + 0 + 0 | 4 + 1 + 3 | 6 + 1 + 1 |
| 261 | 0 + 0 + 0 | 0 + 0 + 0 | 4 + 1 + 3 | 6 + 2 + 1 |
| 262 | 1 + 0 + 0 | 2 + 0 + 0 | 5 + 1 + 3 | 7 + 1 + 1 |
| 263 | 1 + 0 + 0 | 2 + 0 + 0 | 6 + 1 + 3 | 5 + 1 + 1 |
| 264 | 0 + 0 + 0 | 0 + 0 + 0 | 4 + 1 + 3 | 6 + 2 + 1 |
| 265 | 0 + 0 + 0 | 0 + 0 + 0 | 5 + 1 + 3 | 7 + 2 + 1 |
| 271 | 0 + 0 + 1 | 0 + 0 + 1 | 7 + 4 + 1 | 8 + 6 + 2 |
| 274 | 0 + 0 + 0 | 0 + 0 + 0 | 5 + 4 + 1 | 5 + 4 + 2 |
| 398 | 1 + 0 + 0 | 1 + 0 + 0 | 7 + 1 + 0 | 7 + 1 + 0 |
| 550 | 0 + 0 + 0 | 0 + 0 + 0 | 4 + 0 + 3 | 6 + 0 + 1 |
| 551 | 0 + 0 + 0 | 0 + 0 + 0 | 4 + 1 + 3 | 6 + 1 + 1 |
| 552 | 1 + 0 + 0 | 2 + 0 + 0 | 5 + 0 + 3 | 7 + 0 + 1 |
| 553 | 1 + 0 + 0 | 2 + 0 + 0 | 6 + 0 + 3 | 5 + 0 + 1 |
| 554 | 0 + 0 + 0 | 0 + 0 + 0 | 4 + 1 + 3 | 6 + 1 + 1 |
| 555 | 0 + 0 + 0 | 0 + 0 + 0 | 5 + 1 + 3 | 7 + 1 + 1 |
| 561 | 0 + 0 + 1 | 0 + 0 + 1 | 7 + 4 + 1 | 8 + 6 + 2 |
| 564 | 0 + 0 + 0 | 0 + 0 + 0 | 5 + 4 + 1 | 5 + 5 + 2 |

Example 78

Peptide Variants

This example illustrates the design of variant peptide sequences with increased stability, decreased regions of immunogenicity, and the substitution of a tyrosine for spectrophotometric reporting as compared to a parent peptide sequence. Potential mutations to the parent peptide sequence, SEQ ID NO: 108, that may result in a peptide with increased stability, decreased immunogenicity, or increased absorbance at 270-280 nm (such as the substitution to a tyrosine or tryptophan residue for spectrophotometric reporting) were identified based on information from multiple sequence alignment from EXAMPLE 76 and immunogenicity testing from EXAMPLE 77.

In SEQ ID NO: 108, residue N7 is at risk for deamidation. Based on the multiple sequence alignment of SEQ ID NO: 316, SEQ ID NO: 317, SEQ ID NO: 321, SEQ ID NO: 333, SEQ ID NO: 337, SEQ ID NO: 338, SEQ ID NO: 340, SEQ ID NO: 398, SEQ ID NO: 483, SEQ ID NO: 486, and SEQ ID NO: 543-SEQ ID NO: 549, the candidate residue mutations to best reduce this risk were N7S and N7G. N7S was determined to be more likely to result in a peptide with desirable properties such as folding and stability as shown by matches in the alignment and conservationist presence in a peptide with high stability (SEQ ID NO: 474).

Residue D18 is at risk for cleavage. Based on the multiple sequence alignment, the candidate residue mutations to best reduce cleavage at D18 are D18E and D18Q. D18E is the preferred choice based on retaining charge.

Residue M25 is at risk for oxidation. Based on the multiple sequence alignment, the candidate residue mutations to best reduce oxidation were M25T and M25A. Based on the immunogenicity score of peptides with each mutation, it was determined that M25T is the better mutation, as it eliminates a significant source of immunogenicity as compared to SEQ ID NO: 108 as well as the variant with M25A, which did not eliminate the predicted immunogenicity of the parent peptide of SEQ ID NO: 108.

Residue N32 is at risk for deamidation, at least in part due to the neighboring residue S33. However, N32 is conserved across Kv1.3 binding cystine-dense peptides in the alignment of EXAMPLE 76, and implicated in receptor binding (Peigneur, S., Biochemistry, 55(32): 2927-35 (2016)). For certain applications, peptides are designed to maintain this binding interaction, and for other applications, peptides are designed to remove this binding interaction. To maintain functionality, one candidate residue mutation based on the multiple sequence alignment is S33R, which would impact deamidation. However, it resulted in a predicted increased immunogenicity score. Another candidate residue mutation is S33G, but this may result in higher deamidation rates. If N32 is mutated, the best candidate residue mutation based the multiple sequence alignment in combination with the immunogenicity score was N32Q despite it having a slight increase in immunogenicity. Other options are N32A, N32S, or N32T. Alternatively, to remove functionality, candidate mutations based on the multiple sequence alignment are N32A and N32L, which are the preferred choices.

For the substitution to a tyrosine for spectrophotometric reporting, the best candidate locations were T38Y (which had the strongest precedence in the multiple sequence alignment and is found in several of the stable peptides (e.g., SEQ ID NO: 474, SEQ ID NO: 544, and SEQ ID NO: 545)), L17Y, and H36Y. However, T38Y may slightly increase immunogenicity with respect to the DR allele. Another option for spectrophometric absorbance is to substitute Trp for the Leu at position 17.

Based on the above analysis, the following short list of potential mutations for SEQ ID NO: 108 were compiled: N7S; D18E; M25T; N32Q, N32A, N32S, N32T, N32L, S33G, and S33R (variants both to retain function and to remove function of binding ion channel); and L17Y, H36Y, and T38Y.

TABLE 8 provides some exemplary sequences using various combinations of these mutations.

TABLE 8

Exemplary Sequence Variants of SEQ ID NO: 108

| SEQ ID NO: | Mutations |
|---|---|
| 108 | Parent |
| 550 | N5S, D16E, M23T, S31G |
| 551 | N5S, D16E, M23T, N30Q |
| 552 | N5S, D16E, M23T, S31R |
| 553 | D16E, M23T |
| 554 | D16E, M23T, N30Q |
| 555 | D16E, M23T, N30Q, T36Y |
| 556 | L15Y, D16E, M23T, N30Q |
| 557 | D16E, M23T, N30Q, H34Y |
| 558 | N5S, D16E, M23T, N30Q, T36Y |
| 559 | N5S, L15Y, D16E, M23T, N30Q |
| 560 | N5S, D16E, M23T, N30Q, H34Y |
| 561 | D16E, M23T, N32A, T36Y |
| 562 | D16E, M23T, N32S, T36Y |
| 563 | D16E, M23T, N32T, T36Y |
| 564 | D16E, M23T, T36Y |

Example 79

Peptide-Budesonide Conjugate

This example describes conjugation of a peptide of any one of SEQ ID NO: 260-SEQ ID NO: 274 or SEQ ID NO: 550-SEQ ID NO: 564 to budesonide. Budesonide is readily conjugated to any peptide disclosed herein via standard chemistries such as those described in, but not limited to, Bioconjugate Techniques by Greg Hermanson (Elsevier Inc., 3$^{rd}$ edition, 2013) or by any of the methods described in EXAMPLES 25-28.

The peptide-budesonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration and homing of peptide-budesonide conjugates, the inflammation in the cartilage and/or kidney tissues is alleviated.

Example 80

Peptide-Dexamethasone Conjugate

This example describes conjugation of a peptide of any one of SEQ ID NO: 260-SEQ ID NO: 274 or SEQ ID NO: 550-SEQ ID NO: 564 to dexamethasone. Dexamethasone is readily conjugated to any peptide disclosed herein via standard chemistries such as those described in, but not limited to, Bioconjugate Techniques by Greg Hermanson (Elsevier Inc., 3$^{rd}$ edition, 2013) or by any of the methods described in EXAMPLES 25-28.

The peptide-dexamethasone conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration and homing of peptide-dexamethasone conjugates, the inflammation in the cartilage and/or kidney tissues is alleviated.

Example 81

Peptide-Triamcinalone Acetonide Conjugate

This example describes conjugation of a peptide of any one of SEQ ID NO: 260-SEQ ID NO: 274 or SEQ ID NO: 550-SEQ ID NO: 564 to triamicinalone acetonide. Triamicinalone acetonide is readily conjugated to any peptide disclosed herein via standard chemistries such as those described in, but not limited to, Bioconjugate Techniques by Greg Hermanson (Elsevier Inc., 3$^{rd}$ edition, 2013) or by any of the methods described in EXAMPLES 25-28.

The peptide-triamicinalone acetonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration and homing of peptide-triamicinalone acetonide conjugates, the inflammation in the cartilage and/or kidney tissues is alleviated.

Example 82

Peptide-Desciclesonide Acetonide Conjugate

This example describes conjugation of a peptide of any one of SEQ ID NO: 260-SEQ ID NO: 274 or SEQ ID NO: 550-SEQ ID NO: 564 to desciclesonide acetonide. Desciclesonide acetonide is readily conjugated to any peptide disclosed herein via standard chemistries such as those described in, but not limited to, Bioconjugate Techniques by Greg Hermanson (Elsevier Inc., 3$^{rd}$ edition, 2013) or by any of the methods described in EXAMPLES 25-28.

The peptide-desciclesonide acetonide conjugates are administered to a subject in need thereof and home, target, are directed to, are retained by, accumulate in, migrate to, and/or bind to cartilage and/or kidneys. The subject is a human or animal and has inflammation in the cartilage or kidney tissues. Upon administration and homing of peptide-desciclesonide acetonide conjugates, the inflammation in the cartilage and/or kidney tissues is alleviated.

Example 83

Method of Peptide Synthesis

This example describes the synthesis of SEQ ID NO: 106, SEQ ID NO: 108, and SEQ ID NO: 187.

A peptide of SEQ ID NO: 108 was made using Solid Phase Peptide Synthesis (SPPS). After release of the peptide from the solid phase, the peptide was purified prior to folding by oxidation in solution. The folded peptide was further purified by reversed-phase chromatography and lyophilized as a TFA salt. The final SEQ ID NO: 108 peptide product had a purity of 96.1% and a mass of 4,301.7 Da, which confirmed its identity as a peptide of SEQ ID NO: 108.

A peptide of SEQ ID NO: 106 was made using Solid Phase Peptide Synthesis (SPPS). After release of the peptide from the solid phase, the peptide was folded by oxidation in solution. The folded peptide was purified by reversed-phase chromatography and lyophilized as a TFA salt. The final SEQ ID NO: 106 had a purity of 95.6% and a mass of 4,503.0 Da, which confirmed its identity as a peptide of SEQ ID NO: 106.

A peptide of SEQ ID NO: 187 was made using Solid Phase Peptide Synthesis (SPPS). After release of the peptide from the solid phase, the peptide was folded by oxidation in solution. The folded peptide was purified by reversed-phase chromatography and lyophilized as a TFA salt. The final SEQ ID NO: 187 peptide product had a purity of 95.5% and a mass of 4,154.0 Da, which confirmed its identity as a peptide of SEQ ID NO: 187.

Example 84

Whole Body Autoradiography of Cartilage Homing Peptides

This example illustrates peptide homing to cartilage mice 5 minutes to 48 hours after administration of a radiolabeled peptide. Signal from the radiolabeled peptides was found in all types of cartilage at each time point examined. Each peptide was radiolabeled by methylating lysines at the N-terminus as described in EXAMPLE 2. As such, the peptide may contain methyl or dimethyl lysines and a methylated or dimethlyated amino terminus. A dose of 100 nmol radiolabeled peptide was administered via tail vein injection in Female Harlan athymic nude mice, weighing 20-25 g. The experiment was done in duplicate (n=2 animals per group). Each radiolabeled peptide was allowed to freely circulate within the animal for the described time period before the animals were euthanized and sectioned.

Whole body autoradiography (WBA) sagittal sectioning was performed as follows. At the end of the dosing period, mice were frozen in a hexane/dry ice bath and then embedded in a frozen block of carboxymethylcellulose. Whole animal sagittal slices were prepared that resulted in thin frozen sections for imaging. Sections were allowed to dessicate in a freezer prior to imaging. For the autoradiography imaging, tape mounted thin sections were freeze dried and radioactive samples were exposed to phosphoimager plates. These plates were developed and the signal (densitometry) from each organ was normalized to the signal found in the cardiac blood of each animal. A signal in tissue darker than the signal expected from blood in that tissue indicates accumulation in a region, tissue, structure, or cell.

Figure 14A:
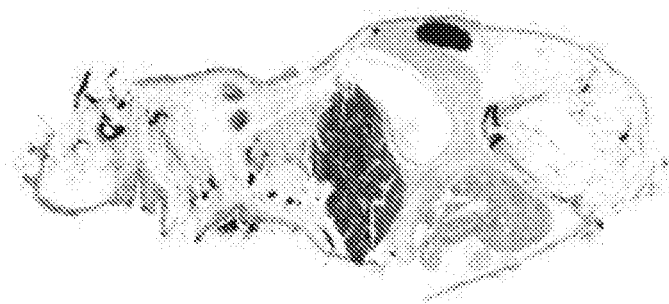
FIG. 14A illustrates the $^{14}C$ signal in a different frozen section of the mouse, 3 hours after administration of 100 nmol of a radiolabeled peptide of SEQ ID NO: 108.
Figure 14B:
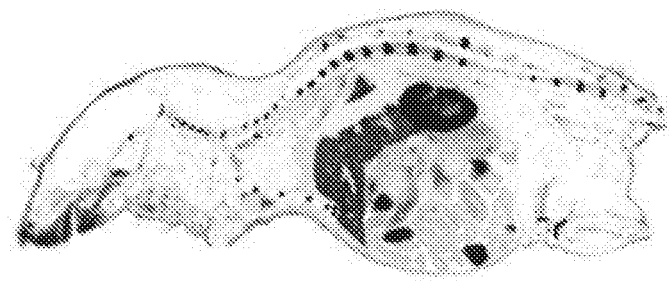
FIG. 14B illustrates the $^{14}C$ signal in a different frozen section of a mouse, 3 hours after administration of 100 nmol of a radiolabeled peptide of SEQ ID NO: 108

FIG. 14 illustrates autoradiography image of frozen sections from a mouse, 3 hours after administration of 100 nmol of a radiolabeled peptide of SEQ ID NO: 108. FIG. 14A illustrates the $^{14}$C signal in a frozen section of a mouse, 3 hours after administration of 100 nmol of a radiolabeled peptide of SEQ ID NO: 108. The $^{14}$C signal identifies the radiolabeled peptide distribution in the cartilage of the mouse. FIG. 14B illustrates the $^{14}$C signal in a different frozen section of a mouse, 3 hours after administration of 100 nmol of a radiolabeled peptide of SEQ ID NO: 108. The $^{14}$C signal identifies the radiolabeled peptide distribution in the cartilage of the mouse.

TABLE 9 shows the signal of radiolabeled peptides of SEQ ID NO: 27 and SEQ ID NO: 108 in intervertebral discs (IVD) and knee joints as a percentage of the blood. Because the peptides may arrive at the joint within five minutes, a therapeutic effect from the peptide or a conjugated active agent may begin quickly. A therapeutic effect could be long lasting, due to continued presence of detected agents at 48 hours and/or due to long lasting pharmacodynamics effects.

TABLE 9

Signal of Radiolabeled Peptides of SEQ ID NO: 27 and SEQ ID NO: 108 in IVD and Knee Joints as a Percentage of Blood

| Hours | SEQ ID NO: 27 IVD | SEQ ID NO: 108 IVD | SEQ ID NO: 108 Knee |
|---|---|---|---|
| 0.08 |  | 164 | 404 |
| 0.5 |  | 369 | 510 |
| 1 |  | 961 | 1114 |
| 3 | 1779 | 3213 | 4059 |
| 8 |  | 3777 | 4990 |
| 24 | 833 | 5391 | 2137 |
| 48 |  | 3320 | 843 |

Figure 15A:
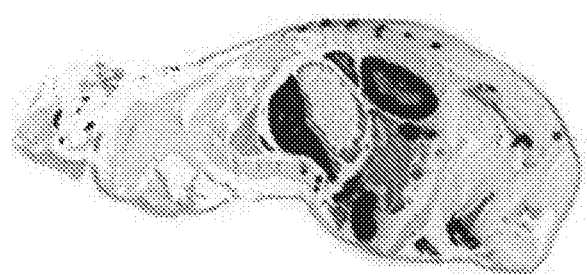
FIG. 15A illustrates the $^{14}C$ signal in a frozen section of a mouse.
Figure 15B:
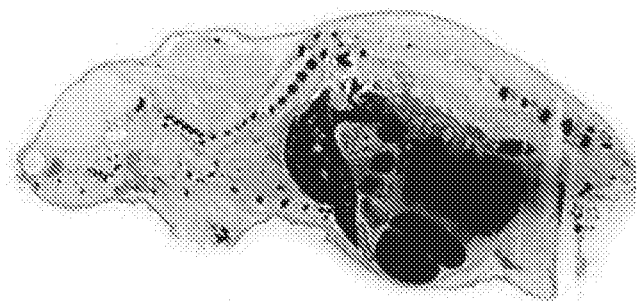
FIG. 15B illustrates the $^{14}C$ signal in a frozen section of the mouse, 3 hours after administration of 100 nmol of a radiolabeled peptide of SEQ ID NO: 106.

FIG. 15 illustrates autoradiography images of frozen sections from a mouse, 3 hours after administration of 100 nmol of a radiolabeled peptide of SEQ ID NO: 106. FIG. 15A illustrates the $^{14}$C signal in a frozen section of a mouse, 3 hours after administration of 100 nmol of a radiolabeled peptide of SEQ ID NO: 106. The $^{14}$C signal identifies the radiolabeled peptide distribution in the cartilage of the mouse. FIG. 15B illustrates the $^{14}$C signal in a frozen section of a different mouse, 3 hours after administration of 100 nmol of a radiolabeled peptide of SEQ ID NO: 106. The $^{14}$C signal identifies the radiolabeled peptide distribution in the cartilage of the mouse.

Figure 16A:
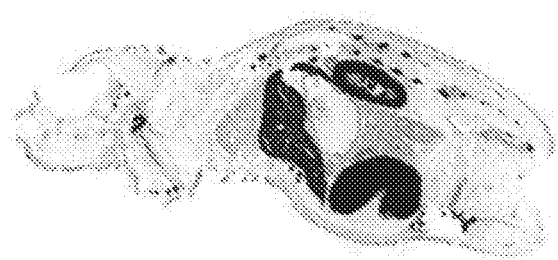
FIG. 16A illustrates the $^{14}C$ signal in a frozen section of the mouse, 3 hours after administration of 100 nmol of a radiolabeled peptide of SEQ ID NO: 187.
Figure 16B:
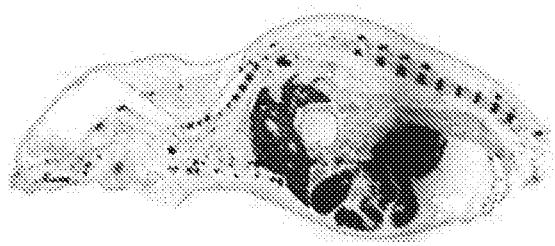
FIG. 16B illustrates the $^{14}C$ signal in a frozen section of the mouse, 3 hours after administration of 100 nmol of a radiolabeled peptide of SEQ ID NO: 187.

FIG. 16 illustrates autoradiography images of frozen sections from a mouse, 3 hours after administration of 100 nmol of a radiolabeled peptide of SEQ ID NO: 187. FIG. 16A illustrates the $^{14}$C signal in a frozen section of the mouse, 3 hours after administration of 100 nmol of a radiolabeled peptide of SEQ ID NO: 187. The $^{14}$C signal identifies the radiolabeled peptide distribution in the cartilage of the mouse. FIG. 16B illustrates the $^{14}$C signal in a frozen section of a different mouse, 3 hours after administration of 100 nmol of a radiolabeled peptide of SEQ ID NO: 187. The $^{14}$C signal identifies the radiolabeled peptide distribution in the cartilage of the mouse.

This data illustrates peptides of SEQ ID NO: 27, SEQ ID NO: 108, SEQ ID NO: 106 and SEQ ID NO: 187 homed to and accumulated in the cartilage of the animals. The peptide of SEQ ID NO: 108 is a K to R variant of a peptide of SEQ ID NO: 27. These data show that K to R variants of cartilage homing peptides retained their cartilage homing properties.

SEQ ID NO: 567 (GSGVPINVRSRGSRDSLDPSR-RAGMRFGRSINSRSHSTP) is a linearized version of SEQ ID NO: 108, where the knotted scaffold of the peptide was removed by mutating out the cysteine residues that form the disulfide bonds of the peptide to serine residues, but retaining the rest of the sequence. TABLE 10 shows quantification of signal as a percentage of signal in blood from a linearized radiolabeled SEQ ID NO: 567 peptide in intervertebral discs (IVD).

TABLE 10

Signal of Radiolabled Peptides of SEQ ID NO: 567 in IVD as a Percentage of Blood

|  | 3 hr Ligated Kidneys | 3 hr Intact Kidneys | 24 hr Intact Kidneys |
|---|---|---|---|
| IVD | 117 | 177 | 104 |

The peptide of SEQ ID NO: 567, a linearized version of the peptide of SEQ ID NO: 108, homed to cartilage to a much lesser extent than the folded knotted peptide (SEQ ID NO: 108). The signal of the folded knotted peptide of SEQ ID NO: 108 was ~20-fold greater at 3 hours and ~50-fold greater at 24 hours (TABLE 9) as compared to the linearized peptide of SEQ ID NO: 567 (TABLE 10). These results indicate that in addition to changes in primary sequence or peptide charge, homing to cartilage can also be related to changes in conformation, or tertiary structure. Namely, in some cases, folded cystine-dense peptides can be exemplary cartilage homers in comparison to unfolded, linearized peptides of the same primary sequence (except for the mutated cysteine residues).

Example 85

Fluorescence of Cartilage Homing Peptides

This example illustrates peptide homing to cartilage mice after administration of a peptide fluorophore conjugate. A peptide of SEQ ID NO: 108 was chemically conjugated to one molecule of Cyanine 5.5, and then imaged using the methods of EXAMPLE 13.

FIG. 10 shows white light images and corresponding whole body fluorescence images of a mouse administered 10 nmol of a peptide of SEQ ID NO: 108 conjugated to a Cy5.5 fluorophore (SEQ ID NO: 108A) at 24 hours post-administration. FIG. 10A illustrates an image of a frozen section of a mouse, 24 hours after administration of 10 nmol of a peptide of SEQ ID NO: 108 conjugated to a Cy5.5 fluorophore (SEQ ID NO: 108A). FIG. 10B illustrates the fluorescence signal in the mouse, corresponding to the section shown in FIG. 10A, 24 hours after administration of 10 nmol of a peptide of SEQ ID NO: 108 conjugated to a Cy5.5 fluorophore (SEQ ID NO: 108A). FIG. 10C illustrates an image of a different frozen section of the mouse, 24 hours after administration of 10 nmol of a peptide of SEQ ID NO: 108 conjugated to a Cy5.5 fluorophore (SEQ ID NO: 108A). FIG. 10D illustrates the fluorescence signal in the mouse, corresponding to the section shown in FIG. 10C, 24 hours after administration of 10 nmol of a peptide of SEQ ID NO: 108 conjugated to a Cy5.5 fluorophore (SEQ ID NO: 108A). FIG. 10E illustrates an image of a different frozen section of the mouse, 24 hours after administration of 10 nmol of a peptide of SEQ ID NO: 108 conjugated to a Cy5.5 fluorophore (SEQ ID NO: 108A). FIG. 10F illustrates a fluorescence signal in the mouse, corresponding to the section shown in FIG. 10E, 24 hours after administration of 10 nmol of a peptide of SEQ ID NO: 108 conjugated to a Cy5.5 fluorophore (SEQ ID NO: 108A).

FIG. 13 shows IVIS fluorescence imaging of an isolated hind limb from a first mouse and an isolated hind limb from a second mouse after administration of 10 nmol SEQ ID NO: 108 peptide conjugated to a Cy5.5 fluorophore (SEQ ID NO: 108A). FIG. 13A shows the right hind limb with skin removed from a first mouse and from a second mouse 3 hours after peptide administration. FIG. 13B shows the right hind limb with muscle removed from a first mouse and from a second mouse 3 hours after peptide administration. FIG. 13C shows the right hind limb with skin removed from a first mouse and from a second mouse 24 hours after peptide administration. FIG. 13D shows the right hind limb with muscle removed from a first mouse and from a second mouse 24 hours after peptide administration. FIG. 13E shows the right hind limb with skin removed from a first mouse and from a second mouse 48 hours after peptide administration. FIG. 13F shows the right hind limb with muscle removed from a first mouse and from a second mouse 48 hours after peptide administration. FIG. 13G shows the right hind limb with skin removed from a first mouse and from a second mouse 72 hours after peptide administration. FIG. 13H shows the right hind limb with muscle removed from a first mouse and from a second mouse 72 hours after peptide administration. Peptide fluorescence was observed in the knee joints of isolated right hind limbs at all time points tested.

Example 86

Peptide Resistance Under Various Conditions

This example illustrates peptide stability under various stress conditions such as high temperature, low pH, reducing agents, and proteases. To determine resistance to high temperatures, cystine-dense peptides (CDPs) were incubated at 0.5 mM in PBS at 75° C. or 100° C. for 1 h and pelleted, and the supernatant was analyzed with reversed-phase chromatography (RPC). To determine resistance to proteolytic digestion, CDPs were mixed with 50 U of porcine pepsin, in simulated gastric fluid at pH 1.0, or 50 U of porcine trypsin in PBS, incubated for 30 minutes at 37° C. and analyzed with RPC. Oxidized and reduced forms (prepared through addition 10 mM DTT) were compared. Circular Dichroism spectroscopy was used in order to measure the secondary structure of peptides with a Jasco J-720W spectropolarimeter in a cell with a 1.0-mm path length, and CDPs were diluted into 20 mM phosphate buffer, pH 7.4, at a concentration of 15-25 μM. These conditions were expected to denature or degrade conventional globular proteins and many peptides. In TABLE 11, "high" resistance indicated a high amount of the peptide remained or was retained as unmodified under the given experimental conditions and "low" resistance indicated a low amount of the peptide remained or was retained unmodified under the given experimental conditions. Notably, the experimental conditions described in this example were more extreme stress conditions than to many standard in vivo or physiologic conditions, in vitro conditions, conditions during manufacturing, and handling conditions. As such, even "low" resistance can indicate meaningful resistance to these stress conditions that may have applicability for a number of uses described herein. The data from these studies are shown in TABLE 11. The peptides tested, SEQ ID NO: 315, SEQ ID NO: 317 and SEQ ID NO: 482, showed high resistance to one or more of the conditions tested.

TABLE 11

Resistance of SEQ ID NO: 317, SEQ ID NO: 315, and SEQ ID NO: 482 to Various Conditions

| SEQ ID NO: | Resistance to Reduction | Resistance to 75° C. | Resistance to 100° C. | Resistance to Pepsin | Resistance to Trypsin |
|---|---|---|---|---|---|
| 27 | High | High | High | High | High |
| 25 | Low | High | Low | High | Low |
| 192 | Low | High | Low | High | Low |

While certain embodiments of the present disclosure have been exemplified or shown and described herein, it will be apparent to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all embodiments of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed:

1. A peptide active agent conjugate, the peptide active agent conjugate comprising:
   a) a peptide comprising a sequence that has at least 90% sequence identity to SEQ ID NO: 398 or a fragment thereof comprising at least 18 amino acid residues that has at least 95% sequence identity to SEQ ID NO: 398; and
   b) an active agent, wherein the active agent is desciclesonide, kineret, a j anus kinase (JAK) inhibitor, tofacitinib, dasatinib, an interleukin-1 (IL-1) inhibitor, an interleukin-1 (IL-1) receptor antagonist, an interleukin-12 (IL-12) antagonist, fibroblast growth factor 18 (FGF-18), insulin-like growth factor 1 (IGF-1), transforming growth factor beta (TFG-β), a cathepsin K inhibitor, an NOD-, LRR- and pyrin domain-containing protein 3 (NLRP3) inflammasome drug, or MCC950.

2. The peptide active agent conjugate of claim 1, wherein the peptide comprises 4 or more cysteine residues.

3. The peptide active agent conjugate of claim 1, wherein the peptide or the fragment thereof comprises three or more disulfide bridges formed between cysteine residues, wherein one of the disulfide bridges passes through a loop formed by two other disulfide bridges.

4. The peptide active agent conjugate of claim 1, wherein the peptide or the fragment thereof comprises 5 to 12 basic residues.

5. The peptide active agent conjugate of claim 1, wherein the peptide or the fragment thereof comprises from 0 to 5 acidic residues.

6. The peptide active agent conjugate of claim 1, wherein the peptide is SEQ ID NO: 398.

7. The peptide active agent conjugate of claim 1, wherein 1, 2, 3, 4, 5, 6, 7, 8, 9, or 10 active agents are linked to the peptide.

8. The peptide active agent conjugate of claim 1, wherein the peptide is linked to the active agent by fusion of the active agent to the peptide at an N-terminus or a C-terminus of the peptide.

9. The peptide active agent conjugate of claim 1, wherein the peptide is linked to the active agent at an N-terminus, at the epsilon amine of an internal lysine residue, at the carboxylic acid of an aspartic acid or glutamic acid residue, or a C-terminus of the peptide by a linker.

10. The peptide active agent conjugate of claim 1, wherein the peptide is linked to the active agent at a non-natural amino acid present in the peptide, wherein the non-natural amino acid is an insertion, appendage, or substitution for another amino acid.

11. The peptide active agent conjugate of claim 1, wherein the peptide is linked to the active agent by a cleavable linker comprising a cleavage site for matrix metalloproteinases, thrombin, cathepsins, or beta-glucuronidase.

12. The peptide active agent conjugate of claim 1, wherein the peptide is linked to the active agent by a linker comprising an amide bond, an ester bond, a carbamate bond, a carbonate bond, a hydrazone bond, an oxime bond, a disulfide bond, a thioester bond, a thioether bond, a triazole, a carbon-carbon bond, or a carbon-nitrogen bond.

13. The peptide active agent conjugate of claim 1, wherein the peptide is linked to the active agent by a hydrolytically labile linker.

14. The peptide active agent conjugate of claim 1, wherein the peptide is linked to the active agent by a pH sensitive, reducible, glutathione-sensitive, or protease cleavable linker.

15. The peptide active agent conjugate of claim 1, wherein the peptide is linked to the active agent by a stable linker.

16. A pharmaceutical composition comprising the peptide active agent conjugate of claim 1, or a salt thereof, and a pharmaceutically acceptable carrier.

17. A method of imaging an organ or body region of a subject comprising administering to the subject a peptide active agent conjugate comprising:
   a) a peptide comprising a sequence that has at least 90% sequence identity to SEQ ID NO: 398 or a fragment thereof comprising at least 18 amino acid residues that has at least 95% sequence identity to SEQ ID NO: 398;
   b) an active agent, wherein the active agent is desciclesonide, kineret, a j anus kinase (JAK) inhibitor, tofacitinib, dasatinib, an interleukin-1 (IL-1) inhibitor, an interleukin-1 (IL-1) receptor antagonist, an interleukin-12 (IL-12) antagonist, fibroblast growth factor 18 (FGF-18), insulin-like growth factor 1 (IGF-1), transforming growth factor beta (TFG-β), a cathepsin K inhibitor, an NOD-, LRR- and pyrin domain-containing protein 3 (NLRP3) inflammasome drug, or MCC950; and
   c) a detectable agent.

18. The method of claim 17, wherein the detectable agent is a fluorophore, a near-infrared dye, a contrast agent, a nanoparticle, a metal-containing nanoparticle, a metal chelate, an X-ray contrast agent, a PET agent, a radioisotope, or a radionuclide chelator.

19. The method of claim 17, further comprising detecting a cancer or diseased region, tissue, structure, or cell.

20. The method of claim 19, further comprising performing surgery on the subject and removing the cancer or diseased region, the tissue, the structure, or the cell.

21. A method of treating a cartilage or kidney disorder in a subject comprising administering to the subject a peptide active agent conjugate comprising:
  a) a peptide comprising a sequence that has at least 90% sequence identity to SEQ ID NO: 398 or a fragment thereof comprising at least 18 amino acid residues that has at least 95% sequence identity to SEQ ID NO: 398; and
  b) an active agent, wherein the active agent is desciclesonide, kineret, a janus kinase (JAK) inhibitor, tofacitinib, dasatinib, an interleukin-1 (IL-1) inhibitor, an interleukin-1 (IL-1) receptor antagonist, an interleukin-12 (IL-12) antagonist, fibroblast growth factor 18 (FGF-18), insulin-like growth factor 1 (IGF-1), transforming growth factor beta (TFG-13), a cathepsin K inhibitor, an NOD-, LRR- and pyrin domain-containing protein 3 (NLRP3) inflammasome drug, or MCC950.

22. The method of claim 21, wherein the disorder is lupus nephritis, rheumatoid arthritis, gout, ankylosing spondylitis, psoriatic arthritis, osteoarthritis, fibrosis, scleroderma, chronic kidney disease, diabetic nephropathy, renal fibrosis, acute kidney injury, or calcium pyrophosphate deposition disease.

23. The method of claim 21, wherein upon administration to the subject the peptide active agent conjugate homes to a cartilage or a kidney of the subject.

24. The method of claim 21, wherein upon administration to the subject, the peptide active agent conjugate homes to proximal tubules of a kidney.

25. The method of claim 21, wherein the administering comprises administering by inhalation, intranasally, orally, topically, parenterally, intravenously, subcutaneously, intraarticularly, intramuscularly administration, intraperitoneally, dermally, transdermally, or a combination thereof.

* * * * *

UNITED STATES PATENT AND TRADEMARK OFFICE
CERTIFICATE OF CORRECTION

PATENT NO. : 11,013,814 B2
APPLICATION NO. : 16/492914
DATED : May 25, 2021
INVENTOR(S) : Julia E. Novak et al.

It is certified that error appears in the above-identified patent and that said Letters Patent is hereby corrected as shown below:

In the Claims

Claim 1, Column 475, Line 32, replace "j anus" with -- janus --

Claim 17, Column 476, Line 58, replace "j anus" with -- janus --

Claim 21, Column 478, Line 2, replace "(TFG-13)" with -- (TFG-$\beta$) --

Signed and Sealed this
Twelfth Day of April, 2022

Drew Hirshfeld
*Performing the Functions and Duties of the
Under Secretary of Commerce for Intellectual Property and
Director of the United States Patent and Trademark Office*